US010856482B2

(12) United States Patent
Van Der Linde et al.

(10) Patent No.: US 10,856,482 B2
(45) Date of Patent: Dec. 8, 2020

(54) MODIFIED CULLIN1 GENE

(71) Applicant: RIJK ZWAAN ZAADTEELT EN ZAADHANDEL B.V., De Lier (NL)

(72) Inventors: Lilian Van Der Linde, De Lier (NL); Sara Movahedi, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 32 days.

(21) Appl. No.: 15/892,500

(22) Filed: Feb. 9, 2018

(65) Prior Publication Data

US 2018/0184604 A1 Jul. 5, 2018

Related U.S. Application Data

(63) Continuation-in-part of application No. PCT/EP2016/071177, filed on Sep. 8, 2016.

(30) Foreign Application Priority Data

Sep. 8, 2015 (NL) ..................................... 2015409

(51) Int. Cl.

| | |
|---|---|
| ***A01H 1/04*** | (2006.01) |
| ***A01H 5/08*** | (2018.01) |
| ***C07K 14/415*** | (2006.01) |
| ***C12N 15/82*** | (2006.01) |
| ***C12Q 1/6895*** | (2018.01) |

(52) U.S. Cl.

CPC ................. *A01H 1/04* (2013.01); *A01H 5/08* (2013.01); *C07K 14/415* (2013.01); *C12N 15/8261* (2013.01); *C12Q 1/6895* (2013.01); *Y02A 40/146* (2018.01)

(58) Field of Classification Search

None

See application file for complete search history.

(56) References Cited

FOREIGN PATENT DOCUMENTS

WO WO 2011/061656 A1 * 5/2011

OTHER PUBLICATIONS

Kano-Murakami et al (1993, "A Rice Homeotic Gene, OSH1, Causes Unusual Phenotypes in Transgenic Tobacco", FEBS 334:365-368).*

Bowie et al, (1990, "Deciphering the Message in Protein Sequences: Tolerance to Amino Acid Substitutions", Science 247:1306-1310).*

McConnell et al, (2001, "Radial Patterning of Arabidopsis Shoots by Class III HD-ZIP and KANADI Genes", Nature 411 (6838):709-713).*

International Search Report and Written Opinion of the International Searching Authority dated Nov. 9, 2016, which issued during prosecution of International Application No. PCT/EP2016/071177.

Genbank. "Database Accession No. XM_004143037", Mar. 23, 2015.

Genbank. "Database Accession No. XM_004229178", Nov. 19, 2014.

Hernandez, et al. "Growth and morphological response of cucumber seedlings to supplemental red and blue photon flux ratios under varied solar daily light integrals" Scientia Horticulturae, Jun. 2014, 173:92-99.

* cited by examiner

*Primary Examiner* — Stuart F Baum

(74) *Attorney, Agent, or Firm* — Duane Morris LLP; Thomas J. Kowalski; Deborah L. Lu

(57) ABSTRACT

The present invention relates to a modified Cullin1 gene which leads to a plant type that enables efficient cultivation and/or is suitable for situations that require smaller portions, or reduces the labour, time and expenses involved with storing, handling and transporting of redundant plant leaves. The invention also relates to plants comprising the modified Cullin1 gene. The modified Cullin1 gene provides plants with a compact growth phenotype, i.e. comprising shorter internode length and/or a smaller leaf area when compared to plants not comprising the modified Cullin1 gene. The invention further relates to the use of the modified Cullin1 gene for the identification and development of a plant showing a compact growth phenotype, i.e. comprising shorter internodes and/or a smaller leaf area.

8 Claims, 77 Drawing Sheets

Specification includes a Sequence Listing.

Fig. 1

ATGACAATGGGCGAGCGGAAGACTATTGACTTGGAGCAGGGATGGGAGTTTATGCAGAAGGGTATC
ACAAAGTTGAAGAACATTCTCGAGGGCTTGCCTGAGCCTCAGTTCAGCTCCGAGGACTACATGATG
CTTTACACTACCAT[A]TATAACATGTGCACCCAAAAGCCGCCGCATGATTACTCCCAGCAGCTGT
ATGATAAATATCGTGAATCTTTTGAAGAGTACATCACTTCTATGGTCTTACCATCCTTGAGGGAGA
AGCACGATGAGTTCATGTTGAGAGAACTAGTAAAAAGGTGGACAAACCATAAAGTCATGGTGAGGT
GGCTTTCTCGCTTCTTCCACTATCTTGATCGGTACTTCATCGCTCGAAGGTCACTTCCACCTCTAA
ATGAAGTTGGCCTCACATGCTTCCGCGAATTGGTGTACAAAGAGCTAAATAGTAAAGTGAGGGATG
CAGTAATTTCATTGATTGATCAAGAACGTGAAGGAGAACAGATTGACAGAGCTCTACTGAAGAATG
TACTAGATATATTTGTGGAAATTGGTATGGGGCAAATGGATTACTATGAAAATGACTTTGAAGCTG
CCATGCTTAAAGATACTGCTGCTTATTACTCTAGGAAGGCTTCCAATTGGATCCTAGAAGATTCTT
GTCCCGATTATATGCTTAAAGCAGAGGAGTGCTTGAAACGAGAAAAGGATAGGGTTTCCCACTATT
TGCACTCTAGTAGCGAGCCAAAGTTGTTGGAGAAAGTTCAACATGAACTATTATCTGTTTATGCTA
CTCAACTGCTGGAAAAAGAGCATTCAGGATGCCATGCATTGCTTAGAGATGACAAGGTGGAAGATT
TGTCAAGGATGTTCCGTCTATTCTCCAAAATACCGAAGGGACTGGATCCAGTTTCCAACATATTTA
AGCAGCATGTAACTGCTGAAGGAACAGCACTGGTCAAACAGGCAGAAGATGCTGCAAGTAACAAGA
AGGCTGAGAAAAAGGACATAGTTGGTCTGCAGGAACAGGTTTTTGTAAGAAAAGTGATTGAGCTTC
ACGACAAGTACTTGGCTTATGTGAATGATTGTTTCCAAAACCACACACTTTTCCATAAGGCTCTCA
AGGAAGCTTTTGAAGTATTTTGCAATAAGGGTGTTGCTGGAAGTTCTAGTGCAGAATTGCTTGCTA
CCTTTTGTGATAACATCCTTAAGAAAGGTGGGAGTGAGAAGTTGAGTGATGAAGCAATCGAGGAGA
CACTTGAGAAGGTTGTGAAGTTGTTGGCATACATTTGCGACAAAGATCTGTTTGCTGAATTCTATA
GAAAAAAACTTGCCCGAAGGCTTCTCTTTGACAAGAGCGCGAACGATGACCACGAGAGAAGTATAT
TGACCAAATTGAAGCAACAATGTGGTGGTCAGTTCACTTCTAAGATGGAGGGAATGGTTACTGATT
TGACTTTGGCAAGGGAGAACCAAACTAGTTTTGAGGAGTATCTGAGCAATAATCCACAAGCGAGTC
CTGGCATCGACCTGACTGTTACTGTTTTAACTACTGGATTTTGGCCAAGCTACAAGTCTTTTGACC
TCAACCTGCCGGCAGAGATGGTAAAGTGTGTTGAAGTTTTCAGAGAGTTTTATCAAACAAAAACCA
AGCATCGAAAACTTACATGGATTTACTCATTGGGTACTTGTAACATCAGTGGAAAATTTGAACCGA
AAACGATGGAGCTGATTGTGACAACTTATCAGGCTTCTGCCCTGTTGCTATTCAATTCTTCGGATA
GACTAAGTTACTCGGAAATCATGACACAATTAAATTTGAGTGACGATGATGTAGTTAGACTACTCC
ACTCGTTGTCATGTGCCAAGTATAAAATTCTTAATAAGGAACCAAATACGAAAACCATCTCTCCGA
ACGATCATTTTGAGTTCAATGCAAAATTCTCCGACAAAATGAGGAGAATAAAGATCCCTCTTCCGC
CTGTGGATGAGAAAAAGAAAGTCATTGAAGATGTTGACAAGGATCGAAGGTATGCTATTGACGCCT
CAATCGTGCGTATCATGAAGAGTCGGAAAGTTCTTGGTCATCAGCAACTAGTGATGGAGTGCGTCG
AGCAATTGGGCCGTATGTTCAAGCCCGATTTCAAGGCGATAAAGAAGAGAATTGAAGACCTGATCA
CTCGGGATTATCTAGAGAGAGACAAAGACAACCCCCACTTGTTTAGGTACTTGGCTTGA

Fig. 2

ATGACAATGGGCGAGCGGAAGACTATTGACTTGGAACAGGGATGGGAGTTTATGCAGAAGGGTATC
ACAAAGTTGAAGAACATTCTTGAGGGCTTGCCTGAGCCCCAGTTCAGCTCCGAGGACTACATGATG
CTTTACACTACCAT[A]TATAACATGTGCACCCAAAAGCCGCCGCATGATTACTCCCAGCAGCTGT
ATGATAAATATCGTGAATCTTTTGAAGAGTACATCACTTCTATGGTCTTACCATCCTTGAGGGAGA
AGCATGACGAGTTCATGTTGAGAGAACTAGTCAAAAGGTGGACAAACCATAAAGTCATGGTGAGGT
GGCTTTCTCGCTTCTTCCACTATCTTGATCGGTACTTCATCGCTCGAAGGTCACTTCCACCTCTAA
ATGAAGTTGGCCTCACATGCTTCCGCGAATTGGTGTACAAAGAGCTAAACAGTAAAGTGAGGGATG
CAGTAATCTCATTGATTGATCAAGAACGTGAAGGAGAACAGATTGACAGAGCTCTACTGAAGAATG
TATTAGATATATTTGTGGAAATTGGTATGGGGCAAATGGATTACTATGAAAATGACTTTGAAGCTG
CCATGCTTAAAGATACTGCTGCTTATTACTCTAGGAAGGCTTCCAATTGGATCCTAGAAGATTCTT
GTCCCGATTATATGCTAAAAGCAGAGGAGTGCTTGAAGCGAGAAAAGGATAGGGTTTCCCACTATT
TGCACTCTAGTAGCGAGCCAAAGTTGTTGGAGAAAGTTCAACACGAACTGTTATCTGTGTATGCTA
CTCAACTGCTGGAAAAAGAGCATTCAGGATGCCATGCATTGCTTAGAGATGACAAGGTGGAAGATT
TGTCAAGGATGTTCCGTCTCTTCTCCAAAATACCGAAGGGATTGGACCCAGTTTCCAACATATTTA
AGCAGCATGTAACTGCTGAAGGAACAGCACTGGTCAAACAGGCAGAAGATGCTGCAAGTAACAAGA
AGGCCGAGAAAAAGGACATAGTTGGTCTGCAGGAACAGGTTTTTGTAAGAAAAGTGATTGAGCTTC
ACGACAAGTACTTGGCTTATGTGAATGATTGTTTCCAAAACCACACACTTTTCCATAAGGCTCTCA
AGGAAGCTTTTGAAGTCTTTTGCAATAAGGGTGTTGCTGGAAGTTCTAGTGCAGAATTGCTTGCTA
CCTTCTGCGATAACATCCTTAAGAAAGGTGGGAGTGAGAAGTTGAGTGATGAAGCAATCGAAGAGA
CACTTGAGAAGGTTGTGAAGTTGTTGGCATACATCTGCGACAAAGATCTGTTTGCTGAATTCTATA
GAAAAAAaCTTGCCCGAAGGCTTCTCTTTGATAAGAGCGCCAACGATGACCACGAGAGAAGTATAT
TGACCAAATTGAAGCAACAATGTGGTGGTCAGTTCACTTCTAAGATGGAGGGAATGGTTACTGATT
TGACTTTGGCAAGGGAGAACCAAACTAGTTTCGAAGAGTATCTGAGCAATAATCCACAAGCTAGTC
CTGGAATCGACCTAACTGTTACTGTTTTGACTACTGGATTTTGGCCAAGCTACAAGTCTTTTGACC
TCAACCTGCCGGCGGAGATGGTAAAGTGTGTTGAAGTTTTCAGAGAGTTTTATCAAACAAAAACCA
AGCATAGAAAACTTACATGGATTTACTCATTGGGTACTTGTAACATCAGTGGAAAATTTGAACCGA
AGACGATGGAGCTGATTGTGACAACATATCAGGCTTCTGCCCTGTTGCTATTCAATTCTTCGGACA
GACTAAGTTACTCCGAAATCATGACACAATTAAATTTGAGTGATGATGATGTTGTTAGACTGCTCC
ACTCATTGTCGTGTGCCAAGTATAAAATTCTTAATAAGGAGCCAAATACGAAAACCATCTCACCGA
ACGATCATTTTGAGTTCAATGCAAAATTCTCCGACAAAATGAGGAGAATAAAGATCCCTCTTCCGC
CTGTGGATGAGAAAAaGAAAGTCATTGAAGATGTTGACAAGGATCGAAGGTATGCTATTGACGCCT
CAATCGTGCGTATCATGAAGAGTCGAAAAGTTCTTGGTCATCAGCAACTAGTGATGGAGTGCGTCG
AGCAATTGGGTCGTATGTTCAAGCCCGATTTCAAGGCGATAAAGAAGAGAATTGAAGACCTGATCA
CTCGGGACTATCTAGAGAGAGACAAAGACAACCCCCACTTGTTTAGGTACTTGGCTTGA

Fig. 3

ATGACAATGGGTGAGCGGAAGACTATTGACTTGGAGCAAGGATGGGAGTTTATGCAGAAGGGAATC
ACAAAATTGAAGAACATTCTGGAAGGATTGCCTGAGCCACAGTTCAGCTCCGAGGACTACATGATG
CTTTACACTACAAT[A]TATAACATGTGTACCCAGAAGCCACCGCATGATTACTCCCAGCAGCTGT
ATGATAAATACCGCGAATCGTTTGAGGAGTACATCAGTTCTATGGTTTTACCATCCTTGAGGGAGA
AGCATGACGAATTTATGTTGAGAGAACTGGTCAAAAGGTGGACCAACCATAAAGTCATGGTGAGGT
GGCTTTCTCGCTTCTTCCACTATCTTGATCGATACTTCATTGCTCGAAGGTCACTTCCACCTCTCA
ATGAAGTTGGCCTCACTTGCTTCCGTGAATTGGTGTACAAAGAGCTAAACAGTAAAGTGAGGGATG
CAGTAATTTCATTGATCGATCAAGAACGTGAAGGAGAGCAGATTGACAGAGCTCTGTTGAAGAACG
TGTTGGATATATTTGTGGAGATTGGGATGGGGCAAATGGATTATTATGAAAATGACTTTGAAGCTG
CCATGCTTAAAGATACTGCTGCTTACTACTCTAGGAAGGCATCAAATTGGATCTTAGAAGATTCTT
GTCCTGATTATATGCTAAAAGCAGAGGAGTGCTTGAGACGAGAAAAGGACCGAGTTTCTCACTATC
TGCACTCTAGTAGCGAGCCAAAGTTATTGGAGAAAGTTCAACATGAACTATTGTCTGTTTATGCTA
CTCAACTGCTGGAGAAAGAGCATTCAGGATGCCATGCATTGCTTAGAGATGACAAGGTGGAAGATT
TGTCAAGGATGTTCCGTCTCTTCTCCAAAATACCCAAGGGATTGGACCCAGTTTCCAACATATTTA
AGCAGCATGTCACTGCTGAAGGAACAGCATTAGTCAAACAGGCAGAAGACGCTGCAAGTAACAAGA
AGGCCGAGAAAAAGGACATCGTTGGTCTGCAAGAACAGGTTTTTGTTAGAAAAGTGATTGAGCTTC
ACGACAAGTACTTGGCATATGTGAATGATTGTTTCCAAAACCACACACTTTTTCACAAGGCTCTCA
AGGAAGCTTTTGAAGTCTTTTGCAATAAGGGTGTTGCTGGAAGTTCTAGTGCAGAATTACTTGCTA
CCTTTTGTGATAACATCCTTAAGAAAGGTGGGAGTGAGAAGTTGAGTGATGAAGCAATTGAGGAAA
CACTCGAGAAGGTCGTGAAATTGCTGGCGTATATCTGCGACAAAGATCTGTTTGCTGAATTCTATA
GAAAAAAACTCGCCCGAAGGCTTCTCTTCGACAAGAGTGCGAATGATGACCACGAGAGAAGTATAC
TGACGAAATTGAAGCAACAATGTGGTGGTCAGTTTACCTCTAAGATGGAGGGAATGGTCACGGATT
TGACACTGGCAAGGGAGAACCAAACTAGTTTTGAGGAATATCTGAGCAATAATCCACAAGCTAGTC
CTGGAATCGACTTGACCGTTACCGTTTTGACCACTGGTTTTTGGCCAAGCTACAAGTCTTTTGACC
TCAACCTGCCGGCGGAGATGGTAAAGTGTGTTGAAGTTTTCAGGGAATTTTATCAAACAAAAACCA
AGCACAGAAAACTTACGTGGATTTACTCGTTGGGTACCTGTAACATCAGCGGAAAATTCGAACCGA
AAACGATGGAGCTGATCGTGACAACCTATCAGGCTTCTGCCCTGCTGCTTTTCAATTCCTCGGATA
AACTAAGTTACTCCGAGATCATGACTCAATTAAACTTGAGTGACGATGATGTTGTTAGACTGCTCC
ACTCGTTGTCGTGTGCGAAGTATAAAATTCTTAACAAGGAGCCAAATACGAAAACCATCTCTCCGA
ACGATCATTTTGAGTTCAACGCAAAATTCTCCGACAAAATGAGGAGAATAAAGATCCCTCTTCCGC
CTGTGGATGAGAAAAAGAAAGTAATAGAAGATGTTGACAAGGATCGAAGATATGCTATCGATGCCT
CGATCGTGCGTATCATGAAGAGTAGGAAAGTTCTGGGTCACCAGCAGTTAGTGATGGAGTGCGTCG
AGCAACTGGGTCGTATGTTCAAGCCTGATTTCAAGGCGATAAAGAAGAGAATCGAAGATCTGATCA
CTCGTGACTATTTAGAGAGAGACAAAGACAACCCCCACTTGTTTAGGTACTTGGCTTGA

Fig. 4

ATGACAATGGGCGAGCGGAAGACTATTGACTTGGAACAAGGATGGGAGTTTATGCAGAAGGGAATC
ACAAAGTTGAAGAACATTCTTGAGGGCTTGCCTGAGCCTCAGTTCAGCTCCGAGGACTACATGATG
CTTTATACCACCAT[A]TACAACATGTGCACACAAAAGCCGCCACATGATTACTCCCAGCAGCTAT
ACGATAAATACCGTGAATCTTTTGAGGAGTATATCACTTCTATGGTCTTACCATCCTTGAGGGAGA
AGCATGACGAGTTCATGTTGAGAGAACTGGTCAAAAGGTGGACGAACCATAAAGTCATGGTGAGGT
GGCTTTCTCGCTTCTTCCACTATCTTGACCGATACTTCATTGCTCGAAGATCACTTCCACCTCTCA
ACGAAGTTGGCCTCACATGCTTCCGTGAATTGGTGTACAAAGAGCTAAACAGTAAAGTGAGGGATG
CAGTAATTTCATTGATTGATCAAGAACGTGAAGGAGAGCAGATTGACAGAGCTCTACTGAAGAATG
TATTAGATATATTTGTGGAAATTGGGATGGGGCAAATGGATTACTATGAAAATGACTTTGAAGCTG
CCATGCTTAAAGATACTGCTGCTTATTACTCTAGGAAGGCTTCCAATTGGATCCTAGAAGATTCTT
GTCCCGATTATATGCTAAAAGCAGAGGAGTGCTTGAAACGAGAAAAGGATAGAGTTTCTCACTATT
TGCACTCTAGTAGCGAGCCAAAGTTATTAGAGAAAGTTCAACATGAACTGTTATCTGTGTATGCTA
CTCAACTGCTGGAAAAAGAGCATTCAGGATGCCATGCATTGCTTAGAGATGACAAGGTGGAAGATT
TGTCAAGGATGTTCCGCCTCTTCTCCAAAATACCCAAGGGATTGGACCCAGTTTCCAACATATTTA
AGCAGCATGTCACTGCTGAAGGAACAGCATTGGTCAAACAGGCAGAAGATGCTGCAAGTAACAAGA
AGGCCGAGAAAAAGGACATAGTTGGTCTGCAGGAACAGGTTTTTGTAAGAAAAGTGATTGAGCTTC
ACGACAAGTACTTGGCTTACGTGAATGATTGTTTCCAAAACCACACACTTTTTCACAAGGCTCTCA
AGGAAGCTTTTGAAGTCTTTTGCAATAAGGGTGTTGCTGGAAGTTCTAGTGCAGAATTACTTGCTA
CCTTTTGTGATAACATCCTTAAGAAAGGTGGGAGCGAGAAGTTGAGTGATGAAGCAATTGAGGAGA
CACTTGAGAAGGTCGTGAAGTTGCTGGCATACATCTGCGACAAAGATCTGTTTGCTGAATTCTATA
GAAAAAAACTTGCCCGAAGGCTTCTCTTTGACAAGAGTGCCAACGATGACCATGAGAGAAGTATAT
TGACCAAATTGAAGCAACAATGTGGTGGCCAGTTCACCTCTAAGATGGAGGGGATGGTCACTGATT
TGACTTTGGCAAGGGAGAACCAAACTAGTTTCGAGGAGTATCTGAGCAATAATCCACAAGCTAGTC
CTGGAATCGACTTGACTGTCACTGTTTTGACTACTGGCTTTTGGCCAAGCTACAAGTCTTTTGACC
TCAACCTGCCGGCAGAGATGGTAAAGTGTGTTGAAGTTTTCAGAGAGTTCTATCAAACAAAAACAA
AGCATAGAAAACTTACATGGATTTACTCATTGGGTACCTGTAACATCAGCGGAAAATTTGAACCGA
AAACGATGGAGCTGATTGTAACAACTTATCAGGCTTCTGCCCTGCTGCTATTCAATTCCTCAGATA
GATTAAGTTATTCCGAGATCATGACACAATTAAATTTGAGTGACGATGATGTTGTTAGACTGCTCC
ACTCATTGTCATGTGCCAAGTATAAAATTCTTAATAAGGAGCCGAACACGAAAACCATCTCTCCGA
ATGATCATTTTGAGTTCAATGCAAAATTCTCCGACAAAATGAGGAGAATAAAGATCCCTCTTCCGC
CTGTGGATGAGAAAAAGAAAGTCATTGAAGATGTTGACAAGGATCGAAGGTATGCTATTGATGCCT
CAATCGTGCGTATCATGAAGAGTCGGAAAGTTCTGGGTCATCAGCAGCTAGTGATGGAGTGCGTCG
AGCAATTGGGTCGTATGTTCAAGCCCGACTTCAAAGCGATAAAGAAGAGAATCGAAGATCTGATCA
CTCGGGACTATTTAGAGAGAGACAAAGACAACCCCCACTTGTTTAGGTACTTGGCTTGA

Fig. 5

ATGAACCAACGCAGCACAATCGATCTGGAACATGGATGGGATTTCATGCAAAAGGGCATCACAAAG
CTGAAGAACATTCTAGAAGGGCTGCCTGAGCCTCAGTTCAGCTCAGAGGACTATATGATGCTGTAT
ACGACAAT[T]TACAACATGTGTACTCAGAAGCCCCCACATGATTATTCTCAACAGCTGTATGACA
AATATCGTGAAGCTTTTGAAGAATATATCACAACGACGGTATTACCTTCTTTGAGAGAAAAACATG
ACGAGTTCATGTTGCGAGAGTTGGTAAAAAGGTGGTCAAACCATAAGGTCATGGTTAGATGGTTAT
CGCGATTCTTCCATTATCTTGACCGTTATTTCATTGCTCGGAGATCACTGCCAGGGCTTAATGAAG
TTGGACTAACTTGCTTCCGCGATCTGGTCTACCAAGAGTTGAATGGAAAAGTCAGGGATGCTGTTA
TATCTCTGATTGATCAAGAGCGTGAGGGAGAGCAAATTGACAGAGCTCTACTGAAGAATGTGCTAG
ATATATTTGTTGAAATTGGAATGGGGTCAATGGATTATTATGAGAATGATTTTGAAGCTGCAATGC
TCAAGGACACTGCGGCTTATTATTCTCGCAAAGCTTCTAACTGGATCCTCGAAGATTCATGTCCAG
ATTATATGCTGAAAGCTGAGGAGTGCTTGAAACGGGAGAAGGATAGGGTCTCCCATTATCTCCATT
CTAGCAGTGAGACAAAGTTGCTTGAGAAAGTGCAACATGAGTTGTTATCTGTGTATGCCAATCAAC
TTCTTGAGAAGGAGCACTCTGGATGCCATGCATTACTTAGAGATGATAAGGTCGATGATTTATCAA
GGATGTATAGACTCTTTTCTAAGATTCCTCGAGGCTTAGAGCCTGTGGCTAATATATTTAAGCAGC
ATGTTACTGCTGAAGGTACAGCTTTGGTGAAACAGGCTGAAGATGCTGCTAGCAACAAAAAGGCAG
AGAAGAGAGATGTGGTTGGTTTGCAGGAACAGGTTTTTGTTCGGAAAGTGATTGAGCTTCATGATA
AATATTTGGCGTATGTGAATAACTGTTTCCAAAACCACACACTTTTTCACAAGGCACTTAAAGAAG
CTTTCGAACTTTTCTGCAACAAGGGTGTTGCTGGTAGCTCAAATGCTGAACTTCTTGCCACATTCT
GCGACAACATTCTCAAAAAAGGCGGGAGTGAAAAATTGAGTGATGAAGCCATTGAAGAGACGCTGG
AGAAGGTGGTAAAGCTGCTGGCTTATATTAGTGATAAGGACTTGTTTGCAGAATTCTATAGGAAAA
AGCTCGCCCGGCGGTTGTTATTTGATAAGAGTGCCAATGATGAACATGAGAGAAGTATCCTAACAA
AGTTGAAGCAGCAGTGTGGAGGTCAGTTCACATCAAAGATGGAGGGAATGGTCACAGATTTGACAT
TGGCAAGGGAAAATCAAGCCAGCTTTGAGGAGTATTTGAGCAATAATCCAACAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGTGTTGAAGTATTCAAGGAGTTTTATCAAACAAAAACGAAGCACA
GGAAACTTACATGGATATACTCTTTGGGAACTTGCAACATAAATGGAAAATTTGAGGCAAAGACTA
TTGAGCTCGTTGTCACTACTTATCAGGCTTCTGCTCTGCTTCTCTTTAATGCATCAGATAGATTGA
GTTATCAGGAAATCATGACGCAATTAAACCTATCAGATGATGATGTTGTTCGGCTTCTTCATTCCC
TTTCATGTGCGAAATACAAGATTCTCAACAAGGAGCCAAGCACCAAAACAATTTCTCCGACTGATG
TCTTTGAGTTCAACTCAAAGTTCACTGACAAAATGAGGAGGATCAAGATACCTCTCCCACCAGTTG
ATGAAAAGAAAAAGGTAATTGAAGACGTTGACAAGGATAGGCGGTATGCTATAGATGCCTCAATTG
TGCGTATTATGAAGAGTCGTAAAGTATTGGGCTACCAGCAACTGGTCATGGAGTGCGTTGAGCAGT
TGGGACGCATGTTCAAGCCTGATGTCAAAGCTATCAAGAAGAGAATTGAAGATCTGATAACTAGAG
ATTACCTAGAGAGGGACAAAGATAACCCAAACTTGTTCAAGTACTTGGCATGA

Fig. 6

ATGAACCAACGAAGCACAATCGATCTGGAACATGGATGGGACTTCATGCAAAGGGGCATTACAAAG
CTGAAGAACATTCTAGAAGGGCTGCCTGAGCCTCAATTCAGCTCAGAGGACTATATGATGCTATAT
ACGACAAT[T]TACAACATGTGTACTCAAAAGCCCCCACATGATTATTCTCAACAGCTGTATGACA
AATATCGTGAAGCTTTTGAAGAATATATCACAACAACGGTATTGCCTTCTTTGAGAGAAAAACATG
ACGAGTTTATGTTGCGAGAGTTGGTAAAAAGGTGGTCAAATCATAAAGTCATGGTCAGATGGTTGT
CAAGATTCTTCCATTACCTTGACCGGTATTTCATTGCCCGGAGATCTCTGCCGGGGCTTAATGAAG
TTGGACTAACTTGCTTCCGCGATCAGGTCTACCAAGAGTTGAATGGAAAAGTCAGGGATGCTGTTA
TATCTCTGATTGATCAAGAGCGTGAGGGAGAGCAAATTGACAGAGCTCTACTTAAGAATGTGCTTG
ATATATTTGTCGAAATTGGAATGGGGTTAATGGATTATTATGAGAATGATTTTGAAGCTGCAATGC
TCAAGGACACAGCGGCTTATTATTCTCGCAAAGCTTCTAATTGGATCCTCGAAGATTCATGTCCGG
ATTATATGCTGAAAGCCGAGGAGTGCTTGAAACGGGAGAAGGATAGGGTCTCTCATTATCTCCATT
CAAGCAGCGAGACGAAGTTGCTTGAGAAAGTGCAACATGAGTTGTTGTCTGTGTATGCCACTCAAC
TTCTTGAGAAGGAGCACTCTGGATGCCATGCGTTACTGAGAGATGATAAGGTTGAAGATTTATCAA
GGATGTATAGGCTCTTTTCTAAGATTTCTCGAGGCTTAGACCCTGTGGCCAATATTTTTAAGCAGC
ATGTTACTGCTGAAGGTACAGCTTTGGTAAAACAGGCTGAAGATGCTGCTAGCAATAAAAAGGCAG
AGAAGAGAGATGTGGTTGGTTTGCAGGAACAGGTTTTTGTTCGGAAAGTGATTGAACTTCATGATA
AATATTTGGCTTATGTGAATAACTGTTTCCAAAACCACACACTTTTTCACAAGGCGCTTAAAGAAG
CTTTTGAGCTTTTCTGCAACAAGGGTGTTGCTGGTAGCTCAAGCGCTGAACTTCTTGCCACCTTCT
GTGACAACATTCTCAAAAAAGGCGGGAGTGAGAAATTGAGTGATGAAGCTATTGAAGAAACGTTGG
AAAAGGTGGTAAAGCTACTAGCTTATATTAGTGATAAGGACTTGTTTGCAGAATTCTATAGGAAAA
AGCTAGCCCGGCGGTTGTTATTTGATAAGAGTGCCAATGATGAACATGAAAGAAGTATCCTAACAA
AGTTGAAGCAGCAGTGTGGGGGGCAGTTCACATCAAAGATGGAGGGAATGGTCACAGATTTGACAT
TGGCAAGGGAAAATCAAGCCAGCTTCGAGGAGTATTTGAGCAATAATCCAATAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGCGTTGAAGTATTTAAGGAGTTCTATCAAACAAAAACAAAGCACA
GGAAACTTACGTGGATATACTCTTTGGGAACTTGCAACATAAATGGAAAATTTGAGCCAAAAACTA
TTGAGCTCGTTGTCACTACTTATCAGGCTTCTGCTCTGCTGCTCTTTAATGCATCAGATAGATTGA
GTTATCAGGAAATCATGACGCAATTAAACCTATCAGATGATGATGTTGTTCGGCTTCTTCATTCCC
TTTCATGTGCGAAGTACAAGATACTCAACAAGGAGCCAAGCACCAAAACAATTTCTCCGACTGATG
TCTTTGAGTTCAACTCAAAGTTCACTGACAAAATGAGGAGGATCAAGATACCTCTCCCTCCTGTTG
ATGAGAAGAAAAAGGTAATTGAAGACGTTGACAAGGATAGGCGGTATGCTATAGATGCTTCAATTG
TGCGTATTATGAAGAGCCGTAAAGTATTGGGCTACCAGCAACTAGTCATGGAGTGCGTTGAGCAGT
TGGGGCGCATGTTCAAGCCTGATGTCAAAGCTATCAAGAAGAGAATCGAAGATTTGATAACTAGAG
ATTACCTAGAGAGGGACAAAGATAATCCAAACCTGTTCAAGTACTTGGCATGA

Fig. 7

ATGAACCAGCGTTCCACAATCAATCTAGAACATGGATGGGACTTCATGCAAAGGGGCATTACAAAG
CTGAAGAACATTCTAGAAGGGCTGCCCGAGCCTCAGTTCAGCTCAGAGGACTATATGATGCTGTAT
ACGACAAT[T]TACAACATGTGTACTCAGAAGCCCCCACATGATTATTCTCAACAGCTGTATGACA
AATATCGTGAAGCTTTTGAAGAATATATCACAACAACGGTATTGCCTTCTTTGAGAGAAAAACATG
ACGAGTTCATGTTGCGAGAGCTGGTAAAAAGGTGGTCAAACCATAAGGTCATGGTCAGATGGTTAT
CGCGATTCTTCCATTATCTTGATCGCTATTTCATTGCCCGGAGATCTCTACCGGGGCTTAATGAAG
TTGGACTAACTTGCTTCCGAGATCTGGTCTACCAAGAGTTGAATGGAAAAGTCAGGGATGCTGTTA
TATCTCTGATTGATCAAGAGCGTGAGGGAGAGCAAATTGACAGAGCTCTACTGAAGAATGTGCTAG
ATATATTTGTTGAAATTGGAATGGGGTCGATGGATTATTATGAGAATGATTTTGAAGCTGCAATGC
TCAAGGACACCGCAGCTTATTATTCTCGCAAAGCTTCTAACTGGATACTTGAAGATTCATGTCCAG
ATTATATGCTGAAAGCCGAGGAGTGCTTGAAACGGGAGAAAGATAGGGTCTCTCACTATCTTCATT
TAAGCAGTGAGACAAAGTTGCTTGAGAAAGTGCAACATGAGTTGTTGTCTGTGTATGCCACTCAAC
TTCTTGAGAAGGAGCACTCTGGGTGCCATGCGTTACTAAGAGATGATAAGGTTGAAGATTTATCAA
GGATGTATAGGCTCTTTTCTAAGATTCCTCGAGGCTTAGACCCTGTGGCTAATATATTTAAGCAGC
ATGTTACTGCTGAAGGTACAGCTTTGGTCAAACAGGCTGAAGATGCTGCTAGCAACAAAAAGGCAG
AGAAAAGAGATGTGGTTGGTTTGCAGGAACAGATTTTTGTTCGGAAAGTGATTGAGCTTCATGATA
AGTATATGGCATATGTGAATAACTGTTTCCAAAACCACACACTTTTTCACAAGGCGCTTAAAGAAG
CTTTCGAACTTTTCTGCAACAAGGGTGTTGCTGGTAGCTCAAGTGCTGAACTTCTTGCCACATTCT
GCGACAATATTCTCAAGAAAGGCGGGAGTGAGAAATTGAGTGATGAAGCCATTGAAGAGACGCTGG
AGAAGGTTGTAAAGCTGCTAGCATATATTAGTGACAAGGACTTGTTTGCAGAATTCTATAGGAAAA
AGCTAGCCCGGCGGTTGTTATTTGATAAGAGTGCCAATGATGAACACGAGAGAAGTATCCTTACAA
AGTTGAAGCAGCAGTGTGGGGGCCAGTTCACATCAAAGATGGAGGGAATGGTGACAGATTTGACAT
TGGCAAGGGAAAATCAAGCCAGCTTTGAGGAGTATTTGAGCAACAATCCAGCAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGCGTTGAAGTATTCAAGGAGTTTTATCAAACAAAAACGAAGCACA
GGAAACTTACGTGGATATACTCTTTGGGAACTTGCAATATAAATGGAAAATTTGAGCCAAAGACTA
TTGAGCTCGTTGTCACTACTTATCAGGCTTCTGCTCTGCTGCTCTTTAATGCATCGGATAGATTGA
GTTATCAGGAAATCATGACGCAACTAAACCTATCAGATGATGATGTTGTTCGGCTTCTTCATTCCC
TTTCATGTGCGAAGTACAAGATTCTCAACAAGGAGCCAAGCACCAAAACAATTTCTCCGACTGATG
TCTTTGAGTTCAATTTTAAGTTCACTGACAAAATGAGGAGGATCAAGATACCTCTCCCTCCTGTTG
ATGAGAAGAAAAAGGTAATTGAAGATGTTGACAAAGATAGGCGGTACGCTATAGATGCTTCAATTG
TGCGTATTATGAAGAGTCGTAAAGTATTGGGCTACCAGCAACTGGTCATGGAGTGTGTTGAGCAGT
TGGGACGTATGTTCAAGCCTGATGTCAAAGCTATCAAGAAGAGAATTGAAGATTTGATAACTAGAG
ATTACCTAGAGAGGGACAAAGATAATCCGAACTTGTTCAAGTACTTGGCATGA

Fig. 8

ATGGAGCGCAAGACGATTGACTTGGACCAAGGATGGGACTATATGCAGACTGGTATCACTAAGCTG
AAACGGATTCTTGAGGGGCTGCCTGAGCCGCAGTTTGACTCTGAGCAATACATGATGCTCTATACG
ACTAT[C]TACAACATGTGCACTCAGAAACCTCCTCATGATTACTCACAGCAGCTTTATGACAAGT
ATCGTGAAGCATTTGAGGAGTATATTCACTCAACTGTTTTGCCTGCTCTAAGGGAGAAGCATGATG
AGTACATGCTGAGGGAGCTGGTTAAGAGATGGTCTAACCATAAAGTTATGGTTCGATGGCTATCCC
GCTTCTTCTACTATCTTGACCGTTACTTCATTGCTCGGAGGTCACTTCCACCCCTGAATGAAGTTG
GCCTGACTTGCTTCCGTGACCTGGTTTATAACGAGTTGCATTCCAAGGTCAAAGATGCTGTAATAG
CACTTGTTGATAAAGAACGGGAGGGTGAGCAGATTGACAGGGCTCTATTGAAAAACGTATTAGACA
TTTATGTAGAGATTGGAATGGGACAGATGGAAAGATACGAGGAGGATTTTGAAAGCTTCATGCTTT
TAGATTCAGCATCTTACTATTCTCGCAAGGCGTCAAGCTGGATCCAAGAAGATTCTTGCCCTGATT
ACATGCTGAAGTCTGAAGAATGTCTTAAGAAGGAGAGGGAGAGAGTGGCTCACTACCTTCACTCAA
GCAGCGAGCCAAAGCTGGTTGAGAAAGTACAACATGAGCTGTTGGTAGTGTATGCAAATCAGCTTC
TAGAAAAAGAGCATTCAGGGTGCCGTGCATTGCTGAGAGATGACAAGGTTGATGACCTCTCCAGGA
TGTACAGGCTTTATCATAAAATTGTGAAAGGTTTGGAACCTGTTGCAAACATATTTAAGCAGCATG
TCACAGCAGAGGGTAACGCACTTGTCCAACAGGCCGAAGACACGGCCACTAATCATGCTGCAAATA
CTGCTAGCGTGCAGGAACAGGTTCTTATCAGAAAAGTGATTGAACTACATGATAAATACATGGTCT
ATGTTGTTGAGTGTTTCCAGAACCACACCCTCTTCCACAAGGCATTGAAAGAGGCATTTGAGATAT
TCTGTAACAAAACAGTCGCTGGAAGTTCTAGTGCTGAATTGCTTGCAACATTTTGCGACAATATTC
TCAAGAAGGGGGGAAGTGAAAAGCTGAGCGATGAAGCTATTGAAGATACCCTTGAGAAGGTGGTCA
AATTGCTTGCTTATATAAGTGACAAGGATCTTTTCGCCGAGTTCTACAGGAAGAAGCTGGCCCGTA
GGCTCTTATTTGATCGCAGTGCTAATGATGATCATGAGAGAAGTATCCTGACAAAGCTCAAGCAAC
AATGTGGTGGGCAGTTTACTTCGAAGATGGAGGGCATGGTGACTGATTTGACATTGGCAAGGGAAA
ACCAAAACAGCTTCGAGGAGTATCTTGGCAATAACCCCGCTGCAAACCCAGGGATTGATTTGACCG
TAACTGTTCTTACCACTGGTTTTTGGCCAAGTTACAAATCATTTGACATAAATCTACCCGCTGAAA
TGGTCAAGTGTGTTGAAGTTTTCAAAGGGTTTTATGAAACAAAGACAAAACATAGGAAACTTACCT
GGATCTACTCACTAGGAACTTGCCACCTCAATGGGAAGTTTGATGTCAAGCCCATTGAGTTAGTTG
TGTCTACATACCAGGCTGCTGTGCTTCTGCTGTTCAACACAACAGACAAATTGAGCTACACTGATA
TCCTAACTCAGCTGAACCTGAGCCACGAAGATCTAGTGAGGTTGCTTCATTCCTTGTCATGTGCTA
GATACAAGATTCTTCTCAAGGAGCCAAGCACAAAGACTGTTTCCCAGTCTGATTCTTTTGAATTCA
ACTCCAAATTCACCGACAGAATGCGGAGAATAAAGATCCCTCTCCCACCTGTTGATGAGAGGAAGA
AAGTTGTGGAAGACGTGGACAAAGACAGACGCTATGCGATTGATGCTGCCATTGTGAGGATCATGA
AGAGCAGGAAAGTATTGGGACATCAACAACTTGTTTCTGAGTGCGTTGAGCAACTTAGCCGAATGT
TCAAGCCTGATATCAAGGCAATCAAGAAGCGCATGGAGGATTTGATAACGAGAGATTATCTGGAGA
GGGACAAGGAGAACGCTAACATGTTTAGGTACTTGGCTTAG

Fig. 9

ATGATGATTGAGCGGAAAACTATAGACCTGGAGCAGGGATGGGACTTTATGCAAAAGGGAATCACA
AAGCTAAAGAATATTTTAGAAGGCTTTCCGGAGCCGCAATTCAGCTCGGAGGATTATATGATGCTT
TATACAACTAT[C]TATAACATGTGTACACAGAAACCTCCACATGATTACTCTCAGCAGCTGTATG
AAAAGTATCGTGAAGCTATTGAGGAGTACATTACTTCTACAGTATTGCCTTCATTGAGAGAGAAGC
ATGATGAATTCATGCTTAGAGAACTTGTGAAGAGATGGTCTAATCATAAGGTCATGGTCAGGTGGC
TTTCTCGATTCTTTCACTATCTTGATCGCTATTTTATTGCTCGGAGGTCACTTCCACCACTTCATG
AAGTTGGACTCACTTGCTTTCGGGACCTGGTTTACCAGGAGATAAATGGGAAAGTAAGGGATGCTG
TAATATCATTGATTAATCAAGAGCGCGAGGGAGAGCAAATTGACCGAGCTTTGTTGAAGAATGTTC
TAGATATATTTGTTGAAGTTGGAATGAGTCAAATGGATTATTATGAGAATGACTTTGAAGCAGACA
TGCTCAAAGATACAGCAGCATACTATTCTCGAAAGGCTTCCAACTGGATCTTAGAAGATTCTTGTC
CAGATTATATGCTCAAAGCGGAAGAGTGTTTGAGACGGGAAAAGGACAGGGTCTCTAACTACCTTC
ATTCTAGTAGTGAACCCAAGTTGCTTGAGAAAGTTCAACATGAGTTACTATCACACTATGCAACTC
AGCTGCTTGAGAAAGAACACTCTGGGTGTCATGCATTGCTTAGGGATGACAAGGTGGCAGATTTAT
CAAGGATGTATAGGCTCTTCTCTAAAATACCTCGAGGCCTAGATCCCGTGTCTAATATTTTCAAGC
AGCATGTTACTGCTGAAGGTACAGCTTTGGTCAAACAAGCAGAAGATGCAGCTAGCAACAAGAAGG
CAGAGAAGAGAGATGTAGTAGGTTTACAAGAACAGGTTTTTGTGAGGAAAATAATTGAATTGCATG
ACAAATACCTTACATACGTAAATGACTGTTTTACAAACCACACTCTCTTCCATAAGGCGCTTAAGG
AGGCTTTTGAAATCTTCTGCAATAAGGGTGTCTCTGGAAGCTCTAGTGCAGAATTACTTGCCACAT
TCTGTGATAATATTCTCAAGAAAGGTGGAAGCGAGAAGTTAAGTGATGAAGCCATTGAGGAAACAC
TTGAGAAGGTTGTAAGGTTGCTTGCTTATATAAGTGACAAAGACTTATTTGCTGAATTTTATAGGA
AAAAGCTTGCACGGCGTCTCTTATTCGACAAGAGTGCCAATGATGAGCATGAGAGAAGTATATTGA
CTAAGCTGAAGCAACAATGTGGGGGTCAATTTACATCAAAGATGGAAGGAATGGTCACTGACTTGA
CGTTGGCAAAGGAAAATCAGTCCAACTTCGAGGAGTACCTCAATAATAATTCAAACGTAAATCCTG
GAATTGACTTGACAGTTACTGTTCTAACCACTGGGTTTTGGCCAAGTTACAAATCTTTCGATCTCA
ACCTCCCAGCAGAGATGGTCAAATGTGTTGAAGTTTTTAGAGAATTCTACCAAACAAAAACAAAGC
ACAGAAAACTGACATGGATATACTCTTTGGGTACTTGTAACATCATTGGAAAATTTGATCCAAAAA
CCATGGAGCTTATTGTGACAACATACCAGGCCTCTGCTCTGCTGCTATTTAACTCTTCTGATAGAC
TTAGTTATAATGAAATAATGACTCAGTTGAACTTGTCGGATGATGATGTTGTCAGACTACTTCATT
CTCTTTCGTGTGCAAAGTACAAGATTCTATCTAAAGAGCCGAACACCAAAACTATATCTCCAACTG
ATTGCTTTCAGTTCAATTCCAAATTTACTGATAAAATGAGGAGGATTAAGATTCCACTTCCCCCAG
TGGATGAGAAGAAAAAGGTAATTGAAGATGTTGATAAAGACAGGCGATATGCTATAGATGCTTCAA
TTGTCCGTATCATGAAGAGCCGCAAAGTTTTGGGTTATCAGCAGCTAGTAATGGAGTGCGTTGAAC
AATTGGGTCGCATGTTTAAGCCTGATGTCAAAGCAATCAAGAAGAGAATCGAAGATTTAATAACTC
GGGATTATCTGGAAAGAGACAAGGACAATGCCAACTTGTTCAGGTATCTGGCATGA

Fig. 10

ATGAACGAGCGGAAGACTATCGATTTGGATAATGGATGGGAATTTATGCAGAAAGGGATCACTAAG
TTGAAGAAGATTCTCGAAGGTCAACCTGAGCCTCAGTTTAGCTCCGAGGACTATATGATGCTTTAC
ACAACTAT[C]TATAATATGTGTACGCAGAAGCCTCCACATGATTATTCTCAACAGCTGTATGACA
AGTACCGTGAGGCCTTTGAGGAGTACATAACTTCAACTGTCCTGCCTTCTTTACGAGAGAAGCATG
ATGAGTTTATGTTGAGAGAGCTCGTGAATAGATGGACAAACCATAAAGTCATGGTCAGGTGGCTTT
CTCGATTCTTTCACTATCTTGATCGGTACTTCATTGCGAGGAGGTCACTTCCTGCACTTCATGAAG
TTGGACTCACGTGCTTCCGGGATCTGGTCTATCAGGAGCTGAAAGTTAAAGTGAGGGATGCTGTAA
TATCTCTGATCGATCAAGAGCGTGAGGGGGAACAGATTGACCGAGCTTTATTAAAGAACGTGTTAG
ATATATTTGTTGAAATCGGAATGAGTCAAATGGATCAATATGAGAATGACTTTGAAGAAGCCATGC
TCACTGATACTGCTGCTTACTATTCTCGAAAAGCTTCAAACTGGATCCTTGAAGATTCTTGTCCTG
ATTATATGTTAAAGGCAGAAGAATGTTTGCGACGAGAGAAGGACAGGGTTTCCCACTACCTACATT
TTAGTAGCGAGCCAAAGTTGCTTGAGAAAGTGCAACATGAGCTGCTATCTGTGTATGCAACCCAAT
TACTCGAGAAGGAACATTCTGGTTGTCATGCATTGCTTAGGGATGACAAGGTGGATGATTTGTCTA
GGATGTACAGACTCTTCTCGAAAATACCTAAAGGCCTGGATCCAGTTTCTTATATTTTTAAGCAGC
ATGTTACAAATGAAGGGATGGCATTGGTTAAACAAGCAGAAGATGCAGCAAGCAACAAGAAGGCAG
AAAAGAGAGACGTGGTTAGTTTACAGGAGCAGGTTTTTGTTAGAAAAATTATTGAATTACATGACA
AATACCTCGCCTATGTGAATGACTGCTTTACAAACCATACTCTTTTCCATAAGGCTCTCAAGGAGG
CTTTTGAAATCTTTTGCAACAAGGGTGTTGCTGGAAGCTCTAATGCTGAACTACTTGCTACTTTCT
GTGATAACATCCTCAAAAAGGGTGGGAGTGAGAAATTAAGTGATGAGGCTATTGAAGAAACACTTG
AGAAGGTAGTAAAATTGTTAGCTTACATTAGCGATAAAGACTTGTTCGCTGAATTTTACAGAAAAA
AGCTTGCACGGAGACTTCTCTTTGATAAGAGTGCAAATGACGAGCATGAACGAAGTATTTTGACTA
AACTAAAGCAACAGTGCGGTGGTCAGTTCACATCGAAAATGGAGGGGATGGTCACAGATTTGACTT
TGGCTAAAGAAAATCAATCCAGCTTTGAGGAGTATCTGGGAAATAATGCCAATGTGAATCCTGGCA
TTGACTTGACGGTTACTGTTCTGACCACTGGCTTCTGGCCTAGTTATAAATCCTTTGATCTCAACC
TTCCTGCTGAGATGGTCAAGTGCGTTGAAGTATTTAGAGAATTTTATCAAACAAAAACGAAGCATA
GAAAGCTCACATGGATATATTCTCTGGGTACTTGTAATATCAATGGAAAATTTGAACCCAAAACCA
TTGAGCTGATTGTGACAACCTACCAGGCCTCTGCTCTCCTGTTATTTAATACTTCTGATAGGTTGA
GTTATCAAGAAATCATGACTCAGTTAAATTTGTCGGATGATGATGTTGTTCGCCTGCTTCATTCCC
TTTCATGTGCCAAGTATAAAATTCTTACTAAAGAGCCGAACAACAAAACAATTTCCCCTACGGATT
ACTTTGAGTTCAACTCCAAGTTCACTGACAAAATGAGGAGAATTAAGATTCCACTACCTCCAGTTG
ATGAGAAGAAAAAGGTAATTGAAGATGTTGACAAGGACCGGCGATATGCCATTGATGCATCTATTG
TCCGCATTATGAAGAGCCGTAAAGTTTTGGGCTACCAACAATTGGTTATGGAATGTGTTGAGCAAT
TGGGACGCATGTTTAAGCCTGATGTCAAAGCAATTAAGAAGAGAATCGAAGATTTAATAACGCGTG
ATTATCTGGAAAGAGACAAGGATAATGCCAACCTTTTCAGATATTTGGCATGA

Fig. 11

ATGAATGAAAGAAAAACAATAGACTTAGAACAAGGATGGGACTTCATGCAGAAAGGCATAACAAAG
TTGAAGAACATTCTAGAAGGTCTTCCCGAGCCACAATTCAGCTCGGAAGATTACATGATGCTCTAC
ACAACCAT[C]TACAATATGTGCACACAAAAACCGCCACATGATTACTCTCAACAATTGTATGACA
AATACCGCGAGTCTTTTGAAGAGTACATTACTTCAACGGTGTTACCTTCTTTAAGAGAGAAGCATG
ATGAGTTTATGCTTAGAGAGCTTGTTAGAAGATGGTCAAATCATAAAGTGATGGTTAGGTGGCTTT
CTAGATTCTTCCATTATCTTGATCGATACTTCATTGCCCGAAGATCTCTTCCACCATTAAATGAAG
TTGGACTTGCGTGTTTTCGTGATCTGGTATACCAAGAGGTGAATGGGAAAGTGAGAGATGCTGTAA
TATCTTTGATTGATCAAGAGCGTGAAGGCGAGCAAATTGACCGAGCATTACTCAAGAATGTTCTAG
ATATATTTGTTGAAATAGGAATGGGACAAATGGAATATTATGAGAATGATTTTGAAGCATCCATGC
TTAATGATACAGCAGCATATTATTCACGCAAAGCTTCCAATTGGATTCTAGAAGATTCTTGTCCAG
ATTATATGCTCAAAGCTGAGGAGTGCTTAAAAAGAGAAAAGGACAGAGTTTCTCATTATCTTCATT
CCAGCAGTGAACCAAAGCTTCTTGAGAAAGTTCAAACAGAGTTATTATCTGTTTATGCAACTCAAT
TGCTTGAAAAGGAGCACTCCGGTTGTCATGCATTACTTAGGGATGACAAGGTTGATGATTTATCAA
GAATGTACAGACTCTTTTCAAAGATACAAAAAGGGCTGGATCCTGTTTCTAGTATGTTTAAGCAGC
ATGTCACTGCTGAAGGCACAACATTGGTTAAACAGGCAGAAGATGCAGCAAGTACTAAGAAGGCTG
AAAAGAGAGACGTGGTTGGCTTACAAGAACAGGTTTTTGTTAGAAAAGTTATCGAGCTTCATGACA
AGTACCTTGCATATGTAAATGACTGTTTTATGAATCATACCCTGTTTCACAAGGCTCTTAAAGAGG
CATTTGAAATATTCTGCAACAAGGGCGTTGCTGGAAGTTCAAGTGCAGAATTACTTGCTACATTTT
GTGATAATATTCTTAAAAAAGGTGGAAGTGAAAAATTGAGTGATGAAGCCATTGAGGACACACTTG
AGAAGGTGGTAAAGTTGCTTGCTTACATCAGCGATAAAGATCTATTTGCAGAGTTTTATAGGAAAA
AACTGGCTAGACGGCTTTTATTTGACAAAAGTGCAAATGATGAGCACGAAAGAAGTATTTTGACAA
AATTGAAACAACAATGTGGCGGTCAATTTACATCAAAAATGGAAGGAATGGTTACAGATTTGACAT
TGGCAAAAGAAAATCAATCACATTTTGAGGAGTATTTGAATAATAATCCCAATGTTAGCCCTGGCA
TTGACTTGACCGTGACTGTGTTGACCACTGGTTTTTGGCCTAGTTACAAATCTTTTGACCTAAATC
TCCCTGCAGAAATGGTCAAATGCGTTGAAGTTTTCAGAGAATTTTATCAAACAAAAACAAAACACA
GAAAACTCACATGGATATATTCATTGGGCACCTGCAATATAAACGGAAAATTCGAACCAAAAACCA
TGGAGCTAATCGTTACAACTTACCAGGCATCTGCTTTATTACTGTTCAACTCATCAGATCGATTGA
GTTATCAAGAAATCATGACTCAATTAAACTTATCAGATGATGATGTTGTTAGACTACTCCATTCAT
TATCATGTGCAAAATATAAAATTTTATTAAAAGAACCAAATACAAAAACAATCTCTCCAACTGATT
TCTTTGAATTCAACTCAAAGTTTACAGATAAAATGAGAAGGATCAAGATTCCTCTACCTCCTGTTG
ATGAAAAGAAAAAAGTAATTGAAGATGTTGACAAAGACCGACGTTATGCAATTGATGCTTCAATTG
TACGGATAATGAAAAGCAGAAAAGTTCTTGGATACCAACAATTGGTCATGGAATGTGTTGAACAAT
TAGGCCGTATGTTTAAGCCTGATGTAAAAGCAATCAAGAAACGTATTGAAGATCTCATAACTCGTG
ATTATCTTGAAAGAGACAAAGAAAATCCAAATTTGTTTCGGTACTTGGCATGA

Fig. 12

ATGAATGAAAGAAAAACAATAGACTTAGAACAAGGATGGGACTTCATGCAAAAAGGCATAACAAAG
TTGAAGAACATTCTAGAAGGTCTTCCCGAGCCACAATTCAGCTCAGAGGATTACATGATGCTCTAC
ACAACCAT[C]TACAATATGTGCACACAAAAACCGCCACATGATTACTCTCAACAATTATATGACA
AATACCGCGAGTCTTTTGAAGAGTACATAACTTCAACGGTGTTACCTTCTTTAAGAGAGAAGCATG
ATGAGTTTATGCTTAGAGAGCTTGTTAGAAGGTGGTCAAATCATAAAGTGATGGTTAGGTGGCTTT
CTAGATTCTTCCATTATCTTGATCGATACTTTATTGCAAGAAGATCTCTTCCACCATTAAATGAAG
TTGGACTTGCGTGTTTTCGTGATCTGGTATACCAAGAGGTGAATGGAAAAGTGAGAGATGCTGTAA
TATCTTTGATTGATCAAGAGCGTGAAGGCGAGCAAATTGACCGAGCATTACTGAAGAATGTTCTAG
ATATATTTGTTGAAATAGGAATGGGACAAATGGAATATTATGAGAATGATTTTGAAGCATCTATGC
TTAATGATACAGCAGCATATTATTCACGCAAAGCTTCCAACTGGATTCTAGAAGATTCTTGTCCAG
ATTATATGCTCAAAGCTGAGGAGTGCTTAAAAAGAGAAAAGGACAGAGTTTCTCATTATCTTCATT
CAAGTAGTGAACCAAAGCTTCTTGAGAAAGTTCAAACAGAGTTATTATCTGTTTATGCAACTCAAT
TGCTCGAAAAGGAACACTCAGGTTGTCATGCATTACTTAGAGATGACAAGGTTGATGATTTATCAA
GAATGTACAGACTCTTTTCAAAGATACAAAAAGGACTGGATCCTGTTTCCAGTATGTTTAAGCAGC
ATGTCACTGCTGAAGGCACAACATTAGTAAAACAAGCAGAAGATGCAGCAAGTACTAAGAAGGCTG
AAAAGAGAGACGTGGTTGGCTTACAGGAACAGGTTTTTGTTAGAAAAGTAATCGAGCTTCATGACA
AGTACCTCGCATATGTAAACGACTGTTTTATGAATCACACATTGTTCCACAAGGCTCTTAAAGAGG
CATTTGAAATATTCTGCAACAAGGGCGTTGCTGGAAGTTCAAGTGCAGAATTACTTGCCACATTTT
GTGATAATATTCTTAAAAAAGGTGGAAGTGAAAAATTGAGTGATGAAGCCATTGAAGACACACTTG
AGAAGGTAGTAAAGTTGCTTGCTTACATCAGCGATAAAGATCTATTTGCAGAGTTTTATAGGAAAA
AACTGGCTAGAAGGCTTTTATTTGACAAAAGTGCAAATGATGAGCATGAAAGAAGTATTTTAACAA
AGTTGAAGCAACAATGTGGTGGTCAGTTTACATCAAAGATGGAAGGAATGGTTACAGATTTAACAC
TGGCAAAAGAAAATCAATCACATTTTGAGGAGTATTTGAATAATAATCCCAATGTTAGCCCTGGCA
TTGACTTGACCGTGACTGTGTTGACCACGGGATTTTGGCCTAGTTACAAATCTTTTGACCTAAATC
TTCCTGCAGAAATGGTCAAATGCGTTGAAGTTTTCAGAGAATTTTATCAAACAAAAACAAAACACA
GAAAACTCACATGGATTTATTCATTGGGCACCTGCAATATTAACGGAAAATTCGAACCAAAAACCA
TGGAGCTAATCGTTACAACTTACCAGGCATCTGCTTTATTGTTATTCAACTCATCAGATCGATTAA
GTTATCAAGAAATCATGACTCAATTAAATTTATCAGATGATGATGTTGTTAGACTACTACATTCAT
TATCATGTGCAAAATATAAAATTTTATTAAAAGAACCAAATACCAAAACAATATCTCCAACCGATT
TCTTTGAATTCAACTCAAAGTTTACAGATAAAATGAGAAGGATCAAGATTCCTCTACCTCCTGTTG
ATGAAAAGAAAAAAGTAATTGAAGATGTTGACAAAGATAGAAGGTATGCAATTGATGCTTCAATTG
TACGAATAATGAAAAGCAGAAAAGTTCTTGGATACCAACAATTGGTTATGGAGTGTGTTGAACAAT
TAGGCCGTATGTTTAAGCCTGATGTAAAAGCAATCAAGAAGCGTATTGAAGATTTGATAACGCGTG
ATTATCTTGAAAGAGACAAAGAAAATCCAAATTTGTTTCGGTACTTGGCATGA

Fig. 13

ATGTCGTTGCACGAAAGGAAAACCATTGATTTGGAGCAGGGATGGGCTTTTATGCAGAAAGGGATC
ACCAAACTGAAGAATATTCTTGATGAGTTGAATGAACCTCAGTTCAGCTCAGAGGATTACATGATG
CTCTATACGACTAT[C]TATAATATGTGTACTCAGAAGCCGCCACATGATTATTCTCAGGAGTTGT
ATGATAAGTACCGAGAGTCCTTTGAAGAGTATATCACTACCACTGTGCTTCCTTCATTGAGAGAAA
AGCATGATGAATACATGTTAAGGGAGCTCGTGAGAAGGTGGTCAAATCATAAAATAATGGTTAGAT
GGCTTTCACGCTTTTTCCATTATCTTGATCGCTACTTTATAGCACGAAGATCATTGCCTGCTCTTA
ATGAAGTCGGTCTCACTTGTTTCCGTGATCTGGTGTACAACGAAGTCCATGGGAAAGTTAAAGATG
CCGTGATCTCATTGATTGACCAAGAGAGGGAAGGGGAGCAAATTGACAGAGCTTTATTAAAGAATG
TTTTGGGTATTTTTGTAGAGATTGGTTTGGGAAGCATGGAATGTTATGAGAATGATTTTGAAACAT
CAATGCTTAATGCTACAGCAGCCTATTATTCACGAAAAGCTTCAAATTGGATTCTAGAAGATTCAT
GTCCAGATTATATGCTAAAAGCCGAGGAGTGCTTAAAACATGAGAAAGATAGAGTTGCTCATTATT
TGCATTCAAGCAGTGAACAGAAGCTGTTAGAGAAAGTGCAACATGAGTTACTTTTCGTATATGCAA
GTCAACTTCTCGAGAAAGAACATTCCGGATGTCATGCATTGCTTCGCGATGACAAGGTGGGAGATC
TTTCACGCATGTATCGGCTGTTCTGTAGAATTACACGTGGTTTGGACCCTGTGTCTCAAATATTTA
AGCAGCATGTGACTGCAGAAGGTACTGCTTTGGTCAAACATGCCGAAGATGCTGCAAGTAACAAGA
AGGCCGAGAAAAAAGACATTGTTGGTTTGCAAGAGCAGGTCTTCGTTAGGAAAGTAATTGAGCTGC
ATGATAAATACTTGGCCTATGTGACTGACTGCTTTCAAAATCACTCTCTATTTCACAAGGCACTTA
AAGAGGCATTCGAGGTATTCTGCAATAAAGGTGTTGCAGGTAGCTCAAGCGCTGAACTTCTGGCTG
CTTTTTGTGACAATATATTGAAGAAGGGTGGAAGCGAGAAACTAAGCGATGAGGCCATAGAGGATA
CTCTTGAGAAGGTTGTAAAACTATTGGCATATATTAGCGATAAAGATCTGTTTGCTGAATTTTACA
GGAAGAAGCTTGCACGAAGATTACTCTTTGACAAAAGTGCTAATGATGACCATGAGAGGAGCATCC
TTACAAAGCTGAAACAGCAATGTGGAGGGCAGTTCACCTCTAAAATGGAAGGCATGGTAACCGATC
TGACACTTGCACGAGAAAATCAATCAAGTTTTGACGATTACCTTAGCAGCAATCCTAAAGCAAATT
CTGGAATTGACTTGACTGTTACAGTCTTAACAACTGGCTTCTGGCCCAGTTACAAGTCTTTTGATC
TCAATCTTCCTGATGAGATGGTAAAATGCGTTGAAATTTTTAAAGAGTTTTACGAGACAAAAACCA
AACACAGAAAACTTACATGGATTTATTCGTTGGGCACTTGCAACATCAATGGCAAGTTCGAAACCA
AGACAATAGAGTTGGTTGTTACAACCTATCAGGCTGCAGTGTTGCTTCTATTCAACTCTGCAGATA
AATTAAGTTATTCTGAGATTGTGCAGCAGCTAAACTTATCTGATGATGATGTAATCAGATTACTTC
ACTCTCTTTCATGCGCTAAATACAAAATTCTCAATAAAGAACCCGCTACCAAGACTATTACCCCGA
ATGATCATTTTGAGTTCAATTCTAAATTCACTGATAGAATGAGAAGGATCAAGATTCCCCTGCCTC
CTGTGGATGAGAAGAAAAAAGTAATTGAAGATGTTGACAAAGACAGAAGATATGCAATTGACGCAT
CCATAGTTCGAATAATGAAAAGTAGAAAAGTTCTTGGTCATCAGCAGCTTGTTTTGGAATGTGTTG
AGCAATTAGGCCGCATGTTTAAGCCTGACTTTAAGGCCATCAAGAAAAGGATTGAAGATCTGATCG
CTAGAGATTATTTGGAGAGGGACAAGGACAATCCAAACCTCTTTAAATATTTGGCCTAA

Fig. 14

ATGAACGAAAGAAAAACAATAGACTTAGAGCAAGGATGGGACTTCATGCAGAAAGGAATAACAAAG
TTGAAGAATATTCTAGAAGGTCTTCCCGAGCCACAATTCAGCTCGGAGGATTACATGATGCTCTAC
ACAACCAT[C]TACAACATGTGTACACAGAAACCACCACATGATTACTCCCAACAGTTGTATGACA
AATATCGTGAGTCTTTTGAAGAGTATATTACTTCAACTGTGTTACCTTCTTTAAGAGAGAAGCATG
ATGAGTTCATGCTGAGAGAGCTTGTTAGAAGGTGGTCAAATCATAAAGTCATGGTGCGGTGGCTTT
CTAGATTCTTCCATTATCTTGACCGATATTTCATTGCCCGAAGATCTCTTCCGCCACTAAATGAAG
TTGGACTTGCCTGTTTTCGTGATCTGGTATACCAAGAGGTGAATGGTAAAGTGAGAGATGCTGTAA
TATCTTTGATTGATCAAGAGCGTGAAGGGGAGCAGATTGATCGAGCTTTACTGAAGAATGTTCTAG
ATATATTTGTTGAGATAGGAATGGGACAAATGGAGTATTATGAGAATGATTTTGAAGCATCCATGC
TTAATGATACAGCAGCATATTATTCACGCAAGGCTTCCAACTGGATTCTAGAAGATTCTTGTCCAG
ATTATATGCTCAAAGCAGAGGAGTGCTTAAAAAGAGAAAAGGACAGAGTGTCTCATTATCTTCATT
CCAGCAGTGAGCCAAAGCTTCTTGAGAAAGTTCAAAATGAGTTATTGTCTGTTTATGCAACTCAAT
TGCTTGAGAAAGAGCACTCAGGTTGTCATGCATTGCTCAGGGATGACAAGGTTGATGATTTATCAA
GAATGTACAGACTCTTTTCAAAGATACCAAAAGGATTGGATCCTGTTTCTAGTATGTTTAAGCAGC
ATGTCACTGCTGAAGGCACAACATTGGTTAAACAAGCAGAAGATGCAGCAAGTACCAAGAAGGCTG
AAAAGAGAGATGTGGTTGGGTTGCAGGAACAGGTTTTTGTTAGAAAAGTTATTGAGCTCCATGACA
AGTACCTGGCATATGTAAATGACTGTTTCATGAACCATACTCTTTTCCACAAGGCTCTTAAAGAGG
CATTTGAAATATTCTGCAACAAGGGTGTTGCTGGAAGTTCAAGTGCAGAGTTACTTGCCACATTTT
GTGATAATATTCTTAAAAAAGGTGGAAGTGAGAAACTGAGCGATGAAGCCATTGAGGACACCCTTG
AGAAGGTAGTAAAGTTGCTTGCCTACATCAGTGATAAAGATCTATTTGCTGAATTTTACAGGAAAA
AACTTGCTAGGAGGCTTTTGTTTGACAAGAGTGCAAACGATGAGCATGAGAGAAGTATTCTCACAA
AGCTGAAGCAACAGTGTGGTGGTCAGTTCACATCAAAGATGGAAGGGATGGTTACAGATTTGACAT
TGGCAAAGGAAAACCAATCCCATTTTGAAGAGTATTTGAACAATAATCCCAATGTCAGCCCTGGAA
TTGACTTGACTGTCACTGTGTTGACTACCGGCTTCTGGCCCAGCTACAAATCTTTTGACCTAAATC
TCCCTGCCGAAATGGTTAAATGCGTTGAAGTTTTCAGAGAATTTTATCAAACAAAAACAAAGCACA
GGAAGCTTACATGGATATATTCATTGGGTACCTGCAATATAAACGGGAAATTTGAACCCAAAACAA
TGGAGCTCATAGTCACAACCTACCAGGCATCTGCTTTATTACTGTTCAACTTATCGGATCGATTGA
GTTATCAAGAAATCATGACTCAGTTGAACTTGTCAGATGATGATGTTGTTAGGCTGCTCCATTCTT
TGTCATGTGCAAAATACAAAATTCTTTTAAAGGAGCCTAATACCAAAACAATCTCTCCAACCGATT
ACTTCGAATTCAACTCCAAGTTTACAGATAAAATGAGGAGGATCAAGATTCCTCTACCTCCTGTGG
ATGAGAAGAAAAAGGTGATTGAGGATGTTGACAAAGACAGACGTTATGCCATTGATGCTTCCATTG
TAAGGATAATGAAGAGCAGAAAGGTGCTTGGATACCAGCAGTTGGTTATGGAGTGTGTTGAACAGT
TGGGACGCATGTTTAAGCCTGATGTAAAAGCAATCAAGAAGCGGATTGAAGATCTGATAACTCGTG
ATTATCTTGAAAGAGACAAAGAGAACCCCAACTTGTTCCGATACTTGGCATGA

Fig. 15

ATGGAGCGGAAGACGATTGATCTGGAACAAGGATGGGACTATATGCAGACTGGGATCACTAAGCTG
AAACGGATTCTTGAAGGATTGCCTGAGCCGCAATTCGACTCTGAGCAGTACATGATGCTTTATACG
ACTAT[C]TACAACATGTGCACCCAGAAACCTCCTCATGATTACTCTCAGCAGCTTTATGACAAGT
ATCGCGAAGCTTTTGAGGAGTACATTGACTCTACTGTTTTGCCTGCTTTGAAGGAGAAGCATGATG
AATACATGCTACGGGAGCTGGTTAAGAGATGGTCTAACCATAAAGTTATGGTTAGATGGCTATCCC
GATTCTTCTACTATCTTGACCGTTACTTCATTGCTCGGAGATCGCTGCCACCGCTTAATGAAGTTG
GGCTCACATGCTTCCGTGACCGGGTGTATAAGGAGTTGCATTCCAAGGTCAAAGATGCTGTAATAG
CACTTGTTGATAAAGAACGGGAAGGCGAGCAGATTGACAGGGCTCTTCTGAAAAACGTATTAGATA
TCTATGTAGAGATTGGAATGGGACAGATGGAAAGATACGAAGTGGATTTTGAAAGCTTCATGCTTT
TGGATTCAGCATCTTACTATTCTCGCAAAGCATCAAACTGGATCCAGGAAGATTCTTGCCCTGATT
ACATGCTGAAGTCTGAAGAATGCCTTAAGAAGGAGAGGGAGAGGGTTGCTCACTACCTTCATTCAA
GCAGCGAGCCAAAGCTGGTTGAGAAAGTACAACATGAGCTGTTGGTTGTCTATGCAAATCAGCTTC
TTGAAAAGGAGCACTCAGGGTGCCGTGCATTGCTGAGAGACGACAAGGTTGACGATCTCTCCAGGA
TGTACAGGCTCTATCATAAAATTGCTAAAGGTTTAGAACCTGTTGCAAACATATTTAAGCAGCATG
TCACAGCCGAGGGTAACGCACTTGTCCAACAGGCCGAAGACACAGCCACTAATCAGGCTGCAAATA
CTGCTAGCGTGCAGGAACAGGTTCTCATCAGAAAAGTGATTGAGCTACATGATAAGTACATGGTCT
ATGTCGTGGAGTGCTTCCAGAACCACACCCTCTTCCACAAGGCTCTGAAAGAGGCATTTGAGATAT
TCTGTAACAAAACAGTCGCTGGAAGTTCAAGTGCAGAACTGCTTGCAACATTCTGCGACAACATCC
TCAAGAAGGGGGGTAGTGAGAAGCTGAGTGACGAAGCTATTGAAGATACGCTTGAGAAGGTTGTCA
AATTGCTTGCTTATATAAGCGACAAGGATCTTTTCGCCGAGTTCTACAGGAAGAAGCTGGCACGTA
GGCTCTTATTTGATCGCAGTGCGAATGATGATCATGAGAGAAGCATCCTTACAAAGCTCAAGCAAC
AATGTGGTGGGCAGTTCACTTCTAAGATGGAGGGCATGGTAACGGACTTGACATTGGCAAGAGAGA
ACCAAACCAGTTTCGAGGAGTATCTAGGCAATAACCCCGCTGCAAACCCAGGGATTGATTTGACCG
TCACTGTTCTTACCACTGGTTTCTGGCCAAGTTACAAATCATTCGACATAAATCTACCAAGTGAAA
TGGTCAAGTGTGTTGAAGTTTTCAAAGGGTTTTATGAGACGAAAACTAAACATAGGAAACTTACAT
GGATCTACTCACTAGGAACTTGTCACCTCAACGGAAAGTTTGATCACAAGCCCATTGAGTTAGTTG
TGTCTACTTACCAGGCTGCTGTGCTTCTGCTGTTCAACACAACAGACAAATTGAGCTACAACGATA
TCCTAACTCAACTGAACCTAAGCCACGAAGATTTAGTGAGGTTGCTTCATTCCCTGTCATGTGCTA
GGTACAAGATCCTTCTCAAGGAGCCAAGCACGAAGACTGTTACACAGACTGATTCATTTGAATTCA
ATGCCAAATTCACGGACAGAATGCGCAGAATCAAGATCCCTCTCCCTCCTGTTGATGAAAGGAAGA
AGGTTGTGGAAGATGTGGACAAAGACAGACGCTATGCGATTGATGCTGCCATTGTTAGGATCATGA
AGAGCAGGAAAGTGTTGGGACATCAACAACTCGTCTCTGAGTGCGTTGAGCAACTTAGCCGAATGT
TCAAGCCTGATATCAAAGCGATCAAGAAGCGTATGGAGGATCTAATTACGAGGGATTATTTGGAGA
GGGACAAGGAGAACCCTAACATGTTTAGGTACTTGGCTTAG

Fig. 16

ATGAACGATCGTAAAGTTATCGAACTAGAGCAAGGATGGGAGTTCATGGGGAAGGGGATTACGAAG
TTGAAAAGGATTTTGGAAGGATTACCAGAGCCGCCTTTTAATTCGGAAGACTACATGATGCTGTAC
ACGACAAT[A]TACAACATGTGTACACAGAAACCCCCTCATGATTACTCTCAACAACTCTATGACA
ATTACAAAGAGGCATTTGTGGATTACATACATTCAACGGTTTTACCTTCTTTGGGGGACAAACATG
ATGAGTTTATGCTGAGAGAGCTTGTGAAGAGATGGTCAAATCATAAAGTAATGGTGAGGTGGTTGT
CTCGCTTCTTCCATTATCTGGATCGGTACTTCATCGCTCGGAGATCGCTTCCTTCTTTGAATGATG
TTGGATTGACGTGCTTCCGTGATCTGGTTTATCAAGAAATATCTGGCAAAGCCAAGGATGCTGTTA
TTGCTCTGATTGATGAAGAAAGAGAGGGTGGGCAAATTGACAGAGCCTTATTGAAGAATGTACTTG
ATATATACGTTGAAATTGGAATGACACAAATGGATTACTACGAAAAGGACTTTGAAGCTCATATGC
TGGATGATACTGCTGCTTATTACTCACGCAAGGCCTCAAGCTGGATTCTGGAGGACTCATGTCCGG
AATACATGTTGAAGTCGGAGGAGTGTTTGAAGAAAGAGAAAGATAGAGTGGCTCATTATCTACATT
CCAGCAGTGAGCCAAAGCTTCTGGAGAAAGTACAAAATGAGTTGCTACTGGTTTACGAAAATCAGT
TGCTTGAGAAGGAGAATTCTGGATGTCGTGCATTGTTGAAAGATGACAAGGTGGAAGATCTTTCCA
GGATGTACAGGCTTTATAGCAAGGTTACCAAAGGGTTGGAACCCATTGGCAGTATCTTCAAACAGC
ATATAACCGATGAAGGAACAGCCCTGGTGCAGCAGGCCGAAGACGCTGCAATTAGCAAGGCTGAAA
ATGCTGGCGGTGGTTCACATGAGCAGGTCTTCGTCAGGAAAGTGATTGAGTTGCATGACAAATTTA
TGACCTATGTTACAGATTGCTTCAACAGCCATACCATCTTTCACAAGGCTCTCAAGGAAGCTTTTG
AGGTATTCTTAAACAAGGGTGTTGCTGGTAGTTCAAGTGCTGAACTTCTAGCTTCATTTTGTGATA
ATATTCTCAAGAAAGGTGGTAGTGAAAAATTAAGTGATGAGGCTATTGAGGATTCACTGGAGAAGG
TGGTGAAGCTTCTCGCATATGTCAGTGATAAAGACCTGTTTGCTGAATTTTACAGAAAGAAGCTCT
CTCGCCGGCTACTCTTTGACAAAAGTGCTAATGATGATCATGAGAGGAGTATTTTAACAAAATTGA
AGCAGCAGTGTGGGGGACAGTTCACATCAAAGATGGAGGGGATGGTGACAGACTTGACATTGGCGA
GGGAGAATCAAACTAATTTTGAGGAATATCTTGGACAAAATACAGATGCCAGTCCTGGTCTTGATT
TGACTGTGACAGTTTTGACCACTGGGTTCTGGCCAAGTTACAAATCTTCTGATCTTAACCTTCCTG
CTGAGATGGTGAGGTGTGTTGAAGTTTTTAAGCAATTTTATCAAACAAAGACAAAACACAGGAAGC
TCACCTGGGTATATTCGTTGGGAAGTTGTAACATTAATGGCAAGTTTGGTCCGAAAACAATTGAAT
TGGTTGTTGGAACTTATCAGGCTGCTGCGCTGATGCTCTTTAACACATCAGATCGACTGAGTTATT
CAGAAATAACGACCCAACTAAATCTAGCTGACGAAGACTTGGTTAGAGTGCTTCAATCTCTATCTT
GCGCAAAGTATAAGATTCTTCTAAAAGAGCCAAGCACAAGAAACGTGATCTCAACTGATTGTTTTT
CATTCAACTCTAATTTTACTGACAGAATGAGGAGGATTAGGATTCCTCTTCCTCCAATGGATGAGA
GGAAAAAGGTTGTTGAAGATGTTGACAAAGATAGAAGATATGCTATTGATGCCTCAATTGTACGCA
TAATGAAAAGTAGGAAGGCTTTGGGATATCAACAATTAATCACGGAGTGTGTGGAGCAGCTAAGCC
GCATGTTCAAGCCTGATTTCAAAGCAATTAAGAAGAGGATCGAGGACTTGATAACCAGAGATTATA
TTGAAAGAGACAAGGAAAACCCTCAGCTATTCCGGTACTTGGCTTGA

Fig. 17

ATGAATGATCGTAAAGTTATTGAACTAGAGCAAGGATGGGAGTTCATGGGGAAGGGGATTACAAAG
TTGAAGAGGATTCTGGAAGGATTGCCAGAGCCACCATTTAATTCTGAAGACTACATGATGTTGTAC
ACGACGAT[A]TACAATATGTGTACTCAGAAACCCCCACATGATTACTCTCAACAGCTCTATGACA
ATTACAAACAGGCTTTTGTGGATTACATCAACTCGACGGTTTTACCTTCTTTGCGGGAGAAGCATG
ATGAGTTTATGTTAAGAGAACTTGTGAAAAGATGGGCAAATCATAAAGTAATGGTCAGGTGGTTGT
CTCGTTTCTTCCATTATCTGGACCGGTATTTCATTGCTCGGAGGTCGCTTCCTTCTTTGAATGAAG
TTGGACTGACTTGTTTCCGTGATCTGGTTTATCAAGAAATATCTGGCAAAGCCAAGGATGCTGTTA
TAGCCCTGATTGATATAGAAAGAGAAGGTGGGCAGATTGACAGATCATTATTGAAAAATGTACTTG
ATATATATGTTGAAATTGGAATGGGACAAATGGATCACTATGAAAAAGACTTTGAAGCTCATATGC
TGGATGATACTGCTGCTTACTACTCGCGCAAAGCGTCTAGCTGGATTCTTGAGGACTCTTGTCCGG
AATACATGTTAAAGTCTGAGGAGTGTTTGAAGAAGGAGAAAGAGAGAGTGGCTAATTATTTACATT
CCAGCAGTGAGCCAAAGCTTCTGGAGAAAGTGCAAAACGAGTTGCTATTGGTTTATGAAAGCCAAT
TGCTTGAGAAGGAGAATTCGGGATGTCGTGCATTACTGAAAGATGACAAGGTGGATGATCTTTCCA
GGATGTACAGGCTTTACAGTAAGGTTACCAAAGGATTGGAACCCATTGGCAGTATCTTCAAACAGC
ATATAACTGATGAAGGAACAGCCTTAGTGCAGCAGGCCGAAGATGCTGCTATCAGCAAGGCTGAAA
ATACTGGTGGTTCACATGAGCAGGTCTTCGTCAGGAAAGTAATAGAGTTGCATGACAAATTCATGA
CTTATGTCACCGATTGCTTCAACAGCCATACCATATTTCACAAGGCTCTTAAGGAGGCTTTTGAGG
TATTTTTGAACAAGGGTGTTGCTGGTAGCTCAAGTGCTGAGTTGCTAGCTACATTCTGTGATAACA
TTCTCAAGAAAGGTGGGAGCGAAAAACTAAGCGATGAGGCTATTGAGGATTCACTTGAGAAGGTGG
TGAAGCTTCTGGCCTATGTCAGTGATAAAGACCTGTTTGCTGAATTTTACAGAAAGAAGCTCTCTC
GCCGGCTACTCTTTGACAAGAGTGCTAATGATGATCATGAAAGAAGTATTTTAACCAAATTGAAGC
AGCAGTGTGGCGGACAATTCACATCAAAGATGGAGGGGATGGTGACAGACTTGACCTTGGCGAGGG
AGAATCAAACTAATTTTGAGGAATATCTTAGTCAGAATCCAGATGCCAGTCCTGGTCTTGATTTGA
CTGTGACTGTTCTGACAACTGGGTTCTGGCCAAGTTACAAATCTTCCGATCTTAACCTTCCCGCTG
AGATGGTGAGGTGTGTTGAAGTTTTTAAGCAGTTCTATTCAACTAAAACAAAGCACAGGAAGCTGA
CCTGGGTTTACTCATTGGGAAGCTGTAATATTAATGGCAAGTTTGGTCCAAAAACTATTGAATTGG
TTGTCGGAACTTATCAGGCTGCTGCTTTGATGCTCTTTAACACATCAGACCGACTGAGTTATTCAG
AGATAGCAACTCAACTAAATTTAGCTGATGAAGATCTGGTTAGAGTGCTTCAATCTTTATCCTGCG
CAAAGTATAAGATTCTTTTAAAGGAGCCAAACACGAAAACCGTGTCCCCGACTGATTGTTTTTCAT
TTAACTCTAGTTTCACTGACAGGATGAGGAGGATAAGAATTCCTCTTCCTCCGATGGATGAGAGGA
AAAAGGTTGTTGAGGATGTTGACAAAGATAGAAGATATGCTATTGATGCCTCAATTGTACGCATAA
TGAAAAGTAGGAAGGTTTTGGGGTACCAGCAATTAATCACAGAGTGTGTGGAGCAGCTAAGCCGCA
TGTTCAAGCCTGATTTCAAGGCAATTAAGAAGAGGATCGAGGACTTAATAACCCGAGATTATATTG
AAAGAGACAAGGAGAACCCGCAGCTATTCCGATACTTGGCTTGA

Fig. 18

MTMGERKTIDLEQGWEFMQKGITKLKNILEGLPEPQFSSEDYMMLYTT[I]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLKREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 19

MTMGERKTIDLEQGWEFMQKGITKLKNILEGLPEPQFSSEDYMMLYTT[I]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLKREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 20

MTMGERKTIDLEQGWEFMQKGITKLKNILEGLPEPQFSSEDYMMLYTT[I]YNMCTQKPPHDYSQQ
LYDKYRESFEEYISSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLRREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DKLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig.21

MTMGERKTIDLEQGWEFMQKGITKLKNILEGLPEPQFSSEDYMMLYTT[I]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLKREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 22

MNQRSTIDLEHGWDFMQKGITKLKNILEGLPEPQFSSEDYMMLYTT[I]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDLVYQELNGKVRDAVISLIDQEREGEQIDRALLKNVLDIFVEIGMGSMDYYENDFEAA
MLKDTAAYYSRKASNWILEDSCPDYMLKAEECLKREKDRVSHYLHSSSETKLLEKVQHELLSVYAN
QLLEKEHSGCHALLRDDKVDDLSRMYRLFSKIPRGLEPVANIFKQHVTAEGTALVKQAEDAASNKK
AEKRDVVGLQEQVFVRKVIELHDKYLAYVNNCFQNHTLFHKALKEAFELFCNKGVAGSSNAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPTANPGIDLTVTVLTTGFWPSYKSFDL
NLPAEMVRCVEVFKEFYQTKTKHRKLTWIYSLGTCNINGKFEAKTIELVVTTYQASALLLFNASDR
LSYQEIMTQLNLSDDDVVRLLHSLSCAKYKILNKEPSTKTISPTDVFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 23

MNQRSTIDLEHGWDFMQRGITKLKNILEGLPEPQFSSEDYMMLYTT[I]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDQVYQELNGKVRDAVISLIDQEREGEQIDRALLKNVLDIFVEIGMGLMDYYENDFEAA
MLKDTAAYYSRKASNWILEDSCPDYMLKAEECLKREKDRVSHYLHSSSETKLLEKVQHELLSVYAT
QLLEKEHSGCHALLRDDKVEDLSRMYRLFSKISRGLDPVANIFKQHVTAEGTALVKQAEDAASNKK
AEKRDVVGLQEQVFVRKVIELHDKYLAYVNNCFQNHTLFHKALKEAFELFCNKGVAGSSSAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPIANPGIDLTVTVLTTGFWPSYKSFDL
NLPAEMVRCVEVFKEFYQTKTKHRKLTWIYSLGTCNINGKFEPKTIELVVTTYQASALLLFNASDR
LSYQEIMTQLNLSDDDVVRLLHSLSCAKYKILNKEPSTKTISPTDVFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 24

MNQRSTINLEHGWDFMQRGITKLKNILEGLPEPQFSSEDYMMLYTT[I]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDLVYQELNGKVRDAVISLIDQEREGEQIDRALLKNVLDIFVEIGMGSMDYYENDFEAA
MLKDTAAYYSRKASNWILEDSCPDYMLKAEECLKREKDRVSHYLHLSSETKLLEKVQHELLSVYAT
QLLEKEHSGCHALLRDDKVEDLSRMYRLFSKIPRGLDPVANIFKQHVTAEGTALVKQAEDAASNKK
AEKRDVVGLQEQIFVRKVIELHDKYMAYVNNCFQNHTLFHKALKEAFELFCNKGVAGSSSAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPAANPGIDLTVTVLTTGFWPSYKSFDL
NLPAEMVRCVEVFKEFYQTKTKHRKLTWIYSLGTCNINGKFEPKTIELVVTTYQASALLLFNASDR
LSYQEIMTQLNLSDDDVVRLLHSLSCAKYKILNKEPSTKTISPTDVFEFNFKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 25

MERKTIDLDQGWDYMQTGITKLKRILEGLPEPQFDSEQYMMLYTT[I]YNMCTQKPPHDYSQQLYD
KYREAFEEYIHSTVLPALREKHDEYMLRELVKRWSNHKVMVRWLSRFFYYLDRYFIARRSLPPLNE
VGLTCFRDLVYNELHSKVKDAVIALVDKEREGEQIDRALLKNVLDIYVEIGMGQMERYEEDFESFM
LLDSASYYSRKASSWIQEDSCPDYMLKSEECLKKERERVAHYLHSSSEPKLVEKVQHELLVVYANQ
LLEKEHSGCRALLRDDKVDDLSRMYRLYHKIVKGLEPVANIFKQHVTAEGNALVQQAEDTATNHAA
NTASVQEQVLIRKVIELHDKYMVYVVECFQNHTLFHKALKEAFEIFCNKTVAGSSSAELLATFCDN
ILKKGGSEKLSDEAIEDTLEKVVKLLAYISDKDLFAEFYRKKLARRLLFDRSANDDHERSILTKLK
QQCGGQFTSKMEGMVTDLTLARENQNSFEEYLGNNPAANPGIDLTVTVLTTGFWPSYKSFDINLPA
EMVKCVEVFKGFYETKTKHRKLTWIYSLGTCHLNGKFDVKPIELVVSTYQAAVLLLFNTTDKLSYT
DILTQLNLSHEDLVRLLHSLSCARYKILLKEPSTKTVSQSDSFEFNSKFTDRMRRIKIPLPPVDER
KKVVEDVDKDRRYAIDAAIVRIMKSRKVLGHQQLVSECVEQLSRMFKPDIKAIKKRMEDLITRDYL
ERDKENANMFRYLA

Fig. 26

MMIERKTIDLEQGWDFMQKGITKLKNILEGFPEPQFSSEDYMMLYTT[I]YNMCTQKPPHDYSQQL
YEKYREAIEEYITSTVLPSLREKHDEFMLRELVKRWSNHKVMVRWLSRFFHYLDRYFIARRSLPPL
HEVGLTCFRDLVYQEINGKVRDAVISLINQEREGEQIDRALLKNVLDIFVEVGMSQMDYYENDFEA
DMLKDTAAYYSRKASNWILEDSCPDYMLKAEECLRREKDRVSNYLHSSSEPKLLEKVQHELLSHYA
TQLLEKEHSGCHALLRDDKVADLSRMYRLFSKIPRGLDPVSNIFKQHVTAEGTALVKQAEDAASNK
KAEKRDVVGLQEQVFVRKIIELHDKYLTYVNDCFTNHTLFHKALKEAFEIFCNKGVSGSSSAELLA
TFCDNILKKGGSEKLSDEAIEETLEKVVRLLAYISDKDLFAEFYRKKLARRLLFDKSANDEHERSI
LTKLKQQCGGQFTSKMEGMVTDLTLAKENQSNFEEYLNNNSNVNPGIDLTVTVLTTGFWPSYKSFD
LNLPAEMVKCVEVFREFYQTKTKHRKLTWIYSLGTCNIIGKFDPKTMELIVTTYQASALLLFNSSD
RLSYNEIMTQLNLSDDDVVRLLHSLSCAKYKILSKEPNTKTISPTDCFQFNSKFTDKMRRIKIPLP
PVDEKKKVIEDVDKDRRYAIDASIVRIMKSRKVLGYQQLVMECVEQLGRMFKPDVKAIKKRIEDLI
TRDYLERDKDNANLFRYLA

Fig. 27

MNERKTIDLDNGWEFMQKGITKLKKILEGQPEPQFSSEDYMMLYTT[I]YNMCTQKPPHDYSQQLY
DKYREAFEEYITSTVLPSLREKHDEFMLRELVNRWTNHKVMVRWLSRFFHYLDRYFIARRSLPALH
EVGLTCFRDLVYQELKVKVRDAVISLIDQEREGEQIDRALLKNVLDIFVEIGMSQMDQYENDFEEA
MLTDTAAYYSRKASNWILEDSCPDYMLKAEECLRREKDRVSHYLHFSSEPKLLEKVQHELLSVYAT
QLLEKEHSGCHALLRDDKVDDLSRMYRLFSKIPKGLDPVSYIFKQHVTNEGMALVKQAEDAASNKK
AEKRDVVSLQEQVFVRKIIELHDKYLAYVNDCFTNHTLFHKALKEAFEIFCNKGVAGSSNAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLAKENQSSFEEYLGNNANVNPGIDLTVTVLTTGFWPSYKSFDL
NLPAEMVKCVEVFREFYQTKTKHRKLTWIYSLGTCNINGKFEPKTIELIVTTYQASALLLFNTSDR
LSYQEIMTQLNLSDDDVVRLLHSLSCAKYKILTKEPNNKTISPTDYFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNANLFRYLA

Fig. 28

MNERKTIDLEQGWDFMQKGITKLKNILEGLPEPQFSSEDYMMLYTT[I]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQTELLSVYAT
QLLEKEHSGCHALLRDDKVDDLSRMYRLFSKIQKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNSSDR
LSYQEIMTQLNLSDDDVVRLLHSLSCAKYKILLKEPNTKTISPTDFFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 29

MNERKTIDLEQGWDFMQKGITKLKNILEGLPEPQFSSEDYMMLYTT[I]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQTELLSVYAT
QLLEKEHSGCHALLRDDKVDDLSRMYRLFSKIQKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNSSDR
LSYQEIMTQLNLSDDDVVRLLHSLSCAKYKILLKEPNTKTISPTDFFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 30

MSLHERKTIDLEQGWAFMQKGITKLKNILDELNEPQFSSEDYMMLYTT[I]YNMCTQKPPHDYSQE
LYDKYRESFEEYITTTVLPSLREKHDEYMLRELVRRWSNHKIMVRWLSRFFHYLDRYFIARRSLPA
LNEVGLTCFRDLVYNEVHGKVKDAVISLIDQEREGEQIDRALLKNVLGIFVEIGLGSMECYENDFE
TSMLNATAAYYSRKASNWILEDSCPDYMLKAEECLKHEKDRVAHYLHSSSEQKLLEKVQHELLFVY
ASQLLEKEHSGCHALLRDDKVGDLSRMYRLFCRITRGLDPVSQIFKQHVTAEGTALVKHAEDAASN
KKAEKKDIVGLQEQVFVRKVIELHDKYLAYVTDCFQNHSLFHKALKEAFEVFCNKGVAGSSSAELL
AAFCDNILKKGGSEKLSDEAIEDTLEKVVKLLAYISDKDLFAEFYRKKLARRLLFDKSANDDHERS
ILTKLKQQCGGQFTSKMEGMVTDLTLARENQSSFDDYLSSNPKANSGIDLTVTVLTTGFWPSYKSF
DLNLPDEMVKCVEIFKEFYETKTKHRKLTWIYSLGTCNINGKFETKTIELVVTTYQAAVLLLFNSA
DKLSYSEIVQQLNLSDDDVIRLLHSLSCAKYKILNKEPATKTITPNDHFEFNSKFTDRMRRIKIPL
PPVDEKKKVIEDVDKDRRYAIDASIVRIMKSRKVLGHQQLVLECVEQLGRMFKPDFKAIKKRIEDL
IARDYLERDKDNPNLFKYLA

Fig. 31

MNERKTIDLEQGWDFMQKGITKLKNILEGLPEPQFSSEDYMMLYTT[I]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQNELLSVYAT
QLLEKEHSGCHALLRDDKVDDLSRMYRLFSKIPKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNLSDR
LSYQEIMTQLNLSDDDVVRLLHSLSCAKYKILLKEPNTKTISPTDYFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 32

MERKTIDLEQGWDYMQTGITKLKRILEGLPEPQFDSEQYMMLYTT[I]YNMCTQKPPHDYSQQLYD
KYREAFEEYIDSTVLPALKEKHDEYMLRELVKRWSNHKVMVRWLSRFFYYLDRYFIARRSLPPLNE
VGLTCFRDRVYKELHSKVKDAVIALVDKEREGEQIDRALLKNVLDIYVEIGMGQMERYEVDFESFM
LLDSASYYSRKASNWIQEDSCPDYMLKSEECLKKERERVAHYLHSSSEPKLVEKVQHELLVVYANQ
LLEKEHSGCRALLRDDKVDDLSRMYRLYHKIAKGLEPVANIFKQHVTAEGNALVQQAEDTATNQAA
NTASVQEQVLIRKVIELHDKYMVYVVECFQNHTLFHKALKEAFEIFCNKTVAGSSSAELLATFCDN
ILKKGGSEKLSDEAIEDTLEKVVKLLAYISDKDLFAEFYRKKLARRLLFDRSANDDHERSILTKLK
QQCGGQFTSKMEGMVTDLTLARENQTSFEEYLGNNPAANPGIDLTVTVLTTGFWPSYKSFDINLPS
EMVKCVEVFKGFYETKTKHRKLTWIYSLGTCHLNGKFDHKPIELVVSTYQAAVLLLFNTTDKLSYN
DILTQLNLSHEDLVRLLHSLSCARYKILLKEPSTKTVTQTDSFEFNAKFTDRMRRIKIPLPPVDER
KKVVEDVDKDRRYAIDAAIVRIMKSRKVLGHQQLVSECVEQLSRMFKPDIKAIKKRMEDLITRDYL
ERDKENPNMFRYLA

Fig. 33

MNDRKVIELEQGWEFMGKGITKLKRILEGLPEPPFNSEDYMMLYTT[I]YNMCTQKPPHDYSQQLY
DNYKEAFVDYIHSTVLPSLGDKHDEFMLRELVKRWSNHKVMVRWLSRFFHYLDRYFIARRSLPSLN
DVGLTCFRDLVYQEISGKAKDAVIALIDEEREGGQIDRALLKNVLDIYVEIGMTQMDYYEKDFEAH
MLDDTAAYYSRKASSWILEDSCPEYMLKSEECLKKEKDRVAHYLHSSSEPKLLEKVQNELLLVYEN
QLLEKENSGCRALLKDDKVEDLSRMYRLYSKVTKGLEPIGSIFKQHITDEGTALVQQAEDAAISKA
ENAGGGSHEQVFVRKVIELHDKFMTYVTDCFNSHTIFHKALKEAFEVFLNKGVAGSSSAELLASFC
DNILKKGGSEKLSDEAIEDSLEKVVKLLAYVSDKDLFAEFYRKKLSRRLLFDKSANDDHERSILTK
LKQQCGGQFTSKMEGMVTDLTLARENQTNFEEYLGQNTDASPGLDLTVTVLTTGFWPSYKSSDLNL
PAEMVRCVEVFKQFYQTKTKHRKLTWVYSLGSCNINGKFGPKTIELVVGTYQAAALMLFNTSDRLS
YSEITTQLNLADEDLVRVLQSLSCAKYKILLKEPSTRNVISTDCFSFNSNFTDRMRRIRIPLPPMD
ERKKVVEDVDKDRRYAIDASIVRIMKSRKALGYQQLITECVEQLSRMFKPDFKAIKKRIEDLITRD
YIERDKENPQLFRYLA

Fig. 34

MNDRKVIELEQGWEFMGKGITKLKRILEGLPEPPFNSEDYMMLYTT[I]YNMCTQKPPHDYSQQLY
DNYKQAFVDYINSTVLPSLREKHDEFMLRELVKRWANHKVMVRWLSRFFHYLDRYFIARRSLPSLN
EVGLTCFRDLVYQEISGKAKDAVIALIDIEREGGQIDRSLLKNVLDIYVEIGMGQMDHYEKDFEAH
MLDDTAAYYSRKASSWILEDSCPEYMLKSEECLKKEKERVANYLHSSSEPKLLEKVQNELLLVYES
QLLEKENSGCRALLKDDKVDDLSRMYRLYSKVTKGLEPIGSIFKQHITDEGTALVQQAEDAAISKA
ENTGGSHEQVFVRKVIELHDKFMTYVTDCFNSHTIFHKALKEAFEVFLNKGVAGSSSAELLATFCD
NILKKGGSEKLSDEAIEDSLEKVVKLLAYVSDKDLFAEFYRKKLSRRLLFDKSANDDHERSILTKL
KQQCGGQFTSKMEGMVTDLTLARENQTNFEEYLSQNPDASPGLDLTVTVLTTGFWPSYKSSDLNLP
AEMVRCVEVFKQFYSTKTKHRKLTWVYSLGSCNINGKFGPKTIELVVGTYQAAALMLFNTSDRLSY
SEIATQLNLADEDLVRVLQSLSCAKYKILLKEPNTKTVSPTDCFSFNSSFTDRMRRIRIPLPPMDE
RKKVVEDVDKDRRYAIDASIVRIMKSRKVLGYQQLITECVEQLSRMFKPDFKAIKKRIEDLITRDY
IERDKENPQLFRYLA

Fig. 35

ATGACAATGGGCGAGCGGAAGACTATTGACTTGGAGCAGGGATGGGAGTTTATGCAGAAGGGTATC
ACAAAGTTGAAGAACATTCTCGAGGGCTTGCCTGAGCCTCAGTTCAGCTCCGAGGACTACATGATG
CTTTACACTACCAT[G]TATAACATGTGCACCCAAAAGCCGCCGCATGATTACTCCCAGCAGCTGT
ATGATAAATATCGTGAATCTTTTGAAGAGTACATCACTTCTATGGTCTTACCATCCTTGAGGGAGA
AGCACGATGAGTTCATGTTGAGAGAACTAGTAAAAAGGTGGACAAACCATAAAGTCATGGTGAGGT
GGCTTTCTCGCTTCTTCCACTATCTTGATCGGTACTTCATCGCTCGAAGGTCACTTCCACCTCTAA
ATGAAGTTGGCCTCACATGCTTCCGCGAATTGGTGTACAAAGAGCTAAATAGTAAAGTGAGGGATG
CAGTAATTTCATTGATTGATCAAGAACGTGAAGGAGAACAGATTGACAGAGCTCTACTGAAGAATG
TACTAGATATATTTGTGGAAATTGGTATGGGGCAAATGGATTACTATGAAAATGACTTTGAAGCTG
CCATGCTTAAAGATACTGCTGCTTATTACTCTAGGAAGGCTTCCAATTGGATCCTAGAAGATTCTT
GTCCCGATTATATGCTTAAAGCAGAGGAGTGCTTGAAACGAGAAAAGGATAGGGTTTCCCACTATT
TGCACTCTAGTAGCGAGCCAAAGTTGTTGGAGAAAGTTCAACATGAACTATTATCTGTTTATGCTA
CTCAACTGCTGGAAAAAGAGCATTCAGGATGCCATGCATTGCTTAGAGATGACAAGGTGGAAGATT
TGTCAAGGATGTTCCGTCTATTCTCCAAAATACCGAAGGGACTGGATCCAGTTTCCAACATATTTA
AGCAGCATGTAACTGCTGAAGGAACAGCACTGGTCAAACAGGCAGAAGATGCTGCAAGTAACAAGA
AGGCTGAGAAAAAGGACATAGTTGGTCTGCAGGAACAGGTTTTTGTAAGAAAAGTGATTGAGCTTC
ACGACAAGTACTTGGCTTATGTGAATGATTGTTTCCAAAACCACACACTTTTCCATAAGGCTCTCA
AGGAAGCTTTTGAAGTATTTTGCAATAAGGGTGTTGCTGGAAGTTCTAGTGCAGAATTGCTTGCTA
CCTTTTGTGATAACATCCTTAAGAAAGGTGGGAGTGAGAAGTTGAGTGATGAAGCAATCGAGGAGA
CACTTGAGAAGGTTGTGAAGTTGTTGGCATACATTTGCGACAAAGATCTGTTTGCTGAATTCTATA
GAAAAAAACTTGCCCGAAGGCTTCTCTTTGACAAGAGCGCGAACGATGACCACGAGAGAAGTATAT
TGACCAAATTGAAGCAACAATGTGGTGGTCAGTTCACTTCTAAGATGGAGGGAATGGTTACTGATT
TGACTTTGGCAAGGGAGAACCAAACTAGTTTTGAGGAGTATCTGAGCAATAATCCACAAGCGAGTC
CTGGCATCGACCTGACTGTTACTGTTTTAACTACTGGATTTTGGCCAAGCTACAAGTCTTTTGACC
TCAACCTGCCGGCAGAGATGGTAAAGTGTGTTGAAGTTTTCAGAGAGTTTTATCAAACAAAAACCA
AGCATCGAAAACTTACATGGATTTACTCATTGGGTACTTGTAACATCAGTGGAAAATTTGAACCGA
AAACGATGGAGCTGATTGTGACAACTTATCAGGCTTCTGCCCTGTTGCTATTCAATTCTTCGGATA
GACTAAGTTACTCGGAAATCATGACACAATTAAATTTGAGTGACGATGATGTAGTTAGACTACTCC
ACTCGTTGTCATGTGCCAAGTATAAAATTCTTAATAAGGAACCAAATACGAAAACCATCTCTCCGA
ACGATCATTTTGAGTTCAATGCAAAATTCTCCGACAAAATGAGGAGAATAAAGATCCCTCTTCCGC
CTGTGGATGAGAAAAAGAAAGTCATTGAAGATGTTGACAAGGATCGAAGGTATGCTATTGACGCCT
CAATCGTGCGTATCATGAAGAGTCGGAAAGTTCTTGGTCATCAGCAACTAGTGATGGAGTGCGTCG
AGCAATTGGGCCGTATGTTCAAGCCCGATTTCAAGGCGATAAAGAAGAGAATTGAAGACCTGATCA
CTCGGGATTATCTAGAGAGAGACAAAGACAACCCCCACTTGTTTAGGTACTTGGCTTGA

Fig. 36

ATGACAATGGGCGAGCGGAAGACTATTGACTTGGAACAGGGATGGGAGTTTATGCAGAAGGGTATC
ACAAAGTTGAAGAACATTCTTGAGGGCTTGCCTGAGCCCCAGTTCAGCTCCGAGGACTACATGATG
CTTTACACTACCAT[G]TATAACATGTGCACCCAAAAGCCGCCGCATGATTACTCCCAGCAGCTGT
ATGATAAATATCGTGAATCTTTTGAAGAGTACATCACTTCTATGGTCTTACCATCCTTGAGGGAGA
AGCATGACGAGTTCATGTTGAGAGAACTAGTCAAAAGGTGGACAAACCATAAAGTCATGGTGAGGT
GGCTTTCTCGCTTCTTCCACTATCTTGATCGGTACTTCATCGCTCGAAGGTCACTTCCACCTCTAA
ATGAAGTTGGCCTCACATGCTTCCGCGAATTGGTGTACAAAGAGCTAAACAGTAAAGTGAGGGATG
CAGTAATCTCATTGATTGATCAAGAACGTGAAGGAGAACAGATTGACAGAGCTCTACTGAAGAATG
TATTAGATATATTTGTGGAAATTGGTATGGGGCAAATGGATTACTATGAAAATGACTTTGAAGCTG
CCATGCTTAAAGATACTGCTGCTTATTACTCTAGGAAGGCTTCCAATTGGATCCTAGAAGATTCTT
GTCCCGATTATATGCTAAAAGCAGAGGAGTGCTTGAAGCGAGAAAAGGATAGGGTTTCCCACTATT
TGCACTCTAGTAGCGAGCCAAAGTTGTTGGAGAAAGTTCAACACGAACTGTTATCTGTGTATGCTA
CTCAACTGCTGGAAAAAGAGCATTCAGGATGCCATGCATTGCTTAGAGATGACAAGGTGGAAGATT
TGTCAAGGATGTTCCGTCTCTTCTCCAAAATACCGAAGGGATTGGACCCAGTTTCCAACATATTTA
AGCAGCATGTAACTGCTGAAGGAACAGCACTGGTCAAACAGGCAGAAGATGCTGCAAGTAACAAGA
AGGCCGAGAAAAAGGACATAGTTGGTCTGCAGGAACAGGTTTTTGTAAGAAAAGTGATTGAGCTTC
ACGACAAGTACTTGGCTTATGTGAATGATTGTTTCCAAAACCACACACTTTTCCATAAGGCTCTCA
AGGAAGCTTTTGAAGTCTTTTGCAATAAGGGTGTTGCTGGAAGTTCTAGTGCAGAATTGCTTGCTA
CCTTCTGCGATAACATCCTTAAGAAAGGTGGGAGTGAGAAGTTGAGTGATGAAGCAATCGAAGAGA
CACTTGAGAAGGTTGTGAAGTTGTTGGCATACATCTGCGACAAAGATCTGTTTGCTGAATTCTATA
GAAAAAAaCTTGCCCGAAGGCTTCTCTTTGATAAGAGCGCCAACGATGACCACGAGAGAAGTATAT
TGACCAAATTGAAGCAACAATGTGGTGGTCAGTTCACTTCTAAGATGGAGGGAATGGTTACTGATT
TGACTTTGGCAAGGGAGAACCAAACTAGTTTCGAAGAGTATCTGAGCAATAATCCACAAGCTAGTC
CTGGAATCGACCTAACTGTTACTGTTTTGACTACTGGATTTTGGCCAAGCTACAAGTCTTTTGACC
TCAACCTGCCGGCGGAGATGGTAAAGTGTGTTGAAGTTTTCAGAGAGTTTTATCAAACAAAAACCA
AGCATAGAAAACTTACATGGATTTACTCATTGGGTACTTGTAACATCAGTGGAAAATTTGAACCGA
AGACGATGGAGCTGATTGTGACAACATATCAGGCTTCTGCCCTGTTGCTATTCAATTCTTCGGACA
GACTAAGTTACTCCGAAATCATGACACAATTAAATTTGAGTGATGATGATGTTGTTAGACTGCTCC
ACTCATTGTCGTGTGCCAAGTATAAAATTCTTAATAAGGAGCCAAATACGAAAACCATCTCACCGA
ACGATCATTTTGAGTTCAATGCAAAATTCTCCGACAAAATGAGGAGAATAAAGATCCCTCTTCCGC
CTGTGGATGAGAAAAaGAAAGTCATTGAAGATGTTGACAAGGATCGAAGGTATGCTATTGACGCCT
CAATCGTGCGTATCATGAAGAGTCGAAAAGTTCTTGGTCATCAGCAACTAGTGATGGAGTGCGTCG
AGCAATTGGGTCGTATGTTCAAGCCCGATTTCAAGGCGATAAAGAAGAGAATTGAAGACCTGATCA
CTCGGGACTATCTAGAGAGAGACAAAGACAACCCCCACTTGTTTAGGTACTTGGCTTGA

Fig. 37

ATGACAATGGGTGAGCGGAAGACTATTGACTTGGAGCAAGGATGGGAGTTTATGCAGAAGGGAATC
ACAAAATTGAAGAACATTCTGGAAGGATTGCCTGAGCCACAGTTCAGCTCCGAGGACTACATGATG
CTTTACACTACAAT[G]TATAACATGTGTACCCAGAAGCCACCGCATGATTACTCCCAGCAGCTGT
ATGATAAATACCGCGAATCGTTTGAGGAGTACATCAGTTCTATGGTTTTACCATCCTTGAGGGAGA
AGCATGACGAATTTATGTTGAGAGAACTGGTCAAAAGGTGGACCAACCATAAAGTCATGGTGAGGT
GGCTTTCTCGCTTCTTCCACTATCTTGATCGATACTTCATTGCTCGAAGGTCACTTCCACCTCTCA
ATGAAGTTGGCCTCACTTGCTTCCGTGAATTGGTGTACAAAGAGCTAAACAGTAAAGTGAGGGATG
CAGTAATTTCATTGATCGATCAAGAACGTGAAGGAGAGCAGATTGACAGAGCTCTGTTGAAGAACG
TGTTGGATATATTTGTGGAGATTGGGATGGGGCAAATGGATTATTATGAAAATGACTTTGAAGCTG
CCATGCTTAAAGATACTGCTGCTTACTACTCTAGGAAGGCATCAAATTGGATCTTAGAAGATTCTT
GTCCTGATTATATGCTAAAAGCAGAGGAGTGCTTGAGACGAGAAAAGGACCGAGTTTCTCACTATC
TGCACTCTAGTAGCGAGCCAAAGTTATTGGAGAAAGTTCAACATGAACTATTGTCTGTTTATGCTA
CTCAACTGCTGGAGAAAGAGCATTCAGGATGCCATGCATTGCTTAGAGATGACAAGGTGGAAGATT
TGTCAAGGATGTTCCGTCTCTTCTCCAAAATACCCAAGGGATTGGACCCAGTTTCCAACATATTTA
AGCAGCATGTCACTGCTGAAGGAACAGCATTAGTCAAACAGGCAGAAGACGCTGCAAGTAACAAGA
AGGCCGAGAAAAAGGACATCGTTGGTCTGCAAGAACAGGTTTTTGTTAGAAAAGTGATTGAGCTTC
ACGACAAGTACTTGGCATATGTGAATGATTGTTTCCAAAACCACACACTTTTTCACAAGGCTCTCA
AGGAAGCTTTTGAAGTCTTTTGCAATAAGGGTGTTGCTGGAAGTTCTAGTGCAGAATTACTTGCTA
CCTTTTGTGATAACATCCTTAAGAAAGGTGGGAGTGAGAAGTTGAGTGATGAAGCAATTGAGGAAA
CACTCGAGAAGGTCGTGAAATTGCTGGCGTATATCTGCGACAAAGATCTGTTTGCTGAATTCTATA
GAAAAAAACTCGCCCGAAGGCTTCTCTTCGACAAGAGTGCGAATGATGACCACGAGAGAAGTATAC
TGACGAAATTGAAGCAACAATGTGGTGGTCAGTTTACCTCTAAGATGGAGGGAATGGTCACGGATT
TGACACTGGCAAGGGAGAACCAAACTAGTTTTGAGGAATATCTGAGCAATAATCCACAAGCTAGTC
CTGGAATCGACTTGACCGTTACCGTTTTGACCACTGGTTTTTGGCCAAGCTACAAGTCTTTTGACC
TCAACCTGCCGGCGGAGATGGTAAAGTGTGTTGAAGTTTTCAGGGAATTTTATCAAACAAAAACCA
AGCACAGAAAACTTACGTGGATTTACTCGTTGGGTACCTGTAACATCAGCGGAAAATTCGAACCGA
AAACGATGGAGCTGATCGTGACAACCTATCAGGCTTCTGCCCTGCTGCTTTTCAATTCCTCGGATA
AACTAAGTTACTCCGAGATCATGACTCAATTAAACTTGAGTGACGATGATGTTGTTAGACTGCTCC
ACTCGTTGTCGTGTGCGAAGTATAAAATTCTTAACAAGGAGCCAAATACGAAAACCATCTCTCCGA
ACGATCATTTTGAGTTCAACGCAAAATTCTCCGACAAAATGAGGAGAATAAAGATCCCTCTTCCGC
CTGTGGATGAGAAAAAGAAAGTAATAGAAGATGTTGACAAGGATCGAAGATATGCTATCGATGCCT
CGATCGTGCGTATCATGAAGAGTAGGAAAGTTCTGGGTCACCAGCAGTTAGTGATGGAGTGCGTCG
AGCAACTGGGTCGTATGTTCAAGCCTGATTTCAAGGCGATAAAGAAGAGAATCGAAGATCTGATCA
CTCGTGACTATTTAGAGAGAGACAAAGACAACCCCCACTTGTTTAGGTACTTGGCTTGA

Fig. 38

ATGACAATGGGCGAGCGGAAGACTATTGACTTGGAACAAGGATGGGAGTTTATGCAGAAGGGAATC
ACAAAGTTGAAGAACATTCTTGAGGGCTTGCCTGAGCCTCAGTTCAGCTCCGAGGACTACATGATG
CTTTATACCACCAT[G]TACAACATGTGCACACAAAAGCCGCCACATGATTACTCCCAGCAGCTAT
ACGATAAATACCGTGAATCTTTTGAGGAGTATATCACTTCTATGGTCTTACCATCCTTGAGGGAGA
AGCATGACGAGTTCATGTTGAGAGAACTGGTCAAAAGGTGGACGAACCATAAAGTCATGGTGAGGT
GGCTTTCTCGCTTCTTCCACTATCTTGACCGATACTTCATTGCTCGAAGATCACTTCCACCTCTCA
ACGAAGTTGGCCTCACATGCTTCCGTGAATTGGTGTACAAAGAGCTAAACAGTAAAGTGAGGGATG
CAGTAATTTCATTGATTGATCAAGAACGTGAAGGAGAGCAGATTGACAGAGCTCTACTGAAGAATG
TATTAGATATATTTGTGGAAATTGGGATGGGGCAAATGGATTACTATGAAAATGACTTTGAAGCTG
CCATGCTTAAAGATACTGCTGCTTATTACTCTAGGAAGGCTTCCAATTGGATCCTAGAAGATTCTT
GTCCCGATTATATGCTAAAAGCAGAGGAGTGCTTGAAACGAGAAAAGGATAGAGTTTCTCACTATT
TGCACTCTAGTAGCGAGCCAAAGTTATTAGAGAAAGTTCAACATGAACTGTTATCTGTGTATGCTA
CTCAACTGCTGGAAAAAGAGCATTCAGGATGCCATGCATTGCTTAGAGATGACAAGGTGGAAGATT
TGTCAAGGATGTTCCGCCTCTTCTCCAAAATACCCAAGGGATTGGACCCAGTTTCCAACATATTTA
AGCAGCATGTCACTGCTGAAGGAACAGCATTGGTCAAACAGGCAGAAGATGCTGCAAGTAACAAGA
AGGCCGAGAAAAAGGACATAGTTGGTCTGCAGGAACAGGTTTTTGTAAGAAAAGTGATTGAGCTTC
ACGACAAGTACTTGGCTTACGTGAATGATTGTTTCCAAAACCACACACTTTTTCACAAGGCTCTCA
AGGAAGCTTTTGAAGTCTTTTGCAATAAGGGTGTTGCTGGAAGTTCTAGTGCAGAATTACTTGCTA
CCTTTTGTGATAACATCCTTAAGAAAGGTGGGAGCGAGAAGTTGAGTGATGAAGCAATTGAGGAGA
CACTTGAGAAGGTCGTGAAGTTGCTGGCATACATCTGCGACAAAGATCTGTTTGCTGAATTCTATA
GAAAAAAACTTGCCCGAAGGCTTCTCTTTGACAAGAGTGCCAACGATGACCATGAGAGAAGTATAT
TGACCAAATTGAAGCAACAATGTGGTGGCCAGTTCACCTCTAAGATGGAGGGGATGGTCACTGATT
TGACTTTGGCAAGGGAGAACCAAACTAGTTTCGAGGAGTATCTGAGCAATAATCCACAAGCTAGTC
CTGGAATCGACTTGACTGTCACTGTTTTGACTACTGGCTTTTGGCCAAGCTACAAGTCTTTTGACC
TCAACCTGCCGGCAGAGATGGTAAAGTGTGTTGAAGTTTTCAGAGAGTTCTATCAAACAAAAACAA
AGCATAGAAAACTTACATGGATTTACTCATTGGGTACCTGTAACATCAGCGGAAAATTTGAACCGA
AAACGATGGAGCTGATTGTAACAACTTATCAGGCTTCTGCCCTGCTGCTATTCAATTCCTCAGATA
GATTAAGTTATTCCGAGATCATGACACAATTAAATTTGAGTGACGATGATGTTGTTAGACTGCTCC
ACTCATTGTCATGTGCCAAGTATAAAATTCTTAATAAGGAGCCGAACACGAAAACCATCTCTCCGA
ATGATCATTTTGAGTTCAATGCAAAATTCTCCGACAAAATGAGGAGAATAAAGATCCCTCTTCCGC
CTGTGGATGAGAAAAAGAAAGTCATTGAAGATGTTGACAAGGATCGAAGGTATGCTATTGATGCCT
CAATCGTGCGTATCATGAAGAGTCGGAAAGTTCTGGGTCATCAGCAGCTAGTGATGGAGTGCGTCG
AGCAATTGGGTCGTATGTTCAAGCCCGACTTCAAAGCGATAAAGAAGAGAATCGAAGATCTGATCA
CTCGGGACTATTTAGAGAGAGACAAAGACAACCCCCACTTGTTTAGGTACTTGGCTTGA

Fig. 39

ATGAACCAACGCAGCACAATCGATCTGGAACATGGATGGGATTTCATGCAAAAGGGCATCACAAAG
CTGAAGAACATTCTAGAAGGGCTGCCTGAGCCTCAGTTCAGCTCAGAGGACTATATGATGCTGTAT
ACGACAAT[G]TACAACATGTGTACTCAGAAGCCCCCACATGATTATTCTCAACAGCTGTATGACA
AATATCGTGAAGCTTTTGAAGAATATATCACAACGACGGTATTACCTTCTTTGAGAGAAAAACATG
ACGAGTTCATGTTGCGAGAGTTGGTAAAAAGGTGGTCAAACCATAAGGTCATGGTTAGATGGTTAT
CGCGATTCTTCCATTATCTTGACCGTTATTTCATTGCTCGGAGATCACTGCCAGGGCTTAATGAAG
TTGGACTAACTTGCTTCCGCGATCTGGTCTACCAAGAGTTGAATGGAAAAGTCAGGGATGCTGTTA
TATCTCTGATTGATCAAGAGCGTGAGGGAGAGCAAATTGACAGAGCTCTACTGAAGAATGTGCTAG
ATATATTTGTTGAAATTGGAATGGGGTCAATGGATTATTATGAGAATGATTTTGAAGCTGCAATGC
TCAAGGACACTGCGGCTTATTATTCTCGCAAAGCTTCTAACTGGATCCTCGAAGATTCATGTCCAG
ATTATATGCTGAAAGCTGAGGAGTGCTTGAAACGGGAGAAGGATAGGGTCTCCCATTATCTCCATT
CTAGCAGTGAGACAAAGTTGCTTGAGAAAGTGCAACATGAGTTGTTATCTGTGTATGCCAATCAAC
TTCTTGAGAAGGAGCACTCTGGATGCCATGCATTACTTAGAGATGATAAGGTCGATGATTTATCAA
GGATGTATAGACTCTTTTCTAAGATTCCTCGAGGCTTAGAGCCTGTGGCTAATATATTTAAGCAGC
ATGTTACTGCTGAAGGTACAGCTTTGGTGAAACAGGCTGAAGATGCTGCTAGCAACAAAAAGGCAG
AGAAGAGAGATGTGGTTGGTTTGCAGGAACAGGTTTTTGTTCGGAAAGTGATTGAGCTTCATGATA
AATATTTGGCGTATGTGAATAACTGTTTCCAAAACCACACACTTTTTCACAAGGCACTTAAAGAAG
CTTTCGAACTTTTCTGCAACAAGGGTGTTGCTGGTAGCTCAAATGCTGAACTTCTTGCCACATTCT
GCGACAACATTCTCAAAAAAGGCGGGAGTGAAAAATTGAGTGATGAAGCCATTGAAGAGACGCTGG
AGAAGGTGGTAAAGCTGCTGGCTTATATTAGTGATAAGGACTTGTTTGCAGAATTCTATAGGAAAA
AGCTCGCCCGGCGGTTGTTATTTGATAAGAGTGCCAATGATGAACATGAGAGAAGTATCCTAACAA
AGTTGAAGCAGCAGTGTGGAGGTCAGTTCACATCAAAGATGGAGGGAATGGTCACAGATTTGACAT
TGGCAAGGGAAAATCAAGCCAGCTTTGAGGAGTATTTGAGCAATAATCCAACAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGTGTTGAAGTATTCAAGGAGTTTTATCAAACAAAAACGAAGCACA
GGAAACTTACATGGATATACTCTTTGGGAACTTGCAACATAAATGGAAAATTTGAGGCAAAGACTA
TTGAGCTCGTTGTCACTACTTATCAGGCTTCTGCTCTGCTTCTCTTTAATGCATCAGATAGATTGA
GTTATCAGGAAATCATGACGCAATTAAACCTATCAGATGATGATGTTGTTCGGCTTCTTCATTCCC
TTTCATGTGCGAAATACAAGATTCTCAACAAGGAGCCAAGCACCAAAACAATTTCTCCGACTGATG
TCTTTGAGTTCAACTCAAAGTTCACTGACAAAATGAGGAGGATCAAGATACCTCTCCCACCAGTTG
ATGAAAAGAAAAAGGTAATTGAAGACGTTGACAAGGATAGGCGGTATGCTATAGATGCCTCAATTG
TGCGTATTATGAAGAGTCGTAAAGTATTGGGCTACCAGCAACTGGTCATGGAGTGCGTTGAGCAGT
TGGGACGCATGTTCAAGCCTGATGTCAAAGCTATCAAGAAGAGAATTGAAGATCTGATAACTAGAG
ATTACCTAGAGAGGGACAAAGATAACCCAAACTTGTTCAAGTACTTGGCATGA

Fig. 40

ATGAACCAACGAAGCACAATCGATCTGGAACATGGATGGGACTTCATGCAAAGGGGCATTACAAAG
CTGAAGAACATTCTAGAAGGGCTGCCTGAGCCTCAATTCAGCTCAGAGGACTATATGATGCTATAT
ACGACAAT[G]TACAACATGTGTACTCAAAAGCCCCCACATGATTATTCTCAACAGCTGTATGACA
AATATCGTGAAGCTTTTGAAGAATATATCACAACAACGGTATTGCCTTCTTTGAGAGAAAAACATG
ACGAGTTTATGTTGCGAGAGTTGGTAAAAAGGTGGTCAAATCATAAAGTCATGGTCAGATGGTTGT
CAAGATTCTTCCATTACCTTGACCGGTATTTCATTGCCCGGAGATCTCTGCCGGGGCTTAATGAAG
TTGGACTAACTTGCTTCCGCGATCAGGTCTACCAAGAGTTGAATGGAAAAGTCAGGGATGCTGTTA
TATCTCTGATTGATCAAGAGCGTGAGGGAGAGCAAATTGACAGAGCTCTACTTAAGAATGTGCTTG
ATATATTTGTCGAAATTGGAATGGGGTTAATGGATTATTATGAGAATGATTTTGAAGCTGCAATGC
TCAAGGACACAGCGGCTTATTATTCTCGCAAAGCTTCTAATTGGATCCTCGAAGATTCATGTCCGG
ATTATATGCTGAAAGCCGAGGAGTGCTTGAAACGGGAGAAGGATAGGGTCTCTCATTATCTCCATT
CAAGCAGCGAGACGAAGTTGCTTGAGAAAGTGCAACATGAGTTGTTGTCTGTGTATGCCACTCAAC
TTCTTGAGAAGGAGCACTCTGGATGCCATGCGTTACTGAGAGATGATAAGGTTGAAGATTTATCAA
GGATGTATAGGCTCTTTTCTAAGATTTCTCGAGGCTTAGACCCTGTGGCCAATATTTTTAAGCAGC
ATGTTACTGCTGAAGGTACAGCTTTGGTAAAACAGGCTGAAGATGCTGCTAGCAATAAAAAGGCAG
AGAAGAGAGATGTGGTTGGTTTGCAGGAACAGGTTTTTGTTCGGAAAGTGATTGAACTTCATGATA
AATATTTGGCTTATGTGAATAACTGTTTCCAAAACCACACACTTTTTCACAAGGCGCTTAAAGAAG
CTTTTGAGCTTTTCTGCAACAAGGGTGTTGCTGGTAGCTCAAGCGCTGAACTTCTTGCCACCTTCT
GTGACAACATTCTCAAAAAAGGCGGGAGTGAGAAATTGAGTGATGAAGCTATTGAAGAAACGTTGG
AAAAGGTGGTAAAGCTACTAGCTTATATTAGTGATAAGGACTTGTTTGCAGAATTCTATAGGAAAA
AGCTAGCCCGGCGGTTGTTATTTGATAAGAGTGCCAATGATGAACATGAAAGAAGTATCCTAACAA
AGTTGAAGCAGCAGTGTGGGGGGCAGTTCACATCAAAGATGGAGGGAATGGTCACAGATTTGACAT
TGGCAAGGGAAAATCAAGCCAGCTTCGAGGAGTATTTGAGCAATAATCCAATAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGCGTTGAAGTATTTAAGGAGTTCTATCAAACAAAAACAAAGCACA
GGAAACTTACGTGGATATACTCTTTGGGAACTTGCAACATAAATGGAAAATTTGAGCCAAAAACTA
TTGAGCTCGTTGTCACTACTTATCAGGCTTCTGCTCTGCTGCTCTTTAATGCATCAGATAGATTGA
GTTATCAGGAAATCATGACGCAATTAAACCTATCAGATGATGATGTTGTTCGGCTTCTTCATTCCC
TTTCATGTGCGAAGTACAAGATACTCAACAAGGAGCCAAGCACCAAAACAATTTCTCCGACTGATG
TCTTTGAGTTCAACTCAAAGTTCACTGACAAAATGAGGAGGATCAAGATACCTCTCCCTCCTGTTG
ATGAGAAGAAAAAGGTAATTGAAGACGTTGACAAGGATAGGCGGTATGCTATAGATGCTTCAATTG
TGCGTATTATGAAGAGCCGTAAAGTATTGGGCTACCAGCAACTAGTCATGGAGTGCGTTGAGCAGT
TGGGGCGCATGTTCAAGCCTGATGTCAAAGCTATCAAGAAGAGAATCGAAGATTTGATAACTAGAG
ATTACCTAGAGAGGGACAAAGATAATCCAAACCTGTTCAAGTACTTGGCATGA

Fig. 41

ATGAACCAGCGTTCCACAATCAATCTAGAACATGGATGGGACTTCATGCAAAGGGGCATTACAAAG
CTGAAGAACATTCTAGAAGGGCTGCCCGAGCCTCAGTTCAGCTCAGAGGACTATATGATGCTGTAT
ACGACAAT[G]TACAACATGTGTACTCAGAAGCCCCCACATGATTATTCTCAACAGCTGTATGACA
AATATCGTGAAGCTTTTGAAGAATATATCACAACAACGGTATTGCCTTCTTTGAGAGAAAAACATG
ACGAGTTCATGTTGCGAGAGCTGGTAAAAAGGTGGTCAAACCATAAGGTCATGGTCAGATGGTTAT
CGCGATTCTTCCATTATCTTGATCGCTATTTCATTGCCCGGAGATCTCTACCGGGGCTTAATGAAG
TTGGACTAACTTGCTTCCGAGATCTGGTCTACCAAGAGTTGAATGGAAAAGTCAGGGATGCTGTTA
TATCTCTGATTGATCAAGAGCGTGAGGGAGAGCAAATTGACAGAGCTCTACTGAAGAATGTGCTAG
ATATATTTGTTGAAATTGGAATGGGGTCGATGGATTATTATGAGAATGATTTTGAAGCTGCAATGC
TCAAGGACACCGCAGCTTATTATTCTCGCAAAGCTTCTAACTGGATACTTGAAGATTCATGTCCAG
ATTATATGCTGAAAGCCGAGGAGTGCTTGAAACGGGAGAAAGATAGGGTCTCTCACTATCTTCATT
TAAGCAGTGAGACAAAGTTGCTTGAGAAAGTGCAACATGAGTTGTTGTCTGTGTATGCCACTCAAC
TTCTTGAGAAGGAGCACTCTGGGTGCCATGCGTTACTAAGAGATGATAAGGTTGAAGATTTATCAA
GGATGTATAGGCTCTTTTCTAAGATTCCTCGAGGCTTAGACCCTGTGGCTAATATATTTAAGCAGC
ATGTTACTGCTGAAGGTACAGCTTTGGTCAAACAGGCTGAAGATGCTGCTAGCAACAAAAAGGCAG
AGAAAAGAGATGTGGTTGGTTTGCAGGAACAGATTTTTGTTCGGAAAGTGATTGAGCTTCATGATA
AGTATATGGCATATGTGAATAACTGTTTCCAAAACCACACACTTTTTCACAAGGCGCTTAAAGAAG
CTTTCGAACTTTTCTGCAACAAGGGTGTTGCTGGTAGCTCAAGTGCTGAACTTCTTGCCACATTCT
GCGACAATATTCTCAAGAAAGGCGGGAGTGAGAAATTGAGTGATGAAGCCATTGAAGAGACGCTGG
AGAAGGTTGTAAAGCTGCTAGCATATATTAGTGACAAGGACTTGTTTGCAGAATTCTATAGGAAAA
AGCTAGCCCGGCGGTTGTTATTTGATAAGAGTGCCAATGATGAACACGAGAGAAGTATCCTTACAA
AGTTGAAGCAGCAGTGTGGGGGCCAGTTCACATCAAAGATGGAGGGAATGGTGACAGATTTGACAT
TGGCAAGGGAAAATCAAGCCAGCTTTGAGGAGTATTTGAGCAACAATCCAGCAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGCGTTGAAGTATTCAAGGAGTTTTATCAAACAAAAACGAAGCACA
GGAAACTTACGTGGATATACTCTTTGGGAACTTGCAATATAAATGGAAAATTTGAGCCAAAGACTA
TTGAGCTCGTTGTCACTACTTATCAGGCTTCTGCTCTGCTGCTCTTTAATGCATCGGATAGATTGA
GTTATCAGGAAATCATGACGCAACTAAACCTATCAGATGATGATGTTGTTCGGCTTCTTCATTCCC
TTTCATGTGCGAAGTACAAGATTCTCAACAAGGAGCCAAGCACCAAAACAATTTCTCCGACTGATG
TCTTTGAGTTCAATTTTAAGTTCACTGACAAAATGAGGAGGATCAAGATACCTCTCCCTCCTGTTG
ATGAGAAGAAAAAGGTAATTGAAGATGTTGACAAAGATAGGCGGTACGCTATAGATGCTTCAATTG
TGCGTATTATGAAGAGTCGTAAAGTATTGGGCTACCAGCAACTGGTCATGGAGTGTGTTGAGCAGT
TGGGACGTATGTTCAAGCCTGATGTCAAAGCTATCAAGAAGAGAATTGAAGATTTGATAACTAGAG
ATTACCTAGAGAGGGACAAAGATAATCCGAACTTGTTCAAGTACTTGGCATGA

Fig. 42

ATGGAGCGCAAGACGATTGACTTGGACCAAGGATGGGACTATATGCAGACTGGTATCACTAAGCTG
AAACGGATTCTTGAGGGGCTGCCTGAGCCGCAGTTTGACTCTGAGCAATACATGATGCTCTATACG
ACTAT[G]TACAACATGTGCACTCAGAAACCTCCTCATGATTACTCACAGCAGCTTTATGACAAGT
ATCGTGAAGCATTTGAGGAGTATATTCACTCAACTGTTTTGCCTGCTCTAAGGGAGAAGCATGATG
AGTACATGCTGAGGGAGCTGGTTAAGAGATGGTCTAACCATAAAGTTATGGTTCGATGGCTATCCC
GCTTCTTCTACTATCTTGACCGTTACTTCATTGCTCGGAGGTCACTTCCACCCCTGAATGAAGTTG
GCCTGACTTGCTTCCGTGACCTGGTTTATAACGAGTTGCATTCCAAGGTCAAAGATGCTGTAATAG
CACTTGTTGATAAAGAACGGGAGGGTGAGCAGATTGACAGGGCTCTATTGAAAAACGTATTAGACA
TTTATGTAGAGATTGGAATGGGACAGATGGAAAGATACGAGGAGGATTTTGAAAGCTTCATGCTTT
TAGATTCAGCATCTTACTATTCTCGCAAGGCGTCAAGCTGGATCCAAGAAGATTCTTGCCCTGATT
ACATGCTGAAGTCTGAAGAATGTCTTAAGAAGGAGAGGGAGAGAGTGGCTCACTACCTTCACTCAA
GCAGCGAGCCAAAGCTGGTTGAGAAAGTACAACATGAGCTGTTGGTAGTGTATGCAAATCAGCTTC
TAGAAAAAGAGCATTCAGGGTGCCGTGCATTGCTGAGAGATGACAAGGTTGATGACCTCTCCAGGA
TGTACAGGCTTTATCATAAAATTGTGAAAGGTTTGGAACCTGTTGCAAACATATTTAAGCAGCATG
TCACAGCAGAGGGTAACGCACTTGTCCAACAGGCCGAAGACACGGCCACTAATCATGCTGCAAATA
CTGCTAGCGTGCAGGAACAGGTTCTTATCAGAAAAGTGATTGAACTACATGATAAATACATGGTCT
ATGTTGTTGAGTGTTTCCAGAACCACACCCTCTTCCACAAGGCATTGAAAGAGGCATTTGAGATAT
TCTGTAACAAAACAGTCGCTGGAAGTTCTAGTGCTGAATTGCTTGCAACATTTTGCGACAATATTC
TCAAGAAGGGGGGAAGTGAAAAGCTGAGCGATGAAGCTATTGAAGATACCCTTGAGAAGGTGGTCA
AATTGCTTGCTTATATAAGTGACAAGGATCTTTTCGCCGAGTTCTACAGGAAGAAGCTGGCCCGTA
GGCTCTTATTTGATCGCAGTGCTAATGATGATCATGAGAGAAGTATCCTGACAAAGCTCAAGCAAC
AATGTGGTGGGCAGTTTACTTCGAAGATGGAGGGCATGGTGACTGATTTGACATTGGCAAGGGAAA
ACCAAAACAGCTTCGAGGAGTATCTTGGCAATAACCCCGCTGCAAACCCAGGGATTGATTTGACCG
TAACTGTTCTTACCACTGGTTTTTGGCCAAGTTACAAATCATTTGACATAAATCTACCCGCTGAAA
TGGTCAAGTGTGTTGAAGTTTTCAAAGGGTTTTATGAAACAAAGACAAAACATAGGAAACTTACCT
GGATCTACTCACTAGGAACTTGCCACCTCAATGGGAAGTTTGATGTCAAGCCCATTGAGTTAGTTG
TGTCTACATACCAGGCTGCTGTGCTTCTGCTGTTCAACACAACAGACAAATTGAGCTACACTGATA
TCCTAACTCAGCTGAACCTGAGCCACGAAGATCTAGTGAGGTTGCTTCATTCCTTGTCATGTGCTA
GATACAAGATTCTTCTCAAGGAGCCAAGCACAAAGACTGTTTCCCAGTCTGATTCTTTTGAATTCA
ACTCCAAATTCACCGACAGAATGCGGAGAATAAAGATCCCTCTCCCACCTGTTGATGAGAGGAAGA
AAGTTGTGGAAGACGTGGACAAAGACAGACGCTATGCGATTGATGCTGCCATTGTGAGGATCATGA
AGAGCAGGAAAGTATTGGGACATCAACAACTTGTTTCTGAGTGCGTTGAGCAACTTAGCCGAATGT
TCAAGCCTGATATCAAGGCAATCAAGAAGCGCATGGAGGATTTGATAACGAGAGATTATCTGGAGA
GGGACAAGGAGAACGCTAACATGTTTAGGTACTTGGCTTAG

Fig. 43

ATGATGATTGAGCGGAAAACTATAGACCTGGAGCAGGGATGGGACTTTATGCAAAAGGGAATCACA
AAGCTAAAGAATATTTTAGAAGGCTTTCCGGAGCCGCAATTCAGCTCGGAGGATTATATGATGCTT
TATACAACTAT [G] TATAACATGTGTACACAGAAACCTCCACATGATTACTCTCAGCAGCTGTATG
AAAAGTATCGTGAAGCTATTGAGGAGTACATTACTTCTACAGTATTGCCTTCATTGAGAGAGAAGC
ATGATGAATTCATGCTTAGAGAACTTGTGAAGAGATGGTCTAATCATAAGGTCATGGTCAGGTGGC
TTTCTCGATTCTTTCACTATCTTGATCGCTATTTTATTGCTCGGAGGTCACTTCCACCACTTCATG
AAGTTGGACTCACTTGCTTTCGGGACCTGGTTTACCAGGAGATAAATGGGAAAGTAAGGGATGCTG
TAATATCATTGATTAATCAAGAGCGCGAGGGAGAGCAAATTGACCGAGCTTTGTTGAAGAATGTTC
TAGATATATTTGTTGAAGTTGGAATGAGTCAAATGGATTATTATGAGAATGACTTTGAAGCAGACA
TGCTCAAAGATACAGCAGCATACTATTCTCGAAAGGCTTCCAACTGGATCTTAGAAGATTCTTGTC
CAGATTATATGCTCAAAGCGGAAGAGTGTTTGAGACGGGAAAAGGACAGGGTCTCTAACTACCTTC
ATTCTAGTAGTGAACCCAAGTTGCTTGAGAAAGTTCAACATGAGTTACTATCACACTATGCAACTC
AGCTGCTTGAGAAAGAACACTCTGGGTGTCATGCATTGCTTAGGGATGACAAGGTGGCAGATTTAT
CAAGGATGTATAGGCTCTTCTCTAAAATACCTCGAGGCCTAGATCCCGTGTCTAATATTTTCAAGC
AGCATGTTACTGCTGAAGGTACAGCTTTGGTCAAACAAGCAGAAGATGCAGCTAGCAACAAGAAGG
CAGAGAAGAGAGATGTAGTAGGTTTACAAGAACAGGTTTTTGTGAGGAAAATAATTGAATTGCATG
ACAAATACCTTACATACGTAAATGACTGTTTTACAAACCACACTCTCTTCCATAAGGCGCTTAAGG
AGGCTTTTGAAATCTTCTGCAATAAGGGTGTCTCTGGAAGCTCTAGTGCAGAATTACTTGCCACAT
TCTGTGATAATATTCTCAAGAAAGGTGGAAGCGAGAAGTTAAGTGATGAAGCCATTGAGGAAACAC
TTGAGAAGGTTGTAAGGTTGCTTGCTTATATAAGTGACAAAGACTTATTTGCTGAATTTTATAGGA
AAAAGCTTGCACGGCGTCTCTTATTCGACAAGAGTGCCAATGATGAGCATGAGAGAAGTATATTGA
CTAAGCTGAAGCAACAATGTGGGGGTCAATTTACATCAAAGATGGAAGGAATGGTCACTGACTTGA
CGTTGGCAAAGGAAAATCAGTCCAACTTCGAGGAGTACCTCAATAATAATTCAAACGTAAATCCTG
GAATTGACTTGACAGTTACTGTTCTAACCACTGGGTTTTGGCCAAGTTACAAATCTTTCGATCTCA
ACCTCCCAGCAGAGATGGTCAAATGTGTTGAAGTTTTTAGAGAATTCTACCAAACAAAAACAAAGC
ACAGAAAACTGACATGGATATACTCTTTGGGTACTTGTAACATCATTGGAAAATTTGATCCAAAAA
CCATGGAGCTTATTGTGACAACATACCAGGCCTCTGCTCTGCTGCTATTTAACTCTTCTGATAGAC
TTAGTTATAATGAAATAATGACTCAGTTGAACTTGTCGGATGATGATGTTGTCAGACTACTTCATT
CTCTTTCGTGTGCAAAGTACAAGATTCTATCTAAAGAGCCGAACACCAAAACTATATCTCCAACTG
ATTGCTTTCAGTTCAATTCCAAATTTACTGATAAAATGAGGAGGATTAAGATTCCACTTCCCCCAG
TGGATGAGAAGAAAAAGGTAATTGAAGATGTTGATAAAGACAGGCGATATGCTATAGATGCTTCAA
TTGTCCGTATCATGAAGAGCCGCAAAGTTTTGGGTTATCAGCAGCTAGTAATGGAGTGCGTTGAAC
AATTGGGTCGCATGTTTAAGCCTGATGTCAAAGCAATCAAGAAGAGAATCGAAGATTTAATAACTC
GGGATTATCTGGAAAGAGACAAGGACAATGCCAACTTGTTCAGGTATCTGGCATGA

Fig. 44

ATGAACGAGCGGAAGACTATCGATTTGGATAATGGATGGGAATTTATGCAGAAAGGGATCACTAAG
TTGAAGAAGATTCTCGAAGGTCAACCTGAGCCTCAGTTTAGCTCCGAGGACTATATGATGCTTTAC
ACAACTAT[G]TATAATATGTGTACGCAGAAGCCTCCACATGATTATTCTCAACAGCTGTATGACA
AGTACCGTGAGGCCTTTGAGGAGTACATAACTTCAACTGTCCTGCCTTCTTTACGAGAGAAGCATG
ATGAGTTTATGTTGAGAGAGCTCGTGAATAGATGGACAAACCATAAAGTCATGGTCAGGTGGCTTT
CTCGATTCTTTCACTATCTTGATCGGTACTTCATTGCGAGGAGGTCACTTCCTGCACTTCATGAAG
TTGGACTCACGTGCTTCCGGGATCTGGTCTATCAGGAGCTGAAAGTTAAAGTGAGGGATGCTGTAA
TATCTCTGATCGATCAAGAGCGTGAGGGGGAACAGATTGACCGAGCTTTATTAAAGAACGTGTTAG
ATATATTTGTTGAAATCGGAATGAGTCAAATGGATCAATATGAGAATGACTTTGAAGAAGCCATGC
TCACTGATACTGCTGCTTACTATTCTCGAAAAGCTTCAAACTGGATCCTTGAAGATTCTTGTCCTG
ATTATATGTTAAAGGCAGAAGAATGTTTGCGACGAGAGAAGGACAGGGTTTCCCACTACCTACATT
TTAGTAGCGAGCCAAAGTTGCTTGAGAAAGTGCAACATGAGCTGCTATCTGTGTATGCAACCCAAT
TACTCGAGAAGGAACATTCTGGTTGTCATGCATTGCTTAGGGATGACAAGGTGGATGATTTGTCTA
GGATGTACAGACTCTTCTCGAAAATACCTAAAGGCCTGGATCCAGTTTCTTATATTTTTAAGCAGC
ATGTTACAAATGAAGGGATGGCATTGGTTAAACAAGCAGAAGATGCAGCAAGCAACAAGAAGGCAG
AAAAGAGAGACGTGGTTAGTTTACAGGAGCAGGTTTTTGTTAGAAAAATTATTGAATTACATGACA
AATACCTCGCCTATGTGAATGACTGCTTTACAAACCATACTCTTTTCCATAAGGCTCTCAAGGAGG
CTTTTGAAATCTTTTGCAACAAGGGTGTTGCTGGAAGCTCTAATGCTGAACTACTTGCTACTTTCT
GTGATAACATCCTCAAAAAGGGTGGGAGTGAGAAATTAAGTGATGAGGCTATTGAAGAAACACTTG
AGAAGGTAGTAAAATTGTTAGCTTACATTAGCGATAAAGACTTGTTCGCTGAATTTTACAGAAAAA
AGCTTGCACGGAGACTTCTCTTTGATAAGAGTGCAAATGACGAGCATGAACGAAGTATTTTGACTA
AACTAAAGCAACAGTGCGGTGGTCAGTTCACATCGAAAATGGAGGGGATGGTCACAGATTTGACTT
TGGCTAAAGAAAATCAATCCAGCTTTGAGGAGTATCTGGGAAATAATGCCAATGTGAATCCTGGCA
TTGACTTGACGGTTACTGTTCTGACCACTGGCTTCTGGCCTAGTTATAAATCCTTTGATCTCAACC
TTCCTGCTGAGATGGTCAAGTGCGTTGAAGTATTTAGAGAATTTTATCAAACAAAAACGAAGCATA
GAAAGCTCACATGGATATATTCTCTGGGTACTTGTAATATCAATGGAAAATTTGAACCCAAAACCA
TTGAGCTGATTGTGACAACCTACCAGGCCTCTGCTCTCCTGTTATTTAATACTTCTGATAGGTTGA
GTTATCAAGAAATCATGACTCAGTTAAATTTGTCGGATGATGATGTTGTTCGCCTGCTTCATTCCC
TTTCATGTGCCAAGTATAAAATTCTTACTAAAGAGCCGAACAACAAAACAATTTCCCCTACGGATT
ACTTTGAGTTCAACTCCAAGTTCACTGACAAAATGAGGAGAATTAAGATTCCACTACCTCCAGTTG
ATGAGAAGAAAAAGGTAATTGAAGATGTTGACAAGGACCGGCGATATGCCATTGATGCATCTATTG
TCCGCATTATGAAGAGCCGTAAAGTTTTGGGCTACCAACAATTGGTTATGGAATGTGTTGAGCAAT
TGGGACGCATGTTTAAGCCTGATGTCAAAGCAATTAAGAAGAGAATCGAAGATTTAATAACGCGTG
ATTATCTGGAAAGAGACAAGGATAATGCCAACCTTTTCAGATATTTGGCATGA

Fig. 45

ATGAATGAAAGAAAAACAATAGACTTAGAACAAGGATGGGACTTCATGCAGAAAGGCATAACAAAG
TTGAAGAACATTCTAGAAGGTCTTCCCGAGCCACAATTCAGCTCGGAAGATTACATGATGCTCTAC
ACAACCAT[G]TACAATATGTGCACACAAAAACCGCCACATGATTACTCTCAACAATTGTATGACA
AATACCGCGAGTCTTTTGAAGAGTACATTACTTCAACGGTGTTACCTTCTTTAAGAGAGAAGCATG
ATGAGTTTATGCTTAGAGAGCTTGTTAGAAGATGGTCAAATCATAAAGTGATGGTTAGGTGGCTTT
CTAGATTCTTCCATTATCTTGATCGATACTTCATTGCCCGAAGATCTCTTCCACCATTAAATGAAG
TTGGACTTGCGTGTTTTCGTGATCTGGTATACCAAGAGGTGAATGGGAAAGTGAGAGATGCTGTAA
TATCTTTGATTGATCAAGAGCGTGAAGGCGAGCAAATTGACCGAGCATTACTCAAGAATGTTCTAG
ATATATTTGTTGAAATAGGAATGGGACAAATGGAATATTATGAGAATGATTTTGAAGCATCCATGC
TTAATGATACAGCAGCATATTATTCACGCAAAGCTTCCAATTGGATTCTAGAAGATTCTTGTCCAG
ATTATATGCTCAAAGCTGAGGAGTGCTTAAAAAGAGAAAAGGACAGAGTTTCTCATTATCTTCATT
CCAGCAGTGAACCAAAGCTTCTTGAGAAAGTTCAAACAGAGTTATTATCTGTTTATGCAACTCAAT
TGCTTGAAAAGGAGCACTCCGGTTGTCATGCATTACTTAGGGATGACAAGGTTGATGATTTATCAA
GAATGTACAGACTCTTTTCAAAGATACAAAAAGGGCTGGATCCTGTTTCTAGTATGTTTAAGCAGC
ATGTCACTGCTGAAGGCACAACATTGGTTAAACAGGCAGAAGATGCAGCAAGTACTAAGAAGGCTG
AAAAGAGAGACGTGGTTGGCTTACAAGAACAGGTTTTTGTTAGAAAAGTTATCGAGCTTCATGACA
AGTACCTTGCATATGTAAATGACTGTTTTATGAATCATACCCTGTTTCACAAGGCTCTTAAAGAGG
CATTTGAAATATTCTGCAACAAGGGCGTTGCTGGAAGTTCAAGTGCAGAATTACTTGCTACATTTT
GTGATAATATTCTTAAAAAAGGTGGAAGTGAAAAATTGAGTGATGAAGCCATTGAGGACACACTTG
AGAAGGTGGTAAAGTTGCTTGCTTACATCAGCGATAAAGATCTATTTGCAGAGTTTTATAGGAAAA
AACTGGCTAGACGGCTTTTATTTGACAAAAGTGCAAATGATGAGCACGAAAGAAGTATTTTGACAA
AATTGAAACAACAATGTGGCGGTCAATTTACATCAAAAATGGAAGGAATGGTTACAGATTTGACAT
TGGCAAAAGAAAATCAATCACATTTTGAGGAGTATTTGAATAATAATCCCAATGTTAGCCCTGGCA
TTGACTTGACCGTGACTGTGTTGACCACTGGTTTTTGGCCTAGTTACAAATCTTTTGACCTAAATC
TCCCTGCAGAAATGGTCAAATGCGTTGAAGTTTTCAGAGAATTTTATCAAACAAAAACAAAACACA
GAAAACTCACATGGATATATTCATTGGGCACCTGCAATATAAACGGAAAATTCGAACCAAAAACCA
TGGAGCTAATCGTTACAACTTACCAGGCATCTGCTTTATTACTGTTCAACTCATCAGATCGATTGA
GTTATCAAGAAATCATGACTCAATTAAACTTATCAGATGATGATGTTGTTAGACTACTCCATTCAT
TATCATGTGCAAAATATAAAATTTTATTAAAAGAACCAAATACAAAAACAATCTCTCCAACTGATT
TCTTTGAATTCAACTCAAAGTTTACAGATAAAATGAGAAGGATCAAGATTCCTCTACCTCCTGTTG
ATGAAAAGAAAAAAGTAATTGAAGATGTTGACAAAGACCGACGTTATGCAATTGATGCTTCAATTG
TACGGATAATGAAAAGCAGAAAAGTTCTTGGATACCAACAATTGGTCATGGAATGTGTTGAACAAT
TAGGCCGTATGTTTAAGCCTGATGTAAAAGCAATCAAGAAACGTATTGAAGATCTCATAACTCGTG
ATTATCTTGAAAGAGACAAAGAAAATCCAAATTTGTTTCGGTACTTGGCATGA

Fig. 46

ATGAATGAAAGAAAAACAATAGACTTAGAACAAGGATGGGACTTCATGCAAAAAGGCATAACAAAG
TTGAAGAACATTCTAGAAGGTCTTCCCGAGCCACAATTCAGCTCAGAGGATTACATGATGCTCTAC
ACAACCAT[G]TACAATATGTGCACACAAAAACCGCCACATGATTACTCTCAACAATTATATGACA
AATACCGCGAGTCTTTTGAAGAGTACATAACTTCAACGGTGTTACCTTCTTTAAGAGAGAAGCATG
ATGAGTTTATGCTTAGAGAGCTTGTTAGAAGGTGGTCAAATCATAAAGTGATGGTTAGGTGGCTTT
CTAGATTCTTCCATTATCTTGATCGATACTTTATTGCAAGAAGATCTCTTCCACCATTAAATGAAG
TTGGACTTGCGTGTTTTCGTGATCTGGTATACCAAGAGGTGAATGGAAAAGTGAGAGATGCTGTAA
TATCTTTGATTGATCAAGAGCGTGAAGGCGAGCAAATTGACCGAGCATTACTGAAGAATGTTCTAG
ATATATTTGTTGAAATAGGAATGGGACAAATGGAATATTATGAGAATGATTTTGAAGCATCTATGC
TTAATGATACAGCAGCATATTATTCACGCAAAGCTTCCAACTGGATTCTAGAAGATTCTTGTCCAG
ATTATATGCTCAAAGCTGAGGAGTGCTTAAAAAGAGAAAAGGACAGAGTTTCTCATTATCTTCATT
CAAGTAGTGAACCAAAGCTTCTTGAGAAAGTTCAAACAGAGTTATTATCTGTTTATGCAACTCAAT
TGCTCGAAAAGGAACACTCAGGTTGTCATGCATTACTTAGAGATGACAAGGTTGATGATTTATCAA
GAATGTACAGACTCTTTTCAAAGATACAAAAAGGACTGGATCCTGTTTCCAGTATGTTTAAGCAGC
ATGTCACTGCTGAAGGCACAACATTAGTAAAACAAGCAGAAGATGCAGCAAGTACTAAGAAGGCTG
AAAAGAGAGACGTGGTTGGCTTACAGGAACAGGTTTTTGTTAGAAAAGTAATCGAGCTTCATGACA
AGTACCTCGCATATGTAAACGACTGTTTTATGAATCACACATTGTTCCACAAGGCTCTTAAAGAGG
CATTTGAAATATTCTGCAACAAGGGCGTTGCTGGAAGTTCAAGTGCAGAATTACTTGCCACATTTT
GTGATAATATTCTTAAAAAAGGTGGAAGTGAAAAATTGAGTGATGAAGCCATTGAAGACACACTTG
AGAAGGTAGTAAAGTTGCTTGCTTACATCAGCGATAAAGATCTATTTGCAGAGTTTTATAGGAAAA
AACTGGCTAGAAGGCTTTTATTTGACAAAAGTGCAAATGATGAGCATGAAAGAAGTATTTTAACAA
AGTTGAAGCAACAATGTGGTGGTCAGTTTACATCAAAGATGGAAGGAATGGTTACAGATTTAACAC
TGGCAAAAGAAAATCAATCACATTTTGAGGAGTATTTGAATAATAATCCCAATGTTAGCCCTGGCA
TTGACTTGACCGTGACTGTGTTGACCACGGGATTTTGGCCTAGTTACAAATCTTTTGACCTAAATC
TTCCTGCAGAAATGGTCAAATGCGTTGAAGTTTTCAGAGAATTTTATCAAACAAAAACAAAACACA
GAAAACTCACATGGATTTATTCATTGGGCACCTGCAATATTAACGGAAAATTCGAACCAAAAACCA
TGGAGCTAATCGTTACAACTTACCAGGCATCTGCTTTATTGTTATTCAACTCATCAGATCGATTAA
GTTATCAAGAAATCATGACTCAATTAAATTTATCAGATGATGATGTTGTTAGACTACTACATTCAT
TATCATGTGCAAAATATAAAATTTTATTAAAAGAACCAAATACCAAAACAATATCTCCAACCGATT
TCTTTGAATTCAACTCAAAGTTTACAGATAAAATGAGAAGGATCAAGATTCCTCTACCTCCTGTTG
ATGAAAAGAAAAAAGTAATTGAAGATGTTGACAAAGATAGAAGGTATGCAATTGATGCTTCAATTG
TACGAATAATGAAAAGCAGAAAAGTTCTTGGATACCAACAATTGGTTATGGAGTGTGTTGAACAAT
TAGGCCGTATGTTTAAGCCTGATGTAAAAGCAATCAAGAAGCGTATTGAAGATTTGATAACGCGTG
ATTATCTTGAAAGAGACAAAGAAAATCCAAATTTGTTTCGGTACTTGGCATGA

Fig. 47

ATGTCGTTGCACGAAAGGAAAACCATTGATTTGGAGCAGGGATGGGCTTTTATGCAGAAAGGGATC
ACCAAACTGAAGAATATTCTTGATGAGTTGAATGAACCTCAGTTCAGCTCAGAGGATTACATGATG
CTCTATACGACTAT[G]TATAATATGTGTACTCAGAAGCCGCCACATGATTATTCTCAGGAGTTGT
ATGATAAGTACCGAGAGTCCTTTGAAGAGTATATCACTACCACTGTGCTTCCTTCATTGAGAGAAA
AGCATGATGAATACATGTTAAGGGAGCTCGTGAGAAGGTGGTCAAATCATAAAATAATGGTTAGAT
GGCTTTCACGCTTTTTCCATTATCTTGATCGCTACTTTATAGCACGAAGATCATTGCCTGCTCTTA
ATGAAGTCGGTCTCACTTGTTTCCGTGATCTGGTGTACAACGAAGTCCATGGGAAAGTTAAAGATG
CCGTGATCTCATTGATTGACCAAGAGAGGGAAGGGGAGCAAATTGACAGAGCTTTATTAAAGAATG
TTTTGGGTATTTTTGTAGAGATTGGTTTGGGAAGCATGGAATGTTATGAGAATGATTTTGAAACAT
CAATGCTTAATGCTACAGCAGCCTATTATTCACGAAAAGCTTCAAATTGGATTCTAGAAGATTCAT
GTCCAGATTATATGCTAAAAGCCGAGGAGTGCTTAAAACATGAGAAAGATAGAGTTGCTCATTATT
TGCATTCAAGCAGTGAACAGAAGCTGTTAGAGAAAGTGCAACATGAGTTACTTTTCGTATATGCAA
GTCAACTTCTCGAGAAAGAACATTCCGGATGTCATGCATTGCTTCGCGATGACAAGGTGGGAGATC
TTTCACGCATGTATCGGCTGTTCTGTAGAATTACACGTGGTTTGGACCCTGTGTCTCAAATATTTA
AGCAGCATGTGACTGCAGAAGGTACTGCTTTGGTCAAACATGCCGAAGATGCTGCAAGTAACAAGA
AGGCCGAGAAAAAAGACATTGTTGGTTTGCAAGAGCAGGTCTTCGTTAGGAAAGTAATTGAGCTGC
ATGATAAATACTTGGCCTATGTGACTGACTGCTTTCAAAATCACTCTCTATTTCACAAGGCACTTA
AAGAGGCATTCGAGGTATTCTGCAATAAAGGTGTTGCAGGTAGCTCAAGCGCTGAACTTCTGGCTG
CTTTTTGTGACAATATATTGAAGAAGGGTGGAAGCGAGAAACTAAGCGATGAGGCCATAGAGGATA
CTCTTGAGAAGGTTGTAAAACTATTGGCATATATTAGCGATAAAGATCTGTTTGCTGAATTTTACA
GGAAGAAGCTTGCACGAAGATTACTCTTTGACAAAAGTGCTAATGATGACCATGAGAGGAGCATCC
TTACAAAGCTGAAACAGCAATGTGGAGGGCAGTTCACCTCTAAAATGGAAGGCATGGTAACCGATC
TGACACTTGCACGAGAAAATCAATCAAGTTTTGACGATTACCTTAGCAGCAATCCTAAAGCAAATT
CTGGAATTGACTTGACTGTTACAGTCTTAACAACTGGCTTCTGGCCCAGTTACAAGTCTTTTGATC
TCAATCTTCCTGATGAGATGGTAAAATGCGTTGAAATTTTTAAAGAGTTTTACGAGACAAAAAACCA
AACACAGAAAACTTACATGGATTTATTCGTTGGGCACTTGCAACATCAATGGCAAGTTCGAAACCA
AGACAATAGAGTTGGTTGTTACAACCTATCAGGCTGCAGTGTTGCTTCTATTCAACTCTGCAGATA
AATTAAGTTATTCTGAGATTGTGCAGCAGCTAAACTTATCTGATGATGATGTAATCAGATTACTTC
ACTCTCTTTCATGCGCTAAATACAAAATTCTCAATAAAGAACCCGCTACCAAGACTATTACCCCGA
ATGATCATTTTGAGTTCAATTCTAAATTCACTGATAGAATGAGAAGGATCAAGATTCCCCTGCCTC
CTGTGGATGAGAAGAAAAAAGTAATTGAAGATGTTGACAAAGACAGAAGATATGCAATTGACGCAT
CCATAGTTCGAATAATGAAAAGTAGAAAAGTTCTTGGTCATCAGCAGCTTGTTTTGGAATGTGTTG
AGCAATTAGGCCGCATGTTTAAGCCTGACTTTAAGGCCATCAAGAAAAGGATTGAAGATCTGATCG
CTAGAGATTATTTGGAGAGGGACAAGGACAATCCAAACCTCTTTAAATATTTGGCCTAA

Fig. 48

ATGAACGAAAGAAAAACAATAGACTTAGAGCAAGGATGGGACTTCATGCAGAAAGGAATAACAAAG
TTGAAGAATATTCTAGAAGGTCTTCCCGAGCCACAATTCAGCTCGGAGGATTACATGATGCTCTAC
ACAACCAT[G]TACAACATGTGTACACAGAAACCACCACATGATTACTCCCAACAGTTGTATGACA
AATATCGTGAGTCTTTTGAAGAGTATATTACTTCAACTGTGTTACCTTCTTTAAGAGAGAAGCATG
ATGAGTTCATGCTGAGAGAGCTTGTTAGAAGGTGGTCAAATCATAAAGTCATGGTGCGGTGGCTTT
CTAGATTCTTCCATTATCTTGACCGATATTTCATTGCCCGAAGATCTCTTCCGCCACTAAATGAAG
TTGGACTTGCCTGTTTTCGTGATCTGGTATACCAAGAGGTGAATGGTAAAGTGAGAGATGCTGTAA
TATCTTTGATTGATCAAGAGCGTGAAGGGGAGCAGATTGATCGAGCTTTACTGAAGAATGTTCTAG
ATATATTTGTTGAGATAGGAATGGGACAAATGGAGTATTATGAGAATGATTTTGAAGCATCCATGC
TTAATGATACAGCAGCATATTATTCACGCAAGGCTTCCAACTGGATTCTAGAAGATTCTTGTCCAG
ATTATATGCTCAAAGCAGAGGAGTGCTTAAAAAGAGAAAAGGACAGAGTGTCTCATTATCTTCATT
CCAGCAGTGAGCCAAAGCTTCTTGAGAAAGTTCAAAATGAGTTATTGTCTGTTTATGCAACTCAAT
TGCTTGAGAAAGAGCACTCAGGTTGTCATGCATTGCTCAGGGATGACAAGGTTGATGATTTATCAA
GAATGTACAGACTCTTTTCAAAGATACCAAAAGGATTGGATCCTGTTTCTAGTATGTTTAAGCAGC
ATGTCACTGCTGAAGGCACAACATTGGTTAAACAAGCAGAAGATGCAGCAAGTACCAAGAAGGCTG
AAAAGAGAGATGTGGTTGGGTTGCAGGAACAGGTTTTTGTTAGAAAAGTTATTGAGCTCCATGACA
AGTACCTGGCATATGTAAATGACTGTTTCATGAACCATACTCTTTTCCACAAGGCTCTTAAAGAGG
CATTTGAAATATTCTGCAACAAGGGTGTTGCTGGAAGTTCAAGTGCAGAGTTACTTGCCACATTTT
GTGATAATATTCTTAAAAAAGGTGGAAGTGAGAAACTGAGCGATGAAGCCATTGAGGACACCCTTG
AGAAGGTAGTAAAGTTGCTTGCCTACATCAGTGATAAAGATCTATTTGCTGAATTTTACAGGAAAA
AACTTGCTAGGAGGCTTTTGTTTGACAAGAGTGCAAACGATGAGCATGAGAGAAGTATTCTCACAA
AGCTGAAGCAACAGTGTGGTGGTCAGTTCACATCAAAGATGGAAGGGATGGTTACAGATTTGACAT
TGGCAAAGGAAAACCAATCCCATTTTGAAGAGTATTTGAACAATAATCCCAATGTCAGCCCTGGAA
TTGACTTGACTGTCACTGTGTTGACTACCGGCTTCTGGCCCAGCTACAAATCTTTTGACCTAAATC
TCCCTGCCGAAATGGTTAAATGCGTTGAAGTTTTCAGAGAATTTTATCAAACAAAAACAAAGCACA
GGAAGCTTACATGGATATATTCATTGGGTACCTGCAATATAAACGGGAAATTTGAACCCAAAACAA
TGGAGCTCATAGTCACAACCTACCAGGCATCTGCTTTATTACTGTTCAACTTATCGGATCGATTGA
GTTATCAAGAAATCATGACTCAGTTGAACTTGTCAGATGATGATGTTGTTAGGCTGCTCCATTCTT
TGTCATGTGCAAAATACAAAATTCTTTTAAAGGAGCCTAATACCAAAACAATCTCTCCAACCGATT
ACTTCGAATTCAACTCCAAGTTTACAGATAAAATGAGGAGGATCAAGATTCCTCTACCTCCTGTGG
ATGAGAAGAAAAAGGTGATTGAGGATGTTGACAAAGACAGACGTTATGCCATTGATGCTTCCATTG
TAAGGATAATGAAGAGCAGAAAGGTGCTTGGATACCAGCAGTTGGTTATGGAGTGTGTTGAACAGT
TGGGACGCATGTTTAAGCCTGATGTAAAAGCAATCAAGAAGCGGATTGAAGATCTGATAACTCGTG
ATTATCTTGAAAGAGACAAAGAGAACCCCAACTTGTTCCGATACTTGGCATGA

Fig. 49

ATGGAGCGGAAGACGATTGATCTGGAACAAGGATGGGACTATATGCAGACTGGGATCACTAAGCTG
AAACGGATTCTTGAAGGATTGCCTGAGCCGCAATTCGACTCTGAGCAGTACATGATGCTTTATACG
ACTAT[G]TACAACATGTGCACCCAGAAACCTCCTCATGATTACTCTCAGCAGCTTTATGACAAGT
ATCGCGAAGCTTTTGAGGAGTACATTGACTCTACTGTTTTGCCTGCTTTGAAGGAGAAGCATGATG
AATACATGCTACGGGAGCTGGTTAAGAGATGGTCTAACCATAAAGTTATGGTTAGATGGCTATCCC
GATTCTTCTACTATCTTGACCGTTACTTCATTGCTCGGAGATCGCTGCCACCGCTTAATGAAGTTG
GGCTCACATGCTTCCGTGACCGGGTGTATAAGGAGTTGCATTCCAAGGTCAAAGATGCTGTAATAG
CACTTGTTGATAAAGAACGGGAAGGCGAGCAGATTGACAGGGCTCTTCTGAAAAACGTATTAGATA
TCTATGTAGAGATTGGAATGGGACAGATGGAAAGATACGAAGTGGATTTTGAAAGCTTCATGCTTT
TGGATTCAGCATCTTACTATTCTCGCAAAGCATCAAACTGGATCCAGGAAGATTCTTGCCCTGATT
ACATGCTGAAGTCTGAAGAATGCCTTAAGAAGGAGAGGGAGAGGGTTGCTCACTACCTTCATTCAA
GCAGCGAGCCAAAGCTGGTTGAGAAAGTACAACATGAGCTGTTGGTTGTCTATGCAAATCAGCTTC
TTGAAAAGGAGCACTCAGGGTGCCGTGCATTGCTGAGAGACGACAAGGTTGACGATCTCTCCAGGA
TGTACAGGCTCTATCATAAAATTGCTAAAGGTTTAGAACCTGTTGCAAACATATTTAAGCAGCATG
TCACAGCCGAGGGTAACGCACTTGTCCAACAGGCCGAAGACACAGCCACTAATCAGGCTGCAAATA
CTGCTAGCGTGCAGGAACAGGTTCTCATCAGAAAAGTGATTGAGCTACATGATAAGTACATGGTCT
ATGTCGTGGAGTGCTTCCAGAACCACACCCTCTTCCACAAGGCTCTGAAAGAGGCATTTGAGATAT
TCTGTAACAAAACAGTCGCTGGAAGTTCAAGTGCAGAACTGCTTGCAACATTCTGCGACAACATCC
TCAAGAAGGGGGGTAGTGAGAAGCTGAGTGACGAAGCTATTGAAGATACGCTTGAGAAGGTTGTCA
AATTGCTTGCTTATATAAGCGACAAGGATCTTTTCGCCGAGTTCTACAGGAAGAAGCTGGCACGTA
GGCTCTTATTTGATCGCAGTGCGAATGATGATCATGAGAGAAGCATCCTTACAAAGCTCAAGCAAC
AATGTGGTGGGCAGTTCACTTCTAAGATGGAGGGCATGGTAACGGACTTGACATTGGCAAGAGAGA
ACCAAACCAGTTTCGAGGAGTATCTAGGCAATAACCCCGCTGCAAACCCAGGGATTGATTTGACCG
TCACTGTTCTTACCACTGGTTTCTGGCCAAGTTACAAATCATTCGACATAAATCTACCAAGTGAAA
TGGTCAAGTGTGTTGAAGTTTTCAAAGGGTTTTATGAGACGAAAACTAAACATAGGAAACTTACAT
GGATCTACTCACTAGGAACTTGTCACCTCAACGGAAAGTTTGATCACAAGCCCATTGAGTTAGTTG
TGTCTACTTACCAGGCTGCTGTGCTTCTGCTGTTCAACACAACAGACAAATTGAGCTACAACGATA
TCCTAACTCAACTGAACCTAAGCCACGAAGATTTAGTGAGGTTGCTTCATTCCCTGTCATGTGCTA
GGTACAAGATCCTTCTCAAGGAGCCAAGCACGAAGACTGTTACACAGACTGATTCATTTGAATTCA
ATGCCAAATTCACGGACAGAATGCGCAGAATCAAGATCCCTCTCCCTCCTGTTGATGAAAGGAAGA
AGGTTGTGGAAGATGTGGACAAAGACAGACGCTATGCGATTGATGCTGCCATTGTTAGGATCATGA
AGAGCAGGAAAGTGTTGGGACATCAACAACTCGTCTCTGAGTGCGTTGAGCAACTTAGCCGAATGT
TCAAGCCTGATATCAAAGCGATCAAGAAGCGTATGGAGGATCTAATTACGAGGGATTATTTGGAGA
GGGACAAGGAGAACCCTAACATGTTTAGGTACTTGGCTTAG

Fig. 50

ATGAACGATCGTAAAGTTATCGAACTAGAGCAAGGATGGGAGTTCATGGGGAAGGGGATTACGAAG
TTGAAAAGGATTTTGGAAGGATTACCAGAGCCGCCTTTTAATTCGGAAGACTACATGATGCTGTAC
ACGACAAT[G]TACAACATGTGTACACAGAAACCCCCTCATGATTACTCTCAACAACTCTATGACA
ATTACAAAGAGGCATTTGTGGATTACATACATTCAACGGTTTTACCTTCTTTGGGGGACAAACATG
ATGAGTTTATGCTGAGAGAGCTTGTGAAGAGATGGTCAAATCATAAAGTAATGGTGAGGTGGTTGT
CTCGCTTCTTCCATTATCTGGATCGGTACTTCATCGCTCGGAGATCGCTTCCTTCTTTGAATGATG
TTGGATTGACGTGCTTCCGTGATCTGGTTTATCAAGAAATATCTGGCAAAGCCAAGGATGCTGTTA
TTGCTCTGATTGATGAAGAAAGAGAGGGTGGGCAAATTGACAGAGCCTTATTGAAGAATGTACTTG
ATATATACGTTGAAATTGGAATGACACAAATGGATTACTACGAAAAGGACTTTGAAGCTCATATGC
TGGATGATACTGCTGCTTATTACTCACGCAAGGCCTCAAGCTGGATTCTGGAGGACTCATGTCCGG
AATACATGTTGAAGTCGGAGGAGTGTTTGAAGAAAGAGAAAGATAGAGTGGCTCATTATCTACATT
CCAGCAGTGAGCCAAAGCTTCTGGAGAAAGTACAAAATGAGTTGCTACTGGTTTACGAAAATCAGT
TGCTTGAGAAGGAGAATTCTGGATGTCGTGCATTGTTGAAAGATGACAAGGTGGAAGATCTTTCCA
GGATGTACAGGCTTTATAGCAAGGTTACCAAAGGGTTGGAACCCATTGGCAGTATCTTCAAACAGC
ATATAACCGATGAAGGAACAGCCCTGGTGCAGCAGGCCGAAGACGCTGCAATTAGCAAGGCTGAAA
ATGCTGGCGGTGGTTCACATGAGCAGGTCTTCGTCAGGAAAGTGATTGAGTTGCATGACAAATTTA
TGACCTATGTTACAGATTGCTTCAACAGCCATACCATCTTTCACAAGGCTCTCAAGGAAGCTTTTG
AGGTATTCTTAAACAAGGGTGTTGCTGGTAGTTCAAGTGCTGAACTTCTAGCTTCATTTTGTGATA
ATATTCTCAAGAAAGGTGGTAGTGAAAAATTAAGTGATGAGGCTATTGAGGATTCACTGGAGAAGG
TGGTGAAGCTTCTCGCATATGTCAGTGATAAAGACCTGTTTGCTGAATTTTACAGAAAGAAGCTCT
CTCGCCGGCTACTCTTTGACAAAAGTGCTAATGATGATCATGAGAGGAGTATTTTAACAAAATTGA
AGCAGCAGTGTGGGGGACAGTTCACATCAAAGATGGAGGGGATGGTGACAGACTTGACATTGGCGA
GGGAGAATCAAACTAATTTTGAGGAATATCTTGGACAAAATACAGATGCCAGTCCTGGTCTTGATT
TGACTGTGACAGTTTTGACCACTGGGTTCTGGCCAAGTTACAAATCTTCTGATCTTAACCTTCCTG
CTGAGATGGTGAGGTGTGTTGAAGTTTTTAAGCAATTTTATCAAACAAAGACAAAACACAGGAAGC
TCACCTGGGTATATTCGTTGGGAAGTTGTAACATTAATGGCAAGTTTGGTCCGAAAACAATTGAAT
TGGTTGTTGGAACTTATCAGGCTGCTGCGCTGATGCTCTTTAACACATCAGATCGACTGAGTTATT
CAGAAATAACGACCCAACTAAATCTAGCTGACGAAGACTTGGTTAGAGTGCTTCAATCTCTATCTT
GCGCAAAGTATAAGATTCTTCTAAAAGAGCCAAGCACAAGAAACGTGATCTCAACTGATTGTTTTT
CATTCAACTCTAATTTTACTGACAGAATGAGGAGGATTAGGATTCCTCTTCCTCCAATGGATGAGA
GGAAAAAGGTTGTTGAAGATGTTGACAAAGATAGAAGATATGCTATTGATGCCTCAATTGTACGCA
TAATGAAAAGTAGGAAGGCTTTGGGATATCAACAATTAATCACGGAGTGTGTGGAGCAGCTAAGCC
GCATGTTCAAGCCTGATTTCAAAGCAATTAAGAAGAGGATCGAGGACTTGATAACCAGAGATTATA
TTGAAAGAGACAAGGAAAACCCTCAGCTATTCCGGTACTTGGCTTGA

Fig. 51

ATGAATGATCGTAAAGTTATTGAACTAGAGCAAGGATGGGAGTTCATGGGGAAGGGGATTACAAAG
TTGAAGAGGATTCTGGAAGGATTGCCAGAGCCACCATTTAATTCTGAAGACTACATGATGTTGTAC
ACGACGAT[G]TACAATATGTGTACTCAGAAACCCCCACATGATTACTCTCAACAGCTCTATGACA
ATTACAAACAGGCTTTTGTGGATTACATCAACTCGACGGTTTTACCTTCTTTGCGGGAGAAGCATG
ATGAGTTTATGTTAAGAGAACTTGTGAAAAGATGGGCAAATCATAAAGTAATGGTCAGGTGGTTGT
CTCGTTTCTTCCATTATCTGGACCGGTATTTCATTGCTCGGAGGTCGCTTCCTTCTTTGAATGAAG
TTGGACTGACTTGTTTCCGTGATCTGGTTTATCAAGAAATATCTGGCAAAGCCAAGGATGCTGTTA
TAGCCCTGATTGATATAGAAAGAGAAGGTGGGCAGATTGACAGATCATTATTGAAAAATGTACTTG
ATATATATGTTGAAATTGGAATGGGACAAATGGATCACTATGAAAAAGACTTTGAAGCTCATATGC
TGGATGATACTGCTGCTTACTACTCGCGCAAAGCGTCTAGCTGGATTCTTGAGGACTCTTGTCCGG
AATACATGTTAAAGTCTGAGGAGTGTTTGAAGAAGGAGAAAGAGAGAGTGGCTAATTATTTACATT
CCAGCAGTGAGCCAAAGCTTCTGGAGAAAGTGCAAAACGAGTTGCTATTGGTTTATGAAAGCCAAT
TGCTTGAGAAGGAGAATTCGGGATGTCGTGCATTACTGAAAGATGACAAGGTGGATGATCTTTCCA
GGATGTACAGGCTTTACAGTAAGGTTACCAAAGGATTGGAACCCATTGGCAGTATCTTCAAACAGC
ATATAACTGATGAAGGAACAGCCTTAGTGCAGCAGGCCGAAGATGCTGCTATCAGCAAGGCTGAAA
ATACTGGTGGTTCACATGAGCAGGTCTTCGTCAGGAAAGTAATAGAGTTGCATGACAAATTCATGA
CTTATGTCACCGATTGCTTCAACAGCCATACCATATTTCACAAGGCTCTTAAGGAGGCTTTTGAGG
TATTTTTGAACAAGGGTGTTGCTGGTAGCTCAAGTGCTGAGTTGCTAGCTACATTCTGTGATAACA
TTCTCAAGAAAGGTGGGAGCGAAAAACTAAGCGATGAGGCTATTGAGGATTCACTTGAGAAGGTGG
TGAAGCTTCTGGCCTATGTCAGTGATAAAGACCTGTTTGCTGAATTTTACAGAAAGAAGCTCTCTC
GCCGGCTACTCTTTGACAAGAGTGCTAATGATGATCATGAAAGAAGTATTTTAACCAAATTGAAGC
AGCAGTGTGGCGGACAATTCACATCAAAGATGGAGGGGATGGTGACAGACTTGACCTTGGCGAGGG
AGAATCAAACTAATTTTGAGGAATATCTTAGTCAGAATCCAGATGCCAGTCCTGGTCTTGATTTGA
CTGTGACTGTTCTGACAACTGGGTTCTGGCCAAGTTACAAATCTTCCGATCTTAACCTTCCCGCTG
AGATGGTGAGGTGTGTTGAAGTTTTTAAGCAGTTCTATTCAACTAAAACAAAGCACAGGAAGCTGA
CCTGGGTTTACTCATTGGGAAGCTGTAATATTAATGGCAAGTTTGGTCCAAAAACTATTGAATTGG
TTGTCGGAACTTATCAGGCTGCTGCTTTGATGCTCTTTAACACATCAGACCGACTGAGTTATTCAG
AGATAGCAACTCAACTAAATTTAGCTGATGAAGATCTGGTTAGAGTGCTTCAATCTTTATCCTGCG
CAAAGTATAAGATTCTTTTAAAGGAGCCAAACACGAAAACCGTGTCCCCGACTGATTGTTTTTCAT
TTAACTCTAGTTTCACTGACAGGATGAGGAGGATAAGAATTCCTCTTCCTCCGATGGATGAGAGGA
AAAAGGTTGTTGAGGATGTTGACAAAGATAGAAGATATGCTATTGATGCCTCAATTGTACGCATAA
TGAAAAGTAGGAAGGTTTTGGGGTACCAGCAATTAATCACAGAGTGTGTGGAGCAGCTAAGCCGCA
TGTTCAAGCCTGATTTCAAGGCAATTAAGAAGAGGATCGAGGACTTAATAACCCGAGATTATATTG
AAAGAGACAAGGAGAACCCGCAGCTATTCCGATACTTGGCTTGA

Fig. 52

MTMGERKTIDLEQGWEFMQKGITKLKNILEGLPEPQFSSEDYMMLYTT[M]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLKREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 53

MTMGERKTIDLEQGWEFMQKGITKLKNILEGLPEPQFSSEDYMMLYTT[M]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLKREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 54

MTMGERKTIDLEQGWEFMQKGITKLKNILEGLPEPQFSSEDYMMLYTT[M]YNMCTQKPPHDYSQQ
LYDKYRESFEEYISSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLRREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DKLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 55

MTMGERKTIDLEQGWEFMQKGITKLKNILEGLPEPQFSSEDYMMLYTT[M]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLKREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 56

MNQRSTIDLEHGWDFMQKGITKLKNILEGLPEPQFSSEDYMMLYTT[M]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDLVYQELNGKVRDAVISLIDQEREGEQIDRALLKNVLDIFVEIGMGSMDYYENDFEAA
MLKDTAAYYSRKASNWILEDSCPDYMLKAEECLKREKDRVSHYLHSSSETKLLEKVQHELLSVYAN
QLLEKEHSGCHALLRDDKVDDLSRMYRLFSKIPRGLEPVANIFKQHVTAEGTALVKQAEDAASNKK
AEKRDVVGLQEQVFVRKVIELHDKYLAYVNNCFQNHTLFHKALKEAFELFCNKGVAGSSNAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPTANPGIDLTVTVLTTGFWPSYKSFDL
NLPAEMVRCVEVFKEFYQTKTKHRKLTWIYSLGTCNINGKFEAKTIELVVTTYQASALLLFNASDR
LSYQEIMTQLNLSDDDVVRLLHSLSCAKYKILNKEPSTKTISPTDVFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 57

MNQRSTIDLEHGWDFMQRGITKLKNILEGLPEPQFSSEDYMMLYTT[M]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDQVYQELNGKVRDAVISLIDQEREGEQIDRALLKNVLDIFVEIGMGLMDYYENDFEAA
MLKDTAAYYSRKASNWILEDSCPDYMLKAEECLKREKDRVSHYLHSSSETKLLEKVQHELLSVYAT
QLLEKEHSGCHALLRDDKVEDLSRMYRLFSKISRGLDPVANIFKQHVTAEGTALVKQAEDAASNKK
AEKRDVVGLQEQVFVRKVIELHDKYLAYVNNCFQNHTLFHKALKEAFELFCNKGVAGSSSAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPIANPGIDLTVTVLTTGFWPSYKSFDL
NLPAEMVRCVEVFKEFYQTKTKHRKLTWIYSLGTCNINGKFEPKTIELVVTTYQASALLLFNASDR
LSYQEIMTQLNLSDDDVVRLLHSLSCAKYKILNKEPSTKTISPTDVFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 58

MNQRSTINLEHGWDFMQRGITKLKNILEGLPEPQFSSEDYMMLYTT[M]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDLVYQELNGKVRDAVISLIDQEREGEQIDRALLKNVLDIFVEIGMGSMDYYENDFEAA
MLKDTAAYYSRKASNWILEDSCPDYMLKAEECLKREKDRVSHYLHLSSETKLLEKVQHELLSVYAT
QLLEKEHSGCHALLRDDKVEDLSRMYRLFSKIPRGLDPVANIFKQHVTAEGTALVKQAEDAASNKK
AEKRDVVGLQEQIFVRKVIELHDKYMAYVNNCFQNHTLFHKALKEAFELFCNKGVAGSSSAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPAANPGIDLTVTVLTTGFWPSYKSFDL
NLPAEMVRCVEVFKEFYQTKTKHRKLTWIYSLGTCNINGKFEPKTIELVVTTYQASALLLFNASDR
LSYQEIMTQLNLSDDDVVRLLHSLSCAKYKILNKEPSTKTISPTDVFEFNFKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 59

MERKTIDLDQGWDYMQTGITKLKRILEGLPEPQFDSEQYMMLYTT[M]YNMCTQKPPHDYSQQLYD
KYREAFEEYIHSTVLPALREKHDEYMLRELVKRWSNHKVMVRWLSRFFYYLDRYFIARRSLPPLNE
VGLTCFRDLVYNELHSKVKDAVIALVDKEREGEQIDRALLKNVLDIYVEIGMGQMERYEEDFESFM
LLDSASYYSRKASSWIQEDSCPDYMLKSEECLKKERERVAHYLHSSSEPKLVEKVQHELLVVYANQ
LLEKEHSGCRALLRDDKVDDLSRMYRLYHKIVKGLEPVANIFKQHVTAEGNALVQQAEDTATNHAA
NTASVQEQVLIRKVIELHDKYMVYVVECFQNHTLFHKALKEAFEIFCNKTVAGSSSAELLATFCDN
ILKKGGSEKLSDEAIEDTLEKVVKLLAYISDKDLFAEFYRKKLARRLLFDRSANDDHERSILTKLK
QQCGGQFTSKMEGMVTDLTLARENQNSFEEYLGNNPAANPGIDLTVTVLTTGFWPSYKSFDINLPA
EMVKCVEVFKGFYETKTKHRKLTWIYSLGTCHLNGKFDVKPIELVVSTYQAAVLLLFNTTDKLSYT
DILTQLNLSHEDLVRLLHSLSCARYKILLKEPSTKTVSQSDSFEFNSKFTDRMRRIKIPLPPVDER
KKVVEDVDKDRRYAIDAAIVRIMKSRKVLGHQQLVSECVEQLSRMFKPDIKAIKKRMEDLITRDYL
ERDKENANMFRYLA

Fig. 60

MMIERKTIDLEQGWDFMQKGITKLKNILEGFPEPQFSSEDYMMLYTT[M]YNMCTQKPPHDYSQQL
YEKYREAIEEYITSTVLPSLREKHDEFMLRELVKRWSNHKVMVRWLSRFFHYLDRYFIARRSLPPL
HEVGLTCFRDLVYQEINGKVRDAVISLINQEREGEQIDRALLKNVLDIFVEVGMSQMDYYENDFEA
DMLKDTAAYYSRKASNWILEDSCPDYMLKAEECLRREKDRVSNYLHSSSEPKLLEKVQHELLSHYA
TQLLEKEHSGCHALLRDDKVADLSRMYRLFSKIPRGLDPVSNIFKQHVTAEGTALVKQAEDAASNK
KAEKRDVVGLQEQVFVRKIIELHDKYLTYVNDCFTNHTLFHKALKEAFEIFCNKGVSGSSSAELLA
TFCDNILKKGGSEKLSDEAIEETLEKVVRLLAYISDKDLFAEFYRKKLARRLLFDKSANDEHERSI
LTKLKQQCGGQFTSKMEGMVTDLTLAKENQSNFEEYLNNNSNVNPGIDLTVTVLTTGFWPSYKSFD
LNLPAEMVKCVEVFREFYQTKTKHRKLTWIYSLGTCNIIGKFDPKTMELIVTTYQASALLLFNSSD
RLSYNEIMTQLNLSDDDVVRLLHSLSCAKYKILSKEPNTKTISPTDCFQFNSKFTDKMRRIKIPLP
PVDEKKKVIEDVDKDRRYAIDASIVRIMKSRKVLGYQQLVMECVEQLGRMFKPDVKAIKKRIEDLI
TRDYLERDKDNANLFRYLA

Fig. 61

MNERKTIDLDNGWEFMQKGITKLKKILEGQPEPQFSSEDYMMLYTT[M]YNMCTQKPPHDYSQQLY
DKYREAFEEYITSTVLPSLREKHDEFMLRELVNRWTNHKVMVRWLSRFFHYLDRYFIARRSLPALH
EVGLTCFRDLVYQELKVKVRDAVISLIDQEREGEQIDRALLKNVLDIFVEIGMSQMDQYENDFEEA
MLTDTAAYYSRKASNWILEDSCPDYMLKAEECLRREKDRVSHYLHFSSEPKLLEKVQHELLSVYAT
QLLEKEHSGCHALLRDDKVDDLSRMYRLFSKIPKGLDPVSYIFKQHVTNEGMALVKQAEDAASNKK
AEKRDVVSLQEQVFVRKIIELHDKYLAYVNDCFTNHTLFHKALKEAFEIFCNKGVAGSSNAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLAKENQSSFEEYLGNNANVNPGIDLTVTVLTTGFWPSYKSFDL
NLPAEMVKCVEVFREFYQTKTKHRKLTWIYSLGTCNINGKFEPKTIELIVTTYQASALLLFNTSDR
LSYQEIMTQLNLSDDDVVRLLHSLSCAKYKILTKEPNNKTISPTDYFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNANLFRYLA

Fig. 62

MNERKTIDLEQGWDFMQKGITKLKNILEGLPEPQFSSEDYMMLYTT[M]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQTELLSVYAT
QLLEKEHSGCHALLRDDKVDDLSRMYRLFSKIQKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNSSDR
LSYQEIMTQLNLSDDDVVRLLHSLSCAKYKILLKEPNTKTISPTDFFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 63

MNERKTIDLEQGWDFMQKGITKLKNILEGLPEPQFSSEDYMMLYTT[M]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQTELLSVYAT
QLLEKEHSGCHALLRDDKVDDLSRMYRLFSKIQKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNSSDR
LSYQEIMTQLNLSDDDVVRLLHSLSCAKYKILLKEPNTKTISPTDFFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 64

MSLHERKTIDLEQGWAFMQKGITKLKNILDELNEPQFSSEDYMMLYTT[M]YNMCTQKPPHDYSQE
LYDKYRESFEEYITTTVLPSLREKHDEYMLRELVRRWSNHKIMVRWLSRFFHYLDRYFIARRSLPA
LNEVGLTCFRDLVYNEVHGKVKDAVISLIDQEREGEQIDRALLKNVLGIFVEIGLGSMECYENDFE
TSMLNATAAYYSRKASNWILEDSCPDYMLKAEECLKHEKDRVAHYLHSSSEQKLLEKVQHELLFVY
ASQLLEKEHSGCHALLRDDKVGDLSRMYRLFCRITRGLDPVSQIFKQHVTAEGTALVKHAEDAASN
KKAEKKDIVGLQEQVFVRKVIELHDKYLAYVTDCFQNHSLFHKALKEAFEVFCNKGVAGSSSAELL
AAFCDNILKKGGSEKLSDEAIEDTLEKVVKLLAYISDKDLFAEFYRKKLARRLLFDKSANDDHERS
ILTKLKQQCGGQFTSKMEGMVTDLTLARENQSSFDDYLSSNPKANSGIDLTVTVLTTGFWPSYKSF
DLNLPDEMVKCVEIFKEFYETKTKHRKLTWIYSLGTCNINGKFETKTIELVVTTYQAAVLLLFNSA
DKLSYSEIVQQLNLSDDDVIRLLHSLSCAKYKILNKEPATKTITPNDHFEFNSKFTDRMRRIKIPL
PPVDEKKKVIEDVDKDRRYAIDASIVRIMKSRKVLGHQQLVLECVEQLGRMFKPDFKAIKKRIEDL
IARDYLERDKDNPNLFKYLA

Fig. 65

MNERKTIDLEQGWDFMQKGITKLKNILEGLPEPQFSSEDYMMLYTT[M]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQNELLSVYAT
QLLEKEHSGCHALLRDDKVDDLSRMYRLFSKIPKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNLSDR
LSYQEIMTQLNLSDDDVVRLLHSLSCAKYKILLKEPNTKTISPTDYFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 66

MERKTIDLEQGWDYMQTGITKLKRILEGLPEPQFDSEQYMMLYTT[M]YNMCTQKPPHDYSQQLYD
KYREAFEEYIDSTVLPALKEKHDEYMLRELVKRWSNHKVMVRWLSRFFYYLDRYFIARRSLPPLNE
VGLTCFRDRVYKELHSKVKDAVIALVDKEREGEQIDRALLKNVLDIYVEIGMGQMERYEVDFESFM
LLDSASYYSRKASNWIQEDSCPDYMLKSEECLKKERERVAHYLHSSSEPKLVEKVQHELLVVYANQ
LLEKEHSGCRALLRDDKVDDLSRMYRLYHKIAKGLEPVANIFKQHVTAEGNALVQQAEDTATNQAA
NTASVQEQVLIRKVIELHDKYMVYVVECFQNHTLFHKALKEAFEIFCNKTVAGSSSAELLATFCDN
ILKKGGSEKLSDEAIEDTLEKVVKLLAYISDKDLFAEFYRKKLARRLLFDRSANDDHERSILTKLK
QQCGGQFTSKMEGMVTDLTLARENQTSFEEYLGNNPAANPGIDLTVTVLTTGFWPSYKSFDINLPS
EMVKCVEVFKGFYETKTKHRKLTWIYSLGTCHLNGKFDHKPIELVVSTYQAAVLLLFNTTDKLSYN
DILTQLNLSHEDLVRLLHSLSCARYKILLKEPSTKTVTQTDSFEFNAKFTDRMRRIKIPLPPVDER
KKVVEDVDKDRRYAIDAAIVRIMKSRKVLGHQQLVSECVEQLSRMFKPDIKAIKKRMEDLITRDYL
ERDKENPNMFRYLA

Fig. 67

MNDRKVIELEQGWEFMGKGITKLKRILEGLPEPPFNSEDYMMLYTT[M]YNMCTQKPPHDYSQQLY
DNYKEAFVDYIHSTVLPSLGDKHDEFMLRELVKRWSNHKVMVRWLSRFFHYLDRYFIARRSLPSLN
DVGLTCFRDLVYQEISGKAKDAVIALIDEEREGGQIDRALLKNVLDIYVEIGMTQMDYYEKDFEAH
MLDDTAAYYSRKASSWILEDSCPEYMLKSEECLKKEKDRVAHYLHSSSEPKLLEKVQNELLLVYEN
QLLEKENSGCRALLKDDKVEDLSRMYRLYSKVTKGLEPIGSIFKQHITDEGTALVQQAEDAAISKA
ENAGGGSHEQVFVRKVIELHDKFMTYVTDCFNSHTIFHKALKEAFEVFLNKGVAGSSSAELLASFC
DNILKKGGSEKLSDEAIEDSLEKVVKLLAYVSDKDLFAEFYRKKLSRRLLFDKSANDDHERSILTK
LKQQCGGQFTSKMEGMVTDLTLARENQTNFEEYLGQNTDASPGLDLTVTVLTTGFWPSYKSSDLNL
PAEMVRCVEVFKQFYQTKTKHRKLTWVYSLGSCNINGKFGPKTIELVVGTYQAAALMLFNTSDRLS
YSEITTQLNLADEDLVRVLQSLSCAKYKILLKEPSTRNVISTDCFSFNSNFTDRMRRIRIPLPPMD
ERKKVVEDVDKDRRYAIDASIVRIMKSRKALGYQQLITECVEQLSRMFKPDFKAIKKRIEDLITRD
YIERDKENPQLFRYLA

Fig. 68

MNDRKVIELEQGWEFMGKGITKLKRILEGLPEPPFNSEDYMMLYTT[M]YNMCTQKPPHDYSQQLY
DNYKQAFVDYINSTVLPSLREKHDEFMLRELVKRWANHKVMVRWLSRFFHYLDRYFIARRSLPSLN
EVGLTCFRDLVYQEISGKAKDAVIALIDIEREGGQIDRSLLKNVLDIYVEIGMGQMDHYEKDFEAH
MLDDTAAYYSRKASSWILEDSCPEYMLKSEECLKKEKERVANYLHSSSEPKLLEKVQNELLLVYES
QLLEKENSGCRALLKDDKVDDLSRMYRLYSKVTKGLEPIGSIFKQHITDEGTALVQQAEDAAISKA
ENTGGSHEQVFVRKVIELHDKFMTYVTDCFNSHTIFHKALKEAFEVFLNKGVAGSSSAELLATFCD
NILKKGGSEKLSDEAIEDSLEKVVKLLAYVSDKDLFAEFYRKKLSRRLLFDKSANDDHERSILTKL
KQQCGGQFTSKMEGMVTDLTLARENQTNFEEYLSQNPDASPGLDLTVTVLTTGFWPSYKSSDLNLP
AEMVRCVEVFKQFYSTKTKHRKLTWVYSLGSCNINGKFGPKTIELVVGTYQAAALMLFNTSDRLSY
SEIATQLNLADEDLVRVLQSLSCAKYKILLKEPNTKTVSPTDCFSFNSSFTDRMRRIRIPLPPMDE
RKKVVEDVDKDRRYAIDASIVRIMKSRKVLGYQQLITECVEQLSRMFKPDFKAIKKRIEDLITRDY
IERDKENPQLFRYLA

Fig. 69A

```
Brassica_Cull_Cds          -------ATGGAGCGCAAGACGATTGACTTGGACCAAGGATGGGACTATATGCAGACT
Radish_Cull_Cds            -------ATGGAGCGGAAGACGATTGATCTGGAACAAGGATGGGACTATATGCAGACT
Beet_Cull_Cds              ----ATGAATGATCGTAAAGTTATTGAACTAGAGCAAGGATGGGAGTTCATGGGGAAG
Spinach_Cull_Cds           ----ATGAACGATCGTAAAGTTATCGAACTAGAGCAAGGATGGGAGTTCATGGGGAAG
Leek_Cull_Cds              ATGTCGTTGCACGAAAGGAAAACCATTGATTTGGAGCAGGGATGGGCTTTTATGCAGAAA
Squash_Cull_Cds            ATGACAATGGGTGAGCGGAAGACTATTGACTTGGAGCAAGGATGGGAGTTTATGCAGAAG
WaterMelon_Cull_Cds        ATGACAATGGGCGAGCGGAAGACTATTGACTTGGAACAAGGATGGGAGTTTATGCAGAAG
Cucumber_Cull_Cds          ATGACAATGGGCGAGCGGAAGACTATTGACTTGGAGCAGGGATGGGAGTTTATGCAGAAG
Melon_Cull_Cds             ATGACAATGGGCGAGCGGAAGACTATTGACTTGGAACAGGGATGGGAGTTTATGCAGAAG
Tomato_Cull_Cds            ----ATGAACCAACGAAGCACAATCGATCTGGAACATGGATGGGACTTCATGCAAAGG
Eggplant_Cull_Cds          ----ATGAACCAACGCAGCACAATCGATCTGGAACATGGATGGGATTTCATGCAAAAG
Pepper_Cull_Cds            ----ATGAACCAGCGTTCCACAATCAATCTAGAACATGGATGGGACTTCATGCAAAGG
Lettuce_Cull_Cds           ----ATGAACGAAAGAAAAACAATAGACTTAGAGCAAGGATGGGACTTCATGCAGAAA
Chicory_Cull_Cds           ----ATGAATGAAAGAAAAACAATAGACTTAGAACAAGGATGGGACTTCATGCAGAAA
Endive_Cull_Cds            ----ATGAATGAAAGAAAAACAATAGACTTAGAACAAGGATGGGACTTCATGCAAAAA
Carrot_Cull_Cds            -ATGATGATTGAGCGGAAAACTATAGACCTGGAGCAGGGATGGGACTTTATGCAAAAG
Celery_Cull_Cds            ----ATGAACGAGCGGAAGACTATCGATTTGGATAATGGATGGGAATTTATGCAGAAA

Brassica_Cull_Cds          GGTATCACTAAGCTGAAACGGATTCTTGAGGGGCTGCCTGAGCCGCAGTTTGACTCTGAG
Radish_Cull_Cds            GGGATCACTAAGCTGAAACGGATTCTTGAAGGATTGCCTGAGCCGCAATTCGACTCTGAG
Beet_Cull_Cds              GGGATTACAAAGTTGAAGAGGATTCTGGAAGGATTGCCAGAGCCACCATTTAATTCTGAA
Spinach_Cull_Cds           GGGATTACGAAGTTGAAAAGGATTTTGGAAGGATTACCAGAGCCGCCTTTTAATTCGGAA
Leek_Cull_Cds              GGGATCACCAAACTGAAGAATATTCTTGATGAGTTGAATGAACCTCAGTTCAGCTCAGAG
Squash_Cull_Cds            GGAATCACAAAATTGAAGAACATTCTGGAAGGATTGCCTGAGCCACAGTTCAGCTCCGAG
WaterMelon_Cull_Cds        GGAATCACAAAGTTGAAGAACATTCTTGAGGGCTTGCCTGAGCCTCAGTTCAGCTCCGAG
CuCumber_Cull_Cds          GGTATCACAAAGTTGAAGAACATTCTCGAGGGCTTGCCTGAGCCTCAGTTCAGCTCCGAG
Melon_Cull_Cds             GGTATCACAAAGTTGAAGAACATTCTTGAGGGCTTGCCTGAGCCCCAGTTCAGCTCCGAG
Tomato_Cull_Cds            GGCATTACAAAGCTGAAGAACATTCTAGAAGGGCTGCCTGAGCCTCAATTCAGCTCAGAG
Eggplant_Cull_Cds          GGCATCACAAAGCTGAAGAACATTCTAGAAGGGCTGCCTGAGCCTCAGTTCAGCTCAGAG
Pepper_Cull_Cds            GGCATTACAAAGCTGAAGAACATTCTAGAAGGGCTGCCCGAGCCTCAGTTCAGCTCAGAG
Lettuce_Cull_Cds           GGAATAACAAAGTTGAAGAATATTCTAGAAGGTCTTCCCGAGCCACAATTCAGCTCGGAG
Chicory_Cull_Cds           GGCATAACAAAGTTGAAGAACATTCTAGAAGGTCTTCCCGAGCCACAATTCAGCTCGGAA
Endive_Cull_Cds            GGCATAACAAAGTTGAAGAACATTCTAGAAGGTCTTCCCGAGCCACAATTCAGCTCAGAG
Carrot_Cull_Cds            GGAATCACAAAGCTAAAGAATATTTTAGAAGGCTTTCCGGAGCCGCAATTCAGCTCGGAG
Celery_Cull_Cds            GGGATCACTAAGTTGAAGAAGATTCTCGAAGGTCAACCTGAGCCTCAGTTTAGCTCCGAG
```

Fig. 69B

| | |
|---|---|
| Brassica_Cul1_Cds | CAATACATGATGCTCTATACGACTAT[C]TACAACATGTGCACTCAGAAACCTCCTCATGAT |
| Radish_Cul1_Cds | CAGTACATGATGCTTTATACGACTAT[C]TACAACATGTGCACCCAGAAACCTCCTCATGAT |
| Beet_Cul1_Cds | GACTACATGATGTTGTACACGACGAT[A]TACAATATGTGTACTCAGAAACCCCCACATGAT |
| Spinach_Cul1_Cds | GACTACATGATGCTGTACACGACAAT[A]TACAACATGTGTACACAGAAACCCCCTCATGAT |
| Leek_Cul1_Cds | GATTACATGATGCTCTATACGACTAT[C]TATAATATGTGTACTCAGAAGCCGCCACATGAT |
| Squash_Cul1_Cds | GACTACATGATGCTTTACACTACAAT[A]TATAACATGTGTACCCAGAAGCCACCGCATGAT |
| WaterMelon_Cul1_Cds | GACTACATGATGCTTTATACCACCAT[A]TACAACATGTGCACACAAAAGCCGCCACATGAT |
| CuCumber_Cul1_Cds | GACTACATGATGCTTTACACTACCAT[A]TATAACATGTGCACCCAAAAGCCGCCGCATGAT |
| Melon_Cul1_Cds | GACTACATGATGCTTTACACTACCAT[A]TATAACATGTGCACCCAAAAGCCGCCGCATGAT |
| Tomato_Cul1_Cds | GACTATATGATGCTATATACGACAAT[T]TACAACATGTGTACTCAAAAGCCCCCACATGAT |
| Eggplant_Cul1_Cds | GACTATATGATGCTGTATACGACAAT[T]TACAACATGTGTACTCAGAAGCCCCCACATGAT |
| Pepper_Cul1_Cds | GACTATATGATGCTGTATACGACAAT[T]TACAACATGTGTACTCAGAAGCCCCCACATGAT |
| Lettuce_Cul1_Cds | GATTACATGATGCTCTACACAACCAT[C]TACAACATGTGTACACAGAAACCACCACATGAT |
| Chicory_Cul1_Cds | GATTACATGATGCTCTACACAACCAT[C]TACAATATGTGCACACAAAAACCGCCACATGAT |
| Endive_Cul1_Cds | GATTACATGATGCTCTACACAACCAT[C]TACAATATGTGCACACAAAAACCGCCACATGAT |
| Carrot_Cul1_Cds | GATTATATGATGCTTTATACAACTAT[C]TATAACATGTGTACACAGAAACCTCCACATGAT |
| Celery_Cul1_Cds | GACTATATGATGCTTTACACAACTAT[C]TATAATATGTGTACGCAGAAGCCTCCACATGAT |

| | |
|---|---|
| Brassica_Cul1_Cds | TACTCACAGCAGCTTTATGACAAGTATCGTGAAGCATTTGAGGAGTATATTCACTCAACT |
| Radish_Cul1_Cds | TACTCTCAGCAGCTTTATGACAAGTATCGCGAAGCTTTTGAGGAGTACATTGACTCTACT |
| Beet_Cul1_Cds | TACTCTCAACAGCTCTATGACAATTACAAACAGGCTTTTGTGGATTACATCAACTCGACG |
| Spinach_Cul1_Cds | TACTCTCAACAACTCTATGACAATTACAAAGAGGCATTTGTGGATTACATACATTCAACG |
| Leek_Cul1_Cds | TATTCTCAGGAGTTGTATGATAAGTACCGAGAGTCCTTTGAAGAGTATATCACTACCACT |
| Squash_Cul1_Cds | TACTCCCAGCAGCTGTATGATAAATACCGCGAATCGTTTGAGGAGTACATCAGTTCTATG |
| WaterMelon_Cul1_Cds | TACTCCCAGCAGCTATACGATAAATACCGTGAATCTTTTGAGGAGTATATCACTTCTATG |
| CuCumber_Cul1_Cds | TACTCCCAGCAGCTGTATGATAAATATCGTGAATCTTTTGAAGAGTACATCACTTCTATG |
| Melon_Cul1_Cds | TACTCCCAGCAGCTGTATGATAAATATCGTGAATCTTTTGAAGAGTACATCACTTCTATG |
| Tomato_Cul1_Cds | TATTCTCAACAGCTGTATGACAAATATCGTGAAGCTTTTGAAGAATATATCACAACAACG |
| Eggplant_Cul1_Cds | TATTCTCAACAGCTGTATGACAAATATCGTGAAGCTTTTGAAGAATATATCACAACGACG |
| Pepper_Cul1_Cds | TATTCTCAACAGCTGTATGACAAATATCGTGAAGCTTTTGAAGAATATATCACAACAACG |
| Lettuce_Cul1_Cds | TACTCCCAACAGTTGTATGACAAATATCGTGAGTCTTTTGAAGAGTATATTACTTCAACT |
| Chicory_Cul1_Cds | TACTCTCAACAATTGTATGACAAATACCGCGAGTCTTTTGAAGAGTACATTACTTCAACG |
| Endive_Cul1_Cds | TACTCTCAACAATTATATGACAAATACCGCGAGTCTTTTGAAGAGTACATAACTTCAACG |
| Carrot_Cul1_Cds | TACTCTCAGCAGCTGTATGAAAAGTATCGTGAAGCTATTGAGGAGTACATTACTTCTACA |
| Celery_Cul1_Cds | TATTCTCAACAGCTGTATGACAAGTACCGTGAGGCCTTTGAGGAGTACATAACTTCAACT |

Fig. 69C

| | |
|---|---|
| Brassica_Cul1_Cds | GTTTTGCCTGCTCTAAGGGAGAAGCATGATGAGTACATGCTGAGGGAGCTGGTTAAGAGA |
| Radish_Cul1_Cds | GTTTTGCCTGCTTTGAAGGAGAAGCATGATGAATACATGCTACGGGAGCTGGTTAAGAGA |
| Beet_Cul1_Cds | GTTTTACCTTCTTTGCGGGAGAAGCATGATGAGTTTATGTTAAGAGAACTTGTGAAAAGA |
| Spinach_Cul1_Cds | GTTTTACCTTCTTTGGGGGACAAACATGATGAGTTTATGCTGAGAGAGCTTGTGAAGAGA |
| Leek_Cul1_Cds | GTGCTTCCTTCATTGAGAGAAAAGCATGATGAATACATGTTAAGGGAGCTCGTGAGAAGG |
| Squash_Cul1_Cds | GTTTTACCATCCTTGAGGGAGAAGCATGACGAATTTATGTTGAGAGAACTGGTCAAAAGG |
| WaterMelon_Cul1_Cds | GTCTTACCATCCTTGAGGGAGAAGCATGACGAGTTCATGTTGAGAGAACTGGTCAAAAGG |
| CuCumber_Cul1_Cds | GTCTTACCATCCTTGAGGGAGAAGCACGATGAGTTCATGTTGAGAGAACTAGTAAAAAGG |
| Melon_Cul1_Cds | GTCTTACCATCCTTGAGGGAGAAGCATGACGAGTTCATGTTGAGAGAACTAGTCAAAAGG |
| Tomato_Cul1_Cds | GTATTGCCTTCTTTGAGAGAAAAACATGACGAGTTTATGTTGCGAGAGTTGGTAAAAAGG |
| Eggplant_Cul1_Cds | GTATTACCTTCTTTGAGAGAAAAACATGACGAGTTCATGTTGCGAGAGTTGGTAAAAAGG |
| Pepper_Cul1_Cds | GTATTGCCTTCTTTGAGAGAAAAACATGACGAGTTCATGTTGCGAGAGCTGGTAAAAAGG |
| Lettuce_Cul1_Cds | GTGTTACCTTCTTTAAGAGAGAAGCATGATGAGTTCATGCTGAGAGAGCTTGTTAGAAGG |
| Chicory_Cul1_Cds | GTGTTACCTTCTTTAAGAGAGAAGCATGATGAGTTTATGCTTAGAGAGCTTGTTAGAAGA |
| Endive_Cul1_Cds | GTGTTACCTTCTTTAAGAGAGAAGCATGATGAGTTTATGCTTAGAGAGCTTGTTAGAAGG |
| Carrot_Cul1_Cds | GTATTGCCTTCATTGAGAGAGAAGCATGATGAATTCATGCTTAGAGAACTTGTGAAGAGA |
| Celery_Cul1_Cds | GTCCTGCCTTCTTTACGAGAGAAGCATGATGAGTTTATGTTGAGAGAGCTCGTGAATAGA |

| | |
|---|---|
| Brassica_Cul1_Cds | TGGTCTAACCATAAAGTTATGGTTCGATGGCTATCCCGCTTCTTCTACTATCTTGACCGT |
| Radish_Cul1_Cds | TGGTCTAACCATAAAGTTATGGTTAGATGGCTATCCCGATTCTTCTACTATCTTGACCGT |
| Beet_Cul1_Cds | TGGGCAAATCATAAAGTAATGGTCAGGTGGTTGTCTCGTTTCTTCCATTATCTGGACCGG |
| Spinach_Cul1_Cds | TGGTCAAATCATAAAGTAATGGTGAGGTGGTTGTCTCGCTTCTTCCATTATCTGGATCGG |
| Leek_Cul1_Cds | TGGTCAAATCATAAAATAATGGTTAGATGGCTTTCACGCTTTTTCCATTATCTTGATCGC |
| Squash_Cul1_Cds | TGGACCAACCATAAAGTCATGGTGAGGTGGCTTTCTCGCTTCTTCCACTATCTTGATCGA |
| WaterMelon_Cul1_Cds | TGGACGAACCATAAAGTCATGGTGAGGTGGCTTTCTCGCTTCTTCCACTATCTTGACCGA |
| CuCumber_Cul1_Cds | TGGACAAACCATAAAGTCATGGTGAGGTGGCTTTCTCGCTTCTTCCACTATCTTGATCGG |
| Melon_Cul1_Cds | TGGACAAACCATAAAGTCATGGTGAGGTGGCTTTCTCGCTTCTTCCACTATCTTGATCGG |
| Tomato_Cul1_Cds | TGGTCAAATCATAAAGTCATGGTCAGATGGTTGTCAAGATTCTTCCATTACCTTGACCGG |
| Eggplant_Cul1_Cds | TGGTCAAACCATAAGGTCATGGTTAGATGGTTATCGCGATTCTTCCATTATCTTGACCGT |
| Pepper_Cul1_Cds | TGGTCAAACCATAAGGTCATGGTCAGATGGTTATCGCGATTCTTCCATTATCTTGATCGC |
| Lettuce_Cul1_Cds | TGGTCAAATCATAAAGTCATGGTGCGGTGGCTTTCTAGATTCTTCCATTATCTTGACCGA |
| Chicory_Cul1_Cds | TGGTCAAATCATAAAGTGATGGTTAGGTGGCTTTCTAGATTCTTCCATTATCTTGATCGA |
| Endive_Cul1_Cds | TGGTCAAATCATAAAGTGATGGTTAGGTGGCTTTCTAGATTCTTCCATTATCTTGATCGA |
| Carrot_Cul1_Cds | TGGTCTAATCATAAGGTCATGGTCAGGTGGCTTTCTCGATTCTTTCACTATCTTGATCGC |
| Celery_Cul1_Cds | TGGACAAACCATAAAGTCATGGTCAGGTGGCTTTCTCGATTCTTTCACTATCTTGATCGG |

Fig. 69D

| | |
|---|---|
| Brassica_Cul1_Cds | TACTTCATTGCTCGGAGGTCACTTCCACCCCTGAATGAAGTTGGCCTGACTTGCTTCCGT |
| Radish_Cul1_Cds | TACTTCATTGCTCGGAGATCGCTGCCACCGCTTAATGAAGTTGGGCTCACATGCTTCCGT |
| Beet_Cul1_Cds | TATTTCATTGCTCGGAGGTCGCTTCCTTCTTTGAATGAAGTTGGACTGACTTGTTTCCGT |
| Spinach_Cul1_Cds | TACTTCATCGCTCGGAGATCGCTTCCTTCTTTGAATGATGTTGGATTGACGTGCTTCCGT |
| Leek_Cul1_Cds | TACTTTATAGCACGAAGATCATTGCCTGCTCTTAATGAAGTCGGTCTCACTTGTTTCCGT |
| Squash_Cul1_Cds | TACTTCATTGCTCGAAGGTCACTTCCACCTCTCAATGAAGTTGGCCTCACTTGCTTCCGT |
| WaterMelon_Cul1_Cds | TACTTCATTGCTCGAAGATCACTTCCACCTCTCAACGAAGTTGGCCTCACATGCTTCCGT |
| CuCumber_Cul1_Cds | TACTTCATCGCTCGAAGGTCACTTCCACCTCTAAATGAAGTTGGCCTCACATGCTTCCGC |
| Melon_Cul1_Cds | TACTTCATCGCTCGAAGGTCACTTCCACCTCTAAATGAAGTTGGCCTCACATGCTTCCGC |
| Tomato_Cul1_Cds | TATTTCATTGCCCGGAGATCTCTGCCGGGGCTTAATGAAGTTGGACTAACTTGCTTCCGC |
| Eggplant_Cul1_Cds | TATTTCATTGCTCGGAGATCACTGCCAGGGCTTAATGAAGTTGGACTAACTTGCTTCCGC |
| Pepper_Cul1_Cds | TATTTCATTGCCCGGAGATCTCTACCGGGGCTTAATGAAGTTGGACTAACTTGCTTCCGA |
| Lettuce_Cul1_Cds | TATTTCATTGCCCGAAGATCTCTTCCGCCACTAAATGAAGTTGGACTTGCCTGTTTTCGT |
| Chicory_Cul1_Cds | TACTTCATTGCCCGAAGATCTCTTCCACCATTAAATGAAGTTGGACTTGCGTGTTTTCGT |
| Endive_Cul1_Cds | TACTTTATTGCAAGAAGATCTCTTCCACCATTAAATGAAGTTGGACTTGCGTGTTTTCGT |
| Carrot_Cul1_Cds | TATTTTATTGCTCGGAGGTCACTTCCACCACTTCATGAAGTTGGACTCACTTGCTTTCGG |
| Celery_Cul1_Cds | TACTTCATTGCGAGGAGGTCACTTCCTGCACTTCATGAAGTTGGACTCACGTGCTTCCGG |

| | |
|---|---|
| Brassica_Cul1_Cds | GACCTGGTTTATAACGAGTTGCATTCCAAGGTCAAAGATGCTGTAATAGCACTTGTTGAT |
| Radish_Cul1_Cds | GACCGGGTGTATAAGGAGTTGCATTCCAAGGTCAAAGATGCTGTAATAGCACTTGTTGAT |
| Beet_Cul1_Cds | GATCTGGTTTATCAAGAAATATCTGGCAAAGCCAAGGATGCTGTTATAGCCCTGATTGAT |
| Spinach_Cul1_Cds | GATCTGGTTTATCAAGAAATATCTGGCAAAGCCAAGGATGCTGTTATTGCTCTGATTGAT |
| Leek_Cul1_Cds | GATCTGGTGTACAACGAAGTCCATGGGAAAGTTAAAGATGCCGTGATCTCATTGATTGAC |
| Squash_Cul1_Cds | GAATTGGTGTACAAAGAGCTAAACAGTAAAGTGAGGGATGCAGTAATTTCATTGATCGAT |
| WaterMelon_Cul1_Cds | GAATTGGTGTACAAAGAGCTAAACAGTAAAGTGAGGGATGCAGTAATTTCATTGATTGAT |
| CuCumber_Cul1_Cds | GAATTGGTGTACAAAGAGCTAAATAGTAAAGTGAGGGATGCAGTAATTTCATTGATTGAT |
| Melon_Cul1_Cds | GAATTGGTGTACAAAGAGCTAAACAGTAAAGTGAGGGATGCAGTAATCTCATTGATTGAT |
| Tomato_Cul1_Cds | GATCAGGTCTACCAAGAGTTGAATGGAAAAGTCAGGGATGCTGTTATATCTCTGATTGAT |
| Eggplant_Cul1_Cds | GATCTGGTCTACCAAGAGTTGAATGGAAAAGTCAGGGATGCTGTTATATCTCTGATTGAT |
| Pepper_Cul1_Cds | GATCTGGTCTACCAAGAGTTGAATGGAAAAGTCAGGGATGCTGTTATATCTCTGATTGAT |
| Lettuce_Cul1_Cds | GATCTGGTATACCAAGAGGTGAATGGTAAAGTGAGAGATGCTGTAATATCTTTGATTGAT |
| Chicory_Cul1_Cds | GATCTGGTATACCAAGAGGTGAATGGGAAAGTGAGAGATGCTGTAATATCTTTGATTGAT |
| Endive_Cul1_Cds | GATCTGGTATACCAAGAGGTGAATGGAAAAGTGAGAGATGCTGTAATATCTTTGATTGAT |
| Carrot_Cul1_Cds | GACCTGGTTTACCAGGAGATAAATGGGAAAGTAAGGGATGCTGTAATATCATTGATTAAT |
| Celery_Cul1_Cds | GATCTGGTCTATCAGGAGCTGAAAGTTAAAGTGAGGGATGCTGTAATATCTCTGATCGAT |

Fig. 69E

| | |
|---|---|
| Brassica_Cull_Cds | AAAGAACGGGAGGGTGAGCAGATTGACAGGGCTCTATTGAAAAACGTATTAGACATTTAT |
| Radish_Cull_Cds | AAAGAACGGGAAGGCGAGCAGATTGACAGGGCTCTTCTGAAAAACGTATTAGATATCTAT |
| Beet_Cull_Cds | ATAGAAAGAGAAGGTGGGCAGATTGACAGATCATTATTGAAAAATGTACTTGATATATAT |
| Spinach_Cull_Cds | GAAGAAAGAGAGGGTGGGCAAATTGACAGAGCCTTATTGAAGAATGTACTTGATATATAC |
| Leek_Cull_Cds | CAAGAGAGGGAAGGGGAGCAAATTGACAGAGCTTTATTAAAGAATGTTTTGGGTATTTTT |
| Squash_Cull_Cds | CAAGAACGTGAAGGAGAGCAGATTGACAGAGCTCTGTTGAAGAACGTGTTGGATATATTT |
| WaterMelon_Cull_Cds | CAAGAACGTGAAGGAGAGCAGATTGACAGAGCTCTACTGAAGAATGTATTAGATATATTT |
| CuCumber_Cull_Cds | CAAGAACGTGAAGGAGAACAGATTGACAGAGCTCTACTGAAGAATGTACTAGATATATTT |
| Melon_Cull_Cds | CAAGAACGTGAAGGAGAACAGATTGACAGAGCTCTACTGAAGAATGTATTAGATATATTT |
| Tomato_Cull_Cds | CAAGAGCGTGAGGGAGAGCAAATTGACAGAGCTCTACTTAAGAATGTGCTTGATATATTT |
| Eggplant_Cull_Cds | CAAGAGCGTGAGGGAGAGCAAATTGACAGAGCTCTACTGAAGAATGTGCTAGATATATTT |
| Pepper_Cull_Cds | CAAGAGCGTGAGGGAGAGCAAATTGACAGAGCTCTACTGAAGAATGTGCTAGATATATTT |
| Lettuce_Cull_Cds | CAAGAGCGTGAAGGGGAGCAGATTGATCGAGCTTTACTGAAGAATGTTCTAGATATATTT |
| Chicory_Cull_Cds | CAAGAGCGTGAAGGCGAGCAAATTGACCGAGCATTACTCAAGAATGTTCTAGATATATTT |
| Endive_Cull_Cds | CAAGAGCGTGAAGGCGAGCAAATTGACCGAGCATTACTGAAGAATGTTCTAGATATATTT |
| Carrot_Cull_Cds | CAAGAGCGCGAGGGAGAGCAAATTGACCGAGCTTTGTTGAAGAATGTTCTAGATATATTT |
| Celery_Cull_Cds | CAAGAGCGTGAGGGGGAACAGATTGACCGAGCTTTATTAAAGAACGTGTTAGATATATTT |

| | |
|---|---|
| Brassica_Cull_Cds | GTAGAGATTGGAATGGGACAGATGGAAAGATACGAGGAGGATTTTGAAAGCTTCATGCTT |
| Radish_Cull_Cds | GTAGAGATTGGAATGGGACAGATGGAAAGATACGAAGTGGATTTTGAAAGCTTCATGCTT |
| Beet_Cull_Cds | GTTGAAATTGGAATGGGACAAATGGATCACTATGAAAAAGACTTTGAAGCTCATATGCTG |
| Spinach_Cull_Cds | GTTGAAATTGGAATGACACAAATGGATTACTACGAAAAGGACTTTGAAGCTCATATGCTG |
| Leek_Cull_Cds | GTAGAGATTGGTTTGGGAAGCATGGAATGTTATGAGAATGATTTTGAAACATCAATGCTT |
| Squash_Cull_Cds | GTGGAGATTGGGATGGGGCAAATGGATTATTATGAAAATGACTTTGAAGCTGCCATGCTT |
| WaterMelon_Cull_Cds | GTGGAAATTGGGATGGGGCAAATGGATTACTATGAAAATGACTTTGAAGCTGCCATGCTT |
| CuCumber_Cull_Cds | GTGGAAATTGGTATGGGGCAAATGGATTACTATGAAAATGACTTTGAAGCTGCCATGCTT |
| Melon_Cull_Cds | GTGGAAATTGGTATGGGGCAAATGGATTACTATGAAAATGACTTTGAAGCTGCCATGCTT |
| Tomato_Cull_Cds | GTCGAAATTGGAATGGGGTTAATGGATTATTATGAGAATGATTTTGAAGCTGCAATGCTC |
| Eggplant_Cull_Cds | GTTGAAATTGGAATGGGGTCAATGGATTATTATGAGAATGATTTTGAAGCTGCAATGCTC |
| Pepper_Cull_Cds | GTTGAAATTGGAATGGGGTCGATGGATTATTATGAGAATGATTTTGAAGCTGCAATGCTC |
| Lettuce_Cull_Cds | GTTGAGATAGGAATGGGACAAATGGAGTATTATGAGAATGATTTTGAAGCATCCATGCTT |
| Chicory_Cull_Cds | GTTGAAATAGGAATGGGACAAATGGAATATTATGAGAATGATTTTGAAGCATCCATGCTT |
| Endive_Cull_Cds | GTTGAAATAGGAATGGGACAAATGGAATATTATGAGAATGATTTTGAAGCATCTATGCTT |
| Carrot_Cull_Cds | GTTGAAGTTGGAATGAGTCAAATGGATTATTATGAGAATGACTTTGAAGCAGACATGCTC |
| Celery_Cull_Cds | GTTGAAATCGGAATGAGTCAAATGGATCAATATGAGAATGACTTTGAAGAAGCCATGCTC |

Fig. 69F

| | |
|---|---|
| Brassica_Cul1_Cds | TTAGATTCAGCATCTTACTATTCTCGCAAGGCGTCAAGCTGGATCCAAGAAGATTCTTGC |
| Radish_Cul1_Cds | TTGGATTCAGCATCTTACTATTCTCGCAAAGCATCAAACTGGATCCAGGAAGATTCTTGC |
| Beet_Cul1_Cds | GATGATACTGCTGCTTACTACTCGCGCAAAGCGTCTAGCTGGATTCTTGAGGACTCTTGT |
| Spinach_Cul1_Cds | GATGATACTGCTGCTTATTACTCACGCAAGGCCTCAAGCTGGATTCTGGAGGACTCATGT |
| Leek_Cul1_Cds | AATGCTACAGCAGCCTATTATTCACGAAAAGCTTCAAATTGGATTCTAGAAGATTCATGT |
| Squash_Cul1_Cds | AAAGATACTGCTGCTTACTACTCTAGGAAGGCATCAAATTGGATCTTAGAAGATTCTTGT |
| WaterMelon_Cul1_Cds | AAAGATACTGCTGCTTATTACTCTAGGAAGGCTTCCAATTGGATCCTAGAAGATTCTTGT |
| CuCumber_Cul1_Cds | AAAGATACTGCTGCTTATTACTCTAGGAAGGCTTCCAATTGGATCCTAGAAGATTCTTGT |
| Melon_Cul1_Cds | AAAGATACTGCTGCTTATTACTCTAGGAAGGCTTCCAATTGGATCCTAGAAGATTCTTGT |
| Tomato_Cul1_Cds | AAGGACACAGCGGCTTATTATTCTCGCAAAGCTTCTAATTGGATCCTCGAAGATTCATGT |
| Eggplant_Cul1_Cds | AAGGACACTGCGGCTTATTATTCTCGCAAAGCTTCTAACTGGATCCTCGAAGATTCATGT |
| Pepper_Cul1_Cds | AAGGACACCGCAGCTTATTATTCTCGCAAAGCTTCTAACTGGATACTTGAAGATTCATGT |
| Lettuce_Cul1_Cds | AATGATACAGCAGCATATTATTCACGCAAGGCTTCCAACTGGATTCTAGAAGATTCTTGT |
| Chicory_Cul1_Cds | AATGATACAGCAGCATATTATTCACGCAAAGCTTCCAATTGGATTCTAGAAGATTCTTGT |
| Endive_Cul1_Cds | AATGATACAGCAGCATATTATTCACGCAAAGCTTCCAACTGGATTCTAGAAGATTCTTGT |
| Carrot_Cul1_Cds | AAAGATACAGCAGCATACTATTCTCGAAAGGCTTCCAACTGGATCTTAGAAGATTCTTGT |
| Celery_Cul1_Cds | ACTGATACTGCTGCTTACTATTCTCGAAAAGCTTCAAACTGGATCCTTGAAGATTCTTGT |

| | |
|---|---|
| Brassica_Cul1_Cds | CCTGATTACATGCTGAAGTCTGAAGAATGTCTTAAGAAGGAGAGGGAGAGAGTGGCTCAC |
| Radish_Cul1_Cds | CCTGATTACATGCTGAAGTCTGAAGAATGCCTTAAGAAGGAGAGGGAGAGGGTTGCTCAC |
| Beet_Cul1_Cds | CCGGAATACATGTTAAAGTCTGAGGAGTGTTTGAAGAAGGAGAAAGAGAGAGTGGCTAAT |
| Spinach_Cul1_Cds | CCGGAATACATGTTGAAGTCGGAGGAGTGTTTGAAGAAAGAGAAAGATAGAGTGGCTCAT |
| Leek_Cul1_Cds | CCAGATTATATGCTAAAAGCCGAGGAGTGCTTAAAACATGAGAAAGATAGAGTTGCTCAT |
| Squash_Cul1_Cds | CCTGATTATATGCTAAAAGCAGAGGAGTGCTTGAGACGAGAAAAGGACCGAGTTTCTCAC |
| WaterMelon_Cul1_Cds | CCCGATTATATGCTAAAAGCAGAGGAGTGCTTGAAACGAGAAAAGGATAGAGTTTCTCAC |
| CuCumber_Cul1_Cds | CCCGATTATATGCTTAAAGCAGAGGAGTGCTTGAAACGAGAAAAGGATAGGGTTTCCCAC |
| Melon_Cul1_Cds | CCCGATTATATGCTAAAAGCAGAGGAGTGCTTGAAGCGAGAAAAGGATAGGGTTTCCCAC |
| Tomato_Cul1_Cds | CCGGATTATATGCTGAAAGCCGAGGAGTGCTTGAAACGGGAGAAGGATAGGGTCTCTCAT |
| Eggplant_Cul1_Cds | CCAGATTATATGCTGAAAGCTGAGGAGTGCTTGAAACGGGAGAAGGATAGGGTCTCCCAT |
| Pepper_Cul1_Cds | CCAGATTATATGCTGAAAGCCGAGGAGTGCTTGAAACGGGAGAAAGATAGGGTCTCTCAC |
| Lettuce_Cul1_Cds | CCAGATTATATGCTCAAAGCAGAGGAGTGCTTAAAAAGAGAAAAGGACAGAGTGTCTCAT |
| Chicory_Cul1_Cds | CCAGATTATATGCTCAAAGCTGAGGAGTGCTTAAAAAGAGAAAAGGACAGAGTTTCTCAT |
| Endive_Cul1_Cds | CCAGATTATATGCTCAAAGCTGAGGAGTGCTTAAAAAGAGAAAAGGACAGAGTTTCTCAT |
| Carrot_Cul1_Cds | CCAGATTATATGCTCAAAGCGGAAGAGTGTTTGAGACGGGAAAAGGACAGGGTCTCTAAC |
| Celery_Cul1_Cds | CCTGATTATATGTTAAAGGCAGAAGAATGTTTGCGACGAGAGAAGGACAGGGTTTCCCAC |

Fig. 69G

| | |
|---|---|
| Brassica_Cul1_Cds | TACCTTCACTCAAGCAGCGAGCCAAAGCTGGTTGAGAAAGTACAACATGAGCTGTTGGTA |
| Radish_Cul1_Cds | TACCTTCATTCAAGCAGCGAGCCAAAGCTGGTTGAGAAAGTACAACATGAGCTGTTGGTT |
| Beet_Cul1_Cds | TATTTACATTCCAGCAGTGAGCCAAAGCTTCTGGAGAAAGTGCAAAACGAGTTGCTATTG |
| Spinach_Cul1_Cds | TATCTACATTCCAGCAGTGAGCCAAAGCTTCTGGAGAAAGTACAAAATGAGTTGCTACTG |
| Leek_Cul1_Cds | TATTTGCATTCAAGCAGTGAACAGAAGCTGTTAGAGAAAGTGCAACATGAGTTACTTTTC |
| Squash_Cul1_Cds | TATCTGCACTCTAGTAGCGAGCCAAAGTTATTGGAGAAAGTTCAACATGAACTATTGTCT |
| WaterMelon_Cul1_Cds | TATTTGCACTCTAGTAGCGAGCCAAAGTTATTAGAGAAAGTTCAACATGAACTGTTATCT |
| CuCumber_Cul1_Cds | TATTTGCACTCTAGTAGCGAGCCAAAGTTGTTGGAGAAAGTTCAACATGAACTATTATCT |
| Melon_Cul1_Cds | TATTTGCACTCTAGTAGCGAGCCAAAGTTGTTGGAGAAAGTTCAACACGAACTGTTATCT |
| Tomato_Cul1_Cds | TATCTCCATTCAAGCAGCGAGACGAAGTTGCTTGAGAAAGTGCAACATGAGTTGTTGTCT |
| Eggplant_Cul1_Cds | TATCTCCATTCTAGCAGTGAGACAAAGTTGCTTGAGAAAGTGCAACATGAGTTGTTATCT |
| Pepper_Cul1_Cds | TATCTTCATTTAAGCAGTGAGACAAAGTTGCTTGAGAAAGTGCAACATGAGTTGTTGTCT |
| Lettuce_Cul1_Cds | TATCTTCATTCCAGCAGTGAGCCAAAGCTTCTTGAGAAAGTTCAAAATGAGTTATTGTCT |
| Chicory_Cul1_Cds | TATCTTCATTCCAGCAGTGAACCAAAGCTTCTTGAGAAAGTTCAAACAGAGTTATTATCT |
| Endive_Cul1_Cds | TATCTTCATTCAAGTAGTGAACCAAAGCTTCTTGAGAAAGTTCAAACAGAGTTATTATCT |
| Carrot_Cul1_Cds | TACCTTCATTCTAGTAGTGAACCCAAGTTGCTTGAGAAAGTTCAACATGAGTTACTATCA |
| Celery_Cul1_Cds | TACCTACATTTTAGTAGCGAGCCAAAGTTGCTTGAGAAAGTGCAACATGAGCTGCTATCT |

| | |
|---|---|
| Brassica_Cul1_Cds | GTGTATGCAAATCAGCTTCTAGAAAAAGAGCATTCAGGGTGCCGTGCATTGCTGAGAGAT |
| Radish_Cul1_Cds | GTCTATGCAAATCAGCTTCTTGAAAAGGAGCACTCAGGGTGCCGTGCATTGCTGAGAGAC |
| Beet_Cul1_Cds | GTTTATGAAAGCCAATTGCTTGAGAAGGAGAATTCGGGATGTCGTGCATTACTGAAAGAT |
| Spinach_Cul1_Cds | GTTTACGAAAATCAGTTGCTTGAGAAGGAGAATTCTGGATGTCGTGCATTGTTGAAAGAT |
| Leek_Cul1_Cds | GTATATGCAAGTCAACTTCTCGAGAAAGAACATTCCGGATGTCATGCATTGCTTCGCGAT |
| Squash_Cul1_Cds | GTTTATGCTACTCAACTGCTGGAGAAAGAGCATTCAGGATGCCATGCATTGCTTAGAGAT |
| WaterMelon_Cul1_Cds | GTGTATGCTACTCAACTGCTGGAAAAAGAGCATTCAGGATGCCATGCATTGCTTAGAGAT |
| CuCumber_Cul1_Cds | GTTTATGCTACTCAACTGCTGGAAAAAGAGCATTCAGGATGCCATGCATTGCTTAGAGAT |
| Melon_Cul1_Cds | GTGTATGCTACTCAACTGCTGGAAAAAGAGCATTCAGGATGCCATGCATTGCTTAGAGAT |
| Tomato_Cul1_Cds | GTGTATGCCACTCAACTTCTTGAGAAGGAGCACTCTGGATGCCATGCGTTACTGAGAGAT |
| Eggplant_Cul1_Cds | GTGTATGCCAATCAACTTCTTGAGAAGGAGCACTCTGGATGCCATGCATTACTTAGAGAT |
| Pepper_Cul1_Cds | GTGTATGCCACTCAACTTCTTGAGAAGGAGCACTCTGGGTGCCATGCGTTACTAAGAGAT |
| Lettuce_Cul1_Cds | GTTTATGCAACTCAATTGCTTGAGAAAGAGCACTCAGGTTGTCATGCATTGCTCAGGGAT |
| Chicory_Cul1_Cds | GTTTATGCAACTCAATTGCTTGAAAAGGAGCACTCCGGTTGTCATGCATTACTTAGGGAT |
| Endive_Cul1_Cds | GTTTATGCAACTCAATTGCTCGAAAAGGAACACTCAGGTTGTCATGCATTACTTAGAGAT |
| Carrot_Cul1_Cds | CACTATGCAACTCAGCTGCTTGAGAAAGAACACTCTGGGTGTCATGCATTGCTTAGGGAT |
| Celery_Cul1_Cds | GTGTATGCAACCCAATTACTCGAGAAGGAACATTCTGGTTGTCATGCATTGCTTAGGGAT |

Fig. 69H

```
Brassica_Cul1_Cds        GACAAGGTTGATGACCTCTCCAGGATGTACAGGCTTTATCATAAAATTGTGAAAGGTTTG
Radish_Cul1_Cds          GACAAGGTTGACGATCTCTCCAGGATGTACAGGCTCTATCATAAAATTGCTAAAGGTTTA
Beet_Cul1_Cds            GACAAGGTGGATGATCTTTCCAGGATGTACAGGCTTTACAGTAAGGTTACCAAAGGATTG
Spinach_Cul1_Cds         GACAAGGTGGAAGATCTTTCCAGGATGTACAGGCTTTATAGCAAGGTTACCAAAGGGTTG
Leek_Cul1_Cds            GACAAGGTGGGAGATCTTTCACGCATGTATCGGCTGTTCTGTAGAATTACACGTGGTTTG
Squash_Cul1_Cds          GACAAGGTGGAAGATTTGTCAAGGATGTTCCGTCTCTTCTCCAAAATACCCAAGGGATTG
WaterMelon_Cul1_Cds      GACAAGGTGGAAGATTTGTCAAGGATGTTCCGCCTCTTCTCCAAAATACCCAAGGGATTG
CuCumber_Cul1_Cds        GACAAGGTGGAAGATTTGTCAAGGATGTTCCGTCTATTCTCCAAAATACCGAAGGGACTG
Melon_Cul1_Cds           GACAAGGTGGAAGATTTGTCAAGGATGTTCCGTCTCTTCTCCAAAATACCGAAGGGATTG
Tomato_Cul1_Cds          GATAAGGTTGAAGATTTATCAAGGATGTATAGGCTCTTTTCTAAGATTTCTCGAGGCTTA
Eggplant_Cul1_Cds        GATAAGGTCGATGATTTATCAAGGATGTATAGACTCTTTTCTAAGATTCCTCGAGGCTTA
Pepper_Cul1_Cds          GATAAGGTTGAAGATTTATCAAGGATGTATAGGCTCTTTTCTAAGATTCCTCGAGGCTTA
Lettuce_Cul1_Cds         GACAAGGTTGATGATTTATCAAGAATGTACAGACTCTTTTCAAAGATACCAAAAGGATTG
Chicory_Cul1_Cds         GACAAGGTTGATGATTTATCAAGAATGTACAGACTCTTTTCAAAGATACAAAAAGGGCTG
Endive_Cul1_Cds          GACAAGGTTGATGATTTATCAAGAATGTACAGACTCTTTTCAAAGATACAAAAAGGACTG
Carrot_Cul1_Cds          GACAAGGTGGCAGATTTATCAAGGATGTATAGGCTCTTCTCTAAAATACCTCGAGGCCTA
Celery_Cul1_Cds          GACAAGGTGGATGATTTGTCTAGGATGTACAGACTCTTCTCGAAAATACCTAAAGGCCTG


Brassica_Cul1_Cds        GAACCTGTTGCAAACATATTTAAGCAGCATGTCACAGCAGAGGGTAACGCACTTGTCCAA
Radish_Cul1_Cds          GAACCTGTTGCAAACATATTTAAGCAGCATGTCACAGCCGAGGGTAACGCACTTGTCCAA
Beet_Cul1_Cds            GAACCCATTGGCAGTATCTTCAAACAGCATATAACTGATGAAGGAACAGCCTTAGTGCAG
Spinach_Cul1_Cds         GAACCCATTGGCAGTATCTTCAAACAGCATATAACCGATGAAGGAACAGCCCTGGTGCAG
Leek_Cul1_Cds            GACCCTGTGTCTCAAATATTTAAGCAGCATGTGACTGCAGAAGGTACTGCTTTGGTCAAA
Squash_Cul1_Cds          GACCCAGTTTCCAACATATTTAAGCAGCATGTCACTGCTGAAGGAACAGCATTAGTCAAA
WaterMelon_Cul1_Cds      GACCCAGTTTCCAACATATTTAAGCAGCATGTCACTGCTGAAGGAACAGCATTGGTCAAA
CuCumber_Cul1_Cds        GATCCAGTTTCCAACATATTTAAGCAGCATGTAACTGCTGAAGGAACAGCACTGGTCAAA
Melon_Cul1_Cds           GACCCAGTTTCCAACATATTTAAGCAGCATGTAACTGCTGAAGGAACAGCACTGGTCAAA
Tomato_Cul1_Cds          GACCCTGTGGCCAATATTTTTAAGCAGCATGTTACTGCTGAAGGTACAGCTTTGGTAAAA
Eggplant_Cul1_Cds        GAGCCTGTGGCTAATATATTTAAGCAGCATGTTACTGCTGAAGGTACAGCTTTGGTGAAA
Pepper_Cul1_Cds          GACCCTGTGGCTAATATATTTAAGCAGCATGTTACTGCTGAAGGTACAGCTTTGGTCAAA
Lettuce_Cul1_Cds         GATCCTGTTTCTAGTATGTTTAAGCAGCATGTCACTGCTGAAGGCACAACATTGGTTAAA
Chicory_Cul1_Cds         GATCCTGTTTCTAGTATGTTTAAGCAGCATGTCACTGCTGAAGGCACAACATTGGTTAAA
Endive_Cul1_Cds          GATCCTGTTTCCAGTATGTTTAAGCAGCATGTCACTGCTGAAGGCACAACATTAGTAAAA
Carrot_Cul1_Cds          GATCCCGTGTCTAATATTTTCAAGCAGCATGTTACTGCTGAAGGTACAGCTTTGGTCAAA
Celery_Cul1_Cds          GATCCAGTTTCTTATATTTTTAAGCAGCATGTTACAAATGAAGGGATGGCATTGGTTAAA
```

Fig. 69I

```
Brassica_Cul1_Cds         CAGGCCGAAGACACGGCCACTAATCATGCTGCA-------AATACTGCTAGCGTGCAG
Radish_Cul1_Cds           CAGGCCGAAGACACAGCCACTAATCAGGCTGCA-------AATACTGCTAGCGTGCAG
Beet_Cul1_Cds             CAGGCCGAAGATGCTGCTATCAGCAAGGCTGAA------AATACT-GGTGGTTCACAT
Spinach_Cul1_Cds          CAGGCCGAAGACGCTGCAATTAGCAAGGCTGAA----AATGCTGGCGGTGGTTCACAT
Leek_Cul1_Cds           CATGCCGAAGATGCTGCAAGTAACAAGAAGGCCGAGAAAAAAGACATTGTTGGTTTGCAA
Squash_Cul1_Cds         CAGGCAGAAGACGCTGCAAGTAACAAGAAGGCCGAGAAAAAGGACATCGTTGGTCTGCAA
WaterMelon_Cul1_Cds     CAGGCAGAAGATGCTGCAAGTAACAAGAAGGCCGAGAAAAAGGACATAGTTGGTCTGCAG
CuCumber_Cul1_Cds       CAGGCAGAAGATGCTGCAAGTAACAAGAAGGCTGAGAAAAAGGACATAGTTGGTCTGCAG
Melon_Cul1_Cds          CAGGCAGAAGATGCTGCAAGTAACAAGAAGGCCGAGAAAAAGGACATAGTTGGTCTGCAG
Tomato_Cul1_Cds         CAGGCTGAAGATGCTGCTAGCAATAAAAAGGCAGAGAAGAGAGATGTGGTTGGTTTGCAG
Eggplant_Cul1_Cds       CAGGCTGAAGATGCTGCTAGCAACAAAAAGGCAGAGAAGAGAGATGTGGTTGGTTTGCAG
Pepper_Cul1_Cds         CAGGCTGAAGATGCTGCTAGCAACAAAAAGGCAGAGAAAAGAGATGTGGTTGGTTTGCAG
Lettuce_Cul1_Cds        CAAGCAGAAGATGCAGCAAGTACCAAGAAGGCTGAAAAGAGAGATGTGGTTGGGTTGCAG
Chicory_Cul1_Cds        CAGGCAGAAGATGCAGCAAGTACTAAGAAGGCTGAAAAGAGAGACGTGGTTGGCTTACAA
Endive_Cul1_Cds         CAAGCAGAAGATGCAGCAAGTACTAAGAAGGCTGAAAAGAGAGACGTGGTTGGCTTACAG
Carrot_Cul1_Cds         CAAGCAGAAGATGCAGCTAGCAACAAGAAGGCAGAGAAGAGAGATGTAGTAGGTTTACAA
Celery_Cul1_Cds         CAAGCAGAAGATGCAGCAAGCAACAAGAAGGCAGAAAAGAGAGACGTGGTTAGTTTACAG

Brassica_Cul1_Cds       GAACAGGTTCTTATCAGAAAAGTGATTGAACTACATGATAAATACATGGTCTATGTTGTT
Radish_Cul1_Cds         GAACAGGTTCTCATCAGAAAAGTGATTGAGCTACATGATAAGTACATGGTCTATGTCGTG
Beet_Cul1_Cds           GAGCAGGTCTTCGTCAGGAAAGTAATAGAGTTGCATGACAAATTCATGACTTATGTCACC
Spinach_Cul1_Cds        GAGCAGGTCTTCGTCAGGAAAGTGATTGAGTTGCATGACAAATTTATGACCTATGTTACA
Leek_Cul1_Cds           GAGCAGGTCTTCGTTAGGAAAGTAATTGAGCTGCATGATAAATACTTGGCCTATGTGACT
Squash_Cul1_Cds         GAACAGGTTTTTGTTAGAAAAGTGATTGAGCTTCACGACAAGTACTTGGCATATGTGAAT
WaterMelon_Cul1_Cds     GAACAGGTTTTTGTAAGAAAAGTGATTGAGCTTCACGACAAGTACTTGGCTTACGTGAAT
CuCumber_Cul1_Cds       GAACAGGTTTTTGTAAGAAAAGTGATTGAGCTTCACGACAAGTACTTGGCTTATGTGAAT
Melon_Cul1_Cds          GAACAGGTTTTTGTAAGAAAAGTGATTGAGCTTCACGACAAGTACTTGGCTTATGTGAAT
Tomato_Cul1_Cds         GAACAGGTTTTTGTTCGGAAAGTGATTGAACTTCATGATAAATATTTGGCTTATGTGAAT
Eggplant_Cul1_Cds       GAACAGGTTTTTGTTCGGAAAGTGATTGAGCTTCATGATAAATATTTGGCGTATGTGAAT
Pepper_Cul1_Cds         GAACAGATTTTTGTTCGGAAAGTGATTGAGCTTCATGATAAGTATATGGCATATGTGAAT
Lettuce_Cul1_Cds        GAACAGGTTTTTGTTAGAAAAGTTATTGAGCTCCATGACAAGTACCTGGCATATGTAAAT
Chicory_Cul1_Cds        GAACAGGTTTTTGTTAGAAAAGTTATCGAGCTTCATGACAAGTACCTTGCATATGTAAAT
Endive_Cul1_Cds         GAACAGGTTTTTGTTAGAAAAGTAATCGAGCTTCATGACAAGTACCTCGCATATGTAAAC
Carrot_Cul1_Cds         GAACAGGTTTTTGTGAGGAAAATAATTGAATTGCATGACAAATACCTTACATACGTAAAT
Celery_Cul1_Cds         GAGCAGGTTTTTGTTAGAAAAATTATTGAATTACATGACAAATACCTCGCCTATGTGAAT
```

Fig. 69J

| | |
|---|---|
| Brassica_Cul1_Cds | GAGTGTTTCCAGAACCACACCCTCTTCCACAAGGCATTGAAAGAGGCATTTGAGATATTC |
| Radish_Cul1_Cds | GAGTGCTTCCAGAACCACACCCTCTTCCACAAGGCTCTGAAAGAGGCATTTGAGATATTC |
| Beet_Cul1_Cds | GATTGCTTCAACAGCCATACCATATTTCACAAGGCTCTTAAGGAGGCTTTTGAGGTATTT |
| Spinach_Cul1_Cds | GATTGCTTCAACAGCCATACCATCTTTCACAAGGCTCTCAAGGAAGCTTTTGAGGTATTC |
| Leek_Cul1_Cds | GACTGCTTTCAAAATCACTCTCTATTTCACAAGGCACTTAAAGAGGCATTCGAGGTATTC |
| Squash_Cul1_Cds | GATTGTTTCCAAAACCACACACTTTTTCACAAGGCTCTCAAGGAAGCTTTTGAAGTCTTT |
| WaterMelon_Cul1_Cds | GATTGTTTCCAAAACCACACACTTTTTCACAAGGCTCTCAAGGAAGCTTTTGAAGTCTTT |
| CuCumber_Cul1_Cds | GATTGTTTCCAAAACCACACACTTTTCCATAAGGCTCTCAAGGAAGCTTTTGAAGTATTT |
| Melon_Cul1_Cds | GATTGTTTCCAAAACCACACACTTTTCCATAAGGCTCTCAAGGAAGCTTTTGAAGTCTTT |
| Tomato_Cul1_Cds | AACTGTTTCCAAAACCACACACTTTTTCACAAGGCGCTTAAAGAAGCTTTTGAGCTTTTC |
| Eggplant_Cul1_Cds | AACTGTTTCCAAAACCACACACTTTTTCACAAGGCACTTAAAGAAGCTTTCGAACTTTTC |
| Pepper_Cul1_Cds | AACTGTTTCCAAAACCACACACTTTTTCACAAGGCGCTTAAAGAAGCTTTCGAACTTTTC |
| Lettuce_Cul1_Cds | GACTGTTTCATGAACCATACTCTTTTCCACAAGGCTCTTAAAGAGGCATTTGAAATATTC |
| Chicory_Cul1_Cds | GACTGTTTTATGAATCATACCCTGTTTCACAAGGCTCTTAAAGAGGCATTTGAAATATTC |
| Endive_Cul1_Cds | GACTGTTTTATGAATCACACATTGTTCCACAAGGCTCTTAAAGAGGCATTTGAAATATTC |
| Carrot_Cul1_Cds | GACTGTTTTACAAACCACACTCTCTTCCATAAGGCGCTTAAGGAGGCTTTTGAAATCTTC |
| Celery_Cul1_Cds | GACTGCTTTACAAACCATACTCTTTTCCATAAGGCTCTCAAGGAGGCTTTTGAAATCTTT |

| | |
|---|---|
| Brassica_Cul1_Cds | TGTAACAAAACAGTCGCTGGAAGTTCTAGTGCTGAATTGCTTGCAACATTTTGCGACAAT |
| Radish_Cul1_Cds | TGTAACAAAACAGTCGCTGGAAGTTCAAGTGCAGAACTGCTTGCAACATTCTGCGACAAC |
| Beet_Cul1_Cds | TTGAACAAGGGTGTTGCTGGTAGCTCAAGTGCTGAGTTGCTAGCTACATTCTGTGATAAC |
| Spinach_Cul1_Cds | TTAAACAAGGGTGTTGCTGGTAGTTCAAGTGCTGAACTTCTAGCTTCATTTTGTGATAAT |
| Leek_Cul1_Cds | TGCAATAAAGGTGTTGCAGGTAGCTCAAGCGCTGAACTTCTGGCTGCTTTTTGTGACAAT |
| Squash_Cul1_Cds | TGCAATAAGGGTGTTGCTGGAAGTTCTAGTGCAGAATTACTTGCTACCTTTTGTGATAAC |
| WaterMelon_Cul1_Cds | TGCAATAAGGGTGTTGCTGGAAGTTCTAGTGCAGAATTACTTGCTACCTTTTGTGATAAC |
| CuCumber_Cul1_Cds | TGCAATAAGGGTGTTGCTGGAAGTTCTAGTGCAGAATTGCTTGCTACCTTTTGTGATAAC |
| Melon_Cul1_Cds | TGCAATAAGGGTGTTGCTGGAAGTTCTAGTGCAGAATTGCTTGCTACCTTCTGCGATAAC |
| Tomato_Cul1_Cds | TGCAACAAGGGTGTTGCTGGTAGCTCAAGCGCTGAACTTCTTGCCACCTTCTGTGACAAC |
| Eggplant_Cul1_Cds | TGCAACAAGGGTGTTGCTGGTAGCTCAAATGCTGAACTTCTTGCCACATTCTGCGACAAC |
| Pepper_Cul1_Cds | TGCAACAAGGGTGTTGCTGGTAGCTCAAGTGCTGAACTTCTTGCCACATTCTGCGACAAT |
| Lettuce_Cul1_Cds | TGCAACAAGGGTGTTGCTGGAAGTTCAAGTGCAGAGTTACTTGCCACATTTTGTGATAAT |
| Chicory_Cul1_Cds | TGCAACAAGGGCGTTGCTGGAAGTTCAAGTGCAGAATTACTTGCTACATTTTGTGATAAT |
| Endive_Cul1_Cds | TGCAACAAGGGCGTTGCTGGAAGTTCAAGTGCAGAATTACTTGCCACATTTTGTGATAAT |
| Carrot_Cul1_Cds | TGCAATAAGGGTGTCTCTGGAAGCTCTAGTGCAGAATTACTTGCCACATTCTGTGATAAT |
| Celery_Cul1_Cds | TGCAACAAGGGTGTTGCTGGAAGCTCTAATGCTGAACTACTTGCTACTTTCTGTGATAAC |

Fig. 69K

```
Brassica_Cul1_Cds      ATTCTCAAGAAGGGGGGAAGTGAAAAGCTGAGCGATGAAGCTATTGAAGATACCCTTGAG
Radish_Cul1_Cds        ATCCTCAAGAAGGGGGGTAGTGAGAAGCTGAGTGACGAAGCTATTGAAGATACGCTTGAG
Beet_Cul1_Cds          ATTCTCAAGAAAGGTGGGAGCGAAAAACTAAGCGATGAGGCTATTGAGGATTCACTTGAG
Spinach_Cul1_Cds       ATTCTCAAGAAAGGTGGTAGTGAAAAATTAAGTGATGAGGCTATTGAGGATTCACTGGAG
Leek_Cul1_Cds          ATATTGAAGAAGGGTGGAAGCGAGAAACTAAGCGATGAGGCCATAGAGGATACTCTTGAG
Squash_Cul1_Cds        ATCCTTAAGAAAGGTGGGAGTGAGAAGTTGAGTGATGAAGCAATTGAGGAAACACTCGAG
WaterMelon_Cul1_Cds    ATCCTTAAGAAAGGTGGGAGCGAGAAGTTGAGTGATGAAGCAATTGAGGAGACACTTGAG
CuCumber_Cul1_Cds      ATCCTTAAGAAAGGTGGGAGTGAGAAGTTGAGTGATGAAGCAATCGAGGAGACACTTGAG
Melon_Cul1_Cds         ATCCTTAAGAAAGGTGGGAGTGAGAAGTTGAGTGATGAAGCAATCGAAGAGACACTTGAG
Tomato_Cul1_Cds        ATTCTCAAAAAAGGCGGGAGTGAGAAATTGAGTGATGAAGCTATTGAAGAAACGTTGGAA
Eggplant_Cul1_Cds      ATTCTCAAAAAAGGCGGGAGTGAAAAATTGAGTGATGAAGCCATTGAAGAGACGCTGGAG
Pepper_Cul1_Cds        ATTCTCAAGAAAGGCGGGAGTGAGAAATTGAGTGATGAAGCCATTGAAGAGACGCTGGAG
Lettuce_Cul1_Cds       ATTCTTAAAAAAGGTGGAAGTGAGAAACTGAGCGATGAAGCCATTGAGGACACCCTTGAG
Chicory_Cul1_Cds       ATTCTTAAAAAAGGTGGAAGTGAAAAATTGAGTGATGAAGCCATTGAGGACACACTTGAG
Endive_Cul1_Cds        ATTCTTAAAAAAGGTGGAAGTGAAAAATTGAGTGATGAAGCCATTGAAGACACACTTGAG
Carrot_Cul1_Cds        ATTCTCAAGAAAGGTGGAAGCGAGAAGTTAAGTGATGAAGCCATTGAGGAAACACTTGAG
Celery_Cul1_Cds        ATCCTCAAAAAGGGTGGGAGTGAGAAATTAAGTGATGAGGCTATTGAAGAAACACTTGAG

Brassica_Cul1_Cds      AAGGTGGTCAAATTGCTTGCTTATATAAGTGACAAGGATCTTTTCGCCGAGTTCTACAGG
Radish_Cul1_Cds        AAGGTTGTCAAATTGCTTGCTTATATAAGCGACAAGGATCTTTTCGCCGAGTTCTACAGG
Beet_Cul1_Cds          AAGGTGGTGAAGCTTCTGGCCTATGTCAGTGATAAAGACCTGTTTGCTGAATTTTACAGA
Spinach_Cul1_Cds       AAGGTGGTGAAGCTTCTCGCATATGTCAGTGATAAAGACCTGTTTGCTGAATTTTACAGA
Leek_Cul1_Cds          AAGGTTGTAAAACTATTGGCATATATTAGCGATAAAGATCTGTTTGCTGAATTTTACAGG
Squash_Cul1_Cds        AAGGTCGTGAAATTGCTGGCGTATATCTGCGACAAAGATCTGTTTGCTGAATTCTATAGA
WaterMelon_Cul1_Cds    AAGGTCGTGAAGTTGCTGGCATACATCTGCGACAAAGATCTGTTTGCTGAATTCTATAGA
CuCumber_Cul1_Cds      AAGGTTGTGAAGTTGTTGGCATACATTTGCGACAAAGATCTGTTTGCTGAATTCTATAGA
Melon_Cul1_Cds         AAGGTTGTGAAGTTGTTGGCATACATCTGCGACAAAGATCTGTTTGCTGAATTCTATAGA
Tomato_Cul1_Cds        AAGGTGGTAAAGCTACTAGCTTATATTAGTGATAAGGACTTGTTTGCAGAATTCTATAGG
Eggplant_Cul1_Cds      AAGGTGGTAAAGCTGCTGGCTTATATTAGTGATAAGGACTTGTTTGCAGAATTCTATAGG
Pepper_Cul1_Cds        AAGGTTGTAAAGCTGCTAGCATATATTAGTGACAAGGACTTGTTTGCAGAATTCTATAGG
Lettuce_Cul1_Cds       AAGGTAGTAAAGTTGCTTGCCTACATCAGTGATAAAGATCTATTTGCTGAATTTTACAGG
Chicory_Cul1_Cds       AAGGTGGTAAAGTTGCTTGCTTACATCAGCGATAAAGATCTATTTGCAGAGTTTTATAGG
Endive_Cul1_Cds        AAGGTAGTAAAGTTGCTTGCTTACATCAGCGATAAAGATCTATTTGCAGAGTTTTATAGG
Carrot_Cul1_Cds        AAGGTTGTAAGGTTGCTTGCTTATATAAGTGACAAAGACTTATTTGCTGAATTTTATAGG
Celery_Cul1_Cds        AAGGTAGTAAAATTGTTAGCTTACATTAGCGATAAAGACTTGTTCGCTGAATTTTACAGA
```

Fig. 69L

| | |
|---|---|
| Brassica_Cul1_Cds | AAGAAGCTGGCCCGTAGGCTCTTATTTGATCGCAGTGCTAATGATGATCATGAGAGAAGT |
| Radish_Cul1_Cds | AAGAAGCTGGCACGTAGGCTCTTATTTGATCGCAGTGCGAATGATGATCATGAGAGAAGC |
| Beet_Cul1_Cds | AAGAAGCTCTCTCGCCGGCTACTCTTTGACAAGAGTGCTAATGATGATCATGAAAGAAGT |
| Spinach_Cul1_Cds | AAGAAGCTCTCTCGCCGGCTACTCTTTGACAAAAGTGCTAATGATGATCATGAGAGGAGT |
| Leek_Cul1_Cds | AAGAAGCTTGCACGAAGATTACTCTTTGACAAAAGTGCTAATGATGACCATGAGAGGAGC |
| Squash_Cul1_Cds | AAAAAACTCGCCCGAAGGCTTCTCTTCGACAAGAGTGCGAATGATGACCACGAGAGAAGT |
| WaterMelon_Cul1_Cds | AAAAAACTTGCCCGAAGGCTTCTCTTTGACAAGAGTGCCAACGATGACCATGAGAGAAGT |
| CuCumber_Cul1_Cds | AAAAAACTTGCCCGAAGGCTTCTCTTTGACAAGAGCGCGAACGATGACCACGAGAGAAGT |
| Melon_Cul1_Cds | AAAAAACTTGCCCGAAGGCTTCTCTTTGATAAGAGCGCCAACGATGACCACGAGAGAAGT |
| Tomato_Cul1_Cds | AAAAAGCTAGCCCGGCGGTTGTTATTTGATAAGAGTGCCAATGATGAACATGAAAGAAGT |
| Eggplant_Cul1_Cds | AAAAAGCTCGCCCGGCGGTTGTTATTTGATAAGAGTGCCAATGATGAACATGAGAGAAGT |
| Pepper_Cul1_Cds | AAAAAGCTAGCCCGGCGGTTGTTATTTGATAAGAGTGCCAATGATGAACACGAGAGAAGT |
| Lettuce_Cul1_Cds | AAAAAACTTGCTAGGAGGCTTTTGTTTGACAAGAGTGCAAACGATGAGCATGAGAGAAGT |
| Chicory_Cul1_Cds | AAAAAACTGGCTAGACGGCTTTTATTTGACAAAAGTGCAAATGATGAGCACGAAAGAAGT |
| Endive_Cul1_Cds | AAAAAACTGGCTAGAAGGCTTTTATTTGACAAAAGTGCAAATGATGAGCATGAAAGAAGT |
| Carrot_Cul1_Cds | AAAAAGCTTGCACGGCGTCTCTTATTCGACAAGAGTGCCAATGATGAGCATGAGAGAAGT |
| Celery_Cul1_Cds | AAAAAGCTTGCACGGAGACTTCTCTTTGATAAGAGTGCAAATGACGAGCATGAACGAAGT |

| | |
|---|---|
| Brassica_Cul1_Cds | ATCCTGACAAAGCTCAAGCAACAATGTGGTGGGCAGTTTACTTCGAAGATGGAGGGCATG |
| Radish_Cul1_Cds | ATCCTTACAAAGCTCAAGCAACAATGTGGTGGGCAGTTCACTTCTAAGATGGAGGGCATG |
| Beet_Cul1_Cds | ATTTTAACCAAATTGAAGCAGCAGTGTGGCGGACAATTCACATCAAAGATGGAGGGGATG |
| Spinach_Cul1_Cds | ATTTTAACAAAATTGAAGCAGCAGTGTGGGGGACAGTTCACATCAAAGATGGAGGGGATG |
| Leek_Cul1_Cds | ATCCTTACAAAGCTGAAACAGCAATGTGGAGGGCAGTTCACCTCTAAAATGGAAGGCATG |
| Squash_Cul1_Cds | ATACTGACGAAATTGAAGCAACAATGTGGTGGTCAGTTTACCTCTAAGATGGAGGGAATG |
| WaterMelon_Cul1_Cds | ATATTGACCAAATTGAAGCAACAATGTGGTGGCCAGTTCACCTCTAAGATGGAGGGGATG |
| CuCumber_Cul1_Cds | ATATTGACCAAATTGAAGCAACAATGTGGTGGTCAGTTCACTTCTAAGATGGAGGGAATG |
| Melon_Cul1_Cds | ATATTGACCAAATTGAAGCAACAATGTGGTGGTCAGTTCACTTCTAAGATGGAGGGAATG |
| Tomato_Cul1_Cds | ATCCTAACAAAGTTGAAGCAGCAGTGTGGGGGGCAGTTCACATCAAAGATGGAGGGAATG |
| Eggplant_Cul1_Cds | ATCCTAACAAAGTTGAAGCAGCAGTGTGGAGGTCAGTTCACATCAAAGATGGAGGGAATG |
| Pepper_Cul1_Cds | ATCCTTACAAAGTTGAAGCAGCAGTGTGGGGGCCAGTTCACATCAAAGATGGAGGGAATG |
| Lettuce_Cul1_Cds | ATTCTCACAAAGCTGAAGCAACAGTGTGGTGGTCAGTTCACATCAAAGATGGAAGGGATG |
| Chicory_Cul1_Cds | ATTTTGACAAAATTGAAACAACAATGTGGCGGTCAATTTACATCAAAAATGGAAGGAATG |
| Endive_Cul1_Cds | ATTTTAACAAAGTTGAAGCAACAATGTGGTGGTCAGTTTACATCAAAGATGGAAGGAATG |
| Carrot_Cul1_Cds | ATATTGACTAAGCTGAAGCAACAATGTGGGGGTCAATTTACATCAAAGATGGAAGGAATG |
| Celery_Cul1_Cds | ATTTTGACTAAACTAAAGCAACAGTGCGGTGGTCAGTTCACATCGAAAATGGAGGGGATG |

Fig. 69M

| | |
|---|---|
| Brassica_Cul1_Cds | GTGACTGATTTGACATTGGCAAGGGAAAACCAAAACAGCTTCGAGGAGTATCTTGGCAAT |
| Radish_Cul1_Cds | GTAACGGACTTGACATTGGCAAGAGAGAACCAAACCAGTTTCGAGGAGTATCTAGGCAAT |
| Beet_Cul1_Cds | GTGACAGACTTGACCTTGGCGAGGGAGAATCAAACTAATTTTGAGGAATATCTTAGTCAG |
| Spinach_Cul1_Cds | GTGACAGACTTGACATTGGCGAGGGAGAATCAAACTAATTTTGAGGAATATCTTGGACAA |
| Leek_Cul1_Cds | GTAACCGATCTGACACTTGCACGAGAAAATCAATCAAGTTTTGACGATTACCTTAGCAGC |
| Squash_Cul1_Cds | GTCACGGATTTGACACTGGCAAGGGAGAACCAAACTAGTTTTGAGGAATATCTGAGCAAT |
| WaterMelon_Cul1_Cds | GTCACTGATTTGACTTTGGCAAGGGAGAACCAAACTAGTTTCGAGGAGTATCTGAGCAAT |
| CuCumber_Cul1_Cds | GTTACTGATTTGACTTTGGCAAGGGAGAACCAAACTAGTTTTGAGGAGTATCTGAGCAAT |
| Melon_Cul1_Cds | GTTACTGATTTGACTTTGGCAAGGGAGAACCAAACTAGTTTCGAAGAGTATCTGAGCAAT |
| Tomato_Cul1_Cds | GTCACAGATTTGACATTGGCAAGGGAAAATCAAGCCAGCTTCGAGGAGTATTTGAGCAAT |
| Eggplant_Cul1_Cds | GTCACAGATTTGACATTGGCAAGGGAAAATCAAGCCAGCTTTGAGGAGTATTTGAGCAAT |
| Pepper_Cul1_Cds | GTGACAGATTTGACATTGGCAAGGGAAAATCAAGCCAGCTTTGAGGAGTATTTGAGCAAC |
| Lettuce_Cul1_Cds | GTTACAGATTTGACATTGGCAAAGGAAAACCAATCCCATTTTGAAGAGTATTTGAACAAT |
| Chicory_Cul1_Cds | GTTACAGATTTGACATTGGCAAAAGAAAATCAATCACATTTTGAGGAGTATTTGAATAAT |
| Endive_Cul1_Cds | GTTACAGATTTAACACTGGCAAAAGAAAATCAATCACATTTTGAGGAGTATTTGAATAAT |
| Carrot_Cul1_Cds | GTCACTGACTTGACGTTGGCAAAGGAAAATCAGTCCAACTTCGAGGAGTACCTCAATAAT |
| Celery_Cul1_Cds | GTCACAGATTTGACTTTGGCTAAAGAAAATCAATCCAGCTTTGAGGAGTATCTGGGAAAT |

| | |
|---|---|
| Brassica_Cul1_Cds | AACCCCGCTGCAAACCCAGGGATTGATTTGACCGTAACTGTTCTTACCACTGGTTTTTGG |
| Radish_Cul1_Cds | AACCCCGCTGCAAACCCAGGGATTGATTTGACCGTCACTGTTCTTACCACTGGTTTCTGG |
| Beet_Cul1_Cds | AATCCAGATGCCAGTCCTGGTCTTGATTTGACTGTGACTGTTCTGACAACTGGGTTCTGG |
| Spinach_Cul1_Cds | AATACAGATGCCAGTCCTGGTCTTGATTTGACTGTGACAGTTTTGACCACTGGGTTCTGG |
| Leek_Cul1_Cds | AATCCTAAAGCAAATTCTGGAATTGACTTGACTGTTACAGTCTTAACAACTGGCTTCTGG |
| Squash_Cul1_Cds | AATCCACAAGCTAGTCCTGGAATCGACTTGACCGTTACCGTTTTGACCACTGGTTTTTGG |
| WaterMelon_Cul1_Cds | AATCCACAAGCTAGTCCTGGAATCGACTTGACTGTCACTGTTTTGACTACTGGCTTTTGG |
| CuCumber_Cul1_Cds | AATCCACAAGCGAGTCCTGGCATCGACCTGACTGTTACTGTTTTAACTACTGGATTTTGG |
| Melon_Cul1_Cds | AATCCACAAGCTAGTCCTGGAATCGACCTAACTGTTACTGTTTTGACTACTGGATTTTGG |
| Tomato_Cul1_Cds | AATCCAATAGCAAATCCAGGAATTGACTTGACGGTGACTGTCTTGACTACTGGCTTCTGG |
| Eggplant_Cul1_Cds | AATCCAACAGCAAATCCAGGAATTGACTTGACGGTGACTGTCTTGACTACTGGCTTCTGG |
| Pepper_Cul1_Cds | AATCCAGCAGCAAATCCAGGAATTGACTTGACGGTGACTGTCTTGACTACTGGCTTCTGG |
| Lettuce_Cul1_Cds | AATCCCAATGTCAGCCCTGGAATTGACTTGACTGTCACTGTGTTGACTACCGGCTTCTGG |
| Chicory_Cul1_Cds | AATCCCAATGTTAGCCCTGGCATTGACTTGACCGTGACTGTGTTGACCACTGGTTTTTGG |
| Endive_Cul1_Cds | AATCCCAATGTTAGCCCTGGCATTGACTTGACCGTGACTGTGTTGACCACGGGATTTTGG |
| Carrot_Cul1_Cds | AATTCAAACGTAAATCCTGGAATTGACTTGACAGTTACTGTTCTAACCACTGGGTTTTGG |
| Celery_Cul1_Cds | AATGCCAATGTGAATCCTGGCATTGACTTGACGGTTACTGTTCTGACCACTGGCTTCTGG |

Fig. 69N

```
Brassica_Cul1_Cds          CCAAGTTACAAATCATTTGACATAAATCTACCCGCTGAAATGGTCAAGTGTGTTGAAGTT
Radish_Cul1_Cds            CCAAGTTACAAATCATTCGACATAAATCTACCAAGTGAAATGGTCAAGTGTGTTGAAGTT
Beet_Cul1_Cds              CCAAGTTACAAATCTTCCGATCTTAACCTTCCCGCTGAGATGGTGAGGTGTGTTGAAGTT
Spinach_Cul1_Cds           CCAAGTTACAAATCTTCTGATCTTAACCTTCCTGCTGAGATGGTGAGGTGTGTTGAAGTT
Leek_Cul1_Cds              CCCAGTTACAAGTCTTTTGATCTCAATCTTCCTGATGAGATGGTAAAATGCGTTGAAATT
Squash_Cul1_Cds            CCAAGCTACAAGTCTTTTGACCTCAACCTGCCGGCGGAGATGGTAAAGTGTGTTGAAGTT
WaterMelon_Cul1_Cds        CCAAGCTACAAGTCTTTTGACCTCAACCTGCCGGCAGAGATGGTAAAGTGTGTTGAAGTT
CuCumber_Cul1_Cds          CCAAGCTACAAGTCTTTTGACCTCAACCTGCCGGCAGAGATGGTAAAGTGTGTTGAAGTT
Melon_Cul1_Cds             CCAAGCTACAAGTCTTTTGACCTCAACCTGCCGGCGGAGATGGTAAAGTGTGTTGAAGTT
Tomato_Cul1_Cds            CCTAGCTACAAGTCTTTTGATCTCAACCTCCCAGCAGAAATGGTTAGGTGCGTTGAAGTA
Eggplant_Cul1_Cds          CCTAGCTACAAGTCTTTTGATCTCAACCTCCCAGCAGAAATGGTTAGGTGTGTTGAAGTA
Pepper_Cul1_Cds            CCTAGCTACAAGTCTTTTGATCTCAACCTCCCAGCAGAAATGGTTAGGTGCGTTGAAGTA
Lettuce_Cul1_Cds           CCCAGCTACAAATCTTTTGACCTAAATCTCCCTGCCGAAATGGTTAAATGCGTTGAAGTT
Chicory_Cul1_Cds           CCTAGTTACAAATCTTTTGACCTAAATCTCCCTGCAGAAATGGTCAAATGCGTTGAAGTT
Endive_Cul1_Cds            CCTAGTTACAAATCTTTTGACCTAAATCTTCCTGCAGAAATGGTCAAATGCGTTGAAGTT
Carrot_Cul1_Cds            CCAAGTTACAAATCTTTCGATCTCAACCTCCCAGCAGAGATGGTCAAATGTGTTGAAGTT
Celery_Cul1_Cds            CCTAGTTATAAATCCTTTGATCTCAACCTTCCTGCTGAGATGGTCAAGTGCGTTGAAGTA


Brassica_Cul1_Cds          TTCAAAGGGTTTTATGAAACAAAGACAAAACATAGGAAACTTACCTGGATCTACTCACTA
Radish_Cul1_Cds            TTCAAAGGGTTTTATGAGACGAAAACTAAACATAGGAAACTTACATGGATCTACTCACTA
Beet_Cul1_Cds              TTTAAGCAGTTCTATTCAACTAAAACAAAGCACAGGAAGCTGACCTGGGTTTACTCATTG
Spinach_Cul1_Cds           TTTAAGCAATTTTATCAAACAAAGACAAAACACAGGAAGCTCACCTGGGTATATTCGTTG
Leek_Cul1_Cds              TTTAAAGAGTTTTACGAGACAAAAACCAAACACAGAAAACTTACATGGATTTATTCGTTG
Squash_Cul1_Cds            TTCAGGGAATTTTATCAAACAAAAACCAAGCACAGAAAACTTACGTGGATTTACTCGTTG
WaterMelon_Cul1_Cds        TTCAGAGAGTTCTATCAAACAAAAACAAAGCATAGAAAACTTACATGGATTTACTCATTG
CuCumber_Cul1_Cds          TTCAGAGAGTTTTATCAAACAAAAACCAAGCATCGAAAACTTACATGGATTTACTCATTG
Melon_Cul1_Cds             TTCAGAGAGTTTTATCAAACAAAAACCAAGCATAGAAAACTTACATGGATTTACTCATTG
Tomato_Cul1_Cds            TTTAAGGAGTTCTATCAAACAAAAACAAAGCACAGGAAACTTACGTGGATATACTCTTTG
Eggplant_Cul1_Cds          TTCAAGGAGTTTTATCAAACAAAAACGAAGCACAGGAAACTTACATGGATATACTCTTTG
Pepper_Cul1_Cds            TTCAAGGAGTTTTATCAAACAAAAACGAAGCACAGGAAACTTACGTGGATATACTCTTTG
Lettuce_Cul1_Cds           TTCAGAGAATTTTATCAAACAAAAACAAAGCACAGGAAGCTTACATGGATATATTCATTG
Chicory_Cul1_Cds           TTCAGAGAATTTTATCAAACAAAAACAAAACACAGAAAACTCACATGGATATATTCATTG
Endive_Cul1_Cds            TTCAGAGAATTTTATCAAACAAAAACAAAACACAGAAAACTCACATGGATTTATTCATTG
Carrot_Cul1_Cds            TTTAGAGAATTCTACCAAACAAAAACAAAGCACAGAAAACTGACATGGATATACTCTTTG
Celery_Cul1_Cds            TTTAGAGAATTTTATCAAACAAAAACGAAGCATAGAAAGCTCACATGGATATATTCTCTG
```

Fig. 690

| | |
|---|---|
| Brassica_Cul1_Cds | GGAACTTGCCACCTCAATGGGAAGTTTGATGTCAAGCCCATTGAGTTAGTTGTGTCTACA |
| Radish_Cul1_Cds | GGAACTTGTCACCTCAACGGAAAGTTTGATCACAAGCCCATTGAGTTAGTTGTGTCTACT |
| Beet_Cul1_Cds | GGAAGCTGTAATATTAATGGCAAGTTTGGTCCAAAAACTATTGAATTGGTTGTCGGAACT |
| Spinach_Cul1_Cds | GGAAGTTGTAACATTAATGGCAAGTTTGGTCCGAAAACAATTGAATTGGTTGTTGGAACT |
| Leek_Cul1_Cds | GGCACTTGCAACATCAATGGCAAGTTCGAAACCAAGACAATAGAGTTGGTTGTTACAACC |
| Squash_Cul1_Cds | GGTACCTGTAACATCAGCGGAAAATTCGAACCGAAAACGATGGAGCTGATCGTGACAACC |
| WaterMelon_Cul1_Cds | GGTACCTGTAACATCAGCGGAAAATTTGAACCGAAAACGATGGAGCTGATTGTAACAACT |
| CuCumber_Cul1_Cds | GGTACTTGTAACATCAGTGGAAAATTTGAACCGAAAACGATGGAGCTGATTGTGACAACT |
| Melon_Cul1_Cds | GGTACTTGTAACATCAGTGGAAAATTTGAACCGAAGACGATGGAGCTGATTGTGACAACA |
| Tomato_Cul1_Cds | GGAACTTGCAACATAAATGGAAAATTTGAGCCAAAAACTATTGAGCTCGTTGTCACTACT |
| Eggplant_Cul1_Cds | GGAACTTGCAACATAAATGGAAAATTTGAGGCAAAGACTATTGAGCTCGTTGTCACTACT |
| Pepper_Cul1_Cds | GGAACTTGCAATATAAATGGAAAATTTGAGCCAAAGACTATTGAGCTCGTTGTCACTACT |
| Lettuce_Cul1_Cds | GGTACCTGCAATATAAACGGGAAATTTGAACCCAAAACAATGGAGCTCATAGTCACAACC |
| Chicory_Cul1_Cds | GGCACCTGCAATATAAACGGAAAATTCGAACCAAAAACCATGGAGCTAATCGTTACAACT |
| Endive_Cul1_Cds | GGCACCTGCAATATTAACGGAAAATTCGAACCAAAAACCATGGAGCTAATCGTTACAACT |
| Carrot_Cul1_Cds | GGTACTTGTAACATCATTGGAAAATTTGATCCAAAAACCATGGAGCTTATTGTGACAACA |
| Celery_Cul1_Cds | GGTACTTGTAATATCAATGGAAAATTTGAACCCAAAACCATTGAGCTGATTGTGACAACC |

| | |
|---|---|
| Brassica_Cul1_Cds | TACCAGGCTGCTGTGCTTCTGCTGTTCAACACAACAGACAAATTGAGCTACACTGATATC |
| Radish_Cul1_Cds | TACCAGGCTGCTGTGCTTCTGCTGTTCAACACAACAGACAAATTGAGCTACAACGATATC |
| Beet_Cul1_Cds | TATCAGGCTGCTGCTTTGATGCTCTTTAACACATCAGACCGACTGAGTTATTCAGAGATA |
| Spinach_Cul1_Cds | TATCAGGCTGCTGCGCTGATGCTCTTTAACACATCAGATCGACTGAGTTATTCAGAAATA |
| Leek_Cul1_Cds | TATCAGGCTGCAGTGTTGCTTCTATTCAACTCTGCAGATAAATTAAGTTATTCTGAGATT |
| Squash_Cul1_Cds | TATCAGGCTTCTGCCCTGCTGCTTTTCAATTCCTCGGATAAACTAAGTTACTCCGAGATC |
| WaterMelon_Cul1_Cds | TATCAGGCTTCTGCCCTGCTGCTATTCAATTCCTCAGATAGATTAAGTTATTCCGAGATC |
| CuCumber_Cul1_Cds | TATCAGGCTTCTGCCCTGTTGCTATTCAATTCTTCGGATAGACTAAGTTACTCGGAAATC |
| Melon_Cul1_Cds | TATCAGGCTTCTGCCCTGTTGCTATTCAATTCTTCGGACAGACTAAGTTACTCCGAAATC |
| Tomato_Cul1_Cds | TATCAGGCTTCTGCTCTGCTGCTCTTTAATGCATCAGATAGATTGAGTTATCAGGAAATC |
| Eggplant_Cul1_Cds | TATCAGGCTTCTGCTCTGCTTCTCTTTAATGCATCAGATAGATTGAGTTATCAGGAAATC |
| Pepper_Cul1_Cds | TATCAGGCTTCTGCTCTGCTGCTCTTTAATGCATCGGATAGATTGAGTTATCAGGAAATC |
| Lettuce_Cul1_Cds | TACCAGGCATCTGCTTTATTACTGTTCAACTTATCGGATCGATTGAGTTATCAAGAAATC |
| Chicory_Cul1_Cds | TACCAGGCATCTGCTTTATTACTGTTCAACTCATCAGATCGATTGAGTTATCAAGAAATC |
| Endive_Cul1_Cds | TACCAGGCATCTGCTTTATTGTTATTCAACTCATCAGATCGATTAAGTTATCAAGAAATC |
| Carrot_Cul1_Cds | TACCAGGCCTCTGCTCTGCTGCTATTTAACTCTTCTGATAGACTTAGTTATAATGAAATA |
| Celery_Cul1_Cds | TACCAGGCCTCTGCTCTCCTGTTATTTAATACTTCTGATAGGTTGAGTTATCAAGAAATC |

Fig. 69P

| | |
|---|---|
| Brassica_Cul1_Cds | CTAACTCAGCTGAACCTGAGCCACGAAGATCTAGTGAGGTTGCTTCATTCCTTGTCATGT |
| Radish_Cul1_Cds | CTAACTCAACTGAACCTAAGCCACGAAGATTTAGTGAGGTTGCTTCATTCCCTGTCATGT |
| Beet_Cul1_Cds | GCAACTCAACTAAATTTAGCTGATGAAGATCTGGTTAGAGTGCTTCAATCTTTATCCTGC |
| Spinach_Cul1_Cds | ACGACCCAACTAAATCTAGCTGACGAAGACTTGGTTAGAGTGCTTCAATCTCTATCTTGC |
| Leek_Cul1_Cds | GTGCAGCAGCTAAACTTATCTGATGATGATGTAATCAGATTACTTCACTCTCTTTCATGC |
| Squash_Cul1_Cds | ATGACTCAATTAAACTTGAGTGACGATGATGTTGTTAGACTGCTCCACTCGTTGTCGTGT |
| WaterMelon_Cul1_Cds | ATGACACAATTAAATTTGAGTGACGATGATGTTGTTAGACTGCTCCACTCATTGTCATGT |
| CuCumber_Cul1_Cds | ATGACACAATTAAATTTGAGTGACGATGATGTAGTTAGACTACTCCACTCGTTGTCATGT |
| Melon_Cul1_Cds | ATGACACAATTAAATTTGAGTGATGATGATGTTGTTAGACTGCTCCACTCATTGTCGTGT |
| Tomato_Cul1_Cds | ATGACGCAATTAAACCTATCAGATGATGATGTTGTTCGGCTTCTTCATTCCCTTTCATGT |
| Eggplant_Cul1_Cds | ATGACGCAATTAAACCTATCAGATGATGATGTTGTTCGGCTTCTTCATTCCCTTTCATGT |
| Pepper_Cul1_Cds | ATGACGCAACTAAACCTATCAGATGATGATGTTGTTCGGCTTCTTCATTCCCTTTCATGT |
| Lettuce_Cul1_Cds | ATGACTCAGTTGAACTTGTCAGATGATGATGTTGTTAGGCTGCTCCATTCTTTGTCATGT |
| Chicory_Cul1_Cds | ATGACTCAATTAAACTTATCAGATGATGATGTTGTTAGACTACTCCATTCATTATCATGT |
| Endive_Cul1_Cds | ATGACTCAATTAAATTTATCAGATGATGATGTTGTTAGACTACTACATTCATTATCATGT |
| Carrot_Cul1_Cds | ATGACTCAGTTGAACTTGTCGGATGATGATGTTGTCAGACTACTTCATTCTCTTTCGTGT |
| Celery_Cul1_Cds | ATGACTCAGTTAAATTTGTCGGATGATGATGTTGTTCGCCTGCTTCATTCCCTTTCATGT |

| | |
|---|---|
| Brassica_Cul1_Cds | GCTAGATACAAGATTCTTCTCAAGGAGCCAAGCACAAAGACTGTTTCCCAGTCTGATTCT |
| Radish_Cul1_Cds | GCTAGGTACAAGATCCTTCTCAAGGAGCCAAGCACGAAGACTGTTACACAGACTGATTCA |
| Beet_Cul1_Cds | GCAAAGTATAAGATTCTTTTAAAGGAGCCAAACACGAAAACCGTGTCCCCGACTGATTGT |
| Spinach_Cul1_Cds | GCAAAGTATAAGATTCTTCTAAAAGAGCCAAGCACAAGAAACGTGATCTCAACTGATTGT |
| Leek_Cul1_Cds | GCTAAATACAAAATTCTCAATAAAGAACCCGCTACCAAGACTATTACCCCGAATGATCAT |
| Squash_Cul1_Cds | GCGAAGTATAAAATTCTTAACAAGGAGCCAAATACGAAAACCATCTCTCCGAACGATCAT |
| WaterMelon_Cul1_Cds | GCCAAGTATAAAATTCTTAATAAGGAGCCGAACACGAAAACCATCTCTCCGAATGATCAT |
| CuCumber_Cul1_Cds | GCCAAGTATAAAATTCTTAATAAGGAACCAAATACGAAAACCATCTCTCCGAACGATCAT |
| Melon_Cul1_Cds | GCCAAGTATAAAATTCTTAATAAGGAGCCAAATACGAAAACCATCTCACCGAACGATCAT |
| Tomato_Cul1_Cds | GCGAAGTACAAGATACTCAACAAGGAGCCAAGCACCAAAACAATTTCTCCGACTGATGTC |
| Eggplant_Cul1_Cds | GCGAAATACAAGATTCTCAACAAGGAGCCAAGCACCAAAACAATTTCTCCGACTGATGTC |
| Pepper_Cul1_Cds | GCGAAGTACAAGATTCTCAACAAGGAGCCAAGCACCAAAACAATTTCTCCGACTGATGTC |
| Lettuce_Cul1_Cds | GCAAAATACAAAATTCTTTTAAAGGAGCCTAATACCAAAACAATCTCTCCAACCGATTAC |
| Chicory_Cul1_Cds | GCAAAATATAAAATTTTATTAAAAGAACCAAATACAAAAACAATCTCTCCAACTGATTTC |
| Endive_Cul1_Cds | GCAAAATATAAAATTTTATTAAAAGAACCAAATACCAAAACAATATCTCCAACCGATTTC |
| Carrot_Cul1_Cds | GCAAAGTACAAGATTCTATCTAAAGAGCCGAACACCAAAACTATATCTCCAACTGATTGC |
| Celery_Cul1_Cds | GCCAAGTATAAAATTCTTACTAAAGAGCCGAACAACAAAACAATTTCCCCTACGGATTAC |

Fig. 69Q

| | |
|---|---|
| Brassica_Cull_Cds | TTTGAATTCAACTCCAAATTCACCGACAGAATGCGGAGAATAAAGATCCCTCTCCCACCT |
| Radish_Cull_Cds | TTTGAATTCAATGCCAAATTCACGGACAGAATGCGCAGAATCAAGATCCCTCTCCCTCCT |
| Beet_Cull_Cds | TTTTCATTTAACTCTAGTTTCACTGACAGGATGAGGAGGATAAGAATTCCTCTTCCTCCG |
| Spinach_Cull_Cds | TTTTCATTCAACTCTAATTTTACTGACAGAATGAGGAGGATTAGGATTCCTCTTCCTCCA |
| Leek_Cull_Cds | TTTGAGTTCAATTCTAAATTCACTGATAGAATGAGAAGGATCAAGATTCCCCTGCCTCCT |
| Squash_Cull_Cds | TTTGAGTTCAACGCAAAATTCTCCGACAAAATGAGGAGAATAAAGATCCCTCTTCCGCCT |
| WaterMelon_Cull_Cds | TTTGAGTTCAATGCAAAATTCTCCGACAAAATGAGGAGAATAAAGATCCCTCTTCCGCCT |
| CuCumber_Cull_Cds | TTTGAGTTCAATGCAAAATTCTCCGACAAAATGAGGAGAATAAAGATCCCTCTTCCGCCT |
| Melon_Cull_Cds | TTTGAGTTCAATGCAAAATTCTCCGACAAAATGAGGAGAATAAAGATCCCTCTTCCGCCT |
| Tomato_Cull_Cds | TTTGAGTTCAACTCAAAGTTCACTGACAAAATGAGGAGGATCAAGATACCTCTCCCTCCT |
| Eggplant_Cull_Cds | TTTGAGTTCAACTCAAAGTTCACTGACAAAATGAGGAGGATCAAGATACCTCTCCCACCA |
| Pepper_Cull_Cds | TTTGAGTTCAATTTTAAGTTCACTGACAAAATGAGGAGGATCAAGATACCTCTCCCTCCT |
| Lettuce_Cull_Cds | TTCGAATTCAACTCCAAGTTTACAGATAAAATGAGGAGGATCAAGATTCCTCTACCTCCT |
| Chicory_Cull_Cds | TTTGAATTCAACTCAAAGTTTACAGATAAAATGAGAAGGATCAAGATTCCTCTACCTCCT |
| Endive_Cull_Cds | TTTGAATTCAACTCAAAGTTTACAGATAAAATGAGAAGGATCAAGATTCCTCTACCTCCT |
| Carrot_Cull_Cds | TTTCAGTTCAATTCCAAATTTACTGATAAAATGAGGAGGATTAAGATTCCACTTCCCCCA |
| Celery_Cull_Cds | TTTGAGTTCAACTCCAAGTTCACTGACAAAATGAGGAGAATTAAGATTCCACTACCTCCA |

| | |
|---|---|
| Brassica_Cull_Cds | GTTGATGAGAGGAAGAAAGTTGTGGAAGACGTGGACAAAGACAGACGCTATGCGATTGAT |
| Radish_Cull_Cds | GTTGATGAAAGGAAGAAGGTTGTGGAAGATGTGGACAAAGACAGACGCTATGCGATTGAT |
| Beet_Cull_Cds | ATGGATGAGAGGAAAAAGGTTGTTGAGGATGTTGACAAAGATAGAAGATATGCTATTGAT |
| Spinach_Cull_Cds | ATGGATGAGAGGAAAAAGGTTGTTGAAGATGTTGACAAAGATAGAAGATATGCTATTGAT |
| Leek_Cull_Cds | GTGGATGAGAAGAAAAAAGTAATTGAAGATGTTGACAAAGACAGAAGATATGCAATTGAC |
| Squash_Cull_Cds | GTGGATGAGAAAAAGAAAGTAATAGAAGATGTTGACAAGGATCGAAGATATGCTATCGAT |
| WaterMelon_Cull_Cds | GTGGATGAGAAAAAGAAAGTCATTGAAGATGTTGACAAGGATCGAAGGTATGCTATTGAT |
| CuCumber_Cull_Cds | GTGGATGAGAAAAAGAAAGTCATTGAAGATGTTGACAAGGATCGAAGGTATGCTATTGAC |
| Melon_Cull_Cds | GTGGATGAGAAAAAGAAAGTCATTGAAGATGTTGACAAGGATCGAAGGTATGCTATTGAC |
| Tomato_Cull_Cds | GTTGATGAGAAGAAAAAGGTAATTGAAGACGTTGACAAGGATAGGCGGTATGCTATAGAT |
| Eggplant_Cull_Cds | GTTGATGAAAAGAAAAAGGTAATTGAAGACGTTGACAAGGATAGGCGGTATGCTATAGAT |
| Pepper_Cull_Cds | GTTGATGAGAAGAAAAAGGTAATTGAAGATGTTGACAAAGATAGGCGGTACGCTATAGAT |
| Lettuce_Cull_Cds | GTGGATGAGAAGAAAAAGGTGATTGAGGATGTTGACAAAGACAGACGTTATGCCATTGAT |
| Chicory_Cull_Cds | GTTGATGAAAAGAAAAAAGTAATTGAAGATGTTGACAAAGACCGACGTTATGCAATTGAT |
| Endive_Cull_Cds | GTTGATGAAAAGAAAAAAGTAATTGAAGATGTTGACAAAGATAGAAGGTATGCAATTGAT |
| Carrot_Cull_Cds | GTGGATGAGAAGAAAAAGGTAATTGAAGATGTTGATAAAGACAGGCGATATGCTATAGAT |
| Celery_Cull_Cds | GTTGATGAGAAGAAAAAGGTAATTGAAGATGTTGACAAGGACCGGCGATATGCCATTGAT |

Fig. 69R

```
Brassica_Cull_Cds        GCTGCCATTGTGAGGATCATGAAGAGCAGGAAAGTATTGGGACATCAACAACTTGTTTCT
Radish_Cull_Cds          GCTGCCATTGTTAGGATCATGAAGAGCAGGAAAGTGTTGGGACATCAACAACTCGTCTCT
Beet_Cull_Cds            GCCTCAATTGTACGCATAATGAAAAGTAGGAAGGTTTTGGGGTACCAGCAATTAATCACA
Spinach_Cull_Cds         GCCTCAATTGTACGCATAATGAAAAGTAGGAAGGCTTTGGGATATCAACAATTAATCACG
Leek_Cull_Cds            GCATCCATAGTTCGAATAATGAAAAGTAGAAAAGTTCTTGGTCATCAGCAGCTTGTTTTG
Squash_Cull_Cds          GCCTCGATCGTGCGTATCATGAAGAGTAGGAAAGTTCTGGGTCACCAGCAGTTAGTGATG
WaterMelon_Cull_Cds      GCCTCAATCGTGCGTATCATGAAGAGTCGGAAAGTTCTGGGTCATCAGCAGCTAGTGATG
CuCumber_Cull_Cds        GCCTCAATCGTGCGTATCATGAAGAGTCGGAAAGTTCTTGGTCATCAGCAACTAGTGATG
Melon_Cull_Cds           GCCTCAATCGTGCGTATCATGAAGAGTCGAAAAGTTCTTGGTCATCAGCAACTAGTGATG
Tomato_Cull_Cds          GCTTCAATTGTGCGTATTATGAAGAGCCGTAAAGTATTGGGCTACCAGCAACTAGTCATG
Eggplant_Cull_Cds        GCCTCAATTGTGCGTATTATGAAGAGTCGTAAAGTATTGGGCTACCAGCAACTGGTCATG
Pepper_Cull_Cds          GCTTCAATTGTGCGTATTATGAAGAGTCGTAAAGTATTGGGCTACCAGCAACTGGTCATG
Lettuce_Cull_Cds         GCTTCCATTGTAAGGATAATGAAGAGCAGAAAGGTGCTTGGATACCAGCAGTTGGTTATG
Chicory_Cull_Cds         GCTTCAATTGTACGGATAATGAAAAGCAGAAAAGTTCTTGGATACCAACAATTGGTCATG
Endive_Cull_Cds          GCTTCAATTGTACGAATAATGAAAAGCAGAAAAGTTCTTGGATACCAACAATTGGTTATG
Carrot_Cull_Cds          GCTTCAATTGTCCGTATCATGAAGAGCCGCAAAGTTTTGGGTTATCAGCAGCTAGTAATG
Celery_Cull_Cds          GCATCTATTGTCCGCATTATGAAGAGCCGTAAAGTTTTGGGCTACCAACAATTGGTTATG

Brassica_Cull_Cds        GAGTGCGTTGAGCAACTTAGCCGAATGTTCAAGCCTGATATCAAGGCAATCAAGAAGCGC
Radish_Cull_Cds          GAGTGCGTTGAGCAACTTAGCCGAATGTTCAAGCCTGATATCAAAGCGATCAAGAAGCGT
Beet_Cull_Cds            GAGTGTGTGGAGCAGCTAAGCCGCATGTTCAAGCCTGATTTCAAGGCAATTAAGAAGAGG
Spinach_Cull_Cds         GAGTGTGTGGAGCAGCTAAGCCGCATGTTCAAGCCTGATTTCAAAGCAATTAAGAAGAGG
Leek_Cull_Cds            GAATGTGTTGAGCAATTAGGCCGCATGTTTAAGCCTGACTTTAAGGCCATCAAGAAAAGG
Squash_Cull_Cds          GAGTGCGTCGAGCAACTGGGTCGTATGTTCAAGCCTGATTTCAAGGCGATAAAGAAGAGA
WaterMelon_Cull_Cds      GAGTGCGTCGAGCAATTGGGTCGTATGTTCAAGCCCGACTTCAAAGCGATAAAGAAGAGA
CuCumber_Cull_Cds        GAGTGCGTCGAGCAATTGGGCCGTATGTTCAAGCCCGATTTCAAGGCGATAAAGAAGAGA
Melon_Cull_Cds           GAGTGCGTCGAGCAATTGGGTCGTATGTTCAAGCCCGATTTCAAGGCGATAAAGAAGAGA
Tomato_Cull_Cds          GAGTGCGTTGAGCAGTTGGGGCGCATGTTCAAGCCTGATGTCAAAGCTATCAAGAAGAGA
Eggplant_Cull_Cds        GAGTGCGTTGAGCAGTTGGGACGCATGTTCAAGCCTGATGTCAAAGCTATCAAGAAGAGA
Pepper_Cull_Cds          GAGTGTGTTGAGCAGTTGGGACGTATGTTCAAGCCTGATGTCAAAGCTATCAAGAAGAGA
Lettuce_Cull_Cds         GAGTGTGTTGAACAGTTGGGACGCATGTTTAAGCCTGATGTAAAAGCAATCAAGAAGCGG
Chicory_Cull_Cds         GAATGTGTTGAACAATTAGGCCGTATGTTTAAGCCTGATGTAAAAGCAATCAAGAAACGT
Endive_Cull_Cds          GAGTGTGTTGAACAATTAGGCCGTATGTTTAAGCCTGATGTAAAAGCAATCAAGAAGCGT
Carrot_Cull_Cds          GAGTGCGTTGAACAATTGGGTCGCATGTTTAAGCCTGATGTCAAAGCAATCAAGAAGAGA
Celery_Cull_Cds          GAATGTGTTGAGCAATTGGGACGCATGTTTAAGCCTGATGTCAAAGCAATTAAGAAGAGA
```

Fig. 69S

| | |
|---|---|
| Brassica_Cul1_Cds | ATGGAGGATTTGATAACGAGAGATTATCTGGAGAGGGACAAGGAGAACGCTAACATGTTT |
| Radish_Cul1_Cds | ATGGAGGATCTAATTACGAGGGATTATTTGGAGAGGGACAAGGAGAACCCTAACATGTTT |
| Beet_Cul1_Cds | ATCGAGGACTTAATAACCCGAGATTATATTGAAAGAGACAAGGAGAACCCGCAGCTATTC |
| Spinach_Cul1_Cds | ATCGAGGACTTGATAACCAGAGATTATATTGAAAGAGACAAGGAAAACCCTCAGCTATTC |
| Leek_Cul1_Cds | ATTGAAGATCTGATCGCTAGAGATTATTTGGAGAGGGACAAGGACAATCCAAACCTCTTT |
| Squash_Cul1_Cds | ATCGAAGATCTGATCACTCGTGACTATTTAGAGAGAGACAAAGACAACCCCCACTTGTTT |
| WaterMelon_Cul1_Cds | ATCGAAGATCTGATCACTCGGGACTATTTAGAGAGAGACAAAGACAACCCCCACTTGTTT |
| CuCumber_Cul1_Cds | ATTGAAGACCTGATCACTCGGGATTATCTAGAGAGAGACAAAGACAACCCCCACTTGTTT |
| Melon_Cul1_Cds | ATTGAAGACCTGATCACTCGGGACTATCTAGAGAGAGACAAAGACAACCCCCACTTGTTT |
| Tomato_Cul1_Cds | ATCGAAGATTTGATAACTAGAGATTACCTAGAGAGGGACAAAGATAATCCAAACCTGTTC |
| Eggplant_Cul1_Cds | ATTGAAGATCTGATAACTAGAGATTACCTAGAGAGGGACAAAGATAACCCAAACTTGTTC |
| Pepper_Cul1_Cds | ATTGAAGATTTGATAACTAGAGATTACCTAGAGAGGGACAAAGATAATCCGAACTTGTTC |
| Lettuce_Cul1_Cds | ATTGAAGATCTGATAACTCGTGATTATCTTGAAAGAGACAAAGAGAACCCCAACTTGTTC |
| Chicory_Cul1_Cds | ATTGAAGATCTCATAACTCGTGATTATCTTGAAAGAGACAAAGAAAATCCAAATTTGTTT |
| Endive_Cul1_Cds | ATTGAAGATTTGATAACGCGTGATTATCTTGAAAGAGACAAAGAAAATCCAAATTTGTTT |
| Carrot_Cul1_Cds | ATCGAAGATTTAATAACTCGGGATTATCTGGAAAGAGACAAGGACAATGCCAACTTGTTC |
| Celery_Cul1_Cds | ATCGAAGATTTAATAACGCGTGATTATCTGGAAAGAGACAAGGATAATGCCAACCTTTTC |

| | |
|---|---|
| Brassica_Cul1_Cds | AGGTACTTGGCTTAG |
| Radish_Cul1_Cds | AGGTACTTGGCTTAG |
| Beet_Cul1_Cds | CGATACTTGGCTTGA |
| Spinach_Cul1_Cds | CGGTACTTGGCTTGA |
| Leek_Cul1_Cds | AAATATTTGGCCTAA |
| Squash_Cul1_Cds | AGGTACTTGGCTTGA |
| WaterMelon_Cul1_Cds | AGGTACTTGGCTTGA |
| CuCumber_Cul1_Cds | AGGTACTTGGCTTGA |
| Melon_Cul1_Cds | AGGTACTTGGCTTGA |
| Tomato_Cul1_Cds | AAGTACTTGGCATGA |
| Eggplant_Cul1_Cds | AAGTACTTGGCATGA |
| Pepper_Cul1_Cds | AAGTACTTGGCATGA |
| Lettuce_Cul1_Cds | CGATACTTGGCATGA |
| Chicory_Cul1_Cds | CGGTACTTGGCATGA |
| Endive_Cul1_Cds | CGGTACTTGGCATGA |
| Carrot_Cul1_Cds | AGGTATCTGGCATGA |
| Celery_Cul1_Cds | AGATATTTGGCATGA |
| Endive_Cul1_Cds | CGGTACTTGGCATGA |
| Carrot_Cul1_Cds | AGGTATCTGGCATGA |
| Celery_Cul1_Cds | AGATATTTGGCATGA |

Fig. 70A

```
beet_cul1              --MNDRKVIELEQGWEFMGKGITKLKRILEGLPEPPFNSEDYMMLYTT[I]YNMCTQKPPHD
spinach_cul1           --MNDRKVIELEQGWEFMGKGITKLKRILEGLPEPPFNSEDYMMLYTT[I]YNMCTQKPPHD
arabidopsis_cul1       ---MERKTIDLEQGWDYMQTGITKLKRILEGLNEPAFDSEQYMMLYTT[I]YNMCTQKPPHD
brassica_cul1          ---MERKTIDLDQGWDYMQTGITKLKRILEGLPEPQFDSEQYMMLYTT[I]YNMCTQKPPHD
radish_cul1            ---MERKTIDLEQGWDYMQTGITKLKRILEGLPEPQFDSEQYMMLYTT[I]YNMCTQKPPHD
leek_cul1              MSLHERKTIDLEQGWAFMQKGITKLKNILDELNEPQFSSEDYMMLYTT[I]YNMCTQKPPHD
eggplant_cul1          --MNQRSTIDLEHGWDFMQKGITKLKNILEGLPEPQFSSEDYMMLYTT[I]YNMCTQKPPHD
tomato_cul1            --MNQRSTIDLEHGWDFMQRGITKLKNILEGLPEPQFSSEDYMMLYTT[I]YNMCTQKPPHD
pepper_cul1            --MNQRSTINLEHGWDFMQRGITKLKNILEGLPEPQFSSEDYMMLYTT[I]YNMCTQKPPHD
cucumber_cul1          MTMGERKTIDLEQGWEFMQKGITKLKNILEGLPEPQFSSEDYMMLYTT[I]YNMCTQKPPHD
melon_cul1             MTMGERKTIDLEQGWEFMQKGITKLKNILEGLPEPQFSSEDYMMLYTT[I]YNMCTQKPPHD
watermelon_cul1        MTMGERKTIDLEQGWEFMQKGITKLKNILEGLPEPQFSSEDYMMLYTT[I]YNMCTQKPPHD
squash_cul1            MTMGERKTIDLEQGWEFMQKGITKLKNILEGLPEPQFSSEDYMMLYTT[I]YNMCTQKPPHD
celery_cul1            --MNERKTIDLDNGWEFMQKGITKLKKILEGQPEPQFSSEDYMMLYTT[I]YNMCTQKPPHD
lettuce_cul1           --MNERKTIDLEQGWDFMQKGITKLKNILEGLPEPQFSSEDYMMLYTT[I]YNMCTQKPPHD
endive_cul1            --MNERKTIDLEQGWDFMQKGITKLKNILEGLPEPQFSSEDYMMLYTT[I]YNMCTQKPPHD
chicory_cul1           --MNERKTIDLEQGWDFMQKGITKLKNILEGLPEPQFSSEDYMMLYTT[I]YNMCTQKPPHD
carrot_cul1            -MMIERKTIDLEQGWDFMQKGITKLKNILEGFPEPQFSSEDYMMLYTT[I]YNMCTQKPPHD


beet_cul1              YSQQLYDNYKQAFVDYINSTVLPSLREKHDEFMLRELVKRWANHKVMVRWLSRFFHYLDR
spinach_cul1           YSQQLYDNYKEAFVDYIHSTVLPSLGDKHDEFMLRELVKRWSNHKVMVRWLSRFFHYLDR
arabidopsis_cul1       YSQQLYDKYREAFEEYINSTVLPALREKHDEFMLRELFKRWSNHKVMVRWLSRFFYYLDR
brassica_cul1          YSQQLYDKYREAFEEYIHSTVLPALREKHDEYMLRELVKRWSNHKVMVRWLSRFFYYLDR
radish_cul1            YSQQLYDKYREAFEEYIDSTVLPALKEKHDEYMLRELVKRWSNHKVMVRWLSRFFYYLDR
leek_cul1              YSQELYDKYRESFEEYITTTVLPSLREKHDEYMLRELVRRWSNHKIMVRWLSRFFHYLDR
eggplant_cul1          YSQQLYDKYREAFEEYITTTVLPSLREKHDEFMLRELVKRWSNHKVMVRWLSRFFHYLDR
tomato_cul1            YSQQLYDKYREAFEEYITTTVLPSLREKHDEFMLRELVKRWSNHKVMVRWLSRFFHYLDR
pepper_cul1            YSQQLYDKYREAFEEYITTTVLPSLREKHDEFMLRELVKRWSNHKVMVRWLSRFFHYLDR
cucumber_cul1          YSQQLYDKYRESFEEYITSMVLPSLREKHDEFMLRELVKRWTNHKVMVRWLSRFFHYLDR
melon_cul1             YSQQLYDKYRESFEEYITSMVLPSLREKHDEFMLRELVKRWTNHKVMVRWLSRFFHYLDR
watermelon_cul1        YSQQLYDKYRESFEEYITSMVLPSLREKHDEFMLRELVKRWTNHKVMVRWLSRFFHYLDR
squash_cul1            YSQQLYDKYRESFEEYISSMVLPSLREKHDEFMLRELVKRWTNHKVMVRWLSRFFHYLDR
celery_cul1            YSQQLYDKYREAFEEYITSTVLPSLREKHDEFMLRELVNRWTNHKVMVRWLSRFFHYLDR
lettuce_cul1           YSQQLYDKYRESFEEYITSTVLPSLREKHDEFMLRELVRRWSNHKVMVRWLSRFFHYLDR
endive_cul1            YSQQLYDKYRESFEEYITSTVLPSLREKHDEFMLRELVRRWSNHKVMVRWLSRFFHYLDR
chicory_cul1           YSQQLYDKYRESFEEYITSTVLPSLREKHDEFMLRELVRRWSNHKVMVRWLSRFFHYLDR
carrot_cul1            YSQQLYEKYREAIEEYITSTVLPSLREKHDEFMLRELVKRWSNHKVMVRWLSRFFHYLDR


beet_cul1              YFIARRSLPSLNEVGLTCFRDLVYQEISGKAKDAVIALIDIEREGGQIDRSLLKNVLDIY
spinach_cul1           YFIARRSLPSLNDVGLTCFRDLVYQEISGKAKDAVIALIDEEREGGQIDRALLKNVLDIY
arabidopsis_cul1       YFIARRSLPPLNEVGLTCFRDLVYNELHSKVKQAVIALVDKEREGEQIDRALLKNVLDIY
brassica_cul1          YFIARRSLPPLNEVGLTCFRDLVYNELHSKVKDAVIALVDKEREGEQIDRALLKNVLDIY
radish_cul1            YFIARRSLPPLNEVGLTCFRDRVYKELHSKVKDAVIALVDKEREGEQIDRALLKNVLDIY
leek_cul1              YFIARRSLPALNEVGLTCFRDLVYNEVHGKVKDAVISLIDQEREGEQIDRALLKNVLGIF
eggplant_cul1          YFIARRSLPGLNEVGLTCFRDLVYQELNGKVRDAVISLIDQEREGEQIDRALLKNVLDIF
tomato_cul1            YFIARRSLPGLNEVGLTCFRDQVYQELNGKVRDAVISLIDQEREGEQIDRALLKNVLDIF
```

Fig. 70B

```
pepper_cul1        YFIARRSLPGLNEVGLTCFRDLVYQELNGKVRDAVISLIDQEREGEQIDRALLKNVLDIF
cucumber_cul1      YFIARRSLPPLNEVGLTCFRELVYKELNSKVRDAVISLIDQEREGEQIDRALLKNVLDIF
melon_cul1         YFIARRSLPPLNEVGLTCFRELVYKELNSKVRDAVISLIDQEREGEQIDRALLKNVLDIF
watermelon_cul1    YFIARRSLPPLNEVGLTCFRELVYKELNSKVRDAVISLIDQEREGEQIDRALLKNVLDIF
squash_cul1        YFIARRSLPPLNEVGLTCFRELVYKELNSKVRDAVISLIDQEREGEQIDRALLKNVLDIF
celery_cul1        YFIARRSLPALHEVGLTCFRDLVYQELKVKVRDAVISLIDQEREGEQIDRALLKNVLDIF
lettuce_cul1       YFIARRSLPPLNEVGLACFRDLVYQEVNGKVRDAVISLIDQEREGEQIDRALLKNVLDIF
endive_cul1        YFIARRSLPPLNEVGLACFRDLVYQEVNGKVRDAVISLIDQEREGEQIDRALLKNVLDIF
chicory_cul1       YFIARRSLPPLNEVGLACFRDLVYQEVNGKVRDAVISLIDQEREGEQIDRALLKNVLDIF
carrot_cul1        YFIARRSLPPLHEVGLTCFRDLVYQEINGKVRDAVISLINQEREGEQIDRALLKNVLDIF


beet_cul1          VEIGMGQMDHYEKDFEAHMLDDTAAYYSRKASSWILEDSCPEYMLKSEECLKKEKERVAN
spinach_cul1       VEIGMTQMDYYEKDFEAHMLDDTAAYYSRKASSWILEDSCPEYMLKSEECLKKEKDRVAH
arabidopsis_cul1   VEIGMGQMERYEEDFESFMLQDTSSYYSRKASSWIQEDSCPDYMLKSEECLKKERERVAH
brassica_cul1      VEIGMGQMERYEEDFESFMLLDSASYYSRKASSWIQEDSCPDYMLKSEECLKKERERVAH
radish_cul1        VEIGMGQMERYEVDFESFMLLDSASYYSRKASNWIQEDSCPDYMLKSEECLKKERERVAH
leek_cul1          VEIGLGSMECYENDFETSMLNATAAYYSRKASNWILEDSCPDYMLKAEECLKHEKDRVAH
eggplant_cul1      VEIGMGSMDYYENDFEAAMLKDTAAYYSRKASNWILEDSCPDYMLKAEECLKREKDRVSH
tomato_cul1        VEIGMGLMDYYENDFEAAMLKDTAAYYSRKASNWILEDSCPDYMLKAEECLKREKDRVSH
pepper_cul1        VEIGMGSMDYYENDFEAAMLKDTAAYYSRKASNWILEDSCPDYMLKAEECLKREKDRVSH
cucumber_cul1      VEIGMGQMDYYENDFEAAMLKDTAAYYSRKASNWILEDSCPDYMLKAEECLKREKDRVSH
melon_cul1         VEIGMGQMDYYENDFEAAMLKDTAAYYSRKASNWILEDSCPDYMLKAEECLKREKDRVSH
watermelon_cul1    VEIGMGQMDYYENDFEAAMLKDTAAYYSRKASNWILEDSCPDYMLKAEECLKREKDRVSH
squash_cul1        VEIGMGQMDYYENDFEAAMLKDTAAYYSRKASNWILEDSCPDYMLKAEECLRREKDRVSH
celery_cul1        VEIGMSQMDQYENDFEEAMLTDTAAYYSRKASNWILEDSCPDYMLKAEECLRREKDRVSH
lettuce_cul1       VEIGMGQMEYYENDFEASMLNDTAAYYSRKASNWILEDSCPDYMLKAEECLKREKDRVSH
endive_cul1        VEIGMGQMEYYENDFEASMLNDTAAYYSRKASNWILEDSCPDYMLKAEECLKREKDRVSH
chicory_cul1       VEIGMGQMEYYENDFEASMLNDTAAYYSRKASNWILEDSCPDYMLKAEECLKREKDRVSH
carrot_cul1        VEVGMSQMDYYENDFEADMLKDTAAYYSRKASNWILEDSCPDYMLKAEECLRREKDRVSN


beet_cul1          YLHSSSEPKLLEKVQNELLLVYESQLLEKENSGCRALLKDDKVDDLSRMYRLYSKVTKGL
spinach_cul1       YLHSSSEPKLLEKVQNELLLVYENQLLEKENSGCRALLKDDKVEDLSRMYRLYSKVTKGL
arabidopsis_cul1   YLHSSSEPKLVEKVQHELLVVFASQLLEKEHSGCRALLRDDKVDDLSRMYRLYHKILRGL
brassica_cul1      YLHSSSEPKLVEKVQHELLVVYANQLLEKEHSGCRALLRDDKVDDLSRMYRLYHKIVKGL
radish_cul1        YLHSSSEPKLVEKVQHELLVVYANQLLEKEHSGCRALLRDDKVDDLSRMYRLYHKIAKGL
leek_cul1          YLHSSSEQKLLEKVQHELLFVYASQLLEKEHSGCHALLRDDKVGDLSRMYRLFCRITRGL
eggplant_cul1      YLHSSSETKLLEKVQHELLSVYANQLLEKEHSGCHALLRDDKVDDLSRMYRLFSKIPRGL
tomato_cul1        YLHSSSETKLLEKVQHELLSVYATQLLEKEHSGCHALLRDDKVEDLSRMYRLFSKISRGL
pepper_cul1        YLHLSSETKLLEKVQHELLSVYATQLLEKEHSGCHALLRDDKVEDLSRMYRLFSKIPRGL
cucumber_cul1      YLHSSSEPKLLEKVQHELLSVYATQLLEKEHSGCHALLRDDKVEDLSRMFRLFSKIPKGL
melon_cul1         YLHSSSEPKLLEKVQHELLSVYATQLLEKEHSGCHALLRDDKVEDLSRMFRLFSKIPKGL
watermelon_cul1    YLHSSSEPKLLEKVQHELLSVYATQLLEKEHSGCHALLRDDKVEDLSRMFRLFSKIPKGL
squash_cul1        YLHSSSEPKLLEKVQHELLSVYATQLLEKEHSGCHALLRDDKVEDLSRMFRLFSKIPKGL
celery_cul1        YLHFSSEPKLLEKVQHELLSVYATQLLEKEHSGCHALLRDDKVDDLSRMYRLFSKIPKGL
lettuce_cul1       YLHSSSEPKLLEKVQNELLSVYATQLLEKEHSGCHALLRDDKVDDLSRMYRLFSKIPKGL
endive_cul1        YLHSSSEPKLLEKVQTELLSVYATQLLEKEHSGCHALLRDDKVDDLSRMYRLFSKIQKGL
```

Fig. 70C

```
chicory_cul1        YLHSSSEPKLLEKVQTELLSVYATQLLEKEHSGCHALLRDDKVDDLSRMYRLFSKIQKGL
carrot_cul1         YLHSSSEPKLLEKVQHELLSHYATQLLEKEHSGCHALLRDDKVADLSRMYRLFSKIPRGL


beet_cul1           EPIGSIFKQHITDEGTALVQQAEDAAISKAENT--G-GSHEQVFVRKVIELHDKFMTYVT
spinach_cul1        EPIGSIFKQHITDEGTALVQQAEDAAISKAENA--GGGSHEQVFVRKVIELHDKFMTYVT
arabidopsis_cul1    EPVANIFKQHVTAEGNALVQQAEDTATNQVAN---TASVQEQVLIRKVIELHDKYMVYVT
brassica_cul1       EPVANIFKQHVTAEGNALVQQAEDTATNHAAN---TASVQEQVLIRKVIELHDKYMVYVV
radish_cul1         EPVANIFKQHVTAEGNALVQQAEDTATNQAAN---TASVQEQVLIRKVIELHDKYMVYVV
leek_cul1           DPVSQIFKQHVTAEGTALVKHAEDAASNKKAEKKDIVGLQEQVFVRKVIELHDKYLAYVT
eggplant_cul1       EPVANIFKQHVTAEGTALVKQAEDAASNKKAEKRDVVGLQEQVFVRKVIELHDKYLAYVN
tomato_cul1         DPVANIFKQHVTAEGTALVKQAEDAASNKKAEKRDVVGLQEQVFVRKVIELHDKYLAYVN
pepper_cul1         DPVANIFKQHVTAEGTALVKQAEDAASNKKAEKRDVVGLQEQIFVRKVIELHDKYMAYVN
cucumber_cul1       DPVSNIFKQHVTAEGTALVKQAEDAASNKKAEKKDIVGLQEQVFVRKVIELHDKYLAYVN
melon_cul1          DPVSNIFKQHVTAEGTALVKQAEDAASNKKAEKKDIVGLQEQVFVRKVIELHDKYLAYVN
watermelon_cul1     DPVSNIFKQHVTAEGTALVKQAEDAASNKKAEKKDIVGLQEQVFVRKVIELHDKYLAYVN
squash_cul1         DPVSNIFKQHVTAEGTALVKQAEDAASNKKAEKKDIVGLQEQVFVRKVIELHDKYLAYVN
celery_cul1         DPVSYIFKQHVTNEGMALVKQAEDAASNKKAEKRDVVSLQEQVFVRKIIELHDKYLAYVN
lettuce_cul1        DPVSSMFKQHVTAEGTTLVKQAEDAASTKKAEKRDVVGLQEQVFVRKVIELHDKYLAYVN
endive_cul1         DPVSSMFKQHVTAEGTTLVKQAEDAASTKKAEKRDVVGLQEQVFVRKVIELHDKYLAYVN
chicory_cul1        DPVSSMFKQHVTAEGTTLVKQAEDAASTKKAEKRDVVGLQEQVFVRKVIELHDKYLAYVN
carrot_cul1         DPVSNIFKQHVTAEGTALVKQAEDAASNKKAEKRDVVGLQEQVFVRKIIELHDKYLTYVN


beet_cul1           DCFNSHTIFHKALKEAFEVFLNKGVAGSSSAELLATFCDNILKKGGSEKLSDEAIEDSLE
spinach_cul1        DCFNSHTIFHKALKEAFEVFLNKGVAGSSSAELLASFCDNILKKGGSEKLSDEAIEDSLE
arabidopsis_cul1    ECFQNHTLFHKALKEAFEIFCNKTVAGSSSAELLATFCDNILKKGGSEKLSDEAIEDTLE
brassica_cul1       ECFQNHTLFHKALKEAFEIFCNKTVAGSSSAELLATFCDNILKKGGSEKLSDEAIEDTLE
radish_cul1         ECFQNHTLFHKALKEAFEIFCNKTVAGSSSAELLATFCDNILKKGGSEKLSDEAIEDTLE
leek_cul1           DCFQNHSLFHKALKEAFEVFCNKGVAGSSSAELLAAFCDNILKKGGSEKLSDEAIEDTLE
eggplant_cul1       NCFQNHTLFHKALKEAFELFCNKGVAGSSNAELLATFCDNILKKGGSEKLSDEAIEETLE
tomato_cul1         NCFQNHTLFHKALKEAFELFCNKGVAGSSSAELLATFCDNILKKGGSEKLSDEAIEETLE
pepper_cul1         NCFQNHTLFHKALKEAFELFCNKGVAGSSSAELLATFCDNILKKGGSEKLSDEAIEETLE
cucumber_cul1       DCFQNHTLFHKALKEAFEVFCNKGVAGSSSAELLATFCDNILKKGGSEKLSDEAIEETLE
melon_cul1          DCFQNHTLFHKALKEAFEVFCNKGVAGSSSAELLATFCDNILKKGGSEKLSDEAIEETLE
watermelon_cul1     DCFQNHTLFHKALKEAFEVFCNKGVAGSSSAELLATFCDNILKKGGSEKLSDEAIEETLE
squash_cul1         DCFQNHTLFHKALKEAFEVFCNKGVAGSSSAELLATFCDNILKKGGSEKLSDEAIEETLE
celery_cul1         DCFTNHTLFHKALKEAFEIFCNKGVAGSSNAELLATFCDNILKKGGSEKLSDEAIEETLE
lettuce_cul1        DCFMNHTLFHKALKEAFEIFCNKGVAGSSSAELLATFCDNILKKGGSEKLSDEAIEDTLE
endive_cul1         DCFMNHTLFHKALKEAFEIFCNKGVAGSSSAELLATFCDNILKKGGSEKLSDEAIEDTLE
chicory_cul1        DCFMNHTLFHKALKEAFEIFCNKGVAGSSSAELLATFCDNILKKGGSEKLSDEAIEDTLE
carrot_cul1         DCFTNHTLFHKALKEAFEIFCNKGVSGSSSAELLATFCDNILKKGGSEKLSDEAIEETLE


beet_cul1           KVVKLLAYVSDKDLFAEFYRKKLSRRLLFDKSANDDHERSILTKLKQQCGGQFTSKMEGM
spinach_cul1        KVVKLLAYVSDKDLFAEFYRKKLSRRLLFDKSANDDHERSILTKLKQQCGGQFTSKMEGM
arabidopsis_cul1    KVVKLLAYISDKDLFAEFYRKKLARRLLFDRSANDDHERSILTKLKQQCGGQFTSKMEGM
brassica_cul1       KVVKLLAYISDKDLFAEFYRKKLARRLLFDRSANDDHERSILTKLKQQCGGQFTSKMEGM
```

Fig. 70D

```
radish_cul1          KVVKLLAYISDKDLFAEFYRKKLARRLLFDRSANDDHERSILTKLKQQCGGQFTSKMEGM
leek_cul1            KVVKLLAYISDKDLFAEFYRKKLARRLLFDKSANDDHERSILTKLKQQCGGQFTSKMEGM
eggplant_cul1        KVVKLLAYISDKDLFAEFYRKKLARRLLFDKSANDEHERSILTKLKQQCGGQFTSKMEGM
tomato_cul1          KVVKLLAYISDKDLFAEFYRKKLARRLLFDKSANDEHERSILTKLKQQCGGQFTSKMEGM
pepper_cul1          KVVKLLAYISDKDLFAEFYRKKLARRLLFDKSANDEHERSILTKLKQQCGGQFTSKMEGM
cucumber_cul1        KVVKLLAYICDKDLFAEFYRKKLARRLLFDKSANDDHERSILTKLKQQCGGQFTSKMEGM
melon_cul1           KVVKLLAYICDKDLFAEFYRKKLARRLLFDKSANDDHERSILTKLKQQCGGQFTSKMEGM
watermelon_cul1      KVVKLLAYICDKDLFAEFYRKKLARRLLFDKSANDDHERSILTKLKQQCGGQFTSKMEGM
squash_cul1          KVVKLLAYICDKDLFAEFYRKKLARRLLFDKSANDDHERSILTKLKQQCGGQFTSKMEGM
celery_cul1          KVVKLLAYISDKDLFAEFYRKKLARRLLFDKSANDEHERSILTKLKQQCGGQFTSKMEGM
lettuce_cul1         KVVKLLAYISDKDLFAEFYRKKLARRLLFDKSANDEHERSILTKLKQQCGGQFTSKMEGM
endive_cul1          KVVKLLAYISDKDLFAEFYRKKLARRLLFDKSANDEHERSILTKLKQQCGGQFTSKMEGM
chicory_cul1         KVVKLLAYISDKDLFAEFYRKKLARRLLFDKSANDEHERSILTKLKQQCGGQFTSKMEGM
carrot_cul1          KVVRLLAYISDKDLFAEFYRKKLARRLLFDKSANDEHERSILTKLKQQCGGQFTSKMEGM


beet_cul1            VTDLTLARENQTNFEEYLSQNPDASPGLDLTVTVLTTGFWPSYKSSDLNLPAEMVRCVEV
spinach_cul1         VTDLTLARENQTNFEEYLGQNTDASPGLDLTVTVLTTGFWPSYKSSDLNLPAEMVRCVEV
arabidopsis_cul1     VTDLTLARENQNSFEDYLGSNPAANPGIDLTVTVLTTGFWPSYKSFDINLPSEMIKCVEV
brassica_cul1        VTDLTLARENQNSFEEYLGNNPAANPGIDLTVTVLTTGFWPSYKSFDINLPAEMVKCVEV
radish_cul1          VTDLTLARENQTSFEEYLGNNPAANPGIDLTVTVLTTGFWPSYKSFDINLPSEMVKCVEV
leek_cul1            VTDLTLARENQSSFDDYLSSNPKANSGIDLTVTVLTTGFWPSYKSFDLNLPDEMVKCVEI
eggplant_cul1        VTDLTLARENQASFEEYLSNNPTANPGIDLTVTVLTTGFWPSYKSFDLNLPAEMVRCVEV
tomato_cul1          VTDLTLARENQASFEEYLSNNPIANPGIDLTVTVLTTGFWPSYKSFDLNLPAEMVRCVEV
pepper_cul1          VTDLTLARENQASFEEYLSNNPAANPGIDLTVTVLTTGFWPSYKSFDLNLPAEMVRCVEV
cucumber_cul1        VTDLTLARENQTSFEEYLSNNPQASPGIDLTVTVLTTGFWPSYKSFDLNLPAEMVKCVEV
melon_cul1           VTDLTLARENQTSFEEYLSNNPQASPGIDLTVTVLTTGFWPSYKSFDLNLPAEMVKCVEV
watermelon_cul1      VTDLTLARENQTSFEEYLSNNPQASPGIDLTVTVLTTGFWPSYKSFDLNLPAEMVKCVEV
squash_cul1          VTDLTLARENQTSFEEYLSNNPQASPGIDLTVTVLTTGFWPSYKSFDLNLPAEMVKCVEV
celery_cul1          VTDLTLAKENQSSFEEYLGNNANVNPGIDLTVTVLTTGFWPSYKSFDLNLPAEMVKCVEV
lettuce_cul1         VTDLTLAKENQSHFEEYLNNNPNVSPGIDLTVTVLTTGFWPSYKSFDLNLPAEMVKCVEV
endive_cul1          VTDLTLAKENQSHFEEYLNNNPNVSPGIDLTVTVLTTGFWPSYKSFDLNLPAEMVKCVEV
chicory_cul1         VTDLTLAKENQSHFEEYLNNNPNVSPGIDLTVTVLTTGFWPSYKSFDLNLPAEMVKCVEV
carrot_cul1          VTDLTLAKENQSNFEEYLNNNSNVNPGIDLTVTVLTTGFWPSYKSFDLNLPAEMVKCVEV


beet_cul1            FKQFYSTKTKHRKLTWVYSLGSCNINGKFGPKTIELVVGTYQAAALMLFNTSDRLSYSEI
spinach_cul1         FKQFYQTKTKHRKLTWVYSLGSCNINGKFGPKTIELVVGTYQAAALMLFNTSDRLSYSEI
arabidopsis_cul1     FKGFYETKTKHRKLTWIYSLGTCHINGKFDQKAIELIVSTYQAAVLLLFNTTDKLSYTEI
brassica_cul1        FKGFYETKTKHRKLTWIYSLGTCHLNGKFDVKPIELVVSTYQAAVLLLFNTTDKLSYTDI
radish_cul1          FKGFYETKTKHRKLTWIYSLGTCHLNGKFDHKPIELVVSTYQAAVLLLFNTTDKLSYNDI
leek_cul1            FKEFYETKTKHRKLTWIYSLGTCNINGKFETKTIELVVTTYQAAVLLLFNSADKLSYSEI
eggplant_cul1        FKEFYQTKTKHRKLTWIYSLGTCNINGKFEAKTIELVVTTYQASALLLFNASDRLSYQEI
tomato_cul1          FKEFYQTKTKHRKLTWIYSLGTCNINGKFEPKTIELVVTTYQASALLLFNASDRLSYQEI
pepper_cul1          FKEFYQTKTKHRKLTWIYSLGTCNINGKFEPKTIELVVTTYQASALLLFNASDRLSYQEI
cucumber_cul1        FREFYQTKTKHRKLTWIYSLGTCNISGKFEPKTMELIVTTYQASALLLFNSSDRLSYSEI
melon_cul1           FREFYQTKTKHRKLTWIYSLGTCNISGKFEPKTMELIVTTYQASALLLFNSSDRLSYSEI
watermelon_cul1      FREFYQTKTKHRKLTWIYSLGTCNISGKFEPKTMELIVTTYQASALLLFNSSDRLSYSEI
```

Fig. 70E

```
squash_cul1          FREFYQTKTKHRKLTWIYSLGTCNISGKFEPKTMELIVTTYQASALLLFNSSDKLSYSEI
celery_cul1          FREFYQTKTKHRKLTWIYSLGTCNINGKFEPKTIELIVTTYQASALLLFNTSDRLSYQEI
lettuce_cul1         FREFYQTKTKHRKLTWIYSLGTCNINGKFEPKTMELIVTTYQASALLLFNLSDRLSYQEI
endive_cul1          FREFYQTKTKHRKLTWIYSLGTCNINGKFEPKTMELIVTTYQASALLLFNSSDRLSYQEI
chicory_cul1         FREFYQTKTKHRKLTWIYSLGTCNINGKFEPKTMELIVTTYQASALLLFNSSDRLSYQEI
carrot_cul1          FREFYQTKTKHRKLTWIYSLGTCNIIGKFDPKTMELIVTTYQASALLLFNSSDRLSYNEI

beet_cul1            ATQLNLADEDLVRVLQSLSCAKYKILLKEPNTKTVSPTDCFSFNSSFTDRMRRIRIPLPP
spinach_cul1         TTQLNLADEDLVRVLQSLSCAKYKILLKEPSTRNVISTDCFSFNSNFTDRMRRIRIPLPP
arabidopsis_cul1     LAQLNLSHEDLVRLLHSLSCAKYKILLKEPNTKTVSQNDAFEFNSKFTDRMRRIKIPLPP
brassica_cul1        LTQLNLSHEDLVRLLHSLSCARYKILLKEPSTKTVSQSDSFEFNSKFTDRMRRIKIPLPP
radish_cul1          LTQLNLSHEDLVRLLHSLSCARYKILLKEPSTKTVTQTDSFEFNAKFTDRMRRIKIPLPP
leek_cul1            VQQLNLSDDDVIRLLHSLSCAKYKILNKEPATKTITPNDHFEFNSKFTDRMRRIKIPLPP
eggplant_cul1        MTQLNLSDDDVVRLLHSLSCAKYKILNKEPSTKTISPTDVFEFNSKFTDKMRRIKIPLPP
tomato_cul1          MTQLNLSDDDVVRLLHSLSCAKYKILNKEPSTKTISPTDVFEFNSKFTDKMRRIKIPLPP
pepper_cul1          MTQLNLSDDDVVRLLHSLSCAKYKILNKEPSTKTISPTDVFEFNFKFTDKMRRIKIPLPP
cucumber_cul1        MTQLNLSDDDVVRLLHSLSCAKYKILNKEPNTKTISPNDHFEFNAKFSDKMRRIKIPLPP
melon_cul1           MTQLNLSDDDVVRLLHSLSCAKYKILNKEPNTKTISPNDHFEFNAKFSDKMRRIKIPLPP
watermelon_cul1      MTQLNLSDDDVVRLLHSLSCAKYKILNKEPNTKTISPNDHFEFNAKFSDKMRRIKIPLPP
squash_cul1          MTQLNLSDDDVVRLLHSLSCAKYKILNKEPNTKTISPNDHFEFNAKFSDKMRRIKIPLPP
celery_cul1          MTQLNLSDDDVVRLLHSLSCAKYKILTKEPNNKTISPTDYFEFNSKFTDKMRRIKIPLPP
lettuce_cul1         MTQLNLSDDDVVRLLHSLSCAKYKILLKEPNTKTISPTDYFEFNSKFTDKMRRIKIPLPP
endive_cul1          MTQLNLSDDDVVRLLHSLSCAKYKILLKEPNTKTISPTDFFEFNSKFTDKMRRIKIPLPP
chicory_cul1         MTQLNLSDDDVVRLLHSLSCAKYKILLKEPNTKTISPTDFFEFNSKFTDKMRRIKIPLPP
carrot_cul1          MTQLNLSDDDVVRLLHSLSCAKYKILSKEPNTKTISPTDCFQFNSKFTDKMRRIKIPLPP

beet_cul1            MDERKKVVEDVDKDRRYAIDASIVRIMKSRKVLGYQQLITECVEQLSRMFKPDFKAIKKR
spinach_cul1         MDERKKVVEDVDKDRRYAIDASIVRIMKSRKALGYQQLITECVEQLSRMFKPDFKAIKKR
arabidopsis_cul1     VDERKKVVEDVDKDRRYAIDAAIVRIMKSRKVLGHQQLVSECVEQLSRMFKPDIKAIKKR
brassica_cul1        VDERKKVVEDVDKDRRYAIDAAIVRIMKSRKVLGHQQLVSECVEQLSRMFKPDIKAIKKR
radish_cul1          VDERKKVVEDVDKDRRYAIDAAIVRIMKSRKVLGHQQLVSECVEQLSRMFKPDIKAIKKR
leek_cul1            VDEKKKVIEDVDKDRRYAIDASIVRIMKSRKVLGHQQLVLECVEQLGRMFKPDFKAIKKR
eggplant_cul1        VDEKKKVIEDVDKDRRYAIDASIVRIMKSRKVLGYQQLVMECVEQLGRMFKPDVKAIKKR
tomato_cul1          VDEKKKVIEDVDKDRRYAIDASIVRIMKSRKVLGYQQLVMECVEQLGRMFKPDVKAIKKR
pepper_cul1          VDEKKKVIEDVDKDRRYAIDASIVRIMKSRKVLGYQQLVMECVEQLGRMFKPDVKAIKKR
cucumber_cul1        VDEKKKVIEDVDKDRRYAIDASIVRIMKSRKVLGHQQLVMECVEQLGRMFKPDFKAIKKR
melon_cul1           VDEKKKVIEDVDKDRRYAIDASIVRIMKSRKVLGHQQLVMECVEQLGRMFKPDFKAIKKR
watermelon_cul1      VDEKKKVIEDVDKDRRYAIDASIVRIMKSRKVLGHQQLVMECVEQLGRMFKPDFKAIKKR
squash_cul1          VDEKKKVIEDVDKDRRYAIDASIVRIMKSRKVLGHQQLVMECVEQLGRMFKPDFKAIKKR
celery_cul1          VDEKKKVIEDVDKDRRYAIDASIVRIMKSRKVLGYQQLVMECVEQLGRMFKPDVKAIKKR
lettuce_cul1         VDEKKKVIEDVDKDRRYAIDASIVRIMKSRKVLGYQQLVMECVEQLGRMFKPDVKAIKKR
endive_cul1          VDEKKKVIEDVDKDRRYAIDASIVRIMKSRKVLGYQQLVMECVEQLGRMFKPDVKAIKKR
chicory_cul1         VDEKKKVIEDVDKDRRYAIDASIVRIMKSRKVLGYQQLVMECVEQLGRMFKPDVKAIKKR
carrot_cul1          VDEKKKVIEDVDKDRRYAIDASIVRIMKSRKVLGYQQLVMECVEQLGRMFKPDVKAIKKR
```

Fig. 70F

| | |
|---|---|
| beet_cul1 | IEDLITRDYIERDKENPQLFRYLA |
| spinach_cul1 | IEDLITRDYIERDKENPQLFRYLA |
| arabidopsis_cul1 | MEDLITRDYLERDKENPNMFRYLA |
| brassica_cul1 | MEDLITRDYLERDKENANMFRYLA |
| radish_cul1 | MEDLITRDYLERDKENPNMFRYLA |
| leek_cul1 | IEDLIARDYLERDKDNPNLFKYLA |
| eggplant_cul1 | IEDLITRDYLERDKDNPNLFKYLA |
| tomato_cul1 | IEDLITRDYLERDKDNPNLFKYLA |
| pepper_cul1 | IEDLITRDYLERDKDNPNLFKYLA |
| cucumber_cul1 | IEDLITRDYLERDKDNPHLFRYLA |
| melon_cul1 | IEDLITRDYLERDKDNPHLFRYLA |
| watermelon_cul1 | IEDLITRDYLERDKDNPHLFRYLA |
| squash_cul1 | IEDLITRDYLERDKDNPHLFRYLA |
| celery_cul1 | IEDLITRDYLERDKDNANLFRYLA |
| lettuce_cul1 | IEDLITRDYLERDKENPNLFRYLA |
| endive_cul1 | IEDLITRDYLERDKENPNLFRYLA |
| chicory_cul1 | IEDLITRDYLERDKENPNLFRYLA |
| carrot_cul1 | IEDLITRDYLERDKDNANLFRYLA |

SEQUENCE LISTING

```
<160> NUMBER OF SEQ ID NOS: 69

<210> SEQ ID NO 1
<211> LENGTH: 2235
<212> TYPE: DNA
<213> ORGANISM: Cucumis sativus
<220> FEATURE:
<221> NAME/KEY: source
<222> LOCATION: 1..2235
<223> OTHER INFORMATION: /organism="Cucumis sativus"
      /mol_type="unassigned DNA"

<400> SEQUENCE: 1
```

-continued

```
atgacaatgg gcgagcggaa gactattgac ttggagcagg gatgggagtt tatgcagaag     60
ggtatcacaa agttgaagaa cattctcgag ggcttgcctg agcctcagtt cagctccgag    120
gactacatga tgctttacac taccatatat aacatgtgca cccaaaagcc gccgcatgat    180
tactcccagc agctgtatga taaatatcgt gaatcttttg aagagtacat cacttctatg    240
gtcttaccat ccttgaggga gaagcacgat gagttcatgt tgagagaact agtaaaaagg    300
tggacaaacc ataaagtcat ggtgaggtgg ctttctcgct tcttccacta tcttgatcgg    360
tacttcatcg ctcgaaggtc acttccacct ctaaatgaag ttggcctcac atgcttccgc    420
gaattggtgt acaaagagct aaatagtaaa gtgagggatg cagtaatttc attgattgat    480
caagaacgtg aaggagaaca gattgacaga gctctactga agaatgtact agatatattt    540
gtggaaattg gtatggggca aatggattac tatgaaaatg actttgaagc tgccatgctt    600
aaagatactg ctgcttatta ctctaggaag gcttccaatt ggatcctaga agattcttgt    660
cccgattata tgcttaaagc agaggagtgc ttgaaacgag aaaaggatag ggtttcccac    720
tatttgcact ctagtagcga gccaaagttg ttggagaaag ttcaacatga actattatct    780
gtttatgcta ctcaactgct ggaaaaagag cattcaggat gccatgcatt gcttagagat    840
gacaaggtgg aagatttgtc aaggatgttc cgtctattct ccaaaatacc gaagggactg    900
gatccagttt ccaacatatt taagcagcat gtaactgctg aaggaacagc actggtcaaa    960
caggcagaag atgctgcaag taacaagaag gctgagaaaa aggacatagt tggtctgcag   1020
gaacaggttt ttgtaagaaa agtgattgag cttcacgaca agtacttggc ttatgtgaat   1080
gattgtttcc aaaaccacac acttttccat aaggctctca aggaagcttt tgaagtattt   1140
tgcaataagg gtgttgctgg aagttctagt gcagaattgc ttgctacctt ttgtgataac   1200
atccttaaga aaggtgggag tgagaagttg agtgatgaag caatcgagga gacacttgag   1260
aaggttgtga agttgttggc atacatttgc gacaaagatc tgtttgctga attctataga   1320
aaaaaacttg cccgaaggct tctctttgac aagagcgcga acgatgacca cgagagaagt   1380
atattgacca aattgaagca acaatgtggt ggtcagttca cttctaagat ggagggaatg   1440
gttactgatt tgactttggc aagggagaac caaactagtt ttgaggagta tctgagcaat   1500
aatccacaag cgagtcctgg catcgacctg actgttactg ttttaactac tggattttgg   1560
ccaagctaca agtcttttga cctcaacctg ccggcagaga tggtaaagtg tgttgaagtt   1620
ttcagagagt tttatcaaac aaaaaccaag catcgaaaac ttacatggat ttactcattg   1680
ggtacttgta acatcagtgg aaaatttgaa ccgaaaacga tggagctgat tgtgacaact   1740
tatcaggctt ctgccctgtt gctattcaat tcttcggata gactaagtta ctcggaaatc   1800
atgacacaat taaatttgag tgacgatgat gtagttagac tactccactc gttgtcatgt   1860
gccaagtata aaattcttaa taaggaacca aatacgaaaa ccatctctcc gaacgatcat   1920
tttgagttca atgcaaaatt ctccgacaaa atgaggagaa taaagatccc tcttccgcct   1980
gtggatgaga aaaagaaagt cattgaagat gttgacaagg atcgaaggta tgctattgac   2040
gcctcaatcg tgcgtatcat gaagagtcgg aaagttcttg gtcatcagca actagtgatg   2100
gagtgcgtcg agcaattggg ccgtatgttc aagcccgatt tcaaggcgat aaagaagaga   2160
attgaagacc tgatcactcg ggattatcta gagagagaca aagacaaccc ccacttgttt   2220
aggtacttgg cttga                                                    2235
```

<210> SEQ ID NO 2

-continued

<211> LENGTH: 2235
<212> TYPE: DNA
<213> ORGANISM: Cucumis melo
<220> FEATURE:
<221> NAME/KEY: source
<222> LOCATION: 1..2235
<223> OTHER INFORMATION: /organism="Cucumis melo"
/mol_type="unassigned DNA"

<400> SEQUENCE: 2
atgacaatgg gcgagcggaa gactattgac ttggaacagg gatgggagtt tatgcagaag 60
ggtatcacaa agttgaagaa cattcttgag ggcttgcctg agccccagtt cagctccgag 120
gactacatga tgctttacac taccatatat aacatgtgca cccaaaagcc gccgcatgat 180
tactcccagc agctgtatga taaatatcgt gaatcttttg aagagtacat cacttctatg 240
gtcttaccat ccttgaggga gaagcatgac gagttcatgt tgagagaact agtcaaaagg 300
tggacaaacc ataaagtcat ggtgaggtgg ctttctcgct tcttccacta tcttgatcgg 360
tacttcatcg ctcgaaggtc acttccacct ctaaatgaag ttggcctcac atgcttccgc 420
gaattggtgt acaaagagct aaacagtaaa gtgagggatg cagtaatctc attgattgat 480
caagaacgtg aaggagaaca gattgacaga gctctactga agaatgtatt agatatattt 540
gtggaaattg gtatggggca aatggattac tatgaaaatg actttgaagc tgccatgctt 600
aaagatactg ctgcttatta ctctaggaag gcttccaatt ggatcctaga agattcttgt 660
cccgattata tgctaaaagc agaggagtgc ttgaagcgag aaaaggatag ggtttcccac 720
tatttgcact ctagtagcga gccaaagttg ttggagaaag ttcaacacga actgttatct 780
gtgtatgcta ctcaactgct ggaaaaagag cattcaggat gccatgcatt gcttagagat 840
gacaaggtgg aagatttgtc aaggatgttc cgtctcttct ccaaaatacc gaagggattg 900
gacccagttt ccaacatatt taagcagcat gtaactgctg aaggaacagc actggtcaaa 960
caggcagaag atgctgcaag taacaagaag gccgagaaaa aggacatagt tggtctgcag 1020
gaacaggttt ttgtaagaaa agtgattgag cttcacgaca agtacttggc ttatgtgaat 1080
gattgtttcc aaaaccacac acttttccat aaggctctca aggaagcttt tgaagtcttt 1140
tgcaataagg gtgttgctgg aagttctagt gcagaattgc ttgctacctt ctgcgataac 1200
atccttaaga aaggtgggag tgagaagttg agtgatgaag caatcgaaga gacacttgag 1260
aaggttgtga agttgttggc atacatctgc gacaaagatc tgtttgctga attctataga 1320
aaaaaacttg cccgaaggct tctctttgat aagagcgcca acgatgacca cgagagaagt 1380
atattgacca aattgaagca acaatgtggt ggtcagttca cttctaagat ggagggaatg 1440
gttactgatt tgactttggc aagggagaac caaactagtt tcgaagagta tctgagcaat 1500
aatccacaag ctagtcctgg aatcgaccta actgttactg ttttgactac tggattttgg 1560
ccaagctaca agtcttttga cctcaacctg ccggcggaga tggtaaagtg tgttgaagtt 1620
ttcagagagt tttatcaaac aaaaaccaag catagaaaac ttacatggat ttactcattg 1680
ggtacttgta acatcagtgg aaaatttgaa ccgaagacga tggagctgat tgtgacaaca 1740
tatcaggctt ctgccctgtt gctattcaat tcttcggaca gactaagtta ctccgaaatc 1800
atgacacaat taaatttgag tgatgatgat gttgttagac tgctccactc attgtcgtgt 1860
gccaagtata aaattcttaa taaggagcca aatacgaaaa ccatctcacc gaacgatcat 1920
tttgagttca atgcaaaatt ctccgacaaa atgaggagaa taaagatccc tcttccgcct 1980
gtggatgaga aaaagaaagt cattgaagat gttgacaagg atcgaaggta tgctattgac 2040

-continued

```
gcctcaatcg tgcgtatcat gaagagtcga aaagttcttg gtcatcagca actagtgatg   2100

gagtgcgtcg agcaattggg tcgtatgttc aagcccgatt tcaaggcgat aaagaagaga   2160

attgaagacc tgatcactcg ggactatcta gagagagaca aagacaaccc ccacttgttt   2220

aggtacttgg cttga                                                    2235
```

<210> SEQ ID NO 3
<211> LENGTH: 2235
<212> TYPE: DNA
<213> ORGANISM: Cucurbita pepo
<220> FEATURE:
<221> NAME/KEY: source
<222> LOCATION: 1..2235
<223> OTHER INFORMATION: /organism="Cucurbita pepo"
/mol_type="unassigned DNA"

<400> SEQUENCE: 3

```
atgacaatgg gtgagcggaa gactattgac ttggagcaag gatgggagtt tatgcagaag     60

ggaatcacaa aattgaagaa cattctggaa ggattgcctg agccacagtt cagctccgag    120

gactacatga tgctttacac tacaatatat aacatgtgta cccagaagcc accgcatgat    180

tactcccagc agctgtatga taaataccgc gaatcgtttg aggagtacat cagttctatg    240

gttttaccat ccttgaggga gaagcatgac gaatttatgt tgagagaact ggtcaaaagg    300

tggaccaacc ataaagtcat ggtgaggtgg ctttctcgct tcttccacta tcttgatcga    360

tacttcattg ctcgaaggtc acttccacct ctcaatgaag ttggcctcac ttgcttccgt    420

gaattggtgt acaaagagct aaacagtaaa gtgagggatg cagtaatttc attgatcgat    480

caagaacgtg aaggagagca gattgacaga gctctgttga agaacgtgtt ggatatattt    540

gtggagattg ggatggggca aatggattat tatgaaaatg actttgaagc tgccatgctt    600

aaagatactg ctgcttacta ctctaggaag gcatcaaatt ggatcttaga agattcttgt    660

cctgattata tgctaaaagc agaggagtgc ttgagacgag aaaaggaccg agtttctcac    720

tatctgcact ctagtagcga gccaaagtta ttggagaaag ttcaacatga actattgtct    780

gtttatgcta ctcaactgct ggagaaagag cattcaggat gccatgcatt gcttagagat    840

gacaaggtgg aagatttgtc aaggatgttc cgtctcttct ccaaaatacc caagggattg    900

gacccagttt ccaacatatt taagcagcat gtcactgctg aaggaacagc attagtcaaa    960

caggcagaag acgctgcaag taacaagaag gccgagaaaa aggacatcgt tggtctgcaa   1020

gaacaggttt ttgttagaaa agtgattgag cttcacgaca agtacttggc atatgtgaat   1080

gattgtttcc aaaaccacac actttttcac aaggctctca aggaagcttt tgaagtcttt   1140

tgcaataagg gtgttgctgg aagttctagt gcagaattac ttgctacctt ttgtgataac   1200

atccttaaga aaggtgggag tgagaagttg agtgatgaag caattgagga aacactcgag   1260

aaggtcgtga aattgctggc gtatatctgc gacaaagatc tgtttgctga attctataga   1320

aaaaaactcg cccgaaggct tctcttcgac aagagtgcga atgatgacca cgagagaagt   1380

atactgacga aattgaagca acaatgtggt ggtcagttta cctctaagat ggagggaatg   1440

gtcacggatt tgacactggc aagggagaac caaactagtt ttgaggaata tctgagcaat   1500

aatccacaag ctagtcctgg aatcgacttg accgttaccg ttttgaccac tggtttttgg   1560

ccaagctaca agtcttttga cctcaacctg ccggcggaga tggtaaagtg tgttgaagtt   1620

ttcagggaat tttatcaaac aaaaaaccaag cacagaaaac ttacgtggat ttactcgttg   1680

ggtacctgta acatcagcgg aaaattcgaa ccgaaaacga tggagctgat cgtgacaacc   1740
```

-continued

```
tatcaggctt ctgccctgct gcttttcaat tcctcggata aactaagtta ctccgagatc   1800

atgactcaat taaacttgag tgacgatgat gttgttagac tgctccactc gttgtcgtgt   1860

gcgaagtata aaattcttaa caaggagcca aatacgaaaa ccatctctcc gaacgatcat   1920

tttgagttca acgcaaaatt ctccgacaaa atgaggagaa taaagatccc tcttccgcct   1980

gtggatgaga aaaagaaagt aatagaagat gttgacaagg atcgaagata tgctatcgat   2040

gcctcgatcg tgcgtatcat gaagagtagg aaagttctgg gtcaccagca gttagtgatg   2100

gagtgcgtcg agcaactggg tcgtatgttc aagcctgatt tcaaggcgat aaagaagaga   2160

atcgaagatc tgatcactcg tgactattta gagagagaca aagacaaccc ccacttgttt   2220

aggtacttgg cttga                                                     2235
```

```
<210> SEQ ID NO 4
<211> LENGTH: 2235
<212> TYPE: DNA
<213> ORGANISM: citrillus lanatus
<220> FEATURE:
<221> NAME/KEY: source
<222> LOCATION: 1..2235
<223> OTHER INFORMATION: /organism="citrillus lanatus"
      /mol_type="unassigned DNA"

<400> SEQUENCE: 4

atgacaatgg gcgagcggaa gactattgac ttggaacaag gatgggagtt tatgcagaag     60

ggaatcacaa agttgaagaa cattcttgag ggcttgcctg agcctcagtt cagctccgag    120

gactacatga tgctttatac caccatatac aacatgtgca cacaaaagcc gccacatgat    180

tactcccagc agctatacga taaataccgt gaatcttttg aggagtatat cacttctatg    240

gtcttaccat ccttgaggga gaagcatgac gagttcatgt tgagagaact ggtcaaaagg    300

tggacgaacc ataaagtcat ggtgaggtgg ctttctcgct tcttccacta tcttgaccga    360

tacttcattg ctcgaagatc acttccacct ctcaacgaag ttggcctcac atgcttccgt    420

gaattggtgt acaaagagct aaacagtaaa gtgagggatg cagtaatttc attgattgat    480

caagaacgtg aaggagagca gattgacaga gctctactga agaatgtatt agatatattt    540

gtggaaattg ggatggggca aatggattac tatgaaaatg actttgaagc tgccatgctt    600

aaagatactg ctgcttatta ctctaggaag gcttccaatt ggatcctaga agattcttgt    660

cccgattata tgctaaaagc agaggagtgc ttgaaacgag aaaaggatag agtttctcac    720

tatttgcact ctagtagcga gccaaagtta ttagagaaag ttcaacatga actgttatct    780

gtgtatgcta ctcaactgct ggaaaaagag cattcaggat gccatgcatt gcttagagat    840

gacaaggtgg aagatttgtc aaggatgttc cgcctcttct ccaaaatacc caagggattg    900

gacccagttt ccaacatatt taagcagcat gtcactgctg aaggaacagc attggtcaaa    960

caggcagaag atgctgcaag taacaagaag gccgagaaaa aggacatagt tggtctgcag   1020

gaacaggttt ttgtaagaaa agtgattgag cttcacgaca agtacttggc ttacgtgaat   1080

gattgtttcc aaaaccacac actttttcac aaggctctca aggaagcttt tgaagtcttt   1140

tgcaataagg gtgttgctgg aagttctagt gcagaattac ttgctacctt ttgtgataac   1200

atccttaaga aaggtgggag cgagaagttg agtgatgaag caattgagga gacacttgag   1260

aaggtcgtga agttgctggc atacatctgc gacaaagatc tgtttgctga attctataga   1320

aaaaaacttg cccgaaggct tctctttgac aagagtgcca acgatgacca tgagagaagt   1380

atattgacca aattgaagca acaatgtggt ggccagttca cctctaagat ggaggggatg   1440
```

gtcactgatt tgactttggc aagggagaac caaactagtt tcgaggagta tctgagcaat 1500
aatccacaag ctagtcctgg aatcgacttg actgtcactg ttttgactac tggcttttgg 1560
ccaagctaca agtcttttga cctcaacctg ccggcagaga tggtaaagtg tgttgaagtt 1620
ttcagagagt tctatcaaac aaaaacaaag catagaaaac ttacatggat ttactcattg 1680
ggtacctgta acatcagcgg aaaatttgaa ccgaaaacga tggagctgat tgtaacaact 1740
tatcaggctt ctgccctgct gctattcaat tcctcagata gattaagtta ttccgagatc 1800
atgacacaat taaatttgag tgacgatgat gttgttagac tgctccactc attgtcatgt 1860
gccaagtata aaattcttaa taaggagccg aacacgaaaa ccatctctcc gaatgatcat 1920
tttgagttca atgcaaaatt ctccgacaaa atgaggagaa taaagatccc tcttccgcct 1980
gtggatgaga aaaagaaagt cattgaagat gttgacaagg atcgaaggta tgctattgat 2040
gcctcaatcg tgcgtatcat gaagagtcgg aaagttctgg gtcatcagca gctagtgatg 2100
gagtgcgtcg agcaattggg tcgtatgttc aagcccgact tcaaagcgat aaagaagaga 2160
atcgaagatc tgatcactcg ggactattta gagagagaca aagacaaccc ccacttgttt 2220
aggtacttgg cttga 2235

<210> SEQ ID NO 5
<211> LENGTH: 2229
<212> TYPE: DNA
<213> ORGANISM: Solanum melongena
<220> FEATURE:
<221> NAME/KEY: source
<222> LOCATION: 1..2229
<223> OTHER INFORMATION: /organism="Solanum melongena"
/mol_type="unassigned DNA"

<400> SEQUENCE: 5
atgaaccaac gcagcacaat cgatctggaa catggatggg atttcatgca aaagggcatc 60
acaaagctga agaacattct agaagggctg cctgagcctc agttcagctc agaggactat 120
atgatgctgt atacgacaat ttacaacatg tgtactcaga agccccaca tgattattct 180 caacagctgt atgacaaata tcgtgaagct tttgaagaat atatcacaac gacggtatta 240
ccttctttga gagaaaaaca tgacgagttc atgttgcgag agttggtaaa aaggtggtca 300
aaccataagg tcatggttag atggttatcg cgattcttcc attatcttga ccgttatttc 360
attgctcgga gatcactgcc agggcttaat gaagttggac taacttgctt ccgcgatctg 420
gtctaccaag agttgaatgg aaaagtcagg gatgctgtta tatctctgat tgatcaagag 480
cgtgagggag agcaaattga cagagctcta ctgaagaatg tgctagatat atttgttgaa 540
attggaatgg ggtcaatgga ttattatgag aatgattttg aagctgcaat gctcaaggac 600
actgcggctt attattctcg caaagcttct aactggatcc tcgaagattc atgtccagat 660
tatatgctga aagctgagga gtgcttgaaa cgggagaagg atagggtctc ccattatctc 720
cattctagca gtgagacaaa gttgcttgag aaagtgcaac atgagttgtt atctgtgtat 780
gccaatcaac ttcttgagaa ggagcactct ggatgccatg cattacttag agatgataag 840
gtcgatgatt tatcaaggat gtatagactc ttttctaaga ttcctcgagg cttagagcct 900
gtggctaata tatttaagca gcatgttact gctgaaggta cagctttggt gaaacaggct 960
gaagatgctg ctagcaacaa aaaggcagag aagagagatg tggttggttt gcaggaacag 1020
gtttttgttc ggaaagtgat tgagcttcat gataaatatt tggcgtatgt gaataactgt 1080
ttccaaaacc acacactttt tcacaaggca cttaaagaag ctttcgaact tttctgcaac 1140
aagggtgttg ctggtagctc aaatgctgaa cttcttgcca cattctgcga caacattctc 1200
aaaaaaggcg ggagtgaaaa attgagtgat gaagccattg aagagacgct ggagaaggtg 1260
gtaaagctgc tggcttatat tagtgataag gacttgtttg cagaattcta taggaaaaag 1320
ctcgcccggc ggttgttatt tgataagagt gccaatgatg aacatgagag aagtatccta 1380
acaaagttga agcagcagtg tggaggtcag ttcacatcaa agatggaggg aatggtcaca 1440
gatttgacat tggcaaggga aaatcaagcc agctttgagg agtatttgag caataatcca 1500
acagcaaatc caggaattga cttgacggtg actgtcttga ctactggctt ctggcctagc 1560
tacaagtctt ttgatctcaa cctcccagca gaaatggtta ggtgtgttga agtattcaag 1620
gagttttatc aaacaaaaac gaagcacagg aaacttacat ggatatactc tttgggaact 1680
tgcaacataa atggaaaatt tgaggcaaag actattgagc tcgttgtcac tacttatcag 1740
gcttctgctc tgcttctctt taatgcatca gatagattga gttatcagga aatcatgacg 1800
caattaaacc tatcagatga tgatgttgtt cggcttcttc attccctttc atgtgcgaaa 1860
tacaagattc tcaacaagga gccaagcacc aaaacaattt ctccgactga tgtctttgag 1920
ttcaactcaa agttcactga caaaatgagg aggatcaaga tacctctccc accagttgat 1980
gaaaagaaaa aggtaattga agacgttgac aaggataggc ggtatgctat agatgcctca 2040
attgtgcgta ttatgaagag tcgtaaagta ttgggctacc agcaactggt catggagtgc 2100
gttgagcagt tgggacgcat gttcaagcct gatgtcaaag ctatcaagaa gagaattgaa 2160
gatctgataa ctagagatta cctagagagg gacaaagata acccaaactt gttcaagtac 2220
ttggcatga 2229

<210> SEQ ID NO 6
<211> LENGTH: 2229
<212> TYPE: DNA
<213> ORGANISM: Solanum lycopersicum
<220> FEATURE:
<221> NAME/KEY: source
<222> LOCATION: 1..2229
<223> OTHER INFORMATION: /organism="Solanum lycopersicum"
/mol_type="unassigned DNA"

<400> SEQUENCE: 6
atgaaccaac gaagcacaat cgatctggaa catggatggg acttcatgca aaggggcatt 60
acaaagctga agaacattct agaagggctg cctgagcctc aattcagctc agaggactat 120
atgatgctat atacgacaat ttacaacatg tgtactcaaa agcccccaca tgattattct 180
caacagctgt atgacaaata tcgtgaagct tttgaagaat atatcacaac aacggtattg 240
ccttctttga gagaaaaaca tgacgagttt atgttgcgag agttggtaaa aaggtggtca 300
aatcataaag tcatggtcag atggttgtca agattcttcc attaccttga ccggtatttc 360
attgcccgga gatctctgcc ggggcttaat gaagttggac taacttgctt ccgcgatcag 420
gtctaccaag agttgaatgg aaaagtcagg gatgctgtta tatctctgat tgatcaagag 480
cgtgagggag agcaaattga cagagctcta cttaagaatg tgcttgatat atttgtcgaa 540
attggaatgg ggttaatgga ttattatgag aatgattttg aagctgcaat gctcaaggac 600
acagcggctt attattctcg caaagcttct aattggatcc tcgaagattc atgtccggat 660
tatatgctga aagccgagga gtgcttgaaa cgggagaagg atagggtctc tcattatctc 720
cattcaagca gcgagacgaa gttgcttgag aaagtgcaac atgagttgtt gtctgtgtat 780
gccactcaac ttcttgagaa ggagcactct ggatgccatg cgttactgag agatgataag 840

-continued

```
gttgaagatt tatcaaggat gtataggctc ttttctaaga tttctcgagg cttagaccct    900

gtggccaata tttttaagca gcatgttact gctgaaggta cagctttggt aaaacaggct    960

gaagatgctg ctagcaataa aaaggcagag aagagagatg tggttggttt gcaggaacag   1020

gtttttgttc ggaaagtgat tgaacttcat gataaatatt tggcttatgt gaataactgt   1080

ttccaaaacc acacactttt tcacaaggcg cttaaagaag cttttgagct tttctgcaac   1140

aagggtgttg ctggtagctc aagcgctgaa cttcttgcca ccttctgtga caacattctc   1200

aaaaaaggcg ggagtgagaa attgagtgat gaagctattg aagaaacgtt ggaaaaggtg   1260

gtaaagctac tagcttatat tagtgataag gacttgtttg cagaattcta taggaaaaag   1320

ctagcccggc ggttgttatt tgataagagt gccaatgatg aacatgaaag aagtatccta   1380

acaaagttga agcagcagtg tgggggcag ttcacatcaa agatggaggg aatggtcaca    1440

gatttgacat tggcaaggga aaatcaagcc agcttcgagg agtatttgag caataatcca   1500

atagcaaatc caggaattga cttgacggtg actgtcttga ctactggctt ctggcctagc   1560

tacaagtctt ttgatctcaa cctcccagca gaaatggtta ggtgcgttga agtatttaag   1620

gagttctatc aaacaaaaac aaagcacagg aaacttacgt ggatatactc tttgggaact   1680

tgcaacataa atggaaaatt tgagccaaaa actattgagc tcgttgtcac tacttatcag   1740

gcttctgctc tgctgctctt taatgcatca gatagattga gttatcagga aatcatgacg   1800

caattaaacc tatcagatga tgatgttgtt cggcttcttc attccctttc atgtgcgaag   1860

tacaagatac tcaacaagga gccaagcacc aaaacaattt ctccgactga tgtctttgag   1920

ttcaactcaa agttcactga caaaatgagg aggatcaaga tacctctccc tcctgttgat   1980

gagaagaaaa aggtaattga agacgttgac aaggataggc ggtatgctat agatgcttca   2040

attgtgcgta ttatgaagag ccgtaaagta ttgggctacc agcaactagt catggagtgc   2100

gttgagcagt tggggcgcat gttcaagcct gatgtcaaag ctatcaagaa gagaatcgaa   2160

gatttgataa ctagagatta cctagagagg gacaaagata atccaaacct gttcaagtac   2220

ttggcatga                                                           2229
```

```
<210> SEQ ID NO 7
<211> LENGTH: 2229
<212> TYPE: DNA
<213> ORGANISM: Capsicum annuum
<220> FEATURE:
<221> NAME/KEY: source
<222> LOCATION: 1..2229
<223> OTHER INFORMATION: /organism="Capsicum annuum"
      /mol_type="unassigned DNA"

<400> SEQUENCE: 7

atgaaccagc gttccacaat caatctagaa catggatggg acttcatgca aaggggcatt     60

acaaagctga agaacattct agaagggctg cccgagcctc agttcagctc agaggactat    120

atgatgctgt atacgacaat ttacaacatg tgtactcaga agccccccaca tgattattct    180

caacagctgt atgacaaata tcgtgaagct tttgaagaat atatcacaac aacggtattg    240

ccttctttga gagaaaaaca tgacgagttc atgttgcgag agctggtaaa aaggtggtca    300

aaccataagg tcatggtcag atggttatcg cgattcttcc attatcttga tcgctatttc    360

attgcccgga gatctctacc ggggcttaat gaagttggac taacttgctt ccgagatctg    420

gtctaccaag agttgaatgg aaaagtcagg gatgctgtta tatctctgat tgatcaagag    480

cgtgagggag agcaaattga cagagctcta ctgaagaatg tgctagatat atttgttgaa    540
```

-continued attggaatgg ggtcgatgga ttattatgag aatgattttg aagctgcaat gctcaaggac 600
accgcagctt attattctcg caaagcttct aactggatac ttgaagattc atgtccagat 660
tatatgctga aagccgagga gtgcttgaaa cgggagaaag atagggtctc tcactatctt 720
catttaagca gtgagacaaa gttgcttgag aaagtgcaac atgagttgtt gtctgtgtat 780
gccactcaac ttcttgagaa ggagcactct gggtgccatg cgttactaag agatgataag 840
gttgaagatt tatcaaggat gtataggctc ttttctaaga ttcctcgagg cttagaccct 900
gtggctaata tatttaagca gcatgttact gctgaaggta cagctttggt caaacaggct 960
gaagatgctg ctagcaacaa aaaggcagag aaaagagatg tggttggttt gcaggaacag 1020
atttttgttc ggaaagtgat tgagcttcat gataagtata tggcatatgt gaataactgt 1080
ttccaaaacc acacactttt tcacaaggcg cttaaagaag ctttcgaact tttctgcaac 1140
aagggtgttg ctggtagctc aagtgctgaa cttcttgcca cattctgcga caatattctc 1200
aagaaaggcg ggagtgagaa attgagtgat gaagccattg aagagacgct ggagaaggtt 1260
gtaaagctgc tagcatatat tagtgacaag gacttgtttg cagaattcta taggaaaaag 1320
ctagcccggc ggttgttatt tgataagagt gccaatgatg aacacgagag aagtatcctt 1380
acaaagttga agcagcagtg tgggggccag ttcacatcaa agatggaggg aatggtgaca 1440
gatttgacat tggcaaggga aaatcaagcc agctttgagg agtatttgag caacaatcca 1500
gcagcaaatc caggaattga cttgacggtg actgtcttga ctactggctt ctggcctagc 1560
tacaagtctt ttgatctcaa cctcccagca gaaatggtta ggtgcgttga agtattcaag 1620
gagttttatc aaacaaaaac gaagcacagg aaacttacgt ggatatactc tttgggaact 1680
tgcaatataa atggaaaatt tgagccaaag actattgagc tcgttgtcac tacttatcag 1740
gcttctgctc tgctgctctt taatgcatcg gatagattga gttatcagga aatcatgacg 1800
caactaaacc tatcagatga tgatgttgtt cggcttcttc attccctttc atgtgcgaag 1860
tacaagattc tcaacaagga gccaagcacc aaaacaattt ctccgactga tgtctttgag 1920
ttcaatttta agttcactga caaaatgagg aggatcaaga tacctctccc tcctgttgat 1980
gagaagaaaa aggtaattga agatgttgac aaagataggc ggtacgctat agatgcttca 2040
attgtgcgta ttatgaagag tcgtaaagta ttgggctacc agcaactggt catggagtgt 2100
gttgagcagt tgggacgtat gttcaagcct gatgtcaaag ctatcaagaa gagaattgaa 2160
gatttgataa ctagagatta cctagagagg gacaaagata atccgaactt gttcaagtac 2220
ttggcatga 2229

<210> SEQ ID NO 8
<211> LENGTH: 2217
<212> TYPE: DNA
<213> ORGANISM: Brassica oleracea
<220> FEATURE:
<221> NAME/KEY: source
<222> LOCATION: 1..2217
<223> OTHER INFORMATION: /organism="Brassica oleracea"
/mol_type="unassigned DNA"

<400> SEQUENCE: 8
atggagcgca agacgattga cttggaccaa ggatgggact atatgcagac tggtatcact 60
aagctgaaac ggattcttga ggggctgcct gagccgcagt ttgactctga gcaatacatg 120
atgctctata cgactatcta caacatgtgc actcagaaac ctcctcatga ttactcacag 180
cagctttatg acaagtatcg tgaagcattt gaggagtata ttcactcaac tgttttgcct 240

-continued gctctaaggg agaagcatga tgagtacatg ctgagggagc tggttaagag atggtctaac 300
cataaagtta tggttcgatg gctatcccgc ttcttctact atcttgaccg ttacttcatt 360
gctcggaggt cacttccacc cctgaatgaa gttggcctga cttgcttccg tgacctggtt 420
tataacgagt tgcattccaa ggtcaaagat gctgtaatag cacttgttga taaagaacgg 480
gagggtgagc agattgacag ggctctattg aaaaacgtat tagacattta tgtagagatt 540
ggaatgggac agatggaaag atacgaggag gattttgaaa gcttcatgct tttagattca 600
gcatcttact attctcgcaa ggcgtcaagc tggatccaag aagattcttg ccctgattac 660
atgctgaagt ctgaagaatg tcttaagaag gagagggaga gagtggctca ctaccttcac 720
tcaagcagcg agccaaagct ggttgagaaa gtacaacatg agctgttggt agtgtatgca 780
aatcagcttc tagaaaaaga gcattcaggg tgccgtgcat tgctgagaga tgacaaggtt 840
gatgacctct ccaggatgta caggctttat cataaaattg tgaaaggttt ggaacctgtt 900
gcaaacatat ttaagcagca tgtcacagca gagggtaacg cacttgtcca acaggccgaa 960
gacacggcca ctaatcatgc tgcaaatact gctagcgtgc aggaacaggt tcttatcaga 1020
aaagtgattg aactacatga taaatacatg gtctatgttg ttgagtgttt ccagaaccac 1080
accctcttcc acaaggcatt gaaagaggca tttgagatat tctgtaacaa aacagtcgct 1140
ggaagttcta gtgctgaatt gcttgcaaca ttttgcgaca atattctcaa gaagggggga 1200
agtgaaaagc tgagcgatga agctattgaa gataccccttg agaaggtggt caaattgctt 1260
gcttatataa gtgacaagga tcttttcgcc gagttctaca ggaagaagct ggcccgtagg 1320
ctcttatttg atcgcagtgc taatgatgat catgagagaa gtatcctgac aaagctcaag 1380
caacaatgtg gtgggcagtt tacttcgaag atggagggca tggtgactga tttgacattg 1440
gcaagggaaa accaaaacag cttcgaggag tatcttggca ataaccccgc tgcaaaccca 1500
gggattgatt tgaccgtaac tgttcttacc actggttttt ggccaagtta caaatcattt 1560
gacataaatc tacccgctga aatggtcaag tgtgttgaag ttttcaaagg gttttatgaa 1620
acaaagacaa aacataggaa acttacctgg atctactcac taggaacttg ccacctcaat 1680
gggaagtttg atgtcaagcc cattgagtta gttgtgtcta cataccaggc tgctgtgctt 1740
ctgctgttca acacaacaga caaattgagc tacactgata tcctaactca gctgaacctg 1800
agccacgaag atctagtgag gttgcttcat tccttgtcat gtgctagata caagattctt 1860
ctcaaggagc caagcacaaa gactgtttcc cagtctgatt cttttgaatt caactccaaa 1920
ttcaccgaca gaatgcggag aataaagatc cctctcccac ctgttgatga gaggaagaaa 1980
gttgtggaag acgtggacaa agacagacgc tatgcgattg atgctgccat tgtgaggatc 2040
atgaagagca ggaaagtatt gggacatcaa caacttgttt ctgagtgcgt tgagcaactt 2100
agccgaatgt tcaagcctga tatcaaggca atcaagaagc gcatggagga tttgataacg 2160
agagattatc tggagaggga caaggagaac gctaacatgt ttaggtactt ggcttag 2217

<210> SEQ ID NO 9
<211> LENGTH: 2232
<212> TYPE: DNA
<213> ORGANISM: Daucus carota
<220> FEATURE:
<221> NAME/KEY: source
<222> LOCATION: 1..2232
<223> OTHER INFORMATION: /organism="Daucus carota"
/mol_type="unassigned DNA"

<400> SEQUENCE: 9

-continued

```
atgatgattg agcggaaaac tatagacctg gagcagggat gggactttat gcaaaaggga     60
atcacaaagc taaagaatat tttagaaggc tttccggagc cgcaattcag ctcggaggat    120
tatatgatgc tttatacaac tatctataac atgtgtacac agaaacctcc acatgattac    180
tctcagcagc tgtatgaaaa gtatcgtgaa gctattgagg agtacattac ttctacagta    240
ttgccttcat tgagagagaa gcatgatgaa ttcatgctta gagaacttgt gaagagatgg    300
tctaatcata aggtcatggt caggtggctt tctcgattct ttcactatct tgatcgctat    360
tttattgctc ggaggtcact tccaccactt catgaagttg gactcacttg ctttcgggac    420
ctggtttacc aggagataaa tgggaaagta agggatgctg taatatcatt gattaatcaa    480
gagcgcgagg gagagcaaat tgaccgagct ttgttgaaga atgttctaga tatatttgtt    540
gaagttggaa tgagtcaaat ggattattat gagaatgact ttgaagcaga catgctcaaa    600
gatacagcag catactattc tcgaaaggct tccaactgga tcttagaaga ttcttgtcca    660
gattatatgc tcaaagcgga agagtgtttg agacgggaaa aggacagggt ctctaactac    720
cttcattcta gtagtgaacc caagttgctt gagaaagttc aacatgagtt actatcacac    780
tatgcaactc agctgcttga gaaagaacac tctgggtgtc atgcattgct tagggatgac    840
aaggtggcag atttatcaag gatgtatagg ctcttctcta aaatacctcg aggcctagat    900
cccgtgtcta atattttcaa gcagcatgtt actgctgaag gtacagcttt ggtcaaacaa    960
gcagaagatg cagctagcaa caagaaggca gagaagagag atgtagtagg tttacaagaa   1020
caggtttttg tgaggaaaat aattgaattg catgacaaat accttacata cgtaaatgac   1080
tgttttacaa accacactct cttccataag gcgcttaagg aggcttttga aatcttctgc   1140
aataagggtg tctctggaag ctctagtgca gaattacttg ccacattctg tgataatatt   1200
ctcaagaaag gtggaagcga gaagttaagt gatgaagcca ttgaggaaac acttgagaag   1260
gttgtaaggt tgcttgctta tataagtgac aaagacttat ttgctgaatt ttataggaaa   1320
aagcttgcac ggcgtctctt attcgacaag agtgccaatg atgagcatga gagaagtata   1380
ttgactaagc tgaagcaaca atgtgggggt caatttacat caaagatgga aggaatggtc   1440
actgacttga cgttggcaaa ggaaaatcag tccaacttcg aggagtacct caataataat   1500
tcaaacgtaa atcctggaat tgacttgaca gttactgttc taaccactgg gttttggcca   1560
agttacaaat ctttcgatct caacctccca gcagagatgg tcaaatgtgt tgaagttttt   1620
agagaattct accaaacaaa aacaaagcac agaaaactga catggatata ctctttgggt   1680
acttgtaaca tcattggaaa atttgatcca aaaaccatgg agcttattgt gacaacatac   1740
caggcctctg ctctgctgct atttaactct tctgatagac ttagttataa tgaaataatg   1800
actcagttga acttgtcgga tgatgatgtt gtcagactac ttcattctct ttcgtgtgca   1860
aagtacaaga ttctatctaa agagccgaac accaaaacta tatctccaac tgattgcttt   1920
cagttcaatt ccaaatttac tgataaaatg aggaggatta agattccact tcccccagtg   1980
gatgagaaga aaaaggtaat tgaagatgtt gataaagaca ggcgatatgc tatagatgct   2040
tcaattgtcc gtatcatgaa gagccgcaaa gttttgggtt atcagcagct agtaatggag   2100
tgcgttgaac aattgggtcg catgtttaag cctgatgtca aagcaatcaa gaagagaatc   2160
gaagatttaa taactcggga ttatctggaa agagacaagg acaatgccaa cttgttcagg   2220
tatctggcat ga                                                       2232
```

<210> SEQ ID NO 10
<211> LENGTH: 2229

-continued

<212> TYPE: DNA
<213> ORGANISM: Apium graveolens
<220> FEATURE:
<221> NAME/KEY: source
<222> LOCATION: 1..2229
<223> OTHER INFORMATION: /organism="Apium graveolens"
/mol_type="unassigned DNA"

<400> SEQUENCE: 10
atgaacgagc ggaagactat cgatttggat aatggatggg aatttatgca gaaagggatc 60
actaagttga agaagattct cgaaggtcaa cctgagcctc agtttagctc cgaggactat 120
atgatgcttt acacaactat ctataaatatg tgtacgcaga agcctccaca tgattattct 180
caacagctgt atgacaagta ccgtgaggcc tttgaggagt acataacttc aactgtcctg 240
ccttctttac gagagaagca tgatgagttt atgttgagag agctcgtgaa tagatggaca 300
aaccataaag tcatggtcag gtggctttct cgattctttc actatcttga tcggtacttc 360
attgcgagga ggtcacttcc tgcacttcat gaagttggac tcacgtgctt ccgggatctg 420
gtctatcagg agctgaaagt taaagtgagg gatgctgtaa tatctctgat cgatcaagag 480
cgtgaggggg aacagattga ccgagcttta ttaaagaacg tgttagatat atttgttgaa 540
atcggaatga gtcaaatgga tcaatatgag aatgactttg aagaagccat gctcactgat 600
actgctgctt actattctcg aaaagcttca aactggatcc ttgaagattc ttgtcctgat 660
tatatgttaa aggcagaaga atgtttgcga cgagagaagg acagggtttc ccactaccta 720
cattttagta gcgagccaaa gttgcttgag aaagtgcaac atgagctgct atctgtgtat 780
gcaacccaat tactcgagaa ggaacattct ggttgtcatg cattgcttag ggatgacaag 840
gtggatgatt tgtctaggat gtacagactc ttctcgaaaa tacctaaagg cctggatcca 900
gtttcttata tttttaagca gcatgttaca aatgaaggga tggcattggt taaacaagca 960
gaagatgcag caagcaacaa gaaggcagaa aagagagacg tggttagttt acaggagcag 1020
gtttttgtta gaaaaattat tgaattacat gacaaatacc tcgcctatgt gaatgactgc 1080
tttacaaacc atactctttt ccataaggct ctcaaggagg cttttgaaat cttttgcaac 1140
aagggtgttg ctggaagctc taatgctgaa ctacttgcta ctttctgtga taacatcctc 1200
aaaaagggtg ggagtgagaa attaagtgat gaggctattg aagaaacact tgagaaggta 1260
gtaaaattgt tagcttacat tagcgataaa gacttgttcg ctgaatttta cagaaaaaag 1320
cttgcacgga gacttctctt tgataagagt gcaaatgacg agcatgaacg aagtattttg 1380
actaaactaa agcaacagtg cggtggtcag ttcacatcga aaatggaggg gatggtcaca 1440
gatttgactt tggctaaaga aaatcaatcc agctttgagg agtatctggg aaataatgcc 1500
aatgtgaatc ctggcattga cttgacggtt actgttctga ccactggctt ctggcctagt 1560
tataaatcct ttgatctcaa ccttcctgct gagatggtca agtgcgttga agtatttaga 1620
gaattttatc aaacaaaaac gaagcataga aagctcacat ggatatattc tctgggtact 1680
tgtaatatca atggaaaatt tgaacccaaa accattgagc tgattgtgac aacctaccag 1740
gcctctgctc tcctgttatt taatacttct gataggttga gttatcaaga aatcatgact 1800
cagttaaatt tgtcggatga tgatgttgtt cgcctgcttc attccctttc atgtgccaag 1860
tataaaattc ttactaaaga gccgaacaac aaaacaattt cccctacgga ttactttgag 1920
ttcaactcca agttcactga caaaatgagg agaattaaga ttccactacc tccagttgat 1980
gagaagaaaa aggtaattga agatgttgac aaggaccggc gatatgccat tgatgcatct 2040
attgtccgca ttatgaagag ccgtaaagtt ttgggctacc aacaattggt tatggaatgt 2100

-continued

```
gttgagcaat tgggacgcat gtttaagcct gatgtcaaag caattaagaa gagaatcgaa   2160

gatttaataa cgcgtgatta tctggaaaga gacaaggata atgccaacct tttcagatat   2220

ttggcatga                                                           2229
```

<210> SEQ ID NO 11
<211> LENGTH: 2229
<212> TYPE: DNA
<213> ORGANISM: Cichorium intybus
<220> FEATURE:
<221> NAME/KEY: source
<222> LOCATION: 1..2229
<223> OTHER INFORMATION: /organism="Cichorium intybus"
/mol_type="unassigned DNA"

<400> SEQUENCE: 11

```
atgaatgaaa gaaaaacaat agacttagaa caaggatggg acttcatgca gaaaggcata     60

acaaagttga agaacattct agaaggtctt cccgagccac aattcagctc ggaagattac    120

atgatgctct acacaaccat ctacaatatg tgcacacaaa aaccgccaca tgattactct    180

caacaattgt atgacaaata ccgcgagtct tttgaagagt acattacttc aacggtgtta    240

ccttctttaa gagagaagca tgatgagttt atgcttagag agcttgttag aagatggtca    300

aatcataaag tgatggttag gtggctttct agattcttcc attatcttga tcgatacttc    360

attgcccgaa gatctcttcc accattaaat gaagttggac ttgcgtgttt tcgtgatctg    420

gtataccaag aggtgaatgg gaaagtgaga gatgctgtaa tatctttgat tgatcaagag    480

cgtgaaggcg agcaaattga ccgagcatta ctcaagaatg ttctagatat atttgttgaa    540

ataggaatgg gacaaatgga atattatgag aatgattttg aagcatccat gcttaatgat    600

acagcagcat attattcacg caaagcttcc aattggattc tagaagattc ttgtccagat    660

tatatgctca aagctgagga gtgcttaaaa agagaaaagg acagagtttc tcattatctt    720

cattccagca gtgaaccaaa gcttcttgag aaagttcaaa cagagttatt atctgtttat    780

gcaactcaat tgcttgaaaa ggagcactcc ggttgtcatg cattacttag ggatgacaag    840

gttgatgatt tatcaagaat gtacagactc ttttcaaaga tacaaaaagg gctggatcct    900

gtttctagta tgtttaagca gcatgtcact gctgaaggca caacattggt taaacaggca    960

gaagatgcag caagtactaa gaaggctgaa aagagagacg tggttggctt acaagaacag   1020

gtttttgtta gaaaagttat cgagcttcat gacaagtacc ttgcatatgt aaatgactgt   1080

tttatgaatc ataccctgtt tcacaaggct cttaaagagg catttgaaat attctgcaac   1140

aagggcgttg ctggaagttc aagtgcagaa ttacttgcta cattttgtga taatattctt   1200

aaaaaaggtg gaagtgaaaa attgagtgat gaagccattg aggacacact tgagaaggtg   1260

gtaaagttgc ttgcttacat cagcgataaa gatctatttg cagagtttta taggaaaaaa   1320

ctggctagac ggcttttatt tgacaaaagt gcaaatgatg agcacgaaag aagtattttg   1380

acaaaattga aacaacaatg tggcggtcaa tttacatcaa aaatggaagg aatggttaca   1440

gatttgacat tggcaaaaga aaatcaatca cattttgagg agtatttgaa taataatccc   1500

aatgttagcc ctggcattga cttgaccgtg actgtgttga ccactggttt ttggcctagt   1560

tacaaatctt ttgacctaaa tctccctgca gaaatggtca aatgcgttga agttttcaga   1620

gaattttatc aaacaaaaac aaaacacaga aaactcacat ggatatattc attgggcacc   1680

tgcaatataa acggaaaatt cgaaccaaaa accatggagc taatcgttac aacttaccag   1740

gcatctgctt tattactgtt caactcatca gatcgattga gttatcaaga aatcatgact   1800
```

caattaaact tatcagatga tgatgttgtt agactactcc attcattatc atgtgcaaaa 1860
tataaaattt tattaaaaga accaaataca aaaacaatct ctccaactga tttctttgaa 1920
ttcaactcaa agtttacaga taaaatgaga aggatcaaga ttcctctacc tcctgttgat 1980
gaaaagaaaa aagtaattga agatgttgac aaagaccgac gttatgcaat tgatgcttca 2040
attgtacgga taatgaaaag cagaaaagtt cttggatacc aacaattggt catggaatgt 2100
gttgaacaat taggccgtat gtttaagcct gatgtaaaag caatcaagaa acgtattgaa 2160
gatctcataa ctcgtgatta tcttgaaaga gacaaagaaa atccaaattt gtttcggtac 2220
ttggcatga 2229

<210> SEQ ID NO 12
<211> LENGTH: 2229
<212> TYPE: DNA
<213> ORGANISM: Cichorium endivia
<220> FEATURE:
<221> NAME/KEY: source
<222> LOCATION: 1..2229
<223> OTHER INFORMATION: /organism="Cichorium endivia"
/mol_type="unassigned DNA"

<400> SEQUENCE: 12
atgaatgaaa gaaaaacaat agacttagaa caaggatggg acttcatgca aaaaggcata 60
acaaagttga agaacattct agaaggtctt cccgagccac aattcagctc agaggattac 120
atgatgctct acacaaccat ctacaatatg tgcacacaaa aaccgccaca tgattactct 180
caacaattat atgacaaata ccgcgagtct tttgaagagt acataacttc aacggtgtta 240
ccttctttaa gagagaagca tgatgagttt atgcttagag agcttgttag aaggtggtca 300
aatcataaag tgatggttag gtggctttct agattcttcc attatcttga tcgatacttt 360
attgcaagaa gatctcttcc accattaaat gaagttggac ttgcgtgttt tcgtgatctg 420
gtataccaag aggtgaatgg aaaagtgaga gatgctgtaa tatctttgat tgatcaagag 480
cgtgaaggcg agcaaattga ccgagcatta ctgaagaatg ttctagatat atttgttgaa 540
ataggaatgg gacaaatgga atattatgag aatgattttg aagcatctat gcttaatgat 600
acagcagcat attattcacg caaagcttcc aactggattc tagaagattc ttgtccagat 660
tatatgctca aagctgagga gtgcttaaaa agagaaaagg acagagtttc tcattatctt 720
cattcaagta gtgaaccaaa gcttcttgag aaagttcaaa cagagttatt atctgtttat 780
gcaactcaat tgctcgaaaa ggaacactca ggttgtcatg cattacttag agatgacaag 840
gttgatgatt tatcaagaat gtacagactc ttttcaaaga tacaaaaagg actggatcct 900
gtttccagta tgtttaagca gcatgtcact gctgaaggca caacattagt aaaacaagca 960
gaagatgcag caagtactaa gaaggctgaa aagagagacg tggttggctt acaggaacag 1020
gtttttgtta gaaaagtaat cgagcttcat gacaagtacc tcgcatatgt aaacgactgt 1080
tttatgaatc acacattgtt ccacaaggct cttaaagagg catttgaaat attctgcaac 1140
aagggcgttg ctggaagttc aagtgcagaa ttacttgcca cattttgtga taatattctt 1200
aaaaaaggtg gaagtgaaaa attgagtgat gaagccattg aagacacact tgagaaggta 1260
gtaaagttgc ttgcttacat cagcgataaa gatctatttg cagagtttta taggaaaaaa 1320
ctggctagaa ggcttttatt tgacaaaagt gcaaatgatg agcatgaaag aagtatttta 1380
acaaagttga agcaacaatg tggtggtcag tttacatcaa agatggaagg aatggttaca 1440
gatttaacac tggcaaaaga aaatcaatca cattttgagg agtatttgaa taataatccc 1500

```
aatgttagcc ctggcattga cttgaccgtg actgtgttga ccacgggatt ttggcctagt   1560

tacaaatctt ttgacctaaa tcttcctgca gaaatggtca aatgcgttga agttttcaga   1620

gaattttatc aaacaaaaac aaaacacaga aaactcacat ggatttattc attgggcacc   1680

tgcaatatta acggaaaatt cgaaccaaaa accatggagc taatcgttac aacttaccag   1740

gcatctgctt tattgttatt caactcatca gatcgattaa gttatcaaga aatcatgact   1800

caattaaatt tatcagatga tgatgttgtt agactactac attcattatc atgtgcaaaa   1860

tataaaattt tattaaaaga accaaatacc aaaacaatat ctccaaccga tttctttgaa   1920

ttcaactcaa agtttacaga taaaatgaga aggatcaaga ttcctctacc tcctgttgat   1980

gaaaagaaaa aagtaattga agatgttgac aaagatagaa ggtatgcaat tgatgcttca   2040

attgtacgaa taatgaaaag cagaaaagtt cttggatacc aacaattggt tatggagtgt   2100

gttgaacaat taggccgtat gtttaagcct gatgtaaaag caatcaagaa gcgtattgaa   2160

gatttgataa cgcgtgatta tcttgaaaga gacaaagaaa atccaaattt gtttcggtac   2220

ttggcatga                                                           2229
```

<210> SEQ ID NO 13
<211> LENGTH: 2235
<212> TYPE: DNA
<213> ORGANISM: Allium ampeloprasum
<220> FEATURE:
<221> NAME/KEY: source
<222> LOCATION: 1..2235
<223> OTHER INFORMATION: /organism="Allium ampeloprasum"
/mol_type="unassigned DNA"

<400> SEQUENCE: 13

```
atgtcgttgc acgaaaggaa aaccattgat ttggagcagg gatgggcttt tatgcagaaa     60

gggatcacca aactgaagaa tattcttgat gagttgaatg aacctcagtt cagctcagag    120

gattacatga tgctctatac gactatctat aatatgtgta ctcagaagcc gccacatgat    180

tattctcagg agttgtatga taagtaccga gagtcctttg aagagtatat cactaccact    240

gtgcttcctt cattgagaga aaagcatgat gaatacatgt taagggagct cgtgagaagg    300

tggtcaaatc ataaaataat ggttagatgg ctttcacgct tttccatta tcttgatcgc    360

tactttatag cacgaagatc attgcctgct cttaatgaag tcggtctcac ttgtttccgt    420

gatctggtgt acaacgaagt ccatgggaaa gttaaagatg ccgtgatctc attgattgac    480

caagagaggg aaggggagca aattgacaga gctttattaa agaatgtttt gggtattttt    540

gtagagattg gtttgggaag catggaatgt tatgagaatg attttgaaac atcaatgctt    600

aatgctacag cagcctatta ttcacgaaaa gcttcaaatt ggattctaga agattcatgt    660

ccagattata tgctaaaagc cgaggagtgc ttaaaacatg agaaagatag agttgctcat    720

tatttgcatt caagcagtga acagaagctg ttagagaaag tgcaacatga gttacttttc    780

gtatatgcaa gtcaacttct cgagaaagaa cattccggat gtcatgcatt gcttcgcgat    840

gacaaggtgg gagatctttc acgcatgtat cggctgttct gtagaattac acgtggtttg    900

gaccctgtgt ctcaaatatt taagcagcat gtgactgcag aaggtactgc tttggtcaaa    960

catgccgaag atgctgcaag taacaagaag gccgagaaaa aagacattgt tggtttgcaa   1020

gagcaggtct tcgttaggaa agtaattgag ctgcatgata aatacttggc ctatgtgact   1080

gactgctttc aaaatcactc tctatttcac aaggcactta aagaggcatt cgaggtattc   1140

tgcaataaag gtgttgcagg tagctcaagc gctgaacttc tggctgcttt ttgtgacaat   1200
```

-continued atattgaaga agggtggaag cgagaaacta agcgatgagg ccatagagga tactcttgag 1260
aaggttgtaa aactattggc atatattagc gataaagatc tgtttgctga attttacagg 1320
aagaagcttg cacgaagatt actctttgac aaaagtgcta atgatgacca tgagaggagc 1380
atccttacaa agctgaaaca gcaatgtgga gggcagttca cctctaaaat ggaaggcatg 1440
gtaaccgatc tgacacttgc acgagaaaat caatcaagtt ttgacgatta ccttagcagc 1500
aatcctaaag caaattctgg aattgacttg actgttacag tcttaacaac tggcttctgg 1560
cccagttaca agtcttttga tctcaatctt cctgatgaga tggtaaaatg cgttgaaatt 1620
tttaaagagt tttacgagac aaaaaccaaa cacagaaaac ttacatggat ttattcgttg 1680
ggcacttgca acatcaatgg caagttcgaa accaagacaa tagagttggt tgttacaacc 1740
tatcaggctg cagtgttgct tctattcaac tctgcagata aattaagtta ttctgagatt 1800
gtgcagcagc taaacttatc tgatgatgat gtaatcagat tacttcactc tctttcatgc 1860
gctaaataca aaattctcaa taaagaaccc gctaccaaga ctattacccc gaatgatcat 1920
tttgagttca attctaaatt cactgataga atgagaagga tcaagattcc cctgcctcct 1980
gtggatgaga agaaaaaagt aattgaagat gttgacaaag acagaagata tgcaattgac 2040
gcatccatag ttcgaataat gaaaagtaga aaagttcttg gtcatcagca gcttgttttg 2100
gaatgtgttg agcaattagg ccgcatgttt aagcctgact ttaaggccat caagaaaagg 2160
attgaagatc tgatcgctag agattatttg gagagggaca aggacaatcc aaacctcttt 2220
aaatatttgg cctaa 2235

<210> SEQ ID NO 14
<211> LENGTH: 2229
<212> TYPE: DNA
<213> ORGANISM: Lactuca sativa
<220> FEATURE:
<221> NAME/KEY: source
<222> LOCATION: 1..2229
<223> OTHER INFORMATION: /organism="Lactuca sativa"
/mol_type="unassigned DNA"

<400> SEQUENCE: 14
atgaacgaaa gaaaaacaat agacttagag caaggatggg acttcatgca gaaaggaata 60
acaaagttga agaatattct agaaggtctt cccgagccac aattcagctc ggaggattac 120
atgatgctct acacaaccat ctacaacatg tgtacacaga aaccaccaca tgattactcc 180
caacagttgt atgacaaata tcgtgagtct tttgaagagt atattacttc aactgtgtta 240
ccttctttaa gagagaagca tgatgagttc atgctgagag agcttgttag aaggtggtca 300
aatcataaag tcatggtgcg gtggctttct agattcttcc attatcttga ccgatatttc 360
attgcccgaa gatctcttcc gccactaaat gaagttggac ttgcctgttt tcgtgatctg 420
gtataccaag aggtgaatgg taaagtgaga gatgctgtaa tatctttgat tgatcaagag 480
cgtgaagggg agcagattga tcgagcttta ctgaagaatg ttctagatat atttgttgag 540
ataggaatgg gacaaatgga gtattatgag aatgattttg aagcatccat gcttaatgat 600
acagcagcat attattcacg caaggcttcc aactggattc tagaagattc ttgtccagat 660
tatatgctca aagcagagga gtgcttaaaa agagaaaagg acagagtgtc tcattatctt 720
cattccagca gtgagccaaa gcttcttgag aaagttcaaa atgagttatt gtctgtttat 780
gcaactcaat tgcttgagaa agagcactca ggttgtcatg cattgctcag ggatgacaag 840
gttgatgatt tatcaagaat gtacagactc ttttcaaaga taccaaaagg attggatcct 900
gtttctagta tgtttaagca gcatgtcact gctgaaggca caacattggt taaacaagca 960
gaagatgcag caagtaccaa gaaggctgaa aagagagatg tggttgggtt gcaggaacag 1020
gtttttgtta gaaaagttat tgagctccat gacaagtacc tggcatatgt aaatgactgt 1080
ttcatgaacc atactctttt ccacaaggct cttaaagagg catttgaaat attctgcaac 1140
aagggtgttg ctggaagttc aagtgcagag ttacttgcca cattttgtga taatattctt 1200
aaaaaaggtg gaagtgagaa actgagcgat gaagccattg aggacaccct tgagaaggta 1260
gtaaagttgc ttgcctacat cagtgataaa gatctatttg ctgaatttta caggaaaaaa 1320
cttgctagga ggcttttgtt tgacaagagt gcaaacgatg agcatgagag aagtattctc 1380
acaaagctga agcaacagtg tggtggtcag ttcacatcaa agatggaagg gatggttaca 1440
gatttgacat tggcaaagga aaaccaatcc cattttgaag agtatttgaa caataatccc 1500
aatgtcagcc ctggaattga cttgactgtc actgtgttga ctaccggctt ctggcccagc 1560
tacaaatctt ttgacctaaa tctccctgcc gaaatggtta aatgcgttga agttttcaga 1620
gaattttatc aaacaaaaac aaagcacagg aagcttacat ggatatattc attgggtacc 1680
tgcaatataa acgggaaatt tgaacccaaa acaatggagc tcatagtcac aacctaccag 1740
gcatctgctt tattactgtt caacttatcg gatcgattga gttatcaaga aatcatgact 1800
cagttgaact tgtcagatga tgatgttgtt aggctgctcc attctttgtc atgtgcaaaa 1860
tacaaaattc ttttaaagga gcctaatacc aaaacaatct ctccaaccga ttacttcgaa 1920
ttcaactcca agtttacaga taaaatgagg aggatcaaga ttcctctacc tcctgtggat 1980
gagaagaaaa aggtgattga ggatgttgac aaagacagac gttatgccat tgatgcttcc 2040
attgtaagga taatgaagag cagaaaggtg cttggatacc agcagttggt tatggagtgt 2100
gttgaacagt tgggacgcat gtttaagcct gatgtaaaag caatcaagaa gcggattgaa 2160
gatctgataa ctcgtgatta tcttgaaaga gacaaagaga accccaactt gttccgatac 2220
ttggcatga 2229

<210> SEQ ID NO 15
<211> LENGTH: 2217
<212> TYPE: DNA
<213> ORGANISM: Raphanus sativus
<220> FEATURE:
<221> NAME/KEY: source
<222> LOCATION: 1..2217
<223> OTHER INFORMATION: /organism="Raphanus sativus"
/mol_type="unassigned DNA"

<400> SEQUENCE: 15
atggagcgga agacgattga tctggaacaa ggatgggact atatgcagac tgggatcact 60
aagctgaaac ggattcttga aggattgcct gagccgcaat tcgactctga gcagtacatg 120
atgctttata cgactatcta caacatgtgc acccagaaac ctcctcatga ttactctcag 180
cagctttatg acaagtatcg cgaagctttt gaggagtaca ttgactctac tgttttgcct 240
gctttgaagg agaagcatga tgaatacatg ctacgggagc tggttaagag atggtctaac 300
cataaagtta tggttagatg gctatcccga ttcttctact atcttgaccg ttacttcatt 360
gctcggagat cgctgccacc gcttaatgaa gttgggctca catgcttccg tgaccgggtg 420
tataaggagt tgcattccaa ggtcaaagat gctgtaatag cacttgttga taaagaacgg 480
gaaggcgagc agattgacag ggctcttctg aaaaacgtat tagatatcta tgtagagatt 540
ggaatgggac agatggaaag atacgaagtg gattttgaaa gcttcatgct tttggattca 600

```
gcatcttact attctcgcaa agcatcaaac tggatccagg aagattcttg ccctgattac    660
atgctgaagt ctgaagaatg ccttaagaag gagagggaga gggttgctca ctaccttcat    720
tcaagcagcg agccaaagct ggttgagaaa gtacaacatg agctgttggt tgtctatgca    780
aatcagcttc ttgaaaagga gcactcaggg tgccgtgcat tgctgagaga cgacaaggtt    840
gacgatctct ccaggatgta caggctctat cataaaattg ctaaaggttt agaacctgtt    900
gcaaacatat ttaagcagca tgtcacagcc gagggtaacg cacttgtcca acaggccgaa    960
gacacagcca ctaatcaggc tgcaaatact gctagcgtgc aggaacaggt tctcatcaga   1020
aaagtgattg agctacatga taagtacatg gtctatgtcg tggagtgctt ccagaaccac   1080
accctcttcc acaaggctct gaaagaggca tttgagatat tctgtaacaa aacagtcgct   1140
ggaagttcaa gtgcagaact gcttgcaaca ttctgcgaca acatcctcaa gaagggggggt   1200
agtgagaagc tgagtgacga agctattgaa gatacgcttg agaaggttgt caaattgctt   1260
gcttatataa gcgacaagga tcttttcgcc gagttctaca ggaagaagct ggcacgtagg   1320
ctcttatttg atcgcagtgc gaatgatgat catgagagaa gcatccttac aaagctcaag   1380
caacaatgtg gtgggcagtt cacttctaag atggagggca tggtaacgga cttgacattg   1440
gcaagagaga accaaaccag tttcgaggag tatctaggca ataaccccgc tgcaaaccca   1500
gggattgatt tgaccgtcac tgttcttacc actggtttct ggccaagtta caaatcattc   1560
gacataaatc taccaagtga aatggtcaag tgtgttgaag ttttcaaagg gttttatgag   1620
acgaaaacta aacataggaa acttacatgg atctactcac taggaacttg tcacctcaac   1680
ggaaagtttg atcacaagcc cattgagtta gttgtgtcta cttaccaggc tgctgtgctt   1740
ctgctgttca acacaacaga caaattgagc tacaacgata tcctaactca actgaaccta   1800
agccacgaag atttagtgag gttgcttcat tccctgtcat gtgctaggta caagatcctt   1860
ctcaaggagc caagcacgaa gactgttaca cagactgatt catttgaatt caatgccaaa   1920
ttcacggaca gaatgcgcag aatcaagatc cctctccctc ctgttgatga aaggaagaag   1980
gttgtggaag atgtggacaa agacagacgc tatgcgattg atgctgccat tgttaggatc   2040
atgaagagca ggaaagtgtt gggacatcaa caactcgtct ctgagtgcgt tgagcaactt   2100
agccgaatgt tcaagcctga tatcaaagcg atcaagaagc gtatggagga tctaattacg   2160
agggattatt tggagaggga caaggagaac cctaacatgt ttaggtactt ggcttag      2217
```

<210> SEQ ID NO 16
<211> LENGTH: 2223
<212> TYPE: DNA
<213> ORGANISM: Spinacia oleracea
<220> FEATURE:
<221> NAME/KEY: source
<222> LOCATION: 1..2223
<223> OTHER INFORMATION: /organism="Spinacia oleracea"
/mol_type="unassigned DNA"

<400> SEQUENCE: 16

```
atgaacgatc gtaaagttat cgaactagag caaggatggg agttcatggg gaaggggatt     60
acgaagttga aaaggatttt ggaaggatta ccagagccgc cttttaattc ggaagactac    120
atgatgctgt acacgacaat atacaacatg tgtacacaga aacccccctca tgattactct    180
caacaactct atgacaatta caaagaggca tttgtggatt acatacattc aacggtttta    240
ccttctttgg gggacaaaca tgatgagttt atgctgagag agcttgtgaa gagatggtca    300
aatcataaag taatggtgag gtggttgtct cgcttcttcc attatctgga tcggtacttc    360
```

```
atcgctcgga gatcgcttcc ttctttgaat gatgttggat tgacgtgctt ccgtgatctg    420

gtttatcaag aaatatctgg caaagccaag gatgctgtta ttgctctgat tgatgaagaa    480

agagagggtg ggcaaattga cagagcctta ttgaagaatg tacttgatat atacgttgaa    540

attggaatga cacaaatgga ttactacgaa aaggactttg aagctcatat gctggatgat    600

actgctgctt attactcacg caaggcctca agctggattc tggaggactc atgtccggaa    660

tacatgttga agtcggagga gtgtttgaag aaagagaaag atagagtggc tcattatcta    720

cattccagca gtgagccaaa gcttctggag aaagtacaaa atgagttgct actggtttac    780

gaaaatcagt tgcttgagaa ggagaattct ggatgtcgtg cattgttgaa agatgacaag    840

gtggaagatc tttccaggat gtacaggctt tatagcaagg ttaccaaagg gttggaaccc    900

attggcagta tcttcaaaca gcatataacc gatgaaggaa cagccctggt gcagcaggcc    960

gaagacgctg caattagcaa ggctgaaaat gctggcggtg gttcacatga gcaggtcttc   1020

gtcaggaaag tgattgagtt gcatgacaaa tttatgacct atgttacaga ttgcttcaac   1080

agccatacca tctttcacaa ggctctcaag gaagcttttg aggtattctt aaacaagggt   1140

gttgctggta gttcaagtgc tgaacttcta gcttcatttt gtgataatat tctcaagaaa   1200

ggtggtagtg aaaaattaag tgatgaggct attgaggatt cactggagaa ggtggtgaag   1260

cttctcgcat atgtcagtga taaagacctg tttgctgaat tttacagaaa gaagctctct   1320

cgccggctac tctttgacaa aagtgctaat gatgatcatg agaggagtat tttaacaaaa   1380

ttgaagcagc agtgtggggg acagttcaca tcaaagatgg aggggatggt gacagacttg   1440

acattggcga gggagaatca aactaatttt gaggaatatc ttggacaaaa tacagatgcc   1500

agtcctggtc ttgatttgac tgtgacagtt ttgaccactg ggttctggcc aagttacaaa   1560

tcttctgatc ttaaccttcc tgctgagatg gtgaggtgtg ttgaagtttt taagcaattt   1620

tatcaaacaa agacaaaaca caggaagctc acctgggtat attcgttggg aagttgtaac   1680

attaatggca agtttggtcc gaaaacaatt gaattggttg ttggaactta tcaggctgct   1740

gcgctgatgc tctttaacac atcagatcga ctgagttatt cagaaataac gacccaacta   1800

aatctagctg acgaagactt ggttagagtg cttcaatctc tatcttgcgc aaagtataag   1860

attcttctaa aagagccaag cacaagaaac gtgatctcaa ctgattgttt ttcattcaac   1920

tctaatttta ctgacagaat gaggaggatt aggattcctc ttcctccaat ggatgagagg   1980

aaaaaggttg ttgaagatgt tgacaaagat agaagatatg ctattgatgc ctcaattgta   2040

cgcataatga aaagtaggaa ggctttggga tatcaacaat taatcacgga gtgtgtggag   2100

cagctaagcc gcatgttcaa gcctgatttc aaagcaatta agaagaggat cgaggacttg   2160

ataaccagag attatattga aagagacaag gaaaaccctc agctattccg gtacttggct   2220

tga                                                                  2223
```

<210> SEQ ID NO 17
<211> LENGTH: 2220
<212> TYPE: DNA
<213> ORGANISM: Beta vulgaris
<220> FEATURE:
<221> NAME/KEY: source
<222> LOCATION: 1..2220
<223> OTHER INFORMATION: /organism="Beta vulgaris"
/mol_type="unassigned DNA"

<400> SEQUENCE: 17

```
atgaatgatc gtaaagttat tgaactagag caaggatggg agttcatggg gaaggggatt     60
```

-continued acaaagttga agaggattct ggaaggattg ccagagccac catttaattc tgaagactac 120
atgatgttgt acacgacgat atacaatatg tgtactcaga aaccccccaca tgattactct 180
caacagctct atgacaatta caaacaggct tttgtggatt acatcaactc gacggtttta 240
ccttctttgc gggagaagca tgatgagttt atgttaagag aacttgtgaa aagatgggca 300
aatcataaag taatggtcag gtggttgtct cgtttcttcc attatctgga ccggtatttc 360
attgctcgga ggtcgcttcc ttctttgaat gaagttggac tgacttgttt ccgtgatctg 420
gtttatcaag aaatatctgg caaagccaag gatgctgtta tagccctgat tgatatagaa 480
agagaaggtg ggcagattga cagatcatta ttgaaaaatg tacttgatat atatgttgaa 540
attggaatgg gacaaatgga tcactatgaa aaagactttg aagctcatat gctggatgat 600
actgctgctt actactcgcg caaagcgtct agctggattc ttgaggactc ttgtccggaa 660
tacatgttaa agtctgagga gtgtttgaag aaggagaaag agagagtggc taattattta 720
cattccagca gtgagccaaa gcttctggag aaagtgcaaa acgagttgct attggtttat 780
gaaagccaat tgcttgagaa ggagaattcg ggatgtcgtg cattactgaa agatgacaag 840
gtggatgatc tttccaggat gtacaggctt tacagtaagg ttaccaaagg attggaaccc 900
attggcagta tcttcaaaca gcatataact gatgaaggaa cagccttagt gcagcaggcc 960
gaagatgctg ctatcagcaa ggctgaaaat actggtggtt cacatgagca ggtcttcgtc 1020
aggaaagtaa tagagttgca tgacaaattc atgacttatg tcaccgattg cttcaacagc 1080
cataccatat ttcacaaggc tcttaaggag gcttttgagg tatttttgaa caagggtgtt 1140
gctggtagct caagtgctga gttgctagct acattctgtg ataacattct caagaaaggt 1200
gggagcgaaa aactaagcga tgaggctatt gaggattcac ttgagaaggt ggtgaagctt 1260
ctggcctatg tcagtgataa agacctgttt gctgaatttt acagaaagaa gctctctcgc 1320
cggctactct ttgacaagag tgctaatgat gatcatgaaa gaagtatttt aaccaaattg 1380
aagcagcagt gtggcggaca attcacatca aagatggagg ggatggtgac agacttgacc 1440
ttggcgaggg agaatcaaac taattttgag gaatatctta gtcagaatcc agatgccagt 1500
cctggtcttg atttgactgt gactgttctg acaactgggt tctggccaag ttacaaatct 1560
tccgatctta accttcccgc tgagatggtg aggtgtgttg aagtttttaa gcagttctat 1620
tcaactaaaa caaagcacag gaagctgacc tgggtttact cattgggaag ctgtaatatt 1680
aatggcaagt ttggtccaaa aactattgaa ttggttgtcg gaacttatca ggctgctgct 1740
ttgatgctct ttaacacatc agaccgactg agttattcag agatagcaac tcaactaaat 1800
ttagctgatg aagatctggt tagagtgctt caatctttat cctgcgcaaa gtataagatt 1860
cttttaaagg agccaaacac gaaaaccgtg tccccgactg attgtttttc atttaactct 1920
agtttcactg acaggatgag gaggataaga attcctcttc ctccgatgga tgagaggaaa 1980
aaggttgttg aggatgttga caaagataga agatatgcta ttgatgcctc aattgtacgc 2040
ataatgaaaa gtaggaaggt tttggggtac cagcaattaa tcacagagtg tgtggagcag 2100
ctaagccgca tgttcaagcc tgatttcaag gcaattaaga agaggatcga ggacttaata 2160
acccgagatt atattgaaag agacaaggag aacccgcagc tattccgata cttggcttga 2220

<210> SEQ ID NO 18
<211> LENGTH: 744
<212> TYPE: PRT
<213> ORGANISM: Cucumis sativus

<400> SEQUENCE: 18

```
Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
            20                  25                  30

Pro Glu Pro Gln Phe Ser Ser Glu Asp Tyr Met Met Leu Tyr Thr Thr
        35                  40                  45

Ile Tyr Asn Met Cys Thr Gln Lys Pro Pro His Asp Tyr Ser Gln Gln
    50                  55                  60

Leu Tyr Asp Lys Tyr Arg Glu Ser Phe Glu Glu Tyr Ile Thr Ser Met
65                  70                  75                  80

Val Leu Pro Ser Leu Arg Glu Lys His Asp Glu Phe Met Leu Arg Glu
                85                  90                  95

Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
        115                 120                 125

Pro Pro Leu Asn Glu Val Gly Leu Thr Cys Phe Arg Glu Leu Val Tyr
    130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
            180                 185                 190

Asn Asp Phe Glu Ala Ala Met Leu Lys Asp Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Lys Arg Glu Lys Asp Arg Val Ser His
225                 230                 235                 240

Tyr Leu His Ser Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
            260                 265                 270

Gly Cys His Ala Leu Leu Arg Asp Asp Lys Val Glu Asp Leu Ser Arg
        275                 280                 285

Met Phe Arg Leu Phe Ser Lys Ile Pro Lys Gly Leu Asp Pro Val Ser
    290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Asn Asp Cys Phe Gln Asn His Thr Leu
        355                 360                 365

Phe His Lys Ala Leu Lys Glu Ala Phe Glu Val Phe Cys Asn Lys Gly
    370                 375                 380

Val Ala Gly Ser Ser Ser Ala Glu Leu Leu Ala Thr Phe Cys Asp Asn
385                 390                 395                 400

Ile Leu Lys Lys Gly Gly Ser Glu Lys Leu Ser Asp Glu Ala Ile Glu
                405                 410                 415
```

-continued

```
Glu Thr Leu Glu Lys Val Val Lys Leu Leu Ala Tyr Ile Cys Asp Lys
            420                 425                 430

Asp Leu Phe Ala Glu Phe Tyr Arg Lys Lys Leu Ala Arg Arg Leu Leu
        435                 440                 445

Phe Asp Lys Ser Ala Asn Asp Asp His Glu Arg Ser Ile Leu Thr Lys
    450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Thr Ser Phe Glu Glu
                485                 490                 495

Tyr Leu Ser Asn Asn Pro Gln Ala Ser Pro Gly Ile Asp Leu Thr Val
            500                 505                 510

Thr Val Leu Thr Thr Gly Phe Trp Pro Ser Tyr Lys Ser Phe Asp Leu
        515                 520                 525

Asn Leu Pro Ala Glu Met Val Lys Cys Val Glu Val Phe Arg Glu Phe
    530                 535                 540

Tyr Gln Thr Lys Thr Lys His Arg Lys Leu Thr Trp Ile Tyr Ser Leu
545                 550                 555                 560

Gly Thr Cys Asn Ile Ser Gly Lys Phe Glu Pro Lys Thr Met Glu Leu
                565                 570                 575

Ile Val Thr Thr Tyr Gln Ala Ser Ala Leu Leu Leu Phe Asn Ser Ser
            580                 585                 590

Asp Arg Leu Ser Tyr Ser Glu Ile Met Thr Gln Leu Asn Leu Ser Asp
        595                 600                 605

Asp Asp Val Val Arg Leu Leu His Ser Leu Ser Cys Ala Lys Tyr Lys
    610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Lys Val Ile Glu Asp Val Asp
            660                 665                 670

Lys Asp Arg Arg Tyr Ala Ile Asp Ala Ser Ile Val Arg Ile Met Lys
        675                 680                 685

Ser Arg Lys Val Leu Gly His Gln Gln Leu Val Met Glu Cys Val Glu
    690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
            740


<210> SEQ ID NO 19
<211> LENGTH: 744
<212> TYPE: PRT
<213> ORGANISM: Cucumis melo

<400> SEQUENCE: 19

Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
            20                  25                  30

Pro Glu Pro Gln Phe Ser Ser Glu Asp Tyr Met Met Leu Tyr Thr Thr
```

-continued

```
        35                  40                  45

Ile Tyr Asn Met Cys Thr Gln Lys Pro Pro His Asp Tyr Ser Gln Gln
    50                  55                  60

Leu Tyr Asp Lys Tyr Arg Glu Ser Phe Glu Glu Tyr Ile Thr Ser Met
65                  70                  75                  80

Val Leu Pro Ser Leu Arg Glu Lys His Asp Glu Phe Met Leu Arg Glu
                85                  90                  95

Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
        115                 120                 125

Pro Pro Leu Asn Glu Val Gly Leu Thr Cys Phe Arg Glu Leu Val Tyr
    130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
            180                 185                 190

Asn Asp Phe Glu Ala Ala Met Leu Lys Asp Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Lys Arg Glu Lys Asp Arg Val Ser His
225                 230                 235                 240

Tyr Leu His Ser Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
            260                 265                 270

Gly Cys His Ala Leu Leu Arg Asp Asp Lys Val Glu Asp Leu Ser Arg
        275                 280                 285

Met Phe Arg Leu Phe Ser Lys Ile Pro Lys Gly Leu Asp Pro Val Ser
    290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Asn Asp Cys Phe Gln Asn His Thr Leu
        355                 360                 365

Phe His Lys Ala Leu Lys Glu Ala Phe Glu Val Phe Cys Asn Lys Gly
    370                 375                 380

Val Ala Gly Ser Ser Ser Ala Glu Leu Leu Ala Thr Phe Cys Asp Asn
385                 390                 395                 400

Ile Leu Lys Lys Gly Gly Ser Glu Lys Leu Ser Asp Glu Ala Ile Glu
                405                 410                 415

Glu Thr Leu Glu Lys Val Val Lys Leu Leu Ala Tyr Ile Cys Asp Lys
            420                 425                 430

Asp Leu Phe Ala Glu Phe Tyr Arg Lys Lys Leu Ala Arg Arg Leu Leu
        435                 440                 445

Phe Asp Lys Ser Ala Asn Asp Asp His Glu Arg Ser Ile Leu Thr Lys
    450                 455                 460
```

Leu Lys Gln Gln Cys Gly Gly Gln Phe Thr Ser Lys Met Glu Gly Met
465 470 475 480

Val Thr Asp Leu Thr Leu Ala Arg Glu Asn Gln Thr Ser Phe Glu Glu
485 490 495

Tyr Leu Ser Asn Asn Pro Gln Ala Ser Pro Gly Ile Asp Leu Thr Val
500 505 510

Thr Val Leu Thr Thr Gly Phe Trp Pro Ser Tyr Lys Ser Phe Asp Leu
515 520 525

Asn Leu Pro Ala Glu Met Val Lys Cys Val Glu Val Phe Arg Glu Phe
530 535 540

Tyr Gln Thr Lys Thr Lys His Arg Lys Leu Thr Trp Ile Tyr Ser Leu
545 550 555 560

Gly Thr Cys Asn Ile Ser Gly Lys Phe Glu Pro Lys Thr Met Glu Leu
565 570 575

Ile Val Thr Thr Tyr Gln Ala Ser Ala Leu Leu Leu Phe Asn Ser Ser
580 585 590

Asp Arg Leu Ser Tyr Ser Glu Ile Met Thr Gln Leu Asn Leu Ser Asp
595 600 605

Asp Asp Val Val Arg Leu Leu His Ser Leu Ser Cys Ala Lys Tyr Lys
610 615 620

Ile Leu Asn Lys Glu Pro Asn Thr Lys Thr Ile Ser Pro Asn Asp His
625 630 635 640

Phe Glu Phe Asn Ala Lys Phe Ser Asp Lys Met Arg Arg Ile Lys Ile
645 650 655

Pro Leu Pro Pro Val Asp Glu Lys Lys Lys Val Ile Glu Asp Val Asp
660 665 670

Lys Asp Arg Arg Tyr Ala Ile Asp Ala Ser Ile Val Arg Ile Met Lys
675 680 685

Ser Arg Lys Val Leu Gly His Gln Gln Leu Val Met Glu Cys Val Glu
690 695 700

Gln Leu Gly Arg Met Phe Lys Pro Asp Phe Lys Ala Ile Lys Lys Arg
705 710 715 720

Ile Glu Asp Leu Ile Thr Arg Asp Tyr Leu Glu Arg Asp Lys Asp Asn
725 730 735

Pro His Leu Phe Arg Tyr Leu Ala
740

<210> SEQ ID NO 20
<211> LENGTH: 744
<212> TYPE: PRT
<213> ORGANISM: Cucurbita pepo

<400> SEQUENCE: 20

Met Thr Met Gly Glu Arg Lys Thr Ile Asp Leu Glu Gln Gly Trp Glu
1 5 10 15

Phe Met Gln Lys Gly Ile Thr Lys Leu Lys Asn Ile Leu Glu Gly Leu
20 25 30

Pro Glu Pro Gln Phe Ser Ser Glu Asp Tyr Met Met Leu Tyr Thr Thr
35 40 45

Ile Tyr Asn Met Cys Thr Gln Lys Pro Pro His Asp Tyr Ser Gln Gln
50 55 60

Leu Tyr Asp Lys Tyr Arg Glu Ser Phe Glu Glu Tyr Ile Ser Ser Met
65 70 75 80

Val Leu Pro Ser Leu Arg Glu Lys His Asp Glu Phe Met Leu Arg Glu

-continued

```
                85                  90                  95

Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
        115                 120                 125

Pro Pro Leu Asn Glu Val Gly Leu Thr Cys Phe Arg Glu Leu Val Tyr
    130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
            180                 185                 190

Asn Asp Phe Glu Ala Ala Met Leu Lys Asp Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Arg Arg Glu Lys Asp Arg Val Ser His
225                 230                 235                 240

Tyr Leu His Ser Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
            260                 265                 270

Gly Cys His Ala Leu Leu Arg Asp Asp Lys Val Glu Asp Leu Ser Arg
        275                 280                 285

Met Phe Arg Leu Phe Ser Lys Ile Pro Lys Gly Leu Asp Pro Val Ser
    290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Asn Asp Cys Phe Gln Asn His Thr Leu
        355                 360                 365

Phe His Lys Ala Leu Lys Glu Ala Phe Glu Val Phe Cys Asn Lys Gly
    370                 375                 380

Val Ala Gly Ser Ser Ser Ala Glu Leu Leu Ala Thr Phe Cys Asp Asn
385                 390                 395                 400

Ile Leu Lys Lys Gly Gly Ser Glu Lys Leu Ser Asp Glu Ala Ile Glu
                405                 410                 415

Glu Thr Leu Glu Lys Val Val Lys Leu Leu Ala Tyr Ile Cys Asp Lys
            420                 425                 430

Asp Leu Phe Ala Glu Phe Tyr Arg Lys Lys Leu Ala Arg Arg Leu Leu
        435                 440                 445

Phe Asp Lys Ser Ala Asn Asp Asp His Glu Arg Ser Ile Leu Thr Lys
    450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Thr Ser Phe Glu Glu
                485                 490                 495

Tyr Leu Ser Asn Asn Pro Gln Ala Ser Pro Gly Ile Asp Leu Thr Val
            500                 505                 510
```

Thr Val Leu Thr Thr Gly Phe Trp Pro Ser Tyr Lys Ser Phe Asp Leu
        515                 520                 525

Asn Leu Pro Ala Glu Met Val Lys Cys Val Glu Val Phe Arg Glu Phe
    530                 535                 540

Tyr Gln Thr Lys Thr Lys His Arg Lys Leu Thr Trp Ile Tyr Ser Leu
545                 550                 555                 560

Gly Thr Cys Asn Ile Ser Gly Lys Phe Glu Pro Lys Thr Met Glu Leu
                565                 570                 575

Ile Val Thr Thr Tyr Gln Ala Ser Ala Leu Leu Leu Phe Asn Ser Ser
            580                 585                 590

Asp Lys Leu Ser Tyr Ser Glu Ile Met Thr Gln Leu Asn Leu Ser Asp
        595                 600                 605

Asp Asp Val Val Arg Leu Leu His Ser Leu Ser Cys Ala Lys Tyr Lys
    610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Lys Val Ile Glu Asp Val Asp
            660                 665                 670

Lys Asp Arg Arg Tyr Ala Ile Asp Ala Ser Ile Val Arg Ile Met Lys
        675                 680                 685

Ser Arg Lys Val Leu Gly His Gln Gln Leu Val Met Glu Cys Val Glu
    690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
            740

<210> SEQ ID NO 21
<211> LENGTH: 744
<212> TYPE: PRT
<213> ORGANISM: citrillus lanatus

<400> SEQUENCE: 21

Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
            20                  25                  30

Pro Glu Pro Gln Phe Ser Ser Glu Asp Tyr Met Met Leu Tyr Thr Thr
        35                  40                  45

Ile Tyr Asn Met Cys Thr Gln Lys Pro Pro His Asp Tyr Ser Gln Gln
    50                  55                  60

Leu Tyr Asp Lys Tyr Arg Glu Ser Phe Glu Glu Tyr Ile Thr Ser Met
65                  70                  75                  80

Val Leu Pro Ser Leu Arg Glu Lys His Asp Glu Phe Met Leu Arg Glu
                85                  90                  95

Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
        115                 120                 125

Pro Pro Leu Asn Glu Val Gly Leu Thr Cys Phe Arg Glu Leu Val Tyr

-continued

```
    130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
            180                 185                 190

Asn Asp Phe Glu Ala Ala Met Leu Lys Asp Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Lys Arg Glu Lys Asp Arg Val Ser His
225                 230                 235                 240

Tyr Leu His Ser Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
            260                 265                 270

Gly Cys His Ala Leu Leu Arg Asp Asp Lys Val Glu Asp Leu Ser Arg
        275                 280                 285

Met Phe Arg Leu Phe Ser Lys Ile Pro Lys Gly Leu Asp Pro Val Ser
    290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Asn Asp Cys Phe Gln Asn His Thr Leu
        355                 360                 365

Phe His Lys Ala Leu Lys Glu Ala Phe Glu Val Phe Cys Asn Lys Gly
    370                 375                 380

Val Ala Gly Ser Ser Ser Ala Glu Leu Leu Ala Thr Phe Cys Asp Asn
385                 390                 395                 400

Ile Leu Lys Lys Gly Gly Ser Glu Lys Leu Ser Asp Glu Ala Ile Glu
                405                 410                 415

Glu Thr Leu Glu Lys Val Val Lys Leu Leu Ala Tyr Ile Cys Asp Lys
            420                 425                 430

Asp Leu Phe Ala Glu Phe Tyr Arg Lys Lys Leu Ala Arg Arg Leu Leu
        435                 440                 445

Phe Asp Lys Ser Ala Asn Asp Asp His Glu Arg Ser Ile Leu Thr Lys
    450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Thr Ser Phe Glu Glu
                485                 490                 495

Tyr Leu Ser Asn Asn Pro Gln Ala Ser Pro Gly Ile Asp Leu Thr Val
            500                 505                 510

Thr Val Leu Thr Thr Gly Phe Trp Pro Ser Tyr Lys Ser Phe Asp Leu
        515                 520                 525

Asn Leu Pro Ala Glu Met Val Lys Cys Val Glu Val Phe Arg Glu Phe
    530                 535                 540

Tyr Gln Thr Lys Thr Lys His Arg Lys Leu Thr Trp Ile Tyr Ser Leu
545                 550                 555                 560
```

```
Gly Thr Cys Asn Ile Ser Gly Lys Phe Glu Pro Lys Thr Met Glu Leu
                565                 570                 575

Ile Val Thr Thr Tyr Gln Ala Ser Ala Leu Leu Leu Phe Asn Ser Ser
            580                 585                 590

Asp Arg Leu Ser Tyr Ser Glu Ile Met Thr Gln Leu Asn Leu Ser Asp
        595                 600                 605

Asp Asp Val Val Arg Leu Leu His Ser Leu Ser Cys Ala Lys Tyr Lys
    610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Lys Val Ile Glu Asp Val Asp
            660                 665                 670

Lys Asp Arg Arg Tyr Ala Ile Asp Ala Ser Ile Val Arg Ile Met Lys
        675                 680                 685

Ser Arg Lys Val Leu Gly His Gln Gln Leu Val Met Glu Cys Val Glu
    690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
            740


<210> SEQ ID NO 22
<211> LENGTH: 742
<212> TYPE: PRT
<213> ORGANISM: Solanum melongena

<400> SEQUENCE: 22

Met Asn Gln Arg Ser Thr Ile Asp Leu Glu His Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Gly
        115                 120                 125

Leu Asn Glu Val Gly Leu Thr Cys Phe Arg Asp Leu Val Tyr Gln Glu
    130                 135                 140

Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Ser Met Asp Tyr Tyr Glu Asn Asp
```

```
            180                 185                 190

Phe Glu Ala Ala Met Leu Lys Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Ser Ser Ser Glu Thr Lys Leu Leu Glu Lys Val Gln His Glu Leu
                245                 250                 255

Leu Ser Val Tyr Ala Asn Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Pro Arg Gly Leu Glu Pro Val Ala Asn Ile
    290                 295                 300

Phe Lys Gln His Val Thr Ala Glu Gly Thr Ala Leu Val Lys Gln Ala
305                 310                 315                 320

Glu Asp Ala Ala Ser Asn Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asn Cys Phe Gln Asn His Thr Leu Phe His
        355                 360                 365

Lys Ala Leu Lys Glu Ala Phe Glu Leu Phe Cys Asn Lys Gly Val Ala
    370                 375                 380

Gly Ser Ser Asn Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Arg Glu Asn Gln Ala Ser Phe Glu Glu Tyr Leu
                485                 490                 495

Ser Asn Asn Pro Thr Ala Asn Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Arg Cys Val Glu Val Phe Lys Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Ala Lys Thr Ile Glu Leu Val Val
                565                 570                 575

Thr Thr Tyr Gln Ala Ser Ala Leu Leu Leu Phe Asn Ala Ser Asp Arg
            580                 585                 590

Leu Ser Tyr Gln Glu Ile Met Thr Gln Leu Asn Leu Ser Asp Asp Asp
        595                 600                 605
```

```
Val Val Arg Leu Leu His Ser Leu Ser Cys Ala Lys Tyr Lys Ile Leu
    610                 615                 620

Asn Lys Glu Pro Ser Thr Lys Thr Ile Ser Pro Thr Asp Val Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
                725                 730                 735

Leu Phe Lys Tyr Leu Ala
            740


<210> SEQ ID NO 23
<211> LENGTH: 742
<212> TYPE: PRT
<213> ORGANISM: Solanum lycopersicum

<400> SEQUENCE: 23

Met Asn Gln Arg Ser Thr Ile Asp Leu Glu His Gly Trp Asp Phe Met
1               5                   10                  15

Gln Arg Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Gly
        115                 120                 125

Leu Asn Glu Val Gly Leu Thr Cys Phe Arg Asp Gln Val Tyr Gln Glu
    130                 135                 140

Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Leu Met Asp Tyr Tyr Glu Asn Asp
            180                 185                 190

Phe Glu Ala Ala Met Leu Lys Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
```

```
225                 230                 235                 240

His Ser Ser Ser Glu Thr Lys Leu Leu Glu Lys Val Gln His Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Glu Asp Leu Ser Arg Met Tyr
        275                 280                 285

Arg Leu Phe Ser Lys Ile Ser Arg Gly Leu Asp Pro Val Ala Asn Ile
    290                 295                 300

Phe Lys Gln His Val Thr Ala Glu Gly Thr Ala Leu Val Lys Gln Ala
305                 310                 315                 320

Glu Asp Ala Ala Ser Asn Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asn Cys Phe Gln Asn His Thr Leu Phe His
        355                 360                 365

Lys Ala Leu Lys Glu Ala Phe Glu Leu Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Arg Glu Asn Gln Ala Ser Phe Glu Glu Tyr Leu
                485                 490                 495

Ser Asn Asn Pro Ile Ala Asn Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Arg Cys Val Glu Val Phe Lys Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Ile Glu Leu Val Val
                565                 570                 575

Thr Thr Tyr Gln Ala Ser Ala Leu Leu Leu Phe Asn Ala Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620

Asn Lys Glu Pro Ser Thr Lys Thr Ile Ser Pro Thr Asp Val Phe Glu
625                 630                 635                 640

Phe Asn Ser Lys Phe Thr Asp Lys Met Arg Arg Ile Lys Ile Pro Leu
                645                 650                 655
```

```
Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
                725                 730                 735

Leu Phe Lys Tyr Leu Ala
            740


<210> SEQ ID NO 24
<211> LENGTH: 742
<212> TYPE: PRT
<213> ORGANISM: Capsicum annuum

<400> SEQUENCE: 24

Met Asn Gln Arg Ser Thr Ile Asn Leu Glu His Gly Trp Asp Phe Met
1               5                   10                  15

Gln Arg Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Gly
        115                 120                 125

Leu Asn Glu Val Gly Leu Thr Cys Phe Arg Asp Leu Val Tyr Gln Glu
    130                 135                 140

Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Ser Met Asp Tyr Tyr Glu Asn Asp
            180                 185                 190

Phe Glu Ala Ala Met Leu Lys Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Leu Ser Ser Glu Thr Lys Leu Leu Glu Lys Val Gln His Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Glu Asp Leu Ser Arg Met Tyr
```

-continued

```
        275                 280                 285

Arg Leu Phe Ser Lys Ile Pro Arg Gly Leu Asp Pro Val Ala Asn Ile
    290                 295                 300

Phe Lys Gln His Val Thr Ala Glu Gly Thr Ala Leu Val Lys Gln Ala
305                 310                 315                 320

Glu Asp Ala Ala Ser Asn Lys Lys Ala Glu Lys Arg Asp Val Val Gly
                325                 330                 335

Leu Gln Glu Gln Ile Phe Val Arg Lys Val Ile Glu Leu His Asp Lys
            340                 345                 350

Tyr Met Ala Tyr Val Asn Asn Cys Phe Gln Asn His Thr Leu Phe His
        355                 360                 365

Lys Ala Leu Lys Glu Ala Phe Glu Leu Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Arg Glu Asn Gln Ala Ser Phe Glu Glu Tyr Leu
                485                 490                 495

Ser Asn Asn Pro Ala Ala Asn Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Arg Cys Val Glu Val Phe Lys Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Ile Glu Leu Val Val
                565                 570                 575

Thr Thr Tyr Gln Ala Ser Ala Leu Leu Leu Phe Asn Ala Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620

Asn Lys Glu Pro Ser Thr Lys Thr Ile Ser Pro Thr Asp Val Phe Glu
625                 630                 635                 640

Phe Asn Phe Lys Phe Thr Asp Lys Met Arg Arg Ile Lys Ile Pro Leu
                645                 650                 655

Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700
```

```
Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
                725                 730                 735

Leu Phe Lys Tyr Leu Ala
            740


<210> SEQ ID NO 25
<211> LENGTH: 738
<212> TYPE: PRT
<213> ORGANISM: Brassica oleracea

<400> SEQUENCE: 25

Met Glu Arg Lys Thr Ile Asp Leu Asp Gln Gly Trp Asp Tyr Met Gln
1               5                   10                  15

Thr Gly Ile Thr Lys Leu Lys Arg Ile Leu Glu Gly Leu Pro Glu Pro
            20                  25                  30

Gln Phe Asp Ser Glu Gln Tyr Met Met Leu Tyr Thr Thr Ile Tyr Asn
        35                  40                  45

Met Cys Thr Gln Lys Pro Pro His Asp Tyr Ser Gln Gln Leu Tyr Asp
    50                  55                  60

Lys Tyr Arg Glu Ala Phe Glu Glu Tyr Ile His Ser Thr Val Leu Pro
65                  70                  75                  80

Ala Leu Arg Glu Lys His Asp Glu Tyr Met Leu Arg Glu Leu Val Lys
                85                  90                  95

Arg Trp Ser Asn His Lys Val Met Val Arg Trp Leu Ser Arg Phe Phe
            100                 105                 110

Tyr Tyr Leu Asp Arg Tyr Phe Ile Ala Arg Arg Ser Leu Pro Pro Leu
        115                 120                 125

Asn Glu Val Gly Leu Thr Cys Phe Arg Asp Leu Val Tyr Asn Glu Leu
    130                 135                 140

His Ser Lys Val Lys Asp Ala Val Ile Ala Leu Val Asp Lys Glu Arg
145                 150                 155                 160

Glu Gly Glu Gln Ile Asp Arg Ala Leu Leu Lys Asn Val Leu Asp Ile
                165                 170                 175

Tyr Val Glu Ile Gly Met Gly Gln Met Glu Arg Tyr Glu Glu Asp Phe
            180                 185                 190

Glu Ser Phe Met Leu Leu Asp Ser Ala Ser Tyr Tyr Ser Arg Lys Ala
        195                 200                 205

Ser Ser Trp Ile Gln Glu Asp Ser Cys Pro Asp Tyr Met Leu Lys Ser
    210                 215                 220

Glu Glu Cys Leu Lys Lys Glu Arg Glu Arg Val Ala His Tyr Leu His
225                 230                 235                 240

Ser Ser Ser Glu Pro Lys Leu Val Glu Lys Val Gln His Glu Leu Leu
                245                 250                 255

Val Val Tyr Ala Asn Gln Leu Leu Glu Lys Glu His Ser Gly Cys Arg
            260                 265                 270

Ala Leu Leu Arg Asp Asp Lys Val Asp Asp Leu Ser Arg Met Tyr Arg
        275                 280                 285

Leu Tyr His Lys Ile Val Lys Gly Leu Glu Pro Val Ala Asn Ile Phe
    290                 295                 300

Lys Gln His Val Thr Ala Glu Gly Asn Ala Leu Val Gln Gln Ala Glu
305                 310                 315                 320

Asp Thr Ala Thr Asn His Ala Ala Asn Thr Ala Ser Val Gln Glu Gln
```

-continued

```
                325                 330                 335

Val Leu Ile Arg Lys Val Ile Glu Leu His Asp Lys Tyr Met Val Tyr
            340                 345                 350

Val Val Glu Cys Phe Gln Asn His Thr Leu Phe His Lys Ala Leu Lys
        355                 360                 365

Glu Ala Phe Glu Ile Phe Cys Asn Lys Thr Val Ala Gly Ser Ser Ser
    370                 375                 380

Ala Glu Leu Leu Ala Thr Phe Cys Asp Asn Ile Leu Lys Lys Gly Gly
385                 390                 395                 400

Ser Glu Lys Leu Ser Asp Glu Ala Ile Glu Asp Thr Leu Glu Lys Val
                405                 410                 415

Val Lys Leu Leu Ala Tyr Ile Ser Asp Lys Asp Leu Phe Ala Glu Phe
            420                 425                 430

Tyr Arg Lys Lys Leu Ala Arg Arg Leu Leu Phe Asp Arg Ser Ala Asn
        435                 440                 445

Asp Asp His Glu Arg Ser Ile Leu Thr Lys Leu Lys Gln Gln Cys Gly
    450                 455                 460

Gly Gln Phe Thr Ser Lys Met Glu Gly Met Val Thr Asp Leu Thr Leu
465                 470                 475                 480

Ala Arg Glu Asn Gln Asn Ser Phe Glu Glu Tyr Leu Gly Asn Asn Pro
                485                 490                 495

Ala Ala Asn Pro Gly Ile Asp Leu Thr Val Thr Val Leu Thr Thr Gly
            500                 505                 510

Phe Trp Pro Ser Tyr Lys Ser Phe Asp Ile Asn Leu Pro Ala Glu Met
        515                 520                 525

Val Lys Cys Val Glu Val Phe Lys Gly Phe Tyr Glu Thr Lys Thr Lys
    530                 535                 540

His Arg Lys Leu Thr Trp Ile Tyr Ser Leu Gly Thr Cys His Leu Asn
545                 550                 555                 560

Gly Lys Phe Asp Val Lys Pro Ile Glu Leu Val Val Ser Thr Tyr Gln
                565                 570                 575

Ala Ala Val Leu Leu Leu Phe Asn Thr Thr Asp Lys Leu Ser Tyr Thr
            580                 585                 590

Asp Ile Leu Thr Gln Leu Asn Leu Ser His Glu Asp Leu Val Arg Leu
        595                 600                 605

Leu His Ser Leu Ser Cys Ala Arg Tyr Lys Ile Leu Leu Lys Glu Pro
    610                 615                 620

Ser Thr Lys Thr Val Ser Gln Ser Asp Ser Phe Glu Phe Asn Ser Lys
625                 630                 635                 640

Phe Thr Asp Arg Met Arg Arg Ile Lys Ile Pro Leu Pro Pro Val Asp
                645                 650                 655

Glu Arg Lys Lys Val Val Glu Asp Val Asp Lys Asp Arg Arg Tyr Ala
            660                 665                 670

Ile Asp Ala Ala Ile Val Arg Ile Met Lys Ser Arg Lys Val Leu Gly
        675                 680                 685

His Gln Gln Leu Val Ser Glu Cys Val Glu Gln Leu Ser Arg Met Phe
    690                 695                 700

Lys Pro Asp Ile Lys Ala Ile Lys Lys Arg Met Glu Asp Leu Ile Thr
705                 710                 715                 720

Arg Asp Tyr Leu Glu Arg Asp Lys Glu Asn Ala Asn Met Phe Arg Tyr
                725                 730                 735

Leu Ala
```

<210> SEQ ID NO 26
<211> LENGTH: 743
<212> TYPE: PRT
<213> ORGANISM: Daucus carota

<400> SEQUENCE: 26

```
Met Met Ile Glu Arg Lys Thr Ile Asp Leu Glu Gln Gly Trp Asp Phe
1               5                   10                  15

Met Gln Lys Gly Ile Thr Lys Leu Lys Asn Ile Leu Glu Gly Phe Pro
            20                  25                  30

Glu Pro Gln Phe Ser Ser Glu Asp Tyr Met Met Leu Tyr Thr Thr Ile
        35                  40                  45

Tyr Asn Met Cys Thr Gln Lys Pro Pro His Asp Tyr Ser Gln Gln Leu
    50                  55                  60

Tyr Glu Lys Tyr Arg Glu Ala Ile Glu Glu Tyr Ile Thr Ser Thr Val
65                  70                  75                  80

Leu Pro Ser Leu Arg Glu Lys His Asp Glu Phe Met Leu Arg Glu Leu
                85                  90                  95

Val Lys Arg Trp Ser Asn His Lys Val Met Val Arg Trp Leu Ser Arg
            100                 105                 110

Phe Phe His Tyr Leu Asp Arg Tyr Phe Ile Ala Arg Arg Ser Leu Pro
        115                 120                 125

Pro Leu His Glu Val Gly Leu Thr Cys Phe Arg Asp Leu Val Tyr Gln
    130                 135                 140

Glu Ile Asn Gly Lys Val Arg Asp Ala Val Ile Ser Leu Ile Asn Gln
145                 150                 155                 160

Glu Arg Glu Gly Glu Gln Ile Asp Arg Ala Leu Leu Lys Asn Val Leu
                165                 170                 175

Asp Ile Phe Val Glu Val Gly Met Ser Gln Met Asp Tyr Tyr Glu Asn
            180                 185                 190

Asp Phe Glu Ala Asp Met Leu Lys Asp Thr Ala Ala Tyr Tyr Ser Arg
        195                 200                 205

Lys Ala Ser Asn Trp Ile Leu Glu Asp Ser Cys Pro Asp Tyr Met Leu
    210                 215                 220

Lys Ala Glu Glu Cys Leu Arg Arg Glu Lys Asp Arg Val Ser Asn Tyr
225                 230                 235                 240

Leu His Ser Ser Ser Glu Pro Lys Leu Leu Glu Lys Val Gln His Glu
                245                 250                 255

Leu Leu Ser His Tyr Ala Thr Gln Leu Leu Glu Lys Glu His Ser Gly
            260                 265                 270

Cys His Ala Leu Leu Arg Asp Asp Lys Val Ala Asp Leu Ser Arg Met
        275                 280                 285

Tyr Arg Leu Phe Ser Lys Ile Pro Arg Gly Leu Asp Pro Val Ser Asn
    290                 295                 300

Ile Phe Lys Gln His Val Thr Ala Glu Gly Thr Ala Leu Val Lys Gln
305                 310                 315                 320

Ala Glu Asp Ala Ala Ser Asn Lys Lys Ala Glu Lys Arg Asp Val Val
                325                 330                 335

Gly Leu Gln Glu Gln Val Phe Val Arg Lys Ile Ile Glu Leu His Asp
            340                 345                 350

Lys Tyr Leu Thr Tyr Val Asn Asp Cys Phe Thr Asn His Thr Leu Phe
        355                 360                 365

His Lys Ala Leu Lys Glu Ala Phe Glu Ile Phe Cys Asn Lys Gly Val
    370                 375                 380
```

```
Ser Gly Ser Ser Ser Ala Glu Leu Leu Ala Thr Phe Cys Asp Asn Ile
385                 390                 395                 400

Leu Lys Lys Gly Gly Ser Glu Lys Leu Ser Asp Glu Ala Ile Glu Glu
                405                 410                 415

Thr Leu Glu Lys Val Val Arg Leu Leu Ala Tyr Ile Ser Asp Lys Asp
            420                 425                 430

Leu Phe Ala Glu Phe Tyr Arg Lys Lys Leu Ala Arg Arg Leu Leu Phe
        435                 440                 445

Asp Lys Ser Ala Asn Asp Glu His Glu Arg Ser Ile Leu Thr Lys Leu
    450                 455                 460

Lys Gln Gln Cys Gly Gly Gln Phe Thr Ser Lys Met Glu Gly Met Val
465                 470                 475                 480

Thr Asp Leu Thr Leu Ala Lys Glu Asn Gln Ser Asn Phe Glu Glu Tyr
                485                 490                 495

Leu Asn Asn Asn Ser Asn Val Asn Pro Gly Ile Asp Leu Thr Val Thr
            500                 505                 510

Val Leu Thr Thr Gly Phe Trp Pro Ser Tyr Lys Ser Phe Asp Leu Asn
        515                 520                 525

Leu Pro Ala Glu Met Val Lys Cys Val Glu Val Phe Arg Glu Phe Tyr
    530                 535                 540

Gln Thr Lys Thr Lys His Arg Lys Leu Thr Trp Ile Tyr Ser Leu Gly
545                 550                 555                 560

Thr Cys Asn Ile Ile Gly Lys Phe Asp Pro Lys Thr Met Glu Leu Ile
                565                 570                 575

Val Thr Thr Tyr Gln Ala Ser Ala Leu Leu Leu Phe Asn Ser Ser Asp
            580                 585                 590

Arg Leu Ser Tyr Asn Glu Ile Met Thr Gln Leu Asn Leu Ser Asp Asp
        595                 600                 605

Asp Val Val Arg Leu Leu His Ser Leu Ser Cys Ala Lys Tyr Lys Ile
    610                 615                 620

Leu Ser Lys Glu Pro Asn Thr Lys Thr Ile Ser Pro Thr Asp Cys Phe
625                 630                 635                 640

Gln Phe Asn Ser Lys Phe Thr Asp Lys Met Arg Arg Ile Lys Ile Pro
                645                 650                 655

Leu Pro Pro Val Asp Glu Lys Lys Lys Val Ile Glu Asp Val Asp Lys
            660                 665                 670

Asp Arg Arg Tyr Ala Ile Asp Ala Ser Ile Val Arg Ile Met Lys Ser
        675                 680                 685

Arg Lys Val Leu Gly Tyr Gln Gln Leu Val Met Glu Cys Val Glu Gln
    690                 695                 700

Leu Gly Arg Met Phe Lys Pro Asp Val Lys Ala Ile Lys Lys Arg Ile
705                 710                 715                 720

Glu Asp Leu Ile Thr Arg Asp Tyr Leu Glu Arg Asp Lys Asp Asn Ala
                725                 730                 735

Asn Leu Phe Arg Tyr Leu Ala
            740


<210> SEQ ID NO 27
<211> LENGTH: 742
<212> TYPE: PRT
<213> ORGANISM: Apium graveolens

<400> SEQUENCE: 27

Met Asn Glu Arg Lys Thr Ile Asp Leu Asp Asn Gly Trp Glu Phe Met
```

-continued

```
1               5                   10                  15

Gln Lys Gly Ile Thr Lys Leu Lys Lys Ile Leu Glu Gly Gln Pro Glu
            20                  25                  30

Pro Gln Phe Ser Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Asn Arg Trp Thr Asn His Lys Val Met Val Arg Trp Leu Ser Arg Phe
            100                 105                 110

Phe His Tyr Leu Asp Arg Tyr Phe Ile Ala Arg Arg Ser Leu Pro Ala
        115                 120                 125

Leu His Glu Val Gly Leu Thr Cys Phe Arg Asp Leu Val Tyr Gln Glu
    130                 135                 140

Leu Lys Val Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Ser Gln Met Asp Gln Tyr Glu Asn Asp
            180                 185                 190

Phe Glu Glu Ala Met Leu Thr Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Arg Arg Glu Lys Asp Arg Val Ser His Tyr Leu
225                 230                 235                 240

His Phe Ser Ser Glu Pro Lys Leu Leu Glu Lys Val Gln His Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Pro Lys Gly Leu Asp Pro Val Ser Tyr Ile
    290                 295                 300

Phe Lys Gln His Val Thr Asn Glu Gly Met Ala Leu Val Lys Gln Ala
305                 310                 315                 320

Glu Asp Ala Ala Ser Asn Lys Lys Ala Glu Lys Arg Asp Val Val Ser
                325                 330                 335

Leu Gln Glu Gln Val Phe Val Arg Lys Ile Ile Glu Leu His Asp Lys
            340                 345                 350

Tyr Leu Ala Tyr Val Asn Asp Cys Phe Thr Asn His Thr Leu Phe His
        355                 360                 365

Lys Ala Leu Lys Glu Ala Phe Glu Ile Phe Cys Asn Lys Gly Val Ala
    370                 375                 380

Gly Ser Ser Asn Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415

Leu Glu Lys Val Val Lys Leu Leu Ala Tyr Ile Ser Asp Lys Asp Leu
            420                 425                 430
```

```
Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Lys Glu Asn Gln Ser Ser Phe Glu Glu Tyr Leu
                485                 490                 495

Gly Asn Asn Ala Asn Val Asn Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Lys Cys Val Glu Val Phe Arg Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Ile Glu Leu Ile Val
                565                 570                 575

Thr Thr Tyr Gln Ala Ser Ala Leu Leu Leu Phe Asn Thr Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620

Thr Lys Glu Pro Asn Asn Lys Thr Ile Ser Pro Thr Asp Tyr Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Ala Asn
                725                 730                 735

Leu Phe Arg Tyr Leu Ala
            740


<210> SEQ ID NO 28
<211> LENGTH: 742
<212> TYPE: PRT
<213> ORGANISM: Cichorium intybus

<400> SEQUENCE: 28

Met Asn Glu Arg Lys Thr Ile Asp Leu Glu Gln Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
```

```
    50                  55                  60

Asp Lys Tyr Arg Glu Ser Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Arg Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Pro
        115                 120                 125

Leu Asn Glu Val Gly Leu Ala Cys Phe Arg Asp Leu Val Tyr Gln Glu
    130                 135                 140

Val Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Gln Met Glu Tyr Tyr Glu Asn Asp
            180                 185                 190

Phe Glu Ala Ser Met Leu Asn Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Ser Ser Ser Glu Pro Lys Leu Leu Glu Lys Val Gln Thr Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Gln Lys Gly Leu Asp Pro Val Ser Ser Met
    290                 295                 300

Phe Lys Gln His Val Thr Ala Glu Gly Thr Thr Leu Val Lys Gln Ala
305                 310                 315                 320

Glu Asp Ala Ala Ser Thr Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asp Cys Phe Met Asn His Thr Leu Phe His
        355                 360                 365

Lys Ala Leu Lys Glu Ala Phe Glu Ile Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Asp Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480
```

-continued

```
Asp Leu Thr Leu Ala Lys Glu Asn Gln Ser His Phe Glu Glu Tyr Leu
                485                 490                 495

Asn Asn Asn Pro Asn Val Ser Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Lys Cys Val Glu Val Phe Arg Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Met Glu Leu Ile Val
                565                 570                 575

Thr Thr Tyr Gln Ala Ser Ala Leu Leu Leu Phe Asn Ser Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620

Leu Lys Glu Pro Asn Thr Lys Thr Ile Ser Pro Thr Asp Phe Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Glu Asn Pro Asn
                725                 730                 735

Leu Phe Arg Tyr Leu Ala
            740


<210> SEQ ID NO 29
<211> LENGTH: 742
<212> TYPE: PRT
<213> ORGANISM: Cichorium endivia

<400> SEQUENCE: 29

Met Asn Glu Arg Lys Thr Ile Asp Leu Glu Gln Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
    50                  55                  60

Asp Lys Tyr Arg Glu Ser Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Arg Arg Trp Ser Asn His Lys Val Met Val Arg Trp Leu Ser Arg Phe
```

```
            100                 105                 110

Phe His Tyr Leu Asp Arg Tyr Phe Ile Ala Arg Arg Ser Leu Pro Pro
        115                 120                 125

Leu Asn Glu Val Gly Leu Ala Cys Phe Arg Asp Leu Val Tyr Gln Glu
    130                 135                 140

Val Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Gln Met Glu Tyr Tyr Glu Asn Asp
            180                 185                 190

Phe Glu Ala Ser Met Leu Asn Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Ser Ser Ser Glu Pro Lys Leu Leu Glu Lys Val Gln Thr Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Gln Lys Gly Leu Asp Pro Val Ser Ser Met
    290                 295                 300

Phe Lys Gln His Val Thr Ala Glu Gly Thr Thr Leu Val Lys Gln Ala
305                 310                 315                 320

Glu Asp Ala Ala Ser Thr Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asp Cys Phe Met Asn His Thr Leu Phe His
        355                 360                 365

Lys Ala Leu Lys Glu Ala Phe Glu Ile Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Asp Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Lys Glu Asn Gln Ser His Phe Glu Glu Tyr Leu
                485                 490                 495

Asn Asn Asn Pro Asn Val Ser Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525
```

```
Pro Ala Glu Met Val Lys Cys Val Glu Val Phe Arg Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Met Glu Leu Ile Val
                565                 570                 575

Thr Thr Tyr Gln Ala Ser Ala Leu Leu Leu Phe Asn Ser Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620

Leu Lys Glu Pro Asn Thr Lys Thr Ile Ser Pro Thr Asp Phe Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Glu Asn Pro Asn
                725                 730                 735

Leu Phe Arg Tyr Leu Ala
            740
```

<210> SEQ ID NO 30
<211> LENGTH: 744
<212> TYPE: PRT
<213> ORGANISM: Allium ampeloprasum

<400> SEQUENCE: 30

```
Met Ser Leu His Glu Arg Lys Thr Ile Asp Leu Glu Gln Gly Trp Ala
1               5                   10                  15

Phe Met Gln Lys Gly Ile Thr Lys Leu Lys Asn Ile Leu Asp Glu Leu
            20                  25                  30

Asn Glu Pro Gln Phe Ser Ser Glu Asp Tyr Met Met Leu Tyr Thr Thr
        35                  40                  45

Ile Tyr Asn Met Cys Thr Gln Lys Pro Pro His Asp Tyr Ser Gln Glu
    50                  55                  60

Leu Tyr Asp Lys Tyr Arg Glu Ser Phe Glu Glu Tyr Ile Thr Thr Thr
65                  70                  75                  80

Val Leu Pro Ser Leu Arg Glu Lys His Asp Glu Tyr Met Leu Arg Glu
                85                  90                  95

Leu Val Arg Arg Trp Ser Asn His Lys Ile Met Val Arg Trp Leu Ser
            100                 105                 110

Arg Phe Phe His Tyr Leu Asp Arg Tyr Phe Ile Ala Arg Arg Ser Leu
        115                 120                 125

Pro Ala Leu Asn Glu Val Gly Leu Thr Cys Phe Arg Asp Leu Val Tyr
    130                 135                 140

Asn Glu Val His Gly Lys Val Lys Asp Ala Val Ile Ser Leu Ile Asp
```

-continued

```
145                 150                 155                 160

Gln Glu Arg Glu Gly Glu Gln Ile Asp Arg Ala Leu Leu Lys Asn Val
                165                 170                 175

Leu Gly Ile Phe Val Glu Ile Gly Leu Gly Ser Met Glu Cys Tyr Glu
            180                 185                 190

Asn Asp Phe Glu Thr Ser Met Leu Asn Ala Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Lys His Glu Lys Asp Arg Val Ala His
225                 230                 235                 240

Tyr Leu His Ser Ser Ser Glu Gln Lys Leu Leu Glu Lys Val Gln His
                245                 250                 255

Glu Leu Leu Phe Val Tyr Ala Ser Gln Leu Leu Glu Lys Glu His Ser
            260                 265                 270

Gly Cys His Ala Leu Leu Arg Asp Asp Lys Val Gly Asp Leu Ser Arg
        275                 280                 285

Met Tyr Arg Leu Phe Cys Arg Ile Thr Arg Gly Leu Asp Pro Val Ser
    290                 295                 300

Gln Ile Phe Lys Gln His Val Thr Ala Glu Gly Thr Ala Leu Val Lys
305                 310                 315                 320

His Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Thr Asp Cys Phe Gln Asn His Ser Leu
        355                 360                 365

Phe His Lys Ala Leu Lys Glu Ala Phe Glu Val Phe Cys Asn Lys Gly
    370                 375                 380

Val Ala Gly Ser Ser Ser Ala Glu Leu Leu Ala Ala Phe Cys Asp Asn
385                 390                 395                 400

Ile Leu Lys Lys Gly Gly Ser Glu Lys Leu Ser Asp Glu Ala Ile Glu
                405                 410                 415

Asp Thr Leu Glu Lys Val Val Lys Leu Leu Ala Tyr Ile Ser Asp Lys
            420                 425                 430

Asp Leu Phe Ala Glu Phe Tyr Arg Lys Lys Leu Ala Arg Arg Leu Leu
        435                 440                 445

Phe Asp Lys Ser Ala Asn Asp Asp His Glu Arg Ser Ile Leu Thr Lys
    450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Ser Ser Phe Asp Asp
                485                 490                 495

Tyr Leu Ser Ser Asn Pro Lys Ala Asn Ser Gly Ile Asp Leu Thr Val
            500                 505                 510

Thr Val Leu Thr Thr Gly Phe Trp Pro Ser Tyr Lys Ser Phe Asp Leu
        515                 520                 525

Asn Leu Pro Asp Glu Met Val Lys Cys Val Glu Ile Phe Lys Glu Phe
    530                 535                 540

Tyr Glu Thr Lys Thr Lys His Arg Lys Leu Thr Trp Ile Tyr Ser Leu
545                 550                 555                 560

Gly Thr Cys Asn Ile Asn Gly Lys Phe Glu Thr Lys Thr Ile Glu Leu
                565                 570                 575
```

Val Val Thr Thr Tyr Gln Ala Ala Val Leu Leu Leu Phe Asn Ser Ala
580 585 590

Asp Lys Leu Ser Tyr Ser Glu Ile Val Gln Gln Leu Asn Leu Ser Asp
595 600 605

Asp Asp Val Ile Arg Leu Leu His Ser Leu Ser Cys Ala Lys Tyr Lys
610 615 620

Ile Leu Asn Lys Glu Pro Ala Thr Lys Thr Ile Thr Pro Asn Asp His
625 630 635 640

Phe Glu Phe Asn Ser Lys Phe Thr Asp Arg Met Arg Arg Ile Lys Ile
645 650 655

Pro Leu Pro Pro Val Asp Glu Lys Lys Lys Val Ile Glu Asp Val Asp
660 665 670

Lys Asp Arg Arg Tyr Ala Ile Asp Ala Ser Ile Val Arg Ile Met Lys
675 680 685

Ser Arg Lys Val Leu Gly His Gln Gln Leu Val Leu Glu Cys Val Glu
690 695 700

Gln Leu Gly Arg Met Phe Lys Pro Asp Phe Lys Ala Ile Lys Lys Arg
705 710 715 720

Ile Glu Asp Leu Ile Ala Arg Asp Tyr Leu Glu Arg Asp Lys Asp Asn
725 730 735

Pro Asn Leu Phe Lys Tyr Leu Ala
740

<210> SEQ ID NO 31
<211> LENGTH: 742
<212> TYPE: PRT
<213> ORGANISM: Lactuca sativa

<400> SEQUENCE: 31

Met Asn Glu Arg Lys Thr Ile Asp Leu Glu Gln Gly Trp Asp Phe Met
1 5 10 15

Gln Lys Gly Ile Thr Lys Leu Lys Asn Ile Leu Glu Gly Leu Pro Glu
20 25 30

Pro Gln Phe Ser Ser Glu Asp Tyr Met Met Leu Tyr Thr Thr Ile Tyr
35 40 45

Asn Met Cys Thr Gln Lys Pro Pro His Asp Tyr Ser Gln Gln Leu Tyr
50 55 60

Asp Lys Tyr Arg Glu Ser Phe Glu Glu Tyr Ile Thr Ser Thr Val Leu
65 70 75 80

Pro Ser Leu Arg Glu Lys His Asp Glu Phe Met Leu Arg Glu Leu Val
85 90 95

Arg Arg Trp Ser Asn His Lys Val Met Val Arg Trp Leu Ser Arg Phe
100 105 110

Phe His Tyr Leu Asp Arg Tyr Phe Ile Ala Arg Arg Ser Leu Pro Pro
115 120 125

Leu Asn Glu Val Gly Leu Ala Cys Phe Arg Asp Leu Val Tyr Gln Glu
130 135 140

Val Asn Gly Lys Val Arg Asp Ala Val Ile Ser Leu Ile Asp Gln Glu
145 150 155 160

Arg Glu Gly Glu Gln Ile Asp Arg Ala Leu Leu Lys Asn Val Leu Asp
165 170 175

Ile Phe Val Glu Ile Gly Met Gly Gln Met Glu Tyr Tyr Glu Asn Asp
180 185 190

Phe Glu Ala Ser Met Leu Asn Asp Thr Ala Ala Tyr Tyr Ser Arg Lys

-continued

```
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Ser Ser Ser Glu Pro Lys Leu Leu Glu Lys Val Gln Asn Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Pro Lys Gly Leu Asp Pro Val Ser Ser Met
    290                 295                 300

Phe Lys Gln His Val Thr Ala Glu Gly Thr Thr Leu Val Lys Gln Ala
305                 310                 315                 320

Glu Asp Ala Ala Ser Thr Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asp Cys Phe Met Asn His Thr Leu Phe His
        355                 360                 365

Lys Ala Leu Lys Glu Ala Phe Glu Ile Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Asp Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Lys Glu Asn Gln Ser His Phe Glu Glu Tyr Leu
                485                 490                 495

Asn Asn Asn Pro Asn Val Ser Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Lys Cys Val Glu Val Phe Arg Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Met Glu Leu Ile Val
                565                 570                 575

Thr Thr Tyr Gln Ala Ser Ala Leu Leu Leu Phe Asn Leu Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620
```

```
Leu Lys Glu Pro Asn Thr Lys Thr Ile Ser Pro Thr Asp Tyr Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Glu Asn Pro Asn
                725                 730                 735

Leu Phe Arg Tyr Leu Ala
            740


<210> SEQ ID NO 32
<211> LENGTH: 738
<212> TYPE: PRT
<213> ORGANISM: Raphanus sativus

<400> SEQUENCE: 32

Met Glu Arg Lys Thr Ile Asp Leu Glu Gln Gly Trp Asp Tyr Met Gln
1               5                   10                  15

Thr Gly Ile Thr Lys Leu Lys Arg Ile Leu Glu Gly Leu Pro Glu Pro
            20                  25                  30

Gln Phe Asp Ser Glu Gln Tyr Met Met Leu Tyr Thr Thr Ile Tyr Asn
        35                  40                  45

Met Cys Thr Gln Lys Pro Pro His Asp Tyr Ser Gln Gln Leu Tyr Asp
    50                  55                  60

Lys Tyr Arg Glu Ala Phe Glu Glu Tyr Ile Asp Ser Thr Val Leu Pro
65                  70                  75                  80

Ala Leu Lys Glu Lys His Asp Glu Tyr Met Leu Arg Glu Leu Val Lys
                85                  90                  95

Arg Trp Ser Asn His Lys Val Met Val Arg Trp Leu Ser Arg Phe Phe
            100                 105                 110

Tyr Tyr Leu Asp Arg Tyr Phe Ile Ala Arg Arg Ser Leu Pro Pro Leu
        115                 120                 125

Asn Glu Val Gly Leu Thr Cys Phe Arg Asp Arg Val Tyr Lys Glu Leu
    130                 135                 140

His Ser Lys Val Lys Asp Ala Val Ile Ala Leu Val Asp Lys Glu Arg
145                 150                 155                 160

Glu Gly Glu Gln Ile Asp Arg Ala Leu Leu Lys Asn Val Leu Asp Ile
                165                 170                 175

Tyr Val Glu Ile Gly Met Gly Gln Met Glu Arg Tyr Glu Val Asp Phe
            180                 185                 190

Glu Ser Phe Met Leu Leu Asp Ser Ala Ser Tyr Tyr Ser Arg Lys Ala
        195                 200                 205

Ser Asn Trp Ile Gln Glu Asp Ser Cys Pro Asp Tyr Met Leu Lys Ser
    210                 215                 220

Glu Glu Cys Leu Lys Lys Glu Arg Glu Arg Val Ala His Tyr Leu His
225                 230                 235                 240

Ser Ser Ser Glu Pro Lys Leu Val Glu Lys Val Gln His Glu Leu Leu
```

-continued

```
                245                 250                 255

Val Val Tyr Ala Asn Gln Leu Leu Glu Lys Glu His Ser Gly Cys Arg
            260                 265                 270

Ala Leu Leu Arg Asp Asp Lys Val Asp Asp Leu Ser Arg Met Tyr Arg
        275                 280                 285

Leu Tyr His Lys Ile Ala Lys Gly Leu Glu Pro Val Ala Asn Ile Phe
    290                 295                 300

Lys Gln His Val Thr Ala Glu Gly Asn Ala Leu Val Gln Gln Ala Glu
305                 310                 315                 320

Asp Thr Ala Thr Asn Gln Ala Ala Asn Thr Ala Ser Val Gln Glu Gln
                325                 330                 335

Val Leu Ile Arg Lys Val Ile Glu Leu His Asp Lys Tyr Met Val Tyr
            340                 345                 350

Val Val Glu Cys Phe Gln Asn His Thr Leu Phe His Lys Ala Leu Lys
        355                 360                 365

Glu Ala Phe Glu Ile Phe Cys Asn Lys Thr Val Ala Gly Ser Ser Ser
    370                 375                 380

Ala Glu Leu Leu Ala Thr Phe Cys Asp Asn Ile Leu Lys Lys Gly Gly
385                 390                 395                 400

Ser Glu Lys Leu Ser Asp Glu Ala Ile Glu Asp Thr Leu Glu Lys Val
                405                 410                 415

Val Lys Leu Leu Ala Tyr Ile Ser Asp Lys Asp Leu Phe Ala Glu Phe
            420                 425                 430

Tyr Arg Lys Lys Leu Ala Arg Arg Leu Leu Phe Asp Arg Ser Ala Asn
        435                 440                 445

Asp Asp His Glu Arg Ser Ile Leu Thr Lys Leu Lys Gln Gln Cys Gly
    450                 455                 460

Gly Gln Phe Thr Ser Lys Met Glu Gly Met Val Thr Asp Leu Thr Leu
465                 470                 475                 480

Ala Arg Glu Asn Gln Thr Ser Phe Glu Glu Tyr Leu Gly Asn Asn Pro
                485                 490                 495

Ala Ala Asn Pro Gly Ile Asp Leu Thr Val Thr Val Leu Thr Thr Gly
            500                 505                 510

Phe Trp Pro Ser Tyr Lys Ser Phe Asp Ile Asn Leu Pro Ser Glu Met
        515                 520                 525

Val Lys Cys Val Glu Val Phe Lys Gly Phe Tyr Glu Thr Lys Thr Lys
    530                 535                 540

His Arg Lys Leu Thr Trp Ile Tyr Ser Leu Gly Thr Cys His Leu Asn
545                 550                 555                 560

Gly Lys Phe Asp His Lys Pro Ile Glu Leu Val Val Ser Thr Tyr Gln
                565                 570                 575

Ala Ala Val Leu Leu Leu Phe Asn Thr Thr Asp Lys Leu Ser Tyr Asn
            580                 585                 590

Asp Ile Leu Thr Gln Leu Asn Leu Ser His Glu Asp Leu Val Arg Leu
        595                 600                 605

Leu His Ser Leu Ser Cys Ala Arg Tyr Lys Ile Leu Leu Lys Glu Pro
    610                 615                 620

Ser Thr Lys Thr Val Thr Gln Thr Asp Ser Phe Glu Phe Asn Ala Lys
625                 630                 635                 640

Phe Thr Asp Arg Met Arg Arg Ile Lys Ile Pro Leu Pro Pro Val Asp
                645                 650                 655

Glu Arg Lys Lys Val Val Glu Asp Val Asp Lys Asp Arg Arg Tyr Ala
            660                 665                 670
```

```
Ile Asp Ala Ala Ile Val Arg Ile Met Lys Ser Arg Lys Val Leu Gly
        675                 680                 685

His Gln Gln Leu Val Ser Glu Cys Val Glu Gln Leu Ser Arg Met Phe
    690                 695                 700

Lys Pro Asp Ile Lys Ala Ile Lys Lys Arg Met Glu Asp Leu Ile Thr
705                 710                 715                 720

Arg Asp Tyr Leu Glu Arg Asp Lys Glu Asn Pro Asn Met Phe Arg Tyr
                725                 730                 735

Leu Ala


<210> SEQ ID NO 33
<211> LENGTH: 740
<212> TYPE: PRT
<213> ORGANISM: Spinacia oleracea

<400> SEQUENCE: 33

Met Asn Asp Arg Lys Val Ile Glu Leu Glu Gln Gly Trp Glu Phe Met
1               5                   10                  15

Gly Lys Gly Ile Thr Lys Leu Lys Arg Ile Leu Glu Gly Leu Pro Glu
            20                  25                  30

Pro Pro Phe Asn Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
    50                  55                  60

Asp Asn Tyr Lys Glu Ala Phe Val Asp Tyr Ile His Ser Thr Val Leu
65                  70                  75                  80

Pro Ser Leu Gly Asp Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Ser
        115                 120                 125

Leu Asn Asp Val Gly Leu Thr Cys Phe Arg Asp Leu Val Tyr Gln Glu
    130                 135                 140

Ile Ser Gly Lys Ala Lys Asp Ala Val Ile Ala Leu Ile Asp Glu Glu
145                 150                 155                 160

Arg Glu Gly Gly Gln Ile Asp Arg Ala Leu Leu Lys Asn Val Leu Asp
                165                 170                 175

Ile Tyr Val Glu Ile Gly Met Thr Gln Met Asp Tyr Tyr Glu Lys Asp
            180                 185                 190

Phe Glu Ala His Met Leu Asp Asp Thr Ala Ala Tyr Tyr Ser Arg Lys
        195                 200                 205

Ala Ser Ser Trp Ile Leu Glu Asp Ser Cys Pro Glu Tyr Met Leu Lys
    210                 215                 220

Ser Glu Glu Cys Leu Lys Lys Glu Lys Asp Arg Val Ala His Tyr Leu
225                 230                 235                 240

His Ser Ser Ser Glu Pro Lys Leu Leu Glu Lys Val Gln Asn Glu Leu
                245                 250                 255

Leu Leu Val Tyr Glu Asn Gln Leu Leu Glu Lys Glu Asn Ser Gly Cys
            260                 265                 270

Arg Ala Leu Leu Lys Asp Asp Lys Val Glu Asp Leu Ser Arg Met Tyr
        275                 280                 285

Arg Leu Tyr Ser Lys Val Thr Lys Gly Leu Glu Pro Ile Gly Ser Ile
    290                 295                 300
```

-continued

```
Phe Lys Gln His Ile Thr Asp Glu Gly Thr Ala Leu Val Gln Gln Ala
305                 310                 315                 320

Glu Asp Ala Ala Ile Ser Lys Ala Glu Asn Ala Gly Gly Gly Ser His
                325                 330                 335

Glu Gln Val Phe Val Arg Lys Val Ile Glu Leu His Asp Lys Phe Met
            340                 345                 350

Thr Tyr Val Thr Asp Cys Phe Asn Ser His Thr Ile Phe His Lys Ala
        355                 360                 365

Leu Lys Glu Ala Phe Glu Val Phe Leu Asn Lys Gly Val Ala Gly Ser
    370                 375                 380

Ser Ser Ala Glu Leu Leu Ala Ser Phe Cys Asp Asn Ile Leu Lys Lys
385                 390                 395                 400

Gly Gly Ser Glu Lys Leu Ser Asp Glu Ala Ile Glu Asp Ser Leu Glu
                405                 410                 415

Lys Val Val Lys Leu Leu Ala Tyr Val Ser Asp Lys Asp Leu Phe Ala
            420                 425                 430

Glu Phe Tyr Arg Lys Lys Leu Ser Arg Arg Leu Leu Phe Asp Lys Ser
        435                 440                 445

Ala Asn Asp Asp His Glu Arg Ser Ile Leu Thr Lys Leu Lys Gln Gln
    450                 455                 460

Cys Gly Gly Gln Phe Thr Ser Lys Met Glu Gly Met Val Thr Asp Leu
465                 470                 475                 480

Thr Leu Ala Arg Glu Asn Gln Thr Asn Phe Glu Glu Tyr Leu Gly Gln
                485                 490                 495

Asn Thr Asp Ala Ser Pro Gly Leu Asp Leu Thr Val Thr Val Leu Thr
            500                 505                 510

Thr Gly Phe Trp Pro Ser Tyr Lys Ser Ser Asp Leu Asn Leu Pro Ala
        515                 520                 525

Glu Met Val Arg Cys Val Glu Val Phe Lys Gln Phe Tyr Gln Thr Lys
    530                 535                 540

Thr Lys His Arg Lys Leu Thr Trp Val Tyr Ser Leu Gly Ser Cys Asn
545                 550                 555                 560

Ile Asn Gly Lys Phe Gly Pro Lys Thr Ile Glu Leu Val Val Gly Thr
                565                 570                 575

Tyr Gln Ala Ala Ala Leu Met Leu Phe Asn Thr Ser Asp Arg Leu Ser
            580                 585                 590

Tyr Ser Glu Ile Thr Thr Gln Leu Asn Leu Ala Asp Glu Asp Leu Val
        595                 600                 605

Arg Val Leu Gln Ser Leu Ser Cys Ala Lys Tyr Lys Ile Leu Leu Lys
    610                 615                 620

Glu Pro Ser Thr Arg Asn Val Ile Ser Thr Asp Cys Phe Ser Phe Asn
625                 630                 635                 640

Ser Asn Phe Thr Asp Arg Met Arg Arg Ile Arg Ile Pro Leu Pro Pro
                645                 650                 655

Met Asp Glu Arg Lys Lys Val Val Glu Asp Val Asp Lys Asp Arg Arg
            660                 665                 670

Tyr Ala Ile Asp Ala Ser Ile Val Arg Ile Met Lys Ser Arg Lys Ala
        675                 680                 685

Leu Gly Tyr Gln Gln Leu Ile Thr Glu Cys Val Glu Gln Leu Ser Arg
    690                 695                 700

Met Phe Lys Pro Asp Phe Lys Ala Ile Lys Lys Arg Ile Glu Asp Leu
705                 710                 715                 720
```

```
Ile Thr Arg Asp Tyr Ile Glu Arg Asp Lys Glu Asn Pro Gln Leu Phe
                725                 730                 735

Arg Tyr Leu Ala
            740


<210> SEQ ID NO 34
<211> LENGTH: 739
<212> TYPE: PRT
<213> ORGANISM: Beta vulgaris

<400> SEQUENCE: 34

Met Asn Asp Arg Lys Val Ile Glu Leu Glu Gln Gly Trp Glu Phe Met
1               5                   10                  15

Gly Lys Gly Ile Thr Lys Leu Lys Arg Ile Leu Glu Gly Leu Pro Glu
            20                  25                  30

Pro Pro Phe Asn Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
    50                  55                  60

Asp Asn Tyr Lys Gln Ala Phe Val Asp Tyr Ile Asn Ser Thr Val Leu
65                  70                  75                  80

Pro Ser Leu Arg Glu Lys His Asp Glu Phe Met Leu Arg Glu Leu Val
                85                  90                  95

Lys Arg Trp Ala Asn His Lys Val Met Val Arg Trp Leu Ser Arg Phe
            100                 105                 110

Phe His Tyr Leu Asp Arg Tyr Phe Ile Ala Arg Arg Ser Leu Pro Ser
        115                 120                 125

Leu Asn Glu Val Gly Leu Thr Cys Phe Arg Asp Leu Val Tyr Gln Glu
    130                 135                 140

Ile Ser Gly Lys Ala Lys Asp Ala Val Ile Ala Leu Ile Asp Ile Glu
145                 150                 155                 160

Arg Glu Gly Gly Gln Ile Asp Arg Ser Leu Leu Lys Asn Val Leu Asp
                165                 170                 175

Ile Tyr Val Glu Ile Gly Met Gly Gln Met Asp His Tyr Glu Lys Asp
            180                 185                 190

Phe Glu Ala His Met Leu Asp Asp Thr Ala Ala Tyr Tyr Ser Arg Lys
        195                 200                 205

Ala Ser Ser Trp Ile Leu Glu Asp Ser Cys Pro Glu Tyr Met Leu Lys
    210                 215                 220

Ser Glu Glu Cys Leu Lys Lys Glu Lys Glu Arg Val Ala Asn Tyr Leu
225                 230                 235                 240

His Ser Ser Ser Glu Pro Lys Leu Leu Glu Lys Val Gln Asn Glu Leu
                245                 250                 255

Leu Leu Val Tyr Glu Ser Gln Leu Leu Glu Lys Glu Asn Ser Gly Cys
            260                 265                 270

Arg Ala Leu Leu Lys Asp Asp Lys Val Asp Asp Leu Ser Arg Met Tyr
        275                 280                 285

Arg Leu Tyr Ser Lys Val Thr Lys Gly Leu Glu Pro Ile Gly Ser Ile
    290                 295                 300

Phe Lys Gln His Ile Thr Asp Glu Gly Thr Ala Leu Val Gln Gln Ala
305                 310                 315                 320

Glu Asp Ala Ala Ile Ser Lys Ala Glu Asn Thr Gly Gly Ser His Glu
                325                 330                 335

Gln Val Phe Val Arg Lys Val Ile Glu Leu His Asp Lys Phe Met Thr
            340                 345                 350
```

```
Tyr Val Thr Asp Cys Phe Asn Ser His Thr Ile Phe His Lys Ala Leu
        355                 360                 365

Lys Glu Ala Phe Glu Val Phe Leu Asn Lys Gly Val Ala Gly Ser Ser
    370                 375                 380

Ser Ala Glu Leu Leu Ala Thr Phe Cys Asp Asn Ile Leu Lys Lys Gly
385                 390                 395                 400

Gly Ser Glu Lys Leu Ser Asp Glu Ala Ile Glu Asp Ser Leu Glu Lys
                405                 410                 415

Val Val Lys Leu Leu Ala Tyr Val Ser Asp Lys Asp Leu Phe Ala Glu
            420                 425                 430

Phe Tyr Arg Lys Lys Leu Ser Arg Arg Leu Leu Phe Asp Lys Ser Ala
        435                 440                 445

Asn Asp Asp His Glu Arg Ser Ile Leu Thr Lys Leu Lys Gln Gln Cys
    450                 455                 460

Gly Gly Gln Phe Thr Ser Lys Met Glu Gly Met Val Thr Asp Leu Thr
465                 470                 475                 480

Leu Ala Arg Glu Asn Gln Thr Asn Phe Glu Glu Tyr Leu Ser Gln Asn
                485                 490                 495

Pro Asp Ala Ser Pro Gly Leu Asp Leu Thr Val Thr Val Leu Thr Thr
            500                 505                 510

Gly Phe Trp Pro Ser Tyr Lys Ser Ser Asp Leu Asn Leu Pro Ala Glu
        515                 520                 525

Met Val Arg Cys Val Glu Val Phe Lys Gln Phe Tyr Ser Thr Lys Thr
    530                 535                 540

Lys His Arg Lys Leu Thr Trp Val Tyr Ser Leu Gly Ser Cys Asn Ile
545                 550                 555                 560

Asn Gly Lys Phe Gly Pro Lys Thr Ile Glu Leu Val Val Gly Thr Tyr
                565                 570                 575

Gln Ala Ala Ala Leu Met Leu Phe Asn Thr Ser Asp Arg Leu Ser Tyr
            580                 585                 590

Ser Glu Ile Ala Thr Gln Leu Asn Leu Ala Asp Glu Asp Leu Val Arg
        595                 600                 605

Val Leu Gln Ser Leu Ser Cys Ala Lys Tyr Lys Ile Leu Leu Lys Glu
    610                 615                 620

Pro Asn Thr Lys Thr Val Ser Pro Thr Asp Cys Phe Ser Phe Asn Ser
625                 630                 635                 640

Ser Phe Thr Asp Arg Met Arg Arg Ile Arg Ile Pro Leu Pro Pro Met
                645                 650                 655

Asp Glu Arg Lys Lys Val Val Glu Asp Val Asp Lys Asp Arg Arg Tyr
            660                 665                 670

Ala Ile Asp Ala Ser Ile Val Arg Ile Met Lys Ser Arg Lys Val Leu
        675                 680                 685

Gly Tyr Gln Gln Leu Ile Thr Glu Cys Val Glu Gln Leu Ser Arg Met
    690                 695                 700

Phe Lys Pro Asp Phe Lys Ala Ile Lys Lys Arg Ile Glu Asp Leu Ile
705                 710                 715                 720

Thr Arg Asp Tyr Ile Glu Arg Asp Lys Glu Asn Pro Gln Leu Phe Arg
                725                 730                 735

Tyr Leu Ala
```

<210> SEQ ID NO 35
<211> LENGTH: 2235
<212> TYPE: DNA

<213> ORGANISM: Cucumis sativus
<220> FEATURE:
<221> NAME/KEY: source
<222> LOCATION: 1..2235
<223> OTHER INFORMATION: /organism="Cucumis sativus"
/mol_type="unassigned DNA"

<400> SEQUENCE: 35
atgacaatgg gcgagcggaa gactattgac ttggagcagg gatgggagtt tatgcagaag 60
ggtatcacaa agttgaagaa cattctcgag ggcttgcctg agcctcagtt cagctccgag 120
gactacatga tgctttacac taccatgtat aacatgtgca cccaaaagcc gccgcatgat 180
tactcccagc agctgtatga taaatatcgt gaatcttttg aagagtacat cacttctatg 240
gtcttaccat ccttgaggga gaagcacgat gagttcatgt tgagagaact agtaaaaagg 300
tggacaaacc ataaagtcat ggtgaggtgg ctttctcgct tcttccacta tcttgatcgg 360
tacttcatcg ctcgaaggtc acttccacct ctaaatgaag ttggcctcac atgcttccgc 420
gaattggtgt acaaagagct aaatagtaaa gtgagggatg cagtaatttc attgattgat 480
caagaacgtg aaggagaaca gattgacaga gctctactga agaatgtact agatatattt 540
gtggaaattg gtatggggca aatggattac tatgaaaatg actttgaagc tgccatgctt 600
aaagatactg ctgcttatta ctctaggaag gcttccaatt ggatcctaga agattcttgt 660
cccgattata tgcttaaagc agaggagtgc ttgaaacgag aaaaggatag ggtttcccac 720
tatttgcact ctagtagcga gccaaagttg ttggagaaag ttcaacatga actattatct 780
gtttatgcta ctcaactgct ggaaaaagag cattcaggat gccatgcatt gcttagagat 840
gacaaggtgg aagatttgtc aaggatgttc cgtctattct ccaaaatacc gaagggactg 900
gatccagttt ccaacatatt taagcagcat gtaactgctg aaggaacagc actggtcaaa 960
caggcagaag atgctgcaag taacaagaag gctgagaaaa aggacatagt tggtctgcag 1020
gaacaggttt ttgtaagaaa agtgattgag cttcacgaca agtacttggc ttatgtgaat 1080
gattgtttcc aaaaccacac acttttccat aaggctctca aggaagcttt tgaagtattt 1140
tgcaataagg gtgttgctgg aagttctagt gcagaattgc ttgctacctt ttgtgataac 1200
atccttaaga aaggtgggag tgagaagttg agtgatgaag caatcgagga gacacttgag 1260
aaggttgtga agttgttggc atacatttgc gacaaagatc tgtttgctga attctataga 1320
aaaaaacttg cccgaaggct tctctttgac aagagcgcga acgatgacca cgagagaagt 1380
atattgacca aattgaagca acaatgtggt ggtcagttca cttctaagat ggagggaatg 1440
gttactgatt tgactttggc aagggagaac caaactagtt ttgaggagta tctgagcaat 1500
aatccacaag cgagtcctgg catcgacctg actgttactg ttttaactac tggattttgg 1560
ccaagctaca agtcttttga cctcaacctg ccggcagaga tggtaaagtg tgttgaagtt 1620
ttcagagagt tttatcaaac aaaaaccaag catcgaaaac ttacatggat ttactcattg 1680
ggtacttgta acatcagtgg aaaatttgaa ccgaaaacga tggagctgat tgtgacaact 1740
tatcaggctt ctgccctgtt gctattcaat tcttcggata gactaagtta ctcggaaatc 1800
atgacacaat taaatttgag tgacgatgat gtagttagac tactccactc gttgtcatgt 1860
gccaagtata aaattcttaa taaggaacca aatacgaaaa ccatctctcc gaacgatcat 1920
tttgagttca atgcaaaatt ctccgacaaa atgaggagaa taaagatccc tcttccgcct 1980
gtggatgaga aaaagaaagt cattgaagat gttgacaagg atcgaaggta tgctattgac 2040
gcctcaatcg tgcgtatcat gaagagtcgg aaagttcttg gtcatcagca actagtgatg 2100

-continued gagtgcgtcg agcaattggg ccgtatgttc aagcccgatt tcaaggcgat aaagaagaga 2160
attgaagacc tgatcactcg ggattatcta gagagagaca aagacaaccc ccacttgttt 2220
aggtacttgg cttga 2235

<210> SEQ ID NO 36
<211> LENGTH: 2235
<212> TYPE: DNA
<213> ORGANISM: Cucumis melo
<220> FEATURE:
<221> NAME/KEY: source
<222> LOCATION: 1..2235
<223> OTHER INFORMATION: /organism="Cucumis melo"
/mol_type="unassigned DNA"

<400> SEQUENCE: 36
atgacaatgg gcgagcggaa gactattgac ttggaacagg gatgggagtt tatgcagaag 60
ggtatcacaa agttgaagaa cattcttgag ggcttgcctg agccccagtt cagctccgag 120
gactacatga tgctttacac taccatgtat aacatgtgca cccaaaagcc gccgcatgat 180
tactcccagc agctgtatga taaatatcgt gaatcttttg aagagtacat cacttctatg 240
gtcttaccat ccttgaggga gaagcatgac gagttcatgt tgagagaact agtcaaaagg 300
tggacaaacc ataaagtcat ggtgaggtgg ctttctcgct tcttccacta tcttgatcgg 360
tacttcatcg ctcgaaggtc acttccacct ctaaatgaag ttggcctcac atgcttccgc 420
gaattggtgt acaaagagct aaacagtaaa gtgagggatg cagtaatctc attgattgat 480
caagaacgtg aaggagaaca gattgacaga gctctactga agaatgtatt agatatattt 540
gtggaaattg gtatggggca aatggattac tatgaaaatg actttgaagc tgccatgctt 600
aaagatactg ctgcttatta ctctaggaag gcttccaatt ggatcctaga agattcttgt 660
cccgattata tgctaaaagc agaggagtgc ttgaagcgag aaaaggatag ggtttcccac 720
tatttgcact ctagtagcga gccaaagttg ttggagaaag ttcaacacga actgttatct 780
gtgtatgcta ctcaactgct ggaaaaagag cattcaggat gccatgcatt gcttagagat 840
gacaaggtgg aagatttgtc aaggatgttc cgtctcttct ccaaaatacc gaagggattg 900
gacccagttt ccaacatatt taagcagcat gtaactgctg aaggaacagc actggtcaaa 960
caggcagaag atgctgcaag taacaagaag gccgagaaaa aggacatagt tggtctgcag 1020
gaacaggttt ttgtaagaaa agtgattgag cttcacgaca agtacttggc ttatgtgaat 1080
gattgtttcc aaaaccacac acttttccat aaggctctca aggaagcttt tgaagtcttt 1140
tgcaataagg gtgttgctgg aagttctagt gcagaattgc ttgctacctt ctgcgataac 1200
atccttaaga aaggtgggag tgagaagttg agtgatgaag caatcgaaga gacacttgag 1260
aaggttgtga agttgttggc atacatctgc gacaaagatc tgtttgctga attctataga 1320
aaaaaacttg cccgaaggct tctctttgat aagagcgcca acgatgacca cgagagaagt 1380
atattgacca aattgaagca acaatgtggt ggtcagttca cttctaagat ggagggaatg 1440
gttactgatt tgactttggc aagggagaac caaactagtt tcgaagagta tctgagcaat 1500
aatccacaag ctagtcctgg aatcgaccta actgttactg ttttgactac tggattttgg 1560
ccaagctaca agtcttttga cctcaacctg ccggcggaga tggtaaagtg tgttgaagtt 1620
ttcagagagt tttatcaaac aaaaaaccaag catagaaaac ttacatggat ttactcattg 1680
ggtacttgta acatcagtgg aaaatttgaa ccgaagacga tggagctgat tgtgacaaca 1740
tatcaggctt ctgccctgtt gctattcaat tcttcggaca gactaagtta ctccgaaatc 1800

-continued atgacacaat taaatttgag tgatgatgat gttgttagac tgctccactc attgtcgtgt 1860
gccaagtata aaattcttaa taaggagcca aatacgaaaa ccatctcacc gaacgatcat 1920
tttgagttca atgcaaaatt ctccgacaaa atgaggagaa taaagatccc tcttccgcct 1980
gtggatgaga aaaagaaagt cattgaagat gttgacaagg atcgaaggta tgctattgac 2040
gcctcaatcg tgcgtatcat gaagagtcga aaagttcttg gtcatcagca actagtgatg 2100
gagtgcgtcg agcaattggg tcgtatgttc aagcccgatt tcaaggcgat aaagaagaga 2160
attgaagacc tgatcactcg ggactatcta gagagagaca aagacaaccc ccacttgttt 2220
aggtacttgg cttga 2235

<210> SEQ ID NO 37
<211> LENGTH: 2235
<212> TYPE: DNA
<213> ORGANISM: Cucurbita pepo
<220> FEATURE:
<221> NAME/KEY: source
<222> LOCATION: 1..2235
<223> OTHER INFORMATION: /organism="Cucurbita pepo"
/mol_type="unassigned DNA"

<400> SEQUENCE: 37
atgacaatgg gtgagcggaa gactattgac ttggagcaag gatgggagtt tatgcagaag 60
ggaatcacaa aattgaagaa cattctggaa ggattgcctg agccacagtt cagctccgag 120
gactacatga tgctttacac tacaatgtat aacatgtgta cccagaagcc accgcatgat 180
tactcccagc agctgtatga taaataccgc gaatcgtttg aggagtacat cagttctatg 240
gttttaccat ccttgaggga gaagcatgac gaatttatgt tgagagaact ggtcaaaagg 300
tggaccaacc ataaagtcat ggtgaggtgg ctttctcgct tcttccacta tcttgatcga 360
tacttcattg ctcgaaggtc acttccacct ctcaatgaag ttggcctcac ttgcttccgt 420
gaattggtgt acaaagagct aaacagtaaa gtgagggatg cagtaatttc attgatcgat 480
caagaacgtg aaggagagca gattgacaga gctctgttga agaacgtgtt ggatatattt 540
gtggagattg ggatggggca aatggattat tatgaaaatg actttgaagc tgccatgctt 600
aaagatactg ctgcttacta ctctaggaag gcatcaaatt ggatcttaga agattcttgt 660
cctgattata tgctaaaagc agaggagtgc ttgagacgag aaaaggaccg agtttctcac 720
tatctgcact ctagtagcga gccaaagtta ttggagaaag ttcaacatga actattgtct 780
gtttatgcta ctcaactgct ggagaaagag cattcaggat gccatgcatt gcttagagat 840
gacaaggtgg aagatttgtc aaggatgttc cgtctcttct ccaaaatacc caagggattg 900
gacccagttt ccaacatatt taagcagcat gtcactgctg aaggaacagc attagtcaaa 960
caggcagaag acgctgcaag taacaagaag gccgagaaaa aggacatcgt tggtctgcaa 1020
gaacaggttt ttgttagaaa agtgattgag cttcacgaca agtacttggc atatgtgaat 1080
gattgtttcc aaaaccacac actttttcac aaggctctca aggaagcttt tgaagtcttt 1140
tgcaataagg gtgttgctgg aagttctagt gcagaattac ttgctacctt ttgtgataac 1200
atccttaaga aaggtgggag tgagaagttg agtgatgaag caattgagga aacactcgag 1260
aaggtcgtga aattgctggc gtatatctgc gacaaagatc tgtttgctga attctataga 1320
aaaaaactcg cccgaaggct tctcttcgac aagagtgcga atgatgacca cgagagaagt 1380
atactgacga aattgaagca acaatgtggt ggtcagttta cctctaagat ggagggaatg 1440
gtcacggatt tgacactggc aagggagaac caaactagtt ttgaggaata tctgagcaat 1500

-continued

```
aatccacaag ctagtcctgg aatcgacttg accgttaccg ttttgaccac tggtttttgg   1560

ccaagctaca agtcttttga cctcaacctg ccggcggaga tggtaaagtg tgttgaagtt   1620

ttcagggaat tttatcaaac aaaaaccaag cacagaaaac ttacgtggat ttactcgttg   1680

ggtacctgta acatcagcgg aaaattcgaa ccgaaaacga tggagctgat cgtgacaacc   1740

tatcaggctt ctgccctgct gcttttcaat tcctcggata aactaagtta ctccgagatc   1800

atgactcaat taaacttgag tgacgatgat gttgttagac tgctccactc gttgtcgtgt   1860

gcgaagtata aaattcttaa caaggagcca aatacgaaaa ccatctctcc gaacgatcat   1920

tttgagttca acgcaaaatt ctccgacaaa atgaggagaa taaagatccc tcttccgcct   1980

gtggatgaga aaaagaaagt aatagaagat gttgacaagg atcgaagata tgctatcgat   2040

gcctcgatcg tgcgtatcat gaagagtagg aaagttctgg gtcaccagca gttagtgatg   2100

gagtgcgtcg agcaactggg tcgtatgttc aagcctgatt tcaaggcgat aaagaagaga   2160

atcgaagatc tgatcactcg tgactattta gagagagaca aagacaaccc ccacttgttt   2220

aggtacttgg cttga                                                    2235


<210> SEQ ID NO 38
<211> LENGTH: 2235
<212> TYPE: DNA
<213> ORGANISM: citrillus lanatus
<220> FEATURE:
<221> NAME/KEY: source
<222> LOCATION: 1..2235
<223> OTHER INFORMATION: /organism="citrillus lanatus"
      /mol_type="unassigned DNA"

<400> SEQUENCE: 38

atgacaatgg gcgagcggaa gactattgac ttggaacaag gatgggagtt tatgcagaag     60

ggaatcacaa agttgaagaa cattcttgag ggcttgcctg agcctcagtt cagctccgag    120

gactacatga tgctttatac caccatgtac aacatgtgca cacaaaagcc gccacatgat    180

tactcccagc agctatacga taaataccgt gaatcttttg aggagtatat cacttctatg    240

gtcttaccat ccttgaggga gaagcatgac gagttcatgt tgagagaact ggtcaaaagg    300

tggacgaacc ataaagtcat ggtgaggtgg ctttctcgct tcttccacta tcttgaccga    360

tacttcattg ctcgaagatc acttccacct ctcaacgaag ttggcctcac atgcttccgt    420

gaattggtgt acaaagagct aaacagtaaa gtgagggatg cagtaatttc attgattgat    480

caagaacgtg aaggagagca gattgacaga gctctactga agaatgtatt agatatattt    540

gtggaaattg ggatggggca aatggattac tatgaaaatg actttgaagc tgccatgctt    600

aaagatactg ctgcttatta ctctaggaag gcttccaatt ggatcctaga agattcttgt    660

cccgattata tgctaaaagc agaggagtgc ttgaaacgag aaaaggatag agtttctcac    720

tatttgcact ctagtagcga gccaaagtta ttagagaaag ttcaacatga actgttatct    780

gtgtatgcta ctcaactgct ggaaaaagag cattcaggat gccatgcatt gcttagagat    840

gacaaggtgg aagatttgtc aaggatgttc cgcctcttct ccaaaatacc caagggattg    900

gacccagttt ccaacatatt taagcagcat gtcactgctg aaggaacagc attggtcaaa    960

caggcagaag atgctgcaag taacaagaag gccgagaaaa aggacatagt tggtctgcag   1020

gaacaggttt ttgtaagaaa agtgattgag cttcacgaca agtacttggc ttacgtgaat   1080

gattgtttcc aaaaccacac actttttcac aaggctctca aggaagcttt tgaagtcttt   1140

tgcaataagg gtgttgctgg aagttctagt gcagaattac ttgctacctt ttgtgataac   1200
```

-continued

```
atccttaaga aaggtgggag cgagaagttg agtgatgaag caattgagga gacacttgag   1260

aaggtcgtga agttgctggc atacatctgc gacaaagatc tgtttgctga attctataga   1320

aaaaaacttg cccgaaggct tctctttgac aagagtgcca acgatgacca tgagagaagt   1380

atattgacca aattgaagca acaatgtggt ggccagttca cctctaagat ggaggggatg   1440

gtcactgatt tgactttggc aagggagaac caaactagtt tcgaggagta tctgagcaat   1500

aatccacaag ctagtcctgg aatcgacttg actgtcactg ttttgactac tggcttttgg   1560

ccaagctaca agtcttttga cctcaacctg ccggcagaga tggtaaagtg tgttgaagtt   1620

ttcagagagt tctatcaaac aaaaacaaag catagaaaac ttacatggat ttactcattg   1680

ggtacctgta acatcagcgg aaaatttgaa ccgaaaacga tggagctgat tgtaacaact   1740

tatcaggctt ctgccctgct gctattcaat tcctcagata gattaagtta ttccgagatc   1800

atgacacaat taaatttgag tgacgatgat gttgttagac tgctccactc attgtcatgt   1860

gccaagtata aaattcttaa taaggagccg aacacgaaaa ccatctctcc gaatgatcat   1920

tttgagttca atgcaaaatt ctccgacaaa atgaggagaa taaagatccc tcttccgcct   1980

gtggatgaga aaaagaaagt cattgaagat gttgacaagg atcgaaggta tgctattgat   2040

gcctcaatcg tgcgtatcat gaagagtcgg aaagttctgg gtcatcagca gctagtgatg   2100

gagtgcgtcg agcaattggg tcgtatgttc aagcccgact tcaaagcgat aaagaagaga   2160

atcgaagatc tgatcactcg ggactattta gagagagaca aagacaaccc ccacttgttt   2220

aggtacttgg cttga                                                     2235
```

<210> SEQ ID NO 39
<211> LENGTH: 2229
<212> TYPE: DNA
<213> ORGANISM: Solanum melongena
<220> FEATURE:
<221> NAME/KEY: source
<222> LOCATION: 1..2229
<223> OTHER INFORMATION: /organism="Solanum melongena"
/mol_type="unassigned DNA"

<400> SEQUENCE: 39

```
atgaaccaac gcagcacaat cgatctggaa catggatggg atttcatgca aaagggcatc     60

acaaagctga agaacattct agaagggctg cctgagcctc agttcagctc agaggactat    120

atgatgctgt atacgacaat gtacaacatg tgtactcaga agcccccaca tgattattct    180

caacagctgt atgacaaata tcgtgaagct tttgaagaat atatcacaac gacggtatta    240

ccttctttga gagaaaaaca tgacgagttc atgttgcgag agttggtaaa aaggtggtca    300

aaccataagg tcatggttag atggttatcg cgattcttcc attatcttga ccgttatttc    360

attgctcgga gatcactgcc agggcttaat gaagttggac taacttgctt ccgcgatctg    420

gtctaccaag agttgaatgg aaaagtcagg gatgctgtta tatctctgat tgatcaagag    480

cgtgagggag agcaaattga cagagctcta ctgaagaatg tgctagatat atttgttgaa    540

attggaatgg ggtcaatgga ttattatgag aatgattttg aagctgcaat gctcaaggac    600

actgcggctt attattctcg caaagcttct aactggatcc tcgaagattc atgtccagat    660

tatatgctga aagctgagga gtgcttgaaa cgggagaagg atagggtctc ccattatctc    720

cattctagca gtgagacaaa gttgcttgag aaagtgcaac atgagttgtt atctgtgtat    780

gccaatcaac ttcttgagaa ggagcactct ggatgccatg cattacttag agatgataag    840

gtcgatgatt tatcaaggat gtatagactc ttttctaaga ttcctcgagg cttagagcct    900
```

gtggctaata tatttaagca gcatgttact gctgaaggta cagctttggt gaaacaggct 960
gaagatgctg ctagcaacaa aaaggcagag aagagagatg tggttggttt gcaggaacag 1020
gtttttgttc ggaaagtgat tgagcttcat gataaatatt tggcgtatgt gaataactgt 1080
ttccaaaacc acacactttt tcacaaggca cttaaagaag ctttcgaact tttctgcaac 1140
aagggtgttg ctggtagctc aaatgctgaa cttcttgcca cattctgcga caacattctc 1200
aaaaaaggcg ggagtgaaaa attgagtgat gaagccattg aagagacgct ggagaaggtg 1260
gtaaagctgc tggcttatat tagtgataag gacttgtttg cagaattcta taggaaaaag 1320
ctcgcccggc ggttgttatt tgataagagt gccaatgatg aacatgagag aagtatccta 1380
acaaagttga agcagcagtg tggaggtcag ttcacatcaa agatggaggg aatggtcaca 1440
gatttgacat tggcaaggga aaatcaagcc agctttgagg agtatttgag caataatcca 1500
acagcaaatc caggaattga cttgacggtg actgtcttga ctactggctt ctggcctagc 1560
tacaagtctt ttgatctcaa cctcccagca gaaatggtta ggtgtgttga agtattcaag 1620
gagttttatc aaacaaaaac gaagcacagg aaacttacat ggatatactc tttgggaact 1680
tgcaacataa atggaaaatt tgaggcaaag actattgagc tcgttgtcac tacttatcag 1740
gcttctgctc tgcttctctt taatgcatca gatagattga gttatcagga aatcatgacg 1800
caattaaacc tatcagatga tgatgttgtt cggcttcttc attccctttc atgtgcgaaa 1860
tacaagattc tcaacaagga gccaagcacc aaaacaattt ctccgactga tgtctttgag 1920
ttcaactcaa agttcactga caaaatgagg aggatcaaga tacctctccc accagttgat 1980
gaaaagaaaa aggtaattga agacgttgac aaggataggc ggtatgctat agatgcctca 2040
attgtgcgta ttatgaagag tcgtaaagta ttgggctacc agcaactggt catggagtgc 2100
gttgagcagt tgggacgcat gttcaagcct gatgtcaaag ctatcaagaa gagaattgaa 2160
gatctgataa ctagagatta cctagagagg gacaaagata acccaaactt gttcaagtac 2220
ttggcatga 2229

<210> SEQ ID NO 40
<211> LENGTH: 2229
<212> TYPE: DNA
<213> ORGANISM: Solanum lycopersicum
<220> FEATURE:
<221> NAME/KEY: source
<222> LOCATION: 1..2229
<223> OTHER INFORMATION: /organism="Solanum lycopersicum"
/mol_type="unassigned DNA"

<400> SEQUENCE: 40
atgaaccaac gaagcacaat cgatctggaa catggatggg acttcatgca aaggggcatt 60
acaaagctga agaacattct agaagggctg cctgagcctc aattcagctc agaggactat 120
atgatgctat atacgacaat gtacaacatg tgtactcaaa agcccccaca tgattattct 180
caacagctgt atgacaaata tcgtgaagct tttgaagaat atatcacaac aacggtattg 240
ccttctttga gagaaaaaca tgacgagttt atgttgcgag agttggtaaa aaggtggtca 300
aatcataaag tcatggtcag atggttgtca agattcttcc attaccttga ccggtatttc 360
attgcccgga gatctctgcc ggggcttaat gaagttggac taacttgctt ccgcgatcag 420
gtctaccaag agttgaatgg aaaagtcagg gatgctgtta tatctctgat tgatcaagag 480
cgtgagggag agcaaattga cagagctcta cttaagaatg tgcttgatat atttgtcgaa 540
attggaatgg ggttaatgga ttattatgag aatgattttg aagctgcaat gctcaaggac 600

```
acagcggctt attattctcg caaagcttct aattggatcc tcgaagattc atgtccggat    660

tatatgctga aagccgagga gtgcttgaaa cgggagaagg atagggtctc tcattatctc    720

cattcaagca gcgagacgaa gttgcttgag aaagtgcaac atgagttgtt gtctgtgtat    780

gccactcaac ttcttgagaa ggagcactct ggatgccatg cgttactgag agatgataag    840

gttgaagatt tatcaaggat gtataggctc ttttctaaga tttctcgagg cttagaccct    900

gtggccaata tttttaagca gcatgttact gctgaaggta cagctttggt aaaacaggct    960

gaagatgctg ctagcaataa aaaggcagag aagagagatg tggttggttt gcaggaacag   1020

gtttttgttc ggaaagtgat tgaacttcat gataaatatt tggcttatgt gaataactgt   1080

ttccaaaacc acacactttt tcacaaggcg cttaaagaag cttttgagct tttctgcaac   1140

aagggtgttg ctggtagctc aagcgctgaa cttcttgcca ccttctgtga caacattctc   1200

aaaaaaggcg ggagtgagaa attgagtgat gaagctattg aagaaacgtt ggaaaaggtg   1260

gtaaagctac tagcttatat tagtgataag gacttgtttg cagaattcta taggaaaaag   1320

ctagcccggc ggttgttatt tgataagagt gccaatgatg aacatgaaag aagtatccta   1380

acaaagttga agcagcagtg tgggggggcag ttcacatcaa agatggaggg aatggtcaca   1440

gatttgacat tggcaaggga aaatcaagcc agcttcgagg agtatttgag caataatcca   1500

atagcaaatc caggaattga cttgacggtg actgtcttga ctactggctt ctggcctagc   1560

tacaagtctt ttgatctcaa cctcccagca gaaatggtta ggtgcgttga agtatttaag   1620

gagttctatc aaacaaaaac aaagcacagg aaacttacgt ggatatactc tttgggaact   1680

tgcaacataa atggaaaatt tgagccaaaa actattgagc tcgttgtcac tacttatcag   1740

gcttctgctc tgctgctctt taatgcatca gatagattga gttatcagga aatcatgacg   1800

caattaaacc tatcagatga tgatgttgtt cggcttcttc attccctttc atgtgcgaag   1860

tacaagatac tcaacaagga gccaagcacc aaaacaattt ctccgactga tgtctttgag   1920

ttcaactcaa agttcactga caaaatgagg aggatcaaga tacctctccc tcctgttgat   1980

gagaagaaaa aggtaattga agacgttgac aaggataggc ggtatgctat agatgcttca   2040

attgtgcgta ttatgaagag ccgtaaagta ttgggctacc agcaactagt catggagtgc   2100

gttgagcagt tggggcgcat gttcaagcct gatgtcaaag ctatcaagaa gagaatcgaa   2160

gatttgataa ctagagatta cctagagagg gacaaagata atccaaacct gttcaagtac   2220

ttggcatga                                                           2229
```

```
<210> SEQ ID NO 41
<211> LENGTH: 2229
<212> TYPE: DNA
<213> ORGANISM: Capsicum annuum
<220> FEATURE:
<221> NAME/KEY: source
<222> LOCATION: 1..2229
<223> OTHER INFORMATION: /organism="Capsicum annuum"
      /mol_type="unassigned DNA"

<400> SEQUENCE: 41

atgaaccagc gttccacaat caatctagaa catggatggg acttcatgca aaggggcatt     60

acaaagctga agaacattct agaagggctg cccgagcctc agttcagctc agaggactat    120

atgatgctgt atacgacaat gtacaacatg tgtactcaga agccccccaca tgattattct    180

caacagctgt atgacaaata tcgtgaagct tttgaagaat atatcacaac aacggtattg    240

ccttctttga gagaaaaaca tgacgagttc atgttgcgag agctggtaaa aaggtggtca    300
```

-continued

```
aaccataagg tcatggtcag atggttatcg cgattcttcc attatcttga tcgctatttc    360

attgcccgga gatctctacc ggggcttaat gaagttggac taacttgctt ccgagatctg    420

gtctaccaag agttgaatgg aaaagtcagg gatgctgtta tatctctgat tgatcaagag    480

cgtgagggag agcaaattga cagagctcta ctgaagaatg tgctagatat atttgttgaa    540

attggaatgg ggtcgatgga ttattatgag aatgattttg aagctgcaat gctcaaggac    600

accgcagctt attattctcg caaagcttct aactggatac ttgaagattc atgtccagat    660

tatatgctga aagccgagga gtgcttgaaa cgggagaaag atagggtctc tcactatctt    720

catttaagca gtgagacaaa gttgcttgag aaagtgcaac atgagttgtt gtctgtgtat    780

gccactcaac ttcttgagaa ggagcactct gggtgccatg cgttactaag agatgataag    840

gttgaagatt tatcaaggat gtataggctc ttttctaaga ttcctcgagg cttagaccct    900

gtggctaata tatttaagca gcatgttact gctgaaggta cagctttggt caaacaggct    960

gaagatgctg ctagcaacaa aaaggcagag aaaagagatg tggttggttt gcaggaacag   1020

atttttgttc ggaaagtgat tgagcttcat gataagtata tggcatatgt gaataactgt   1080

ttccaaaacc acacactttt tcacaaggcg cttaaagaag ctttcgaact tttctgcaac   1140

aagggtgttg ctggtagctc aagtgctgaa cttcttgcca cattctgcga caatattctc   1200

aagaaaggcg ggagtgagaa attgagtgat gaagccattg aagagacgct ggagaaggtt   1260

gtaaagctgc tagcatatat tagtgacaag gacttgtttg cagaattcta taggaaaaag   1320

ctagcccggc ggttgttatt tgataagagt gccaatgatg aacacgagag aagtatcctt   1380

acaaagttga agcagcagtg tgggggccag ttcacatcaa agatggaggg aatggtgaca   1440

gatttgacat tggcaaggga aaatcaagcc agctttgagg agtatttgag caacaatcca   1500

gcagcaaatc caggaattga cttgacggtg actgtcttga ctactggctt ctggcctagc   1560

tacaagtctt ttgatctcaa cctcccagca gaaatggtta ggtgcgttga agtattcaag   1620

gagttttatc aaacaaaaac gaagcacagg aaacttacgt ggatatactc tttgggaact   1680

tgcaatataa atggaaaatt tgagccaaag actattgagc tcgttgtcac tacttatcag   1740

gcttctgctc tgctgctctt taatgcatcg gatagattga gttatcagga aatcatgacg   1800

caactaaacc tatcagatga tgatgttgtt cggcttcttc attccctttc atgtgcgaag   1860

tacaagattc tcaacaagga gccaagcacc aaaacaattt ctccgactga tgtctttgag   1920

ttcaatttta agttcactga caaaatgagg aggatcaaga tacctctccc tcctgttgat   1980

gagaagaaaa aggtaattga agatgttgac aaagataggc ggtacgctat agatgcttca   2040

attgtgcgta ttatgaagag tcgtaaagta ttgggctacc agcaactggt catggagtgt   2100

gttgagcagt tgggacgtat gttcaagcct gatgtcaaag ctatcaagaa gagaattgaa   2160

gatttgataa ctagagatta cctagagagg gacaaagata atccgaactt gttcaagtac   2220

ttggcatga                                                           2229
```

```
<210> SEQ ID NO 42
<211> LENGTH: 2217
<212> TYPE: DNA
<213> ORGANISM: Brassica oleracea
<220> FEATURE:
<221> NAME/KEY: source
<222> LOCATION: 1..2217
<223> OTHER INFORMATION: /organism="Brassica oleracea"
      /mol_type="unassigned DNA"

<400> SEQUENCE: 42
```

-continued

```
atggagcgca agacgattga cttggaccaa ggatgggact atatgcagac tggtatcact     60
aagctgaaac ggattcttga ggggctgcct gagccgcagt ttgactctga gcaatacatg    120
atgctctata cgactatgta caacatgtgc actcagaaac ctcctcatga ttactcacag    180
cagctttatg acaagtatcg tgaagcattt gaggagtata ttcactcaac tgttttgcct    240
gctctaaggg agaagcatga tgagtacatg ctgagggagc tggttaagag atggtctaac    300
cataaagtta tggttcgatg gctatcccgc ttcttctact atcttgaccg ttacttcatt    360
gctcggaggt cacttccacc cctgaatgaa gttggcctga cttgcttccg tgacctggtt    420
tataacgagt tgcattccaa ggtcaaagat gctgtaatag cacttgttga taaagaacgg    480
gagggtgagc agattgacag ggctctattg aaaaacgtat tagacattta tgtagagatt    540
ggaatgggac agatggaaag atacgaggag gattttgaaa gcttcatgct tttagattca    600
gcatcttact attctcgcaa ggcgtcaagc tggatccaag aagattcttg ccctgattac    660
atgctgaagt ctgaagaatg tcttaagaag gagagggaga gagtggctca ctaccttcac    720
tcaagcagcg agccaaagct ggttgagaaa gtacaacatg agctgttggt agtgtatgca    780
aatcagcttc tagaaaaaga gcattcaggg tgccgtgcat tgctgagaga tgacaaggtt    840
gatgacctct ccaggatgta caggctttat cataaaattg tgaaaggttt ggaacctgtt    900
gcaaacatat ttaagcagca tgtcacagca gagggtaacg cacttgtcca acaggccgaa    960
gacacggcca ctaatcatgc tgcaaatact gctagcgtgc aggaacaggt tcttatcaga   1020
aaagtgattg aactacatga taaatacatg gtctatgttg ttgagtgttt ccagaaccac   1080
accctcttcc acaaggcatt gaaagaggca tttgagatat tctgtaacaa aacagtcgct   1140
ggaagttcta gtgctgaatt gcttgcaaca ttttgcgaca atattctcaa gaagggggga   1200
agtgaaaagc tgagcgatga agctattgaa gataccottg agaaggtggt caaattgctt   1260
gcttatataa gtgacaagga tcttttcgcc gagttctaca ggaagaagct ggcccgtagg   1320
ctcttatttg atcgcagtgc taatgatgat catgagagaa gtatcctgac aaagctcaag   1380
caacaatgtg gtgggcagtt tacttcgaag atggagggca tggtgactga tttgacattg   1440
gcaagggaaa accaaaacag cttcgaggag tatcttggca ataaccccgc tgcaaaccca   1500
gggattgatt tgaccgtaac tgttcttacc actggttttt ggccaagtta caaatcattt   1560
gacataaatc tacccgctga aatggtcaag tgtgttgaag ttttcaaagg gttttatgaa   1620
acaaagacaa aacataggaa acttacctgg atctactcac taggaacttg ccacctcaat   1680
gggaagtttg atgtcaagcc cattgagtta gttgtgtcta cataccaggc tgctgtgctt   1740
ctgctgttca acacaacaga caaattgagc tacactgata tcctaactca gctgaacctg   1800
agccacgaag atctagtgag gttgcttcat tccttgtcat gtgctagata caagattctt   1860
ctcaaggagc caagcacaaa gactgtttcc cagtctgatt cttttgaatt caactccaaa   1920
ttcaccgaca gaatgcggag aataaagatc cctctcccac ctgttgatga gaggaagaaa   1980
gttgtggaag acgtggacaa agacagacgc tatgcgattg atgctgccat tgtgaggatc   2040
atgaagagca ggaaagtatt gggacatcaa caacttgttt ctgagtgcgt tgagcaactt   2100
agccgaatgt tcaagcctga tatcaaggca atcaagaagc gcatggagga tttgataacg   2160
agagattatc tggagaggga caaggagaac gctaacatgt ttaggtactt ggcttag      2217
```

<210> SEQ ID NO 43
<211> LENGTH: 2232
<212> TYPE: DNA
<213> ORGANISM: Daucus carota
<220> FEATURE:
<221> NAME/KEY: source
<222> LOCATION: 1..2232
<223> OTHER INFORMATION: /organism="Daucus carota"
/mol_type="unassigned DNA"

<400> SEQUENCE: 43
atgatgattg agcggaaaac tatagacctg gagcagggat gggactttat gcaaaaggga 60
atcacaaagc taaagaatat tttagaaggc tttccggagc cgcaattcag ctcggaggat 120
tatatgatgc tttatacaac tatgtataac atgtgtacac agaaacctcc acatgattac 180
tctcagcagc tgtatgaaaa gtatcgtgaa gctattgagg agtacattac ttctacagta 240
ttgccttcat tgagagagaa gcatgatgaa ttcatgctta gagaacttgt gaagagatgg 300
tctaatcata aggtcatggt caggtggctt tctcgattct ttcactatct tgatcgctat 360
tttattgctc ggaggtcact tccaccactt catgaagttg gactcacttg ctttcgggac 420
ctggtttacc aggagataaa tgggaaagta agggatgctg taatatcatt gattaatcaa 480
gagcgcgagg gagagcaaat tgaccgagct ttgttgaaga atgttctaga tatatttgtt 540
gaagttggaa tgagtcaaat ggattattat gagaatgact ttgaagcaga catgctcaaa 600
gatacagcag catactattc tcgaaaggct tccaactgga tcttagaaga ttcttgtcca 660
gattatatgc tcaaagcgga agagtgtttg agacgggaaa aggacagggt ctctaactac 720
cttcattcta gtagtgaacc caagttgctt gagaaagttc aacatgagtt actatcacac 780
tatgcaactc agctgcttga gaaagaacac tctgggtgtc atgcattgct tagggatgac 840
aaggtggcag atttatcaag gatgtatagg ctcttctcta aaatacctcg aggcctagat 900
cccgtgtcta atattttcaa gcagcatgtt actgctgaag gtacagcttt ggtcaaacaa 960
gcagaagatg cagctagcaa caagaaggca gagaagagag atgtagtagg tttacaagaa 1020
caggtttttg tgaggaaaat aattgaattg catgacaaat accttacata cgtaaatgac 1080
tgttttacaa accacactct cttccataag gcgcttaagg aggcttttga aatcttctgc 1140
aataagggtg tctctggaag ctctagtgca gaattacttg ccacattctg tgataatatt 1200
ctcaagaaag gtggaagcga gaagttaagt gatgaagcca ttgaggaaac acttgagaag 1260
gttgtaaggt tgcttgctta tataagtgac aaagacttat ttgctgaatt ttataggaaa 1320
aagcttgcac ggcgtctctt attcgacaag agtgccaatg atgagcatga gagaagtata 1380
ttgactaagc tgaagcaaca atgtgggggt caatttacat caaagatgga aggaatggtc 1440
actgacttga cgttggcaaa ggaaaatcag tccaacttcg aggagtacct caataataat 1500
tcaaacgtaa atcctggaat tgacttgaca gttactgttc taaccactgg gttttggcca 1560
agttacaaat ctttcgatct caacctccca gcagagatgg tcaaatgtgt tgaagttttt 1620
agagaattct accaaacaaa aacaaagcac agaaaactga catggatata ctctttgggt 1680
acttgtaaca tcattggaaa atttgatcca aaaaccatgg agcttattgt gacaacatac 1740
caggcctctg ctctgctgct atttaactct tctgatagac ttagttataa tgaaataatg 1800
actcagttga acttgtcgga tgatgatgtt gtcagactac ttcattctct ttcgtgtgca 1860
aagtacaaga ttctatctaa agagccgaac accaaaacta tatctccaac tgattgcttt 1920
cagttcaatt ccaaatttac tgataaaatg aggaggatta agattccact tcccccagtg 1980
gatgagaaga aaaaggtaat tgaagatgtt gataaagaca ggcgatatgc tatagatgct 2040
tcaattgtcc gtatcatgaa gagccgcaaa gttttgggtt atcagcagct agtaatggag 2100
tgcgttgaac aattgggtcg catgtttaag cctgatgtca aagcaatcaa gaagagaatc 2160
gaagatttaa taactcggga ttatctggaa agagacaagg acaatgccaa cttgttcagg 2220
tatctggcat ga 2232

<210> SEQ ID NO 44
<211> LENGTH: 2229
<212> TYPE: DNA
<213> ORGANISM: Apium graveolens
<220> FEATURE:
<221> NAME/KEY: source
<222> LOCATION: 1..2229
<223> OTHER INFORMATION: /organism="Apium graveolens"
/mol_type="unassigned DNA"

<400> SEQUENCE: 44
atgaacgagc ggaagactat cgatttggat aatggatggg aatttatgca gaaagggatc 60
actaagttga agaagattct cgaaggtcaa cctgagcctc agtttagctc cgaggactat 120
atgatgcttt acacaactat gtataatatg tgtacgcaga agcctccaca tgattattct 180
caacagctgt atgacaagta ccgtgaggcc tttgaggagt acataacttc aactgtcctg 240
ccttctttac gagagaagca tgatgagttt atgttgagag agctcgtgaa tagatggaca 300
aaccataaag tcatggtcag gtggctttct cgattctttc actatcttga tcggtacttc 360
attgcgagga ggtcacttcc tgcacttcat gaagttggac tcacgtgctt ccgggatctg 420
gtctatcagg agctgaaagt taaagtgagg gatgctgtaa tatctctgat cgatcaagag 480
cgtgaggggg aacagattga ccgagcttta ttaaagaacg tgttagatat atttgttgaa 540
atcggaatga gtcaaatgga tcaatatgag aatgactttg aagaagccat gctcactgat 600
actgctgctt actattctcg aaaagcttca aactggatcc ttgaagattc ttgtcctgat 660
tatatgttaa aggcagaaga atgtttgcga cgagagaagg acagggtttc ccactaccta 720
cattttagta gcgagccaaa gttgcttgag aaagtgcaac atgagctgct atctgtgtat 780
gcaacccaat tactcgagaa ggaacattct ggttgtcatg cattgcttag ggatgacaag 840
gtggatgatt tgtctaggat gtacagactc ttctcgaaaa tacctaaagg cctggatcca 900
gtttcttata tttttaagca gcatgttaca aatgaaggga tggcattggt taaacaagca 960
gaagatgcag caagcaacaa gaaggcagaa aagagagacg tggttagttt acaggagcag 1020
gtttttgtta gaaaaattat tgaattacat gacaaatacc tcgcctatgt gaatgactgc 1080
tttacaaacc atactctttt ccataaggct ctcaaggagg cttttgaaat cttttgcaac 1140
aagggtgttg ctggaagctc taatgctgaa ctacttgcta ctttctgtga taacatcctc 1200
aaaaagggtg ggagtgagaa attaagtgat gaggctattg aagaaacact tgagaaggta 1260
gtaaaattgt tagcttacat tagcgataaa gacttgttcg ctgaatttta cagaaaaaag 1320
cttgcacgga gacttctctt tgataagagt gcaaatgacg agcatgaacg aagtattttg 1380
actaaactaa agcaacagtg cggtggtcag ttcacatcga aaatggaggg gatggtcaca 1440
gatttgactt tggctaaaga aaatcaatcc agctttgagg agtatctggg aaataatgcc 1500
aatgtgaatc ctggcattga cttgacggtt actgttctga ccactggctt ctggcctagt 1560
tataaatcct ttgatctcaa ccttcctgct gagatggtca agtgcgttga agtatttaga 1620
gaattttatc aaacaaaaac gaagcataga aagctcacat ggatatattc tctgggtact 1680
tgtaatatca atggaaaatt tgaacccaaa accattgagc tgattgtgac aacctaccag 1740
gcctctgctc tcctgttatt taatacttct gataggttga gttatcaaga aatcatgact 1800
cagttaaatt tgtcggatga tgatgttgtt cgcctgcttc attccctttc atgtgccaag 1860

-continued

```
tataaaattc ttactaaaga gccgaacaac aaaacaattt cccctacgga ttactttgag   1920

ttcaactcca agttcactga caaaatgagg agaattaaga ttccactacc tccagttgat   1980

gagaagaaaa aggtaattga agatgttgac aaggaccggc gatatgccat tgatgcatct   2040

attgtccgca ttatgaagag ccgtaaagtt ttgggctacc aacaattggt tatggaatgt   2100

gttgagcaat tgggacgcat gtttaagcct gatgtcaaag caattaagaa gagaatcgaa   2160

gatttaataa cgcgtgatta tctggaaaga gacaaggata atgccaacct tttcagatat   2220

ttggcatga                                                           2229
```

<210> SEQ ID NO 45
<211> LENGTH: 2229
<212> TYPE: DNA
<213> ORGANISM: Cichorium intybus
<220> FEATURE:
<221> NAME/KEY: source
<222> LOCATION: 1..2229
<223> OTHER INFORMATION: /organism="Cichorium intybus"
/mol_type="unassigned DNA"

<400> SEQUENCE: 45

```
atgaatgaaa gaaaaacaat agacttagaa caaggatggg acttcatgca gaaaggcata     60

acaaagttga agaacattct agaaggtctt cccgagccac aattcagctc ggaagattac    120

atgatgctct acacaaccat gtacaatatg tgcacacaaa aaccgccaca tgattactct    180

caacaattgt atgacaaata ccgcgagtct tttgaagagt acattacttc aacggtgtta    240

ccttctttaa gagagaagca tgatgagttt atgcttagag agcttgttag aagatggtca    300

aatcataaag tgatggttag gtggctttct agattcttcc attatcttga tcgatacttc    360

attgcccgaa gatctcttcc accattaaat gaagttggac ttgcgtgttt tcgtgatctg    420

gtataccaag aggtgaatgg gaaagtgaga gatgctgtaa tatctttgat tgatcaagag    480

cgtgaaggcg agcaaattga ccgagcatta ctcaagaatg ttctagatat atttgttgaa    540

ataggaatgg gacaaatgga atattatgag aatgattttg aagcatccat gcttaatgat    600

acagcagcat attattcacg caaagcttcc aattggattc tagaagattc ttgtccagat    660

tatatgctca aagctgagga gtgcttaaaa agagaaaagg acagagtttc tcattatctt    720

cattccagca gtgaaccaaa gcttcttgag aaagttcaaa cagagttatt atctgtttat    780

gcaactcaat tgcttgaaaa ggagcactcc ggttgtcatg cattacttag ggatgacaag    840

gttgatgatt tatcaagaat gtacagactc ttttcaaaga tacaaaaagg gctggatcct    900

gtttctagta tgtttaagca gcatgtcact gctgaaggca caacattggt taaacaggca    960

gaagatgcag caagtactaa gaaggctgaa aagagagacg tggttggctt acaagaacag   1020

gtttttgtta gaaaagttat cgagcttcat gacaagtacc ttgcatatgt aaatgactgt   1080

tttatgaatc ataccctgtt tcacaaggct cttaaagagg catttgaaat attctgcaac   1140

aagggcgttg ctggaagttc aagtgcagaa ttacttgcta cattttgtga taatattctt   1200

aaaaaaggtg gaagtgaaaa attgagtgat gaagccattg aggacacact tgagaaggtg   1260

gtaaagttgc ttgcttacat cagcgataaa gatctatttg cagagtttta taggaaaaaa   1320

ctggctagac ggcttttatt tgacaaaagt gcaaatgatg agcacgaaag aagtattttg   1380

acaaaattga aacaacaatg tggcggtcaa tttacatcaa aaatggaagg aatggttaca   1440

gatttgacat tggcaaaaga aaatcaatca cattttgagg agtatttgaa taataatccc   1500

aatgttagcc ctggcattga cttgaccgtg actgtgttga ccactggttt ttggcctagt   1560
```

```
tacaaatctt ttgacctaaa tctccctgca gaaatggtca aatgcgttga agttttcaga   1620

gaattttatc aaacaaaaac aaaacacaga aaactcacat ggatatattc attgggcacc   1680

tgcaatataa acggaaaatt cgaaccaaaa accatggagc taatcgttac aacttaccag   1740

gcatctgctt tattactgtt caactcatca gatcgattga gttatcaaga aatcatgact   1800

caattaaact tatcagatga tgatgttgtt agactactcc attcattatc atgtgcaaaa   1860

tataaaattt tattaaaaga accaaataca aaaacaatct ctccaactga tttctttgaa   1920

ttcaactcaa agtttacaga taaaatgaga aggatcaaga ttcctctacc tcctgttgat   1980

gaaaagaaaa aagtaattga agatgttgac aaagaccgac gttatgcaat tgatgcttca   2040

attgtacgga taatgaaaag cagaaaagtt cttggatacc aacaattggt catggaatgt   2100

gttgaacaat taggccgtat gtttaagcct gatgtaaaag caatcaagaa acgtattgaa   2160

gatctcataa ctcgtgatta tcttgaaaga gacaaagaaa atccaaattt gtttcggtac   2220

ttggcatga                                                           2229
```

```
<210> SEQ ID NO 46
<211> LENGTH: 2229
<212> TYPE: DNA
<213> ORGANISM: Cichorium endivia
<220> FEATURE:
<221> NAME/KEY: source
<222> LOCATION: 1..2229
<223> OTHER INFORMATION: /organism="Cichorium endivia"
      /mol_type="unassigned DNA"

<400> SEQUENCE: 46
```

```
atgaatgaaa gaaaaacaat agacttagaa caaggatggg acttcatgca aaaaggcata     60

acaaagttga agaacattct agaaggtctt cccgagccac aattcagctc agaggattac    120

atgatgctct acacaaccat gtacaatatg tgcacacaaa aaccgccaca tgattactct    180

caacaattat atgacaaata ccgcgagtct tttgaagagt acataacttc aacggtgtta    240

ccttctttaa gagagaagca tgatgagttt atgcttagag agcttgttag aaggtggtca    300

aatcataaag tgatggttag gtggctttct agattcttcc attatcttga tcgatacttt    360

attgcaagaa gatctcttcc accattaaat gaagttggac ttgcgtgttt tcgtgatctg    420

gtataccaag aggtgaatgg aaaagtgaga gatgctgtaa tatctttgat tgatcaagag    480

cgtgaaggcg agcaaattga ccgagcatta ctgaagaatg ttctagatat atttgttgaa    540

ataggaatgg gacaaatgga atattatgag aatgattttg aagcatctat gcttaatgat    600

acagcagcat attattcacg caaagcttcc aactggattc tagaagattc ttgtccagat    660

tatatgctca aagctgagga gtgcttaaaa agagaaaagg acagagtttc tcattatctt    720

cattcaagta gtgaaccaaa gcttcttgag aaagttcaaa cagagttatt atctgtttat    780

gcaactcaat tgctcgaaaa ggaacactca ggttgtcatg cattacttag agatgacaag    840

gttgatgatt tatcaagaat gtacagactc ttttcaaaga tacaaaaagg actggatcct    900

gtttccagta tgtttaagca gcatgtcact gctgaaggca caacattagt aaaacaagca    960

gaagatgcag caagtactaa gaaggctgaa aagagagacg tggttggctt acaggaacag   1020

gtttttgtta gaaaagtaat cgagcttcat gacaagtacc tcgcatatgt aaacgactgt   1080

tttatgaatc acacattgtt ccacaaggct cttaaagagg catttgaaat attctgcaac   1140

aagggcgttg ctggaagttc aagtgcagaa ttacttgcca cattttgtga taatattctt   1200

aaaaaaggtg gaagtgaaaa attgagtgat gaagccattg aagacacact tgagaaggta   1260
```

```
gtaaagttgc ttgcttacat cagcgataaa gatctatttg cagagtttta taggaaaaaa   1320

ctggctagaa ggcttttatt tgacaaaagt gcaaatgatg agcatgaaag aagtatttta   1380

acaaagttga agcaacaatg tggtggtcag tttacatcaa agatggaagg aatggttaca   1440

gatttaacac tggcaaaaga aaatcaatca cattttgagg agtatttgaa taataatccc   1500

aatgttagcc ctggcattga cttgaccgtg actgtgttga ccacgggatt ttggcctagt   1560

tacaaatctt ttgacctaaa tcttcctgca gaaatggtca aatgcgttga agttttcaga   1620

gaattttatc aaacaaaaac aaaacacaga aaactcacat ggatttattc attgggcacc   1680

tgcaatatta acggaaaatt cgaaccaaaa accatggagc taatcgttac aacttaccag   1740

gcatctgctt tattgttatt caactcatca gatcgattaa gttatcaaga aatcatgact   1800

caattaaatt tatcagatga tgatgttgtt agactactac attcattatc atgtgcaaaa   1860

tataaaattt tattaaaaga accaaatacc aaaacaatat ctccaaccga tttctttgaa   1920

ttcaactcaa agtttacaga taaaatgaga aggatcaaga ttcctctacc tcctgttgat   1980

gaaaagaaaa aagtaattga agatgttgac aaagatagaa ggtatgcaat tgatgcttca   2040

attgtacgaa taatgaaaag cagaaaagtt cttggatacc aacaattggt tatggagtgt   2100

gttgaacaat taggccgtat gtttaagcct gatgtaaaag caatcaagaa gcgtattgaa   2160

gatttgataa cgcgtgatta tcttgaaaga gacaaagaaa atccaaattt gtttcggtac   2220

ttggcatga                                                            2229
```

<210> SEQ ID NO 47
<211> LENGTH: 2235
<212> TYPE: DNA
<213> ORGANISM: Allium ampeloprasum
<220> FEATURE:
<221> NAME/KEY: source
<222> LOCATION: 1..2235
<223> OTHER INFORMATION: /organism="Allium ampeloprasum"
      /mol_type="unassigned DNA"

<400> SEQUENCE: 47

```
atgtcgttgc acgaaaggaa aaccattgat ttggagcagg gatgggcttt tatgcagaaa     60

gggatcacca aactgaagaa tattcttgat gagttgaatg aacctcagtt cagctcagag    120

gattacatga tgctctatac gactatgtat aatatgtgta ctcagaagcc gccacatgat    180

tattctcagg agttgtatga taagtaccga gagtcctttg aagagtatat cactaccact    240

gtgcttcctt cattgagaga aaagcatgat gaatacatgt taagggagct cgtgagaagg    300

tggtcaaatc ataaaataat ggttagatgg ctttcacgct tttccatta tcttgatcgc    360

tactttatag cacgaagatc attgcctgct cttaatgaag tcggtctcac ttgtttccgt    420

gatctggtgt acaacgaagt ccatgggaaa gttaaagatg ccgtgatctc attgattgac    480

caagagaggg aaggggagca aattgacaga gctttattaa agaatgtttt gggtattttt    540

gtagagattg gtttgggaag catggaatgt tatgagaatg attttgaaac atcaatgctt    600

aatgctacag cagcctatta ttcacgaaaa gcttcaaatt ggattctaga agattcatgt    660

ccagattata tgctaaaagc cgaggagtgc ttaaaacatg agaaagatag agttgctcat    720

tatttgcatt caagcagtga acagaagctg ttagagaaag tgcaacatga gttacttttc    780

gtatatgcaa gtcaacttct cgagaaagaa cattccggat gtcatgcatt gcttcgcgat    840

gacaaggtgg gagatctttc acgcatgtat cggctgttct gtagaattac acgtggtttg    900

gaccctgtgt ctcaaatatt taagcagcat gtgactgcag aaggtactgc tttggtcaaa    960
```

```
catgccgaag atgctgcaag taacaagaag gccgagaaaa aagacattgt tggtttgcaa   1020
gagcaggtct tcgttaggaa agtaattgag ctgcatgata aatacttggc ctatgtgact   1080
gactgctttc aaaatcactc tctatttcac aaggcactta aagaggcatt cgaggtattc   1140
tgcaataaag gtgttgcagg tagctcaagc gctgaacttc tggctgcttt ttgtgacaat   1200
atattgaaga agggtggaag cgagaaacta agcgatgagg ccatagagga tactcttgag   1260
aaggttgtaa aactattggc atatattagc gataaagatc tgtttgctga attttacagg   1320
aagaagcttg cacgaagatt actctttgac aaaagtgcta atgatgacca tgagaggagc   1380
atccttacaa agctgaaaca gcaatgtgga gggcagttca cctctaaaat ggaaggcatg   1440
gtaaccgatc tgacacttgc acgagaaaat caatcaagtt ttgacgatta ccttagcagc   1500
aatcctaaag caaattctgg aattgacttg actgttacag tcttaacaac tggcttctgg   1560
cccagttaca agtcttttga tctcaatctt cctgatgaga tggtaaaatg cgttgaaatt   1620
tttaaagagt tttacgagac aaaaaccaaa cacagaaaac ttacatggat ttattcgttg   1680
ggcacttgca acatcaatgg caagttcgaa accaagacaa tagagttggt tgttacaacc   1740
tatcaggctg cagtgttgct tctattcaac tctgcagata aattaagtta ttctgagatt   1800
gtgcagcagc taaacttatc tgatgatgat gtaatcagat tacttcactc tctttcatgc   1860
gctaaataca aaattctcaa taaagaaccc gctaccaaga ctattacccc gaatgatcat   1920
tttgagttca attctaaatt cactgataga atgagaagga tcaagattcc cctgcctcct   1980
gtggatgaga agaaaaaagt aattgaagat gttgacaaag acagaagata tgcaattgac   2040
gcatccatag ttcgaataat gaaaagtaga aaagttcttg gtcatcagca gcttgttttg   2100
gaatgtgttg agcaattagg ccgcatgttt aagcctgact ttaaggccat caagaaaagg   2160
attgaagatc tgatcgctag agattatttg gagagggaca aggacaatcc aaacctcttt   2220
aaatatttgg cctaa                                                    2235
```

<210> SEQ ID NO 48
<211> LENGTH: 2229
<212> TYPE: DNA
<213> ORGANISM: Lactuca sativa
<220> FEATURE:
<221> NAME/KEY: source
<222> LOCATION: 1..2229
<223> OTHER INFORMATION: /organism="Lactuca sativa"
/mol_type="unassigned DNA"

<400> SEQUENCE: 48

```
atgaacgaaa gaaaaacaat agacttagag caaggatggg acttcatgca gaaaggaata     60
acaaagttga agaatattct agaaggtctt cccgagccac aattcagctc ggaggattac    120
atgatgctct acacaaccat gtacaacatg tgtacacaga aaccaccaca tgattactcc    180
caacagttgt atgacaaata tcgtgagtct tttgaagagt atattacttc aactgtgtta    240
ccttctttaa gagagaagca tgatgagttc atgctgagag agcttgttag aaggtggtca    300
aatcataaag tcatggtgcg gtggctttct agattcttcc attatcttga ccgatatttc    360
attgcccgaa gatctcttcc gccactaaat gaagttggac ttgcctgttt tcgtgatctg    420
gtataccaag aggtgaatgg taaagtgaga gatgctgtaa tatctttgat tgatcaagag    480
cgtgaagggg agcagattga tcgagcttta ctgaagaatg ttctagatat atttgttgag    540
ataggaatgg gacaaatgga gtattatgag aatgattttg aagcatccat gcttaatgat    600
acagcagcat attattcacg caaggcttcc aactggattc tagaagattc ttgtccagat    660
```

```
tatatgctca aagcagagga gtgcttaaaa agagaaaagg acagagtgtc tcattatctt    720
cattccagca gtgagccaaa gcttcttgag aaagttcaaa atgagttatt gtctgtttat    780
gcaactcaat tgcttgagaa agagcactca ggttgtcatg cattgctcag ggatgacaag    840
gttgatgatt tatcaagaat gtacagactc ttttcaaaga taccaaaagg attggatcct    900
gtttctagta tgtttaagca gcatgtcact gctgaaggca caacattggt taaacaagca    960
gaagatgcag caagtaccaa gaaggctgaa aagagagatg tggttgggtt gcaggaacag   1020
gtttttgtta gaaaagttat tgagctccat gacaagtacc tggcatatgt aaatgactgt   1080
ttcatgaacc atactctttt ccacaaggct cttaaagagg catttgaaat attctgcaac   1140
aagggtgttg ctggaagttc aagtgcagag ttacttgcca cattttgtga taatattctt   1200
aaaaaaggtg gaagtgagaa actgagcgat gaagccattg aggacaccct tgagaaggta   1260
gtaaagttgc ttgcctacat cagtgataaa gatctatttg ctgaatttta caggaaaaaa   1320
cttgctagga ggcttttgtt tgacaagagt gcaaacgatg agcatgagag aagtattctc   1380
acaaagctga agcaacagtg tggtggtcag ttcacatcaa agatggaagg gatggttaca   1440
gatttgacat tggcaaagga aaaccaatcc cattttgaag agtatttgaa caataatccc   1500
aatgtcagcc ctggaattga cttgactgtc actgtgttga ctaccggctt ctggcccagc   1560
tacaaatctt ttgacctaaa tctccctgcc gaaatggtta aatgcgttga agttttcaga   1620
gaattttatc aaacaaaaac aaagcacagg aagcttacat ggatatattc attgggtacc   1680
tgcaatataa acgggaaatt tgaacccaaa acaatggagc tcatagtcac aacctaccag   1740
gcatctgctt tattactgtt caacttatcg gatcgattga gttatcaaga aatcatgact   1800
cagttgaact tgtcagatga tgatgttgtt aggctgctcc attctttgtc atgtgcaaaa   1860
tacaaaattc ttttaaagga gcctaatacc aaaacaatct ctccaaccga ttacttcgaa   1920
ttcaactcca agtttacaga taaaatgagg aggatcaaga ttcctctacc tcctgtggat   1980
gagaagaaaa aggtgattga ggatgttgac aaagacagac gttatgccat tgatgcttcc   2040
attgtaagga taatgaagag cagaaaggtg cttggatacc agcagttggt tatggagtgt   2100
gttgaacagt tgggacgcat gtttaagcct gatgtaaaag caatcaagaa gcggattgaa   2160
gatctgataa ctcgtgatta tcttgaaaga gacaaagaga accccaactt gttccgatac   2220
ttggcatga                                                           2229
```

```
<210> SEQ ID NO 49
<211> LENGTH: 2217
<212> TYPE: DNA
<213> ORGANISM: Raphanus sativus
<220> FEATURE:
<221> NAME/KEY: source
<222> LOCATION: 1..2217
<223> OTHER INFORMATION: /organism="Raphanus sativus"
      /mol_type="unassigned DNA"

<400> SEQUENCE: 49
```

```
atggagcgga agacgattga tctggaacaa ggatgggact atatgcagac tgggatcact      60
aagctgaaac ggattcttga aggattgcct gagccgcaat tcgactctga gcagtacatg     120
atgctttata cgactatgta caacatgtgc acccagaaac ctcctcatga ttactctcag     180
cagctttatg acaagtatcg cgaagctttt gaggagtaca ttgactctac tgttttgcct     240
gctttgaagg agaagcatga tgaatacatg ctacgggagc tggttaagag atggtctaac     300
cataaagtta tggttagatg gctatcccga ttcttctact atcttgaccg ttacttcatt     360
```

gctcggagat cgctgccacc gcttaatgaa gttgggctca catgcttccg tgaccgggtg 420
tataaggagt tgcattccaa ggtcaaagat gctgtaatag cacttgttga taaagaacgg 480
gaaggcgagc agattgacag ggctcttctg aaaaacgtat tagatatcta tgtagagatt 540
ggaatgggac agatggaaag atacgaagtg gattttgaaa gcttcatgct tttggattca 600
gcatcttact attctcgcaa agcatcaaac tggatccagg aagattcttg ccctgattac 660
atgctgaagt ctgaagaatg ccttaagaag gagagggaga gggttgctca ctaccttcat 720
tcaagcagcg agccaaagct ggttgagaaa gtacaacatg agctgttggt tgtctatgca 780
aatcagcttc ttgaaaagga gcactcaggg tgccgtgcat tgctgagaga cgacaaggtt 840
gacgatctct ccaggatgta caggctctat cataaaattg ctaaaggttt agaacctgtt 900
gcaaacatat ttaagcagca tgtcacagcc gagggtaacg cacttgtcca acaggccgaa 960
gacacagcca ctaatcaggc tgcaaatact gctagcgtgc aggaacaggt tctcatcaga 1020
aaagtgattg agctacatga taagtacatg gtctatgtcg tggagtgctt ccagaaccac 1080
accctcttcc acaaggctct gaaagaggca tttgagatat tctgtaacaa aacagtcgct 1140
ggaagttcaa gtgcagaact gcttgcaaca ttctgcgaca acatcctcaa gaagggggggt 1200 agtgagaagc tgagtgacga agctattgaa gatacgcttg agaaggttgt caaattgctt 1260
gcttatataa gcgacaagga tcttttcgcc gagttctaca ggaagaagct ggcacgtagg 1320
ctcttatttg atcgcagtgc gaatgatgat catgagagaa gcatccttac aaagctcaag 1380
caacaatgtg gtgggcagtt cacttctaag atggagggca tggtaacgga cttgacattg 1440
gcaagagaga accaaaccag tttcgaggag tatctaggca ataaccccgc tgcaaaccca 1500
gggattgatt tgaccgtcac tgttcttacc actggtttct ggccaagtta caaatcattc 1560
gacataaatc taccaagtga aatggtcaag tgtgttgaag ttttcaaagg gttttatgag 1620
acgaaaacta aacataggaa acttacatgg atctactcac taggaacttg tcacctcaac 1680
ggaaagtttg atcacaagcc cattgagtta gttgtgtcta cttaccaggc tgctgtgctt 1740
ctgctgttca acacaacaga caaattgagc tacaacgata tcctaactca actgaaccta 1800
agccacgaag atttagtgag gttgcttcat tccctgtcat gtgctaggta caagatcctt 1860
ctcaaggagc caagcacgaa gactgttaca cagactgatt catttgaatt caatgccaaa 1920
ttcacggaca gaatgcgcag aatcaagatc cctctccctc ctgttgatga aaggaagaag 1980
gttgtggaag atgtggacaa agacagacgc tatgcgattg atgctgccat tgttaggatc 2040
atgaagagca ggaaagtgtt gggacatcaa caactcgtct ctgagtgcgt tgagcaactt 2100
agccgaatgt tcaagcctga tatcaaagcg atcaagaagc gtatggagga tctaattacg 2160
agggattatt tggagaggga caaggagaac cctaacatgt ttaggtactt ggcttag 2217

<210> SEQ ID NO 50
<211> LENGTH: 2223
<212> TYPE: DNA
<213> ORGANISM: Spinacia oleracea
<220> FEATURE:
<221> NAME/KEY: source
<222> LOCATION: 1..2223
<223> OTHER INFORMATION: /organism="Spinacia oleracea"
/mol_type="unassigned DNA"

<400> SEQUENCE: 50
atgaacgatc gtaaagttat cgaactagag caaggatggg agttcatggg gaaggggatt 60
acgaagttga aaaggatttt ggaaggatta ccagagccgc cttttaattc ggaagactac 120

```
atgatgctgt acacgacaat gtacaacatg tgtacacaga aacccccctca tgattactct    180
caacaactct atgacaatta caaagaggca tttgtggatt acatacattc aacggtttta    240
ccttctttgg gggacaaaca tgatgagttt atgctgagag agcttgtgaa gagatggtca    300
aatcataaag taatggtgag gtggttgtct cgcttcttcc attatctgga tcggtacttc    360
atcgctcgga gatcgcttcc ttctttgaat gatgttggat tgacgtgctt ccgtgatctg    420
gtttatcaag aaatatctgg caaagccaag gatgctgtta ttgctctgat tgatgaagaa    480
agagagggtg ggcaaattga cagagcctta ttgaagaatg tacttgatat atacgttgaa    540
attggaatga cacaaatgga ttactacgaa aaggactttg aagctcatat gctggatgat    600
actgctgctt attactcacg caaggcctca agctggattc tggaggactc atgtccggaa    660
tacatgttga agtcggagga gtgtttgaag aaagagaaag atagagtggc tcattatcta    720
cattccagca gtgagccaaa gcttctggag aaagtacaaa atgagttgct actggtttac    780
gaaaatcagt tgcttgagaa ggagaattct ggatgtcgtg cattgttgaa agatgacaag    840
gtggaagatc tttccaggat gtacaggctt tatagcaagg ttaccaaagg gttggaaccc    900
attggcagta tcttcaaaca gcatataacc gatgaaggaa cagccctggt gcagcaggcc    960
gaagacgctg caattagcaa ggctgaaaat gctggcggtg gttcacatga gcaggtcttc   1020
gtcaggaaag tgattgagtt gcatgacaaa tttatgacct atgttacaga ttgcttcaac   1080
agccatacca tctttcacaa ggctctcaag gaagcttttg aggtattctt aaacaagggt   1140
gttgctggta gttcaagtgc tgaacttcta gcttcatttt gtgataatat tctcaagaaa   1200
ggtggtagtg aaaaattaag tgatgaggct attgaggatt cactggagaa ggtggtgaag   1260
cttctcgcat atgtcagtga taaagacctg tttgctgaat tttacagaaa gaagctctct   1320
cgccggctac tctttgacaa aagtgctaat gatgatcatg agaggagtat tttaacaaaa   1380
ttgaagcagc agtgtggggg acagttcaca tcaaagatgg aggggatggt gacagacttg   1440
acattggcga gggagaatca aactaatttt gaggaatatc ttggacaaaa tacagatgcc   1500
agtcctggtc ttgatttgac tgtgacagtt ttgaccactg ggttctggcc aagttacaaa   1560
tcttctgatc ttaaccttcc tgctgagatg gtgaggtgtg ttgaagtttt taagcaattt   1620
tatcaaacaa agacaaaaca caggaagctc acctgggtat attcgttggg aagttgtaac   1680
attaatggca agtttggtcc gaaaacaatt gaattggttg ttggaactta tcaggctgct   1740
gcgctgatgc tctttaacac atcagatcga ctgagttatt cagaaataac gacccaacta   1800
aatctagctg acgaagactt ggttagagtg cttcaatctc tatcttgcgc aaagtataag   1860
attcttctaa aagagccaag cacaagaaac gtgatctcaa ctgattgttt ttcattcaac   1920
tctaatttta ctgacagaat gaggaggatt aggattcctc ttcctccaat ggatgagagg   1980
aaaaaggttg ttgaagatgt tgacaaagat agaagatatg ctattgatgc ctcaattgta   2040
cgcataatga aaagtaggaa ggctttggga tatcaacaat taatcacgga gtgtgtggag   2100
cagctaagcc gcatgttcaa gcctgatttc aaagcaatta agaagaggat cgaggacttg   2160
ataaccagag attatattga aagagacaag gaaaaccctc agctattccg gtacttggct   2220
tga                                                                 2223
```

<210> SEQ ID NO 51
<211> LENGTH: 2220
<212> TYPE: DNA
<213> ORGANISM: Beta vulgaris
<220> FEATURE:

<221> NAME/KEY: source
<222> LOCATION: 1..2220
<223> OTHER INFORMATION: /organism="Beta vulgaris"
/mol_type="unassigned DNA"

<400> SEQUENCE: 51

```
atgaatgatc gtaaagttat tgaactagag caaggatggg agttcatggg gaaggggatt     60
acaaagttga agaggattct ggaaggattg ccagagccac catttaattc tgaagactac    120
atgatgttgt acacgacgat gtacaatatg tgtactcaga aaccccccaca tgattactct    180
caacagctct atgacaatta caaacaggct tttgtggatt acatcaactc gacggtttta    240
ccttctttgc gggagaagca tgatgagttt atgttaagag aacttgtgaa aagatgggca    300
aatcataaag taatggtcag gtggttgtct cgtttcttcc attatctgga ccggtatttc    360
attgctcgga ggtcgcttcc ttctttgaat gaagttggac tgacttgttt ccgtgatctg    420
gtttatcaag aaatatctgg caaagccaag gatgctgtta tagccctgat tgatatagaa    480
agagaaggtg ggcagattga cagatcatta ttgaaaaatg tacttgatat atatgttgaa    540
attggaatgg gacaaatgga tcactatgaa aaagactttg aagctcatat gctggatgat    600
actgctgctt actactcgcg caaagcgtct agctggattc ttgaggactc ttgtccggaa    660
tacatgttaa agtctgagga gtgtttgaag aaggagaaag agagagtggc taattattta    720
cattccagca gtgagccaaa gcttctggag aaagtgcaaa acgagttgct attggtttat    780
gaaagccaat tgcttgagaa ggagaattcg ggatgtcgtg cattactgaa agatgacaag    840
gtggatgatc tttccaggat gtacaggctt tacagtaagg ttaccaaagg attggaaccc    900
attggcagta tcttcaaaca gcatataact gatgaaggaa cagccttagt gcagcaggcc    960
gaagatgctg ctatcagcaa ggctgaaaat actggtggtt cacatgagca ggtcttcgtc   1020
aggaaagtaa tagagttgca tgacaaattc atgacttatg tcaccgattg cttcaacagc   1080
cataccatat ttcacaaggc tcttaaggag gcttttgagg tatttttgaa caagggtgtt   1140
gctggtagct caagtgctga gttgctagct acattctgtg ataacattct caagaaaggt   1200
gggagcgaaa aactaagcga tgaggctatt gaggattcac ttgagaaggt ggtgaagctt   1260
ctggcctatg tcagtgataa agacctgttt gctgaatttt acagaaagaa gctctctcgc   1320
cggctactct ttgacaagag tgctaatgat gatcatgaaa gaagtatttt aaccaaattg   1380
aagcagcagt gtggcggaca attcacatca aagatggagg ggatggtgac agacttgacc   1440
ttggcgaggg agaatcaaac taattttgag gaatatctta gtcagaatcc agatgccagt   1500
cctggtcttg atttgactgt gactgttctg acaactgggt tctggccaag ttacaaatct   1560
tccgatctta accttcccgc tgagatggtg aggtgtgttg aagtttttaa gcagttctat   1620
tcaactaaaa caaagcacag gaagctgacc tgggtttact cattgggaag ctgtaatatt   1680
aatggcaagt ttggtccaaa aactattgaa ttggttgtcg gaacttatca ggctgctgct   1740
ttgatgctct ttaacacatc agaccgactg agttattcag agatagcaac tcaactaaat   1800
ttagctgatg aagatctggt tagagtgctt caatctttat cctgcgcaaa gtataagatt   1860
cttttaaagg agccaaacac gaaaaccgtg tccccgactg attgtttttc atttaactct   1920
agtttcactg acaggatgag gaggataaga attcctcttc ctccgatgga tgagaggaaa   1980
aaggttgttg aggatgttga caaagataga agatatgcta ttgatgcctc aattgtacgc   2040
ataatgaaaa gtaggaaggt tttggggtac cagcaattaa tcacagagtg tgtggagcag   2100
ctaagccgca tgttcaagcc tgatttcaag gcaattaaga agaggatcga ggacttaata   2160
```

acccgagatt atattgaaag agacaaggag aacccgcagc tattccgata cttggcttga 2220

<210> SEQ ID NO 52
<211> LENGTH: 744
<212> TYPE: PRT
<213> ORGANISM: Cucumis sativus

<400> SEQUENCE: 52

Met Thr Met Gly Glu Arg Lys Thr Ile Asp Leu Glu Gln Gly Trp Glu
1 5 10 15

Phe Met Gln Lys Gly Ile Thr Lys Leu Lys Asn Ile Leu Glu Gly Leu
20 25 30

Pro Glu Pro Gln Phe Ser Ser Glu Asp Tyr Met Met Leu Tyr Thr Thr
35 40 45

Met Tyr Asn Met Cys Thr Gln Lys Pro Pro His Asp Tyr Ser Gln Gln
50 55 60

Leu Tyr Asp Lys Tyr Arg Glu Ser Phe Glu Glu Tyr Ile Thr Ser Met
65 70 75 80

Val Leu Pro Ser Leu Arg Glu Lys His Asp Glu Phe Met Leu Arg Glu
85 90 95

Leu Val Lys Arg Trp Thr Asn His Lys Val Met Val Arg Trp Leu Ser
100 105 110

Arg Phe Phe His Tyr Leu Asp Arg Tyr Phe Ile Ala Arg Arg Ser Leu
115 120 125

Pro Pro Leu Asn Glu Val Gly Leu Thr Cys Phe Arg Glu Leu Val Tyr
130 135 140

Lys Glu Leu Asn Ser Lys Val Arg Asp Ala Val Ile Ser Leu Ile Asp
145 150 155 160

Gln Glu Arg Glu Gly Glu Gln Ile Asp Arg Ala Leu Leu Lys Asn Val
165 170 175

Leu Asp Ile Phe Val Glu Ile Gly Met Gly Gln Met Asp Tyr Tyr Glu
180 185 190

Asn Asp Phe Glu Ala Ala Met Leu Lys Asp Thr Ala Ala Tyr Tyr Ser
195 200 205

Arg Lys Ala Ser Asn Trp Ile Leu Glu Asp Ser Cys Pro Asp Tyr Met
210 215 220

Leu Lys Ala Glu Glu Cys Leu Lys Arg Glu Lys Asp Arg Val Ser His
225 230 235 240

Tyr Leu His Ser Ser Ser Glu Pro Lys Leu Leu Glu Lys Val Gln His
245 250 255

Glu Leu Leu Ser Val Tyr Ala Thr Gln Leu Leu Glu Lys Glu His Ser
260 265 270

Gly Cys His Ala Leu Leu Arg Asp Asp Lys Val Glu Asp Leu Ser Arg
275 280 285

Met Phe Arg Leu Phe Ser Lys Ile Pro Lys Gly Leu Asp Pro Val Ser
290 295 300

Asn Ile Phe Lys Gln His Val Thr Ala Glu Gly Thr Ala Leu Val Lys
305 310 315 320

Gln Ala Glu Asp Ala Ala Ser Asn Lys Lys Ala Glu Lys Lys Asp Ile
325 330 335

Val Gly Leu Gln Glu Gln Val Phe Val Arg Lys Val Ile Glu Leu His
340 345 350

Asp Lys Tyr Leu Ala Tyr Val Asn Asp Cys Phe Gln Asn His Thr Leu
355 360 365

-continued

```
Phe His Lys Ala Leu Lys Glu Ala Phe Glu Val Phe Cys Asn Lys Gly
    370                 375                 380

Val Ala Gly Ser Ser Ser Ala Glu Leu Leu Ala Thr Phe Cys Asp Asn
385                 390                 395                 400

Ile Leu Lys Lys Gly Gly Ser Glu Lys Leu Ser Asp Glu Ala Ile Glu
                405                 410                 415

Glu Thr Leu Glu Lys Val Val Lys Leu Leu Ala Tyr Ile Cys Asp Lys
            420                 425                 430

Asp Leu Phe Ala Glu Phe Tyr Arg Lys Lys Leu Ala Arg Arg Leu Leu
        435                 440                 445

Phe Asp Lys Ser Ala Asn Asp Asp His Glu Arg Ser Ile Leu Thr Lys
    450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Thr Ser Phe Glu Glu
                485                 490                 495

Tyr Leu Ser Asn Asn Pro Gln Ala Ser Pro Gly Ile Asp Leu Thr Val
            500                 505                 510

Thr Val Leu Thr Thr Gly Phe Trp Pro Ser Tyr Lys Ser Phe Asp Leu
        515                 520                 525

Asn Leu Pro Ala Glu Met Val Lys Cys Val Glu Val Phe Arg Glu Phe
    530                 535                 540

Tyr Gln Thr Lys Thr Lys His Arg Lys Leu Thr Trp Ile Tyr Ser Leu
545                 550                 555                 560

Gly Thr Cys Asn Ile Ser Gly Lys Phe Glu Pro Lys Thr Met Glu Leu
                565                 570                 575

Ile Val Thr Thr Tyr Gln Ala Ser Ala Leu Leu Leu Phe Asn Ser Ser
            580                 585                 590

Asp Arg Leu Ser Tyr Ser Glu Ile Met Thr Gln Leu Asn Leu Ser Asp
        595                 600                 605

Asp Asp Val Val Arg Leu Leu His Ser Leu Ser Cys Ala Lys Tyr Lys
    610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Lys Val Ile Glu Asp Val Asp
            660                 665                 670

Lys Asp Arg Arg Tyr Ala Ile Asp Ala Ser Ile Val Arg Ile Met Lys
        675                 680                 685

Ser Arg Lys Val Leu Gly His Gln Gln Leu Val Met Glu Cys Val Glu
    690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
            740
```

<210> SEQ ID NO 53
<211> LENGTH: 744
<212> TYPE: PRT
<213> ORGANISM: Cucumis melo

<400> SEQUENCE: 53

-continued

```
Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
            20                  25                  30

Pro Glu Pro Gln Phe Ser Ser Glu Asp Tyr Met Met Leu Tyr Thr Thr
        35                  40                  45

Met Tyr Asn Met Cys Thr Gln Lys Pro Pro His Asp Tyr Ser Gln Gln
    50                  55                  60

Leu Tyr Asp Lys Tyr Arg Glu Ser Phe Glu Glu Tyr Ile Thr Ser Met
65                  70                  75                  80

Val Leu Pro Ser Leu Arg Glu Lys His Asp Glu Phe Met Leu Arg Glu
                85                  90                  95

Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
        115                 120                 125

Pro Pro Leu Asn Glu Val Gly Leu Thr Cys Phe Arg Glu Leu Val Tyr
    130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
            180                 185                 190

Asn Asp Phe Glu Ala Ala Met Leu Lys Asp Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Lys Arg Glu Lys Asp Arg Val Ser His
225                 230                 235                 240

Tyr Leu His Ser Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
            260                 265                 270

Gly Cys His Ala Leu Leu Arg Asp Asp Lys Val Glu Asp Leu Ser Arg
        275                 280                 285

Met Phe Arg Leu Phe Ser Lys Ile Pro Lys Gly Leu Asp Pro Val Ser
    290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Asn Asp Cys Phe Gln Asn His Thr Leu
        355                 360                 365

Phe His Lys Ala Leu Lys Glu Ala Phe Glu Val Phe Cys Asn Lys Gly
    370                 375                 380

Val Ala Gly Ser Ser Ser Ala Glu Leu Leu Ala Thr Phe Cys Asp Asn
385                 390                 395                 400

Ile Leu Lys Lys Gly Gly Ser Glu Lys Leu Ser Asp Glu Ala Ile Glu
                405                 410                 415
```

```
Glu Thr Leu Glu Lys Val Val Lys Leu Leu Ala Tyr Ile Cys Asp Lys
            420                 425                 430

Asp Leu Phe Ala Glu Phe Tyr Arg Lys Lys Leu Ala Arg Arg Leu Leu
        435                 440                 445

Phe Asp Lys Ser Ala Asn Asp Asp His Glu Arg Ser Ile Leu Thr Lys
    450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Thr Ser Phe Glu Glu
                485                 490                 495

Tyr Leu Ser Asn Asn Pro Gln Ala Ser Pro Gly Ile Asp Leu Thr Val
            500                 505                 510

Thr Val Leu Thr Thr Gly Phe Trp Pro Ser Tyr Lys Ser Phe Asp Leu
        515                 520                 525

Asn Leu Pro Ala Glu Met Val Lys Cys Val Glu Val Phe Arg Glu Phe
    530                 535                 540

Tyr Gln Thr Lys Thr Lys His Arg Lys Leu Thr Trp Ile Tyr Ser Leu
545                 550                 555                 560

Gly Thr Cys Asn Ile Ser Gly Lys Phe Glu Pro Lys Thr Met Glu Leu
                565                 570                 575

Ile Val Thr Thr Tyr Gln Ala Ser Ala Leu Leu Leu Phe Asn Ser Ser
            580                 585                 590

Asp Arg Leu Ser Tyr Ser Glu Ile Met Thr Gln Leu Asn Leu Ser Asp
        595                 600                 605

Asp Asp Val Val Arg Leu Leu His Ser Leu Ser Cys Ala Lys Tyr Lys
    610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Lys Val Ile Glu Asp Val Asp
            660                 665                 670

Lys Asp Arg Arg Tyr Ala Ile Asp Ala Ser Ile Val Arg Ile Met Lys
        675                 680                 685

Ser Arg Lys Val Leu Gly His Gln Gln Leu Val Met Glu Cys Val Glu
    690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
            740


<210> SEQ ID NO 54
<211> LENGTH: 744
<212> TYPE: PRT
<213> ORGANISM: Cucurbita pepo

<400> SEQUENCE: 54

Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
            20                  25                  30

Pro Glu Pro Gln Phe Ser Ser Glu Asp Tyr Met Met Leu Tyr Thr Thr
        35                  40                  45
```

-continued

```
Met Tyr Asn Met Cys Thr Gln Lys Pro Pro His Asp Tyr Ser Gln Gln
    50                  55                  60

Leu Tyr Asp Lys Tyr Arg Glu Ser Phe Glu Glu Tyr Ile Ser Ser Met
65                  70                  75                  80

Val Leu Pro Ser Leu Arg Glu Lys His Asp Glu Phe Met Leu Arg Glu
                85                  90                  95

Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
        115                 120                 125

Pro Pro Leu Asn Glu Val Gly Leu Thr Cys Phe Arg Glu Leu Val Tyr
    130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
            180                 185                 190

Asn Asp Phe Glu Ala Ala Met Leu Lys Asp Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Arg Arg Glu Lys Asp Arg Val Ser His
225                 230                 235                 240

Tyr Leu His Ser Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
            260                 265                 270

Gly Cys His Ala Leu Leu Arg Asp Asp Lys Val Glu Asp Leu Ser Arg
        275                 280                 285

Met Phe Arg Leu Phe Ser Lys Ile Pro Lys Gly Leu Asp Pro Val Ser
    290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Asn Asp Cys Phe Gln Asn His Thr Leu
        355                 360                 365

Phe His Lys Ala Leu Lys Glu Ala Phe Glu Val Phe Cys Asn Lys Gly
    370                 375                 380

Val Ala Gly Ser Ser Ser Ala Glu Leu Leu Ala Thr Phe Cys Asp Asn
385                 390                 395                 400

Ile Leu Lys Lys Gly Gly Ser Glu Lys Leu Ser Asp Glu Ala Ile Glu
                405                 410                 415

Glu Thr Leu Glu Lys Val Val Lys Leu Leu Ala Tyr Ile Cys Asp Lys
            420                 425                 430

Asp Leu Phe Ala Glu Phe Tyr Arg Lys Lys Leu Ala Arg Arg Leu Leu
        435                 440                 445

Phe Asp Lys Ser Ala Asn Asp Asp His Glu Arg Ser Ile Leu Thr Lys
    450                 455                 460
```

Leu Lys Gln Gln Cys Gly Gly Gln Phe Thr Ser Lys Met Glu Gly Met
465 470 475 480

Val Thr Asp Leu Thr Leu Ala Arg Glu Asn Gln Thr Ser Phe Glu Glu
485 490 495

Tyr Leu Ser Asn Asn Pro Gln Ala Ser Pro Gly Ile Asp Leu Thr Val
500 505 510

Thr Val Leu Thr Thr Gly Phe Trp Pro Ser Tyr Lys Ser Phe Asp Leu
515 520 525

Asn Leu Pro Ala Glu Met Val Lys Cys Val Glu Val Phe Arg Glu Phe
530 535 540

Tyr Gln Thr Lys Thr Lys His Arg Lys Leu Thr Trp Ile Tyr Ser Leu
545 550 555 560

Gly Thr Cys Asn Ile Ser Gly Lys Phe Glu Pro Lys Thr Met Glu Leu
565 570 575

Ile Val Thr Thr Tyr Gln Ala Ser Ala Leu Leu Leu Phe Asn Ser Ser
580 585 590

Asp Lys Leu Ser Tyr Ser Glu Ile Met Thr Gln Leu Asn Leu Ser Asp
595 600 605

Asp Asp Val Val Arg Leu Leu His Ser Leu Ser Cys Ala Lys Tyr Lys
610 615 620

Ile Leu Asn Lys Glu Pro Asn Thr Lys Thr Ile Ser Pro Asn Asp His
625 630 635 640

Phe Glu Phe Asn Ala Lys Phe Ser Asp Lys Met Arg Arg Ile Lys Ile
645 650 655

Pro Leu Pro Pro Val Asp Glu Lys Lys Lys Val Ile Glu Asp Val Asp
660 665 670

Lys Asp Arg Arg Tyr Ala Ile Asp Ala Ser Ile Val Arg Ile Met Lys
675 680 685

Ser Arg Lys Val Leu Gly His Gln Gln Leu Val Met Glu Cys Val Glu
690 695 700

Gln Leu Gly Arg Met Phe Lys Pro Asp Phe Lys Ala Ile Lys Lys Arg
705 710 715 720

Ile Glu Asp Leu Ile Thr Arg Asp Tyr Leu Glu Arg Asp Lys Asp Asn
725 730 735

Pro His Leu Phe Arg Tyr Leu Ala
740

<210> SEQ ID NO 55
<211> LENGTH: 744
<212> TYPE: PRT
<213> ORGANISM: citrillus lanatus

<400> SEQUENCE: 55

Met Thr Met Gly Glu Arg Lys Thr Ile Asp Leu Glu Gln Gly Trp Glu
1 5 10 15

Phe Met Gln Lys Gly Ile Thr Lys Leu Lys Asn Ile Leu Glu Gly Leu
20 25 30

Pro Glu Pro Gln Phe Ser Ser Glu Asp Tyr Met Met Leu Tyr Thr Thr
35 40 45

Met Tyr Asn Met Cys Thr Gln Lys Pro Pro His Asp Tyr Ser Gln Gln
50 55 60

Leu Tyr Asp Lys Tyr Arg Glu Ser Phe Glu Glu Tyr Ile Thr Ser Met
65 70 75 80

Val Leu Pro Ser Leu Arg Glu Lys His Asp Glu Phe Met Leu Arg Glu
85 90 95

-continued

```
Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
        115                 120                 125

Pro Pro Leu Asn Glu Val Gly Leu Thr Cys Phe Arg Glu Leu Val Tyr
    130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
            180                 185                 190

Asn Asp Phe Glu Ala Ala Met Leu Lys Asp Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Lys Arg Glu Lys Asp Arg Val Ser His
225                 230                 235                 240

Tyr Leu His Ser Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
            260                 265                 270

Gly Cys His Ala Leu Leu Arg Asp Asp Lys Val Glu Asp Leu Ser Arg
        275                 280                 285

Met Phe Arg Leu Phe Ser Lys Ile Pro Lys Gly Leu Asp Pro Val Ser
    290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Asn Asp Cys Phe Gln Asn His Thr Leu
        355                 360                 365

Phe His Lys Ala Leu Lys Glu Ala Phe Glu Val Phe Cys Asn Lys Gly
    370                 375                 380

Val Ala Gly Ser Ser Ser Ala Glu Leu Leu Ala Thr Phe Cys Asp Asn
385                 390                 395                 400

Ile Leu Lys Lys Gly Gly Ser Glu Lys Leu Ser Asp Glu Ala Ile Glu
                405                 410                 415

Glu Thr Leu Glu Lys Val Val Lys Leu Leu Ala Tyr Ile Cys Asp Lys
            420                 425                 430

Asp Leu Phe Ala Glu Phe Tyr Arg Lys Lys Leu Ala Arg Arg Leu Leu
        435                 440                 445

Phe Asp Lys Ser Ala Asn Asp Asp His Glu Arg Ser Ile Leu Thr Lys
    450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Thr Ser Phe Glu Glu
                485                 490                 495

Tyr Leu Ser Asn Asn Pro Gln Ala Ser Pro Gly Ile Asp Leu Thr Val
            500                 505                 510
```

```
Thr Val Leu Thr Thr Gly Phe Trp Pro Ser Tyr Lys Ser Phe Asp Leu
        515                 520                 525

Asn Leu Pro Ala Glu Met Val Lys Cys Val Glu Val Phe Arg Glu Phe
    530                 535                 540

Tyr Gln Thr Lys Thr Lys His Arg Lys Leu Thr Trp Ile Tyr Ser Leu
545                 550                 555                 560

Gly Thr Cys Asn Ile Ser Gly Lys Phe Glu Pro Lys Thr Met Glu Leu
                565                 570                 575

Ile Val Thr Thr Tyr Gln Ala Ser Ala Leu Leu Leu Phe Asn Ser Ser
            580                 585                 590

Asp Arg Leu Ser Tyr Ser Glu Ile Met Thr Gln Leu Asn Leu Ser Asp
        595                 600                 605

Asp Asp Val Val Arg Leu Leu His Ser Leu Ser Cys Ala Lys Tyr Lys
    610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Lys Val Ile Glu Asp Val Asp
            660                 665                 670

Lys Asp Arg Arg Tyr Ala Ile Asp Ala Ser Ile Val Arg Ile Met Lys
        675                 680                 685

Ser Arg Lys Val Leu Gly His Gln Gln Leu Val Met Glu Cys Val Glu
    690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
            740


<210> SEQ ID NO 56
<211> LENGTH: 742
<212> TYPE: PRT
<213> ORGANISM: Solanum melongena

<400> SEQUENCE: 56

Met Asn Gln Arg Ser Thr Ile Asp Leu Glu His Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Gly
        115                 120                 125

Leu Asn Glu Val Gly Leu Thr Cys Phe Arg Asp Leu Val Tyr Gln Glu
    130                 135                 140
```

```
Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Ser Met Asp Tyr Tyr Glu Asn Asp
            180                 185                 190

Phe Glu Ala Ala Met Leu Lys Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Ser Ser Ser Glu Thr Lys Leu Leu Glu Lys Val Gln His Glu Leu
                245                 250                 255

Leu Ser Val Tyr Ala Asn Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Pro Arg Gly Leu Glu Pro Val Ala Asn Ile
    290                 295                 300

Phe Lys Gln His Val Thr Ala Glu Gly Thr Ala Leu Val Lys Gln Ala
305                 310                 315                 320

Glu Asp Ala Ala Ser Asn Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asn Cys Phe Gln Asn His Thr Leu Phe His
        355                 360                 365

Lys Ala Leu Lys Glu Ala Phe Glu Leu Phe Cys Asn Lys Gly Val Ala
    370                 375                 380

Gly Ser Ser Asn Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Arg Glu Asn Gln Ala Ser Phe Glu Glu Tyr Leu
                485                 490                 495

Ser Asn Asn Pro Thr Ala Asn Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Arg Cys Val Glu Val Phe Lys Glu Phe Tyr Gln
    530                 535                 540

Thr Lys Thr Lys His Arg Lys Leu Thr Trp Ile Tyr Ser Leu Gly Thr
545                 550                 555                 560
```

-continued

```
Cys Asn Ile Asn Gly Lys Phe Glu Ala Lys Thr Ile Glu Leu Val Val
            565                 570                 575

Thr Thr Tyr Gln Ala Ser Ala Leu Leu Leu Phe Asn Ala Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620

Asn Lys Glu Pro Ser Thr Lys Thr Ile Ser Pro Thr Asp Val Phe Glu
625                 630                 635                 640

Phe Asn Ser Lys Phe Thr Asp Lys Met Arg Arg Ile Lys Ile Pro Leu
            645                 650                 655

Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
            725                 730                 735

Leu Phe Lys Tyr Leu Ala
            740


<210> SEQ ID NO 57
<211> LENGTH: 742
<212> TYPE: PRT
<213> ORGANISM: Solanum lycopersicum

<400> SEQUENCE: 57

Met Asn Gln Arg Ser Thr Ile Asp Leu Glu His Gly Trp Asp Phe Met
1               5                   10                  15

Gln Arg Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Gly
        115                 120                 125

Leu Asn Glu Val Gly Leu Thr Cys Phe Arg Asp Gln Val Tyr Gln Glu
    130                 135                 140

Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Leu Met Asp Tyr Tyr Glu Asn Asp
            180                 185                 190
```

```
Phe Glu Ala Ala Met Leu Lys Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Ser Ser Ser Glu Thr Lys Leu Leu Glu Lys Val Gln His Glu Leu
            245                 250                 255

Leu Ser Val Tyr Ala Thr Gln Leu Leu Glu Lys Glu His Ser Gly Cys
            260                 265                 270

His Ala Leu Leu Arg Asp Asp Lys Val Glu Asp Leu Ser Arg Met Tyr
        275                 280                 285

Arg Leu Phe Ser Lys Ile Ser Arg Gly Leu Asp Pro Val Ala Asn Ile
    290                 295                 300

Phe Lys Gln His Val Thr Ala Glu Gly Thr Ala Leu Val Lys Gln Ala
305                 310                 315                 320

Glu Asp Ala Ala Ser Asn Lys Lys Ala Glu Lys Arg Asp Val Val Gly
            325                 330                 335

Leu Gln Glu Gln Val Phe Val Arg Lys Val Ile Glu Leu His Asp Lys
            340                 345                 350

Tyr Leu Ala Tyr Val Asn Asn Cys Phe Gln Asn His Thr Leu Phe His
        355                 360                 365

Lys Ala Leu Lys Glu Ala Phe Glu Leu Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
            405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Arg Glu Asn Gln Ala Ser Phe Glu Glu Tyr Leu
            485                 490                 495

Ser Asn Asn Pro Ile Ala Asn Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Arg Cys Val Glu Val Phe Lys Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Ile Glu Leu Val Val
            565                 570                 575

Thr Thr Tyr Gln Ala Ser Ala Leu Leu Leu Phe Asn Ala Ser Asp Arg
            580                 585                 590

Leu Ser Tyr Gln Glu Ile Met Thr Gln Leu Asn Leu Ser Asp Asp Asp
        595                 600                 605
```

```
Val Val Arg Leu Leu His Ser Leu Ser Cys Ala Lys Tyr Lys Ile Leu
    610                 615                 620

Asn Lys Glu Pro Ser Thr Lys Thr Ile Ser Pro Thr Asp Val Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
                725                 730                 735

Leu Phe Lys Tyr Leu Ala
            740


<210> SEQ ID NO 58
<211> LENGTH: 742
<212> TYPE: PRT
<213> ORGANISM: Capsicum annuum

<400> SEQUENCE: 58

Met Asn Gln Arg Ser Thr Ile Asn Leu Glu His Gly Trp Asp Phe Met
1               5                   10                  15

Gln Arg Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Gly
        115                 120                 125

Leu Asn Glu Val Gly Leu Thr Cys Phe Arg Asp Leu Val Tyr Gln Glu
    130                 135                 140

Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Ser Met Asp Tyr Tyr Glu Asn Asp
            180                 185                 190

Phe Glu Ala Ala Met Leu Lys Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240
```

-continued

```
His Leu Ser Ser Glu Thr Lys Leu Leu Glu Lys Val Gln His Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Glu Asp Leu Ser Arg Met Tyr
        275                 280                 285

Arg Leu Phe Ser Lys Ile Pro Arg Gly Leu Asp Pro Val Ala Asn Ile
    290                 295                 300

Phe Lys Gln His Val Thr Ala Glu Gly Thr Ala Leu Val Lys Gln Ala
305                 310                 315                 320

Glu Asp Ala Ala Ser Asn Lys Lys Ala Glu Lys Arg Asp Val Val Gly
                325                 330                 335

Leu Gln Glu Gln Ile Phe Val Arg Lys Val Ile Glu Leu His Asp Lys
            340                 345                 350

Tyr Met Ala Tyr Val Asn Asn Cys Phe Gln Asn His Thr Leu Phe His
        355                 360                 365

Lys Ala Leu Lys Glu Ala Phe Glu Leu Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Arg Glu Asn Gln Ala Ser Phe Glu Glu Tyr Leu
                485                 490                 495

Ser Asn Asn Pro Ala Ala Asn Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Arg Cys Val Glu Val Phe Lys Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Ile Glu Leu Val Val
                565                 570                 575

Thr Thr Tyr Gln Ala Ser Ala Leu Leu Leu Phe Asn Ala Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620

Asn Lys Glu Pro Ser Thr Lys Thr Ile Ser Pro Thr Asp Val Phe Glu
625                 630                 635                 640

Phe Asn Phe Lys Phe Thr Asp Lys Met Arg Arg Ile Lys Ile Pro Leu
                645                 650                 655
```

-continued

```
Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
                725                 730                 735

Leu Phe Lys Tyr Leu Ala
            740


<210> SEQ ID NO 59
<211> LENGTH: 738
<212> TYPE: PRT
<213> ORGANISM: Brassica oleracea

<400> SEQUENCE: 59

Met Glu Arg Lys Thr Ile Asp Leu Asp Gln Gly Trp Asp Tyr Met Gln
1               5                   10                  15

Thr Gly Ile Thr Lys Leu Lys Arg Ile Leu Glu Gly Leu Pro Glu Pro
            20                  25                  30

Gln Phe Asp Ser Glu Gln Tyr Met Met Leu Tyr Thr Thr Met Tyr Asn
        35                  40                  45

Met Cys Thr Gln Lys Pro Pro His Asp Tyr Ser Gln Gln Leu Tyr Asp
    50                  55                  60

Lys Tyr Arg Glu Ala Phe Glu Glu Tyr Ile His Ser Thr Val Leu Pro
65                  70                  75                  80

Ala Leu Arg Glu Lys His Asp Glu Tyr Met Leu Arg Glu Leu Val Lys
                85                  90                  95

Arg Trp Ser Asn His Lys Val Met Val Arg Trp Leu Ser Arg Phe Phe
            100                 105                 110

Tyr Tyr Leu Asp Arg Tyr Phe Ile Ala Arg Arg Ser Leu Pro Pro Leu
        115                 120                 125

Asn Glu Val Gly Leu Thr Cys Phe Arg Asp Leu Val Tyr Asn Glu Leu
    130                 135                 140

His Ser Lys Val Lys Asp Ala Val Ile Ala Leu Val Asp Lys Glu Arg
145                 150                 155                 160

Glu Gly Glu Gln Ile Asp Arg Ala Leu Leu Lys Asn Val Leu Asp Ile
                165                 170                 175

Tyr Val Glu Ile Gly Met Gly Gln Met Glu Arg Tyr Glu Glu Asp Phe
            180                 185                 190

Glu Ser Phe Met Leu Leu Asp Ser Ala Ser Tyr Tyr Ser Arg Lys Ala
        195                 200                 205

Ser Ser Trp Ile Gln Glu Asp Ser Cys Pro Asp Tyr Met Leu Lys Ser
    210                 215                 220

Glu Glu Cys Leu Lys Lys Glu Arg Glu Arg Val Ala His Tyr Leu His
225                 230                 235                 240

Ser Ser Ser Glu Pro Lys Leu Val Glu Lys Val Gln His Glu Leu Leu
                245                 250                 255

Val Val Tyr Ala Asn Gln Leu Leu Glu Lys Glu His Ser Gly Cys Arg
            260                 265                 270

Ala Leu Leu Arg Asp Asp Lys Val Asp Asp Leu Ser Arg Met Tyr Arg
        275                 280                 285
```

-continued

```
Leu Tyr His Lys Ile Val Lys Gly Leu Glu Pro Val Ala Asn Ile Phe
    290                 295                 300

Lys Gln His Val Thr Ala Glu Gly Asn Ala Leu Val Gln Gln Ala Glu
305                 310                 315                 320

Asp Thr Ala Thr Asn His Ala Ala Asn Thr Ala Ser Val Gln Glu Gln
                325                 330                 335

Val Leu Ile Arg Lys Val Ile Glu Leu His Asp Lys Tyr Met Val Tyr
            340                 345                 350

Val Val Glu Cys Phe Gln Asn His Thr Leu Phe His Lys Ala Leu Lys
        355                 360                 365

Glu Ala Phe Glu Ile Phe Cys Asn Lys Thr Val Ala Gly Ser Ser Ser
    370                 375                 380

Ala Glu Leu Leu Ala Thr Phe Cys Asp Asn Ile Leu Lys Lys Gly Gly
385                 390                 395                 400

Ser Glu Lys Leu Ser Asp Glu Ala Ile Glu Asp Thr Leu Glu Lys Val
                405                 410                 415

Val Lys Leu Leu Ala Tyr Ile Ser Asp Lys Asp Leu Phe Ala Glu Phe
            420                 425                 430

Tyr Arg Lys Lys Leu Ala Arg Arg Leu Leu Phe Asp Arg Ser Ala Asn
        435                 440                 445

Asp Asp His Glu Arg Ser Ile Leu Thr Lys Leu Lys Gln Gln Cys Gly
    450                 455                 460

Gly Gln Phe Thr Ser Lys Met Glu Gly Met Val Thr Asp Leu Thr Leu
465                 470                 475                 480

Ala Arg Glu Asn Gln Asn Ser Phe Glu Glu Tyr Leu Gly Asn Asn Pro
                485                 490                 495

Ala Ala Asn Pro Gly Ile Asp Leu Thr Val Thr Val Leu Thr Thr Gly
            500                 505                 510

Phe Trp Pro Ser Tyr Lys Ser Phe Asp Ile Asn Leu Pro Ala Glu Met
        515                 520                 525

Val Lys Cys Val Glu Val Phe Lys Gly Phe Tyr Glu Thr Lys Thr Lys
    530                 535                 540

His Arg Lys Leu Thr Trp Ile Tyr Ser Leu Gly Thr Cys His Leu Asn
545                 550                 555                 560

Gly Lys Phe Asp Val Lys Pro Ile Glu Leu Val Val Ser Thr Tyr Gln
                565                 570                 575

Ala Ala Val Leu Leu Leu Phe Asn Thr Thr Asp Lys Leu Ser Tyr Thr
            580                 585                 590

Asp Ile Leu Thr Gln Leu Asn Leu Ser His Glu Asp Leu Val Arg Leu
        595                 600                 605

Leu His Ser Leu Ser Cys Ala Arg Tyr Lys Ile Leu Leu Lys Glu Pro
    610                 615                 620

Ser Thr Lys Thr Val Ser Gln Ser Asp Ser Phe Glu Phe Asn Ser Lys
625                 630                 635                 640

Phe Thr Asp Arg Met Arg Arg Ile Lys Ile Pro Leu Pro Pro Val Asp
                645                 650                 655

Glu Arg Lys Lys Val Val Glu Asp Val Asp Lys Asp Arg Arg Tyr Ala
            660                 665                 670

Ile Asp Ala Ala Ile Val Arg Ile Met Lys Ser Arg Lys Val Leu Gly
        675                 680                 685

His Gln Gln Leu Val Ser Glu Cys Val Glu Gln Leu Ser Arg Met Phe
    690                 695                 700
```

Lys Pro Asp Ile Lys Ala Ile Lys Lys Arg Met Glu Asp Leu Ile Thr
705 710 715 720

Arg Asp Tyr Leu Glu Arg Asp Lys Glu Asn Ala Asn Met Phe Arg Tyr
725 730 735

Leu Ala

<210> SEQ ID NO 60
<211> LENGTH: 743
<212> TYPE: PRT
<213> ORGANISM: Daucus carota

<400> SEQUENCE: 60

Met Met Ile Glu Arg Lys Thr Ile Asp Leu Glu Gln Gly Trp Asp Phe
1 5 10 15

Met Gln Lys Gly Ile Thr Lys Leu Lys Asn Ile Leu Glu Gly Phe Pro
20 25 30

Glu Pro Gln Phe Ser Ser Glu Asp Tyr Met Met Leu Tyr Thr Thr Met
35 40 45

Tyr Asn Met Cys Thr Gln Lys Pro Pro His Asp Tyr Ser Gln Gln Leu
50 55 60

Tyr Glu Lys Tyr Arg Glu Ala Ile Glu Glu Tyr Ile Thr Ser Thr Val
65 70 75 80

Leu Pro Ser Leu Arg Glu Lys His Asp Glu Phe Met Leu Arg Glu Leu
85 90 95

Val Lys Arg Trp Ser Asn His Lys Val Met Val Arg Trp Leu Ser Arg
100 105 110

Phe Phe His Tyr Leu Asp Arg Tyr Phe Ile Ala Arg Arg Ser Leu Pro
115 120 125

Pro Leu His Glu Val Gly Leu Thr Cys Phe Arg Asp Leu Val Tyr Gln
130 135 140

Glu Ile Asn Gly Lys Val Arg Asp Ala Val Ile Ser Leu Ile Asn Gln
145 150 155 160

Glu Arg Glu Gly Glu Gln Ile Asp Arg Ala Leu Leu Lys Asn Val Leu
165 170 175

Asp Ile Phe Val Glu Val Gly Met Ser Gln Met Asp Tyr Tyr Glu Asn
180 185 190

Asp Phe Glu Ala Asp Met Leu Lys Asp Thr Ala Ala Tyr Tyr Ser Arg
195 200 205

Lys Ala Ser Asn Trp Ile Leu Glu Asp Ser Cys Pro Asp Tyr Met Leu
210 215 220

Lys Ala Glu Glu Cys Leu Arg Arg Glu Lys Asp Arg Val Ser Asn Tyr
225 230 235 240

Leu His Ser Ser Ser Glu Pro Lys Leu Leu Glu Lys Val Gln His Glu
245 250 255

Leu Leu Ser His Tyr Ala Thr Gln Leu Leu Glu Lys Glu His Ser Gly
260 265 270

Cys His Ala Leu Leu Arg Asp Asp Lys Val Ala Asp Leu Ser Arg Met
275 280 285

Tyr Arg Leu Phe Ser Lys Ile Pro Arg Gly Leu Asp Pro Val Ser Asn
290 295 300

Ile Phe Lys Gln His Val Thr Ala Glu Gly Thr Ala Leu Val Lys Gln
305 310 315 320

Ala Glu Asp Ala Ala Ser Asn Lys Lys Ala Glu Lys Arg Asp Val Val
325 330 335

-continued

```
Gly Leu Gln Glu Gln Val Phe Val Arg Lys Ile Ile Glu Leu His Asp
            340                 345                 350

Lys Tyr Leu Thr Tyr Val Asn Asp Cys Phe Thr Asn His Thr Leu Phe
        355                 360                 365

His Lys Ala Leu Lys Glu Ala Phe Glu Ile Phe Cys Asn Lys Gly Val
    370                 375                 380

Ser Gly Ser Ser Ser Ala Glu Leu Leu Ala Thr Phe Cys Asp Asn Ile
385                 390                 395                 400

Leu Lys Lys Gly Gly Ser Glu Lys Leu Ser Asp Glu Ala Ile Glu Glu
                405                 410                 415

Thr Leu Glu Lys Val Val Arg Leu Leu Ala Tyr Ile Ser Asp Lys Asp
            420                 425                 430

Leu Phe Ala Glu Phe Tyr Arg Lys Lys Leu Ala Arg Arg Leu Leu Phe
        435                 440                 445

Asp Lys Ser Ala Asn Asp Glu His Glu Arg Ser Ile Leu Thr Lys Leu
    450                 455                 460

Lys Gln Gln Cys Gly Gly Gln Phe Thr Ser Lys Met Glu Gly Met Val
465                 470                 475                 480

Thr Asp Leu Thr Leu Ala Lys Glu Asn Gln Ser Asn Phe Glu Glu Tyr
                485                 490                 495

Leu Asn Asn Asn Ser Asn Val Asn Pro Gly Ile Asp Leu Thr Val Thr
            500                 505                 510

Val Leu Thr Thr Gly Phe Trp Pro Ser Tyr Lys Ser Phe Asp Leu Asn
        515                 520                 525

Leu Pro Ala Glu Met Val Lys Cys Val Glu Val Phe Arg Glu Phe Tyr
    530                 535                 540

Gln Thr Lys Thr Lys His Arg Lys Leu Thr Trp Ile Tyr Ser Leu Gly
545                 550                 555                 560

Thr Cys Asn Ile Ile Gly Lys Phe Asp Pro Lys Thr Met Glu Leu Ile
                565                 570                 575

Val Thr Thr Tyr Gln Ala Ser Ala Leu Leu Leu Phe Asn Ser Ser Asp
            580                 585                 590

Arg Leu Ser Tyr Asn Glu Ile Met Thr Gln Leu Asn Leu Ser Asp Asp
        595                 600                 605

Asp Val Val Arg Leu Leu His Ser Leu Ser Cys Ala Lys Tyr Lys Ile
    610                 615                 620

Leu Ser Lys Glu Pro Asn Thr Lys Thr Ile Ser Pro Thr Asp Cys Phe
625                 630                 635                 640

Gln Phe Asn Ser Lys Phe Thr Asp Lys Met Arg Arg Ile Lys Ile Pro
                645                 650                 655

Leu Pro Pro Val Asp Glu Lys Lys Lys Val Ile Glu Asp Val Asp Lys
            660                 665                 670

Asp Arg Arg Tyr Ala Ile Asp Ala Ser Ile Val Arg Ile Met Lys Ser
        675                 680                 685

Arg Lys Val Leu Gly Tyr Gln Gln Leu Val Met Glu Cys Val Glu Gln
    690                 695                 700

Leu Gly Arg Met Phe Lys Pro Asp Val Lys Ala Ile Lys Lys Arg Ile
705                 710                 715                 720

Glu Asp Leu Ile Thr Arg Asp Tyr Leu Glu Arg Asp Lys Asp Asn Ala
                725                 730                 735

Asn Leu Phe Arg Tyr Leu Ala
            740
```

<210> SEQ ID NO 61
<211> LENGTH: 742
<212> TYPE: PRT
<213> ORGANISM: Apium graveolens

<400> SEQUENCE: 61

Met Asn Glu Arg Lys Thr Ile Asp Leu Asp Asn Gly Trp Glu Phe Met
1               5                   10                  15

Gln Lys Gly Ile Thr Lys Leu Lys Lys Ile Leu Glu Gly Gln Pro Glu
            20                  25                  30

Pro Gln Phe Ser Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Asn Arg Trp Thr Asn His Lys Val Met Val Arg Trp Leu Ser Arg Phe
            100                 105                 110

Phe His Tyr Leu Asp Arg Tyr Phe Ile Ala Arg Arg Ser Leu Pro Ala
        115                 120                 125

Leu His Glu Val Gly Leu Thr Cys Phe Arg Asp Leu Val Tyr Gln Glu
    130                 135                 140

Leu Lys Val Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Ser Gln Met Asp Gln Tyr Glu Asn Asp
            180                 185                 190

Phe Glu Glu Ala Met Leu Thr Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Arg Arg Glu Lys Asp Arg Val Ser His Tyr Leu
225                 230                 235                 240

His Phe Ser Ser Glu Pro Lys Leu Leu Glu Lys Val Gln His Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Pro Lys Gly Leu Asp Pro Val Ser Tyr Ile
    290                 295                 300

Phe Lys Gln His Val Thr Asn Glu Gly Met Ala Leu Val Lys Gln Ala
305                 310                 315                 320

Glu Asp Ala Ala Ser Asn Lys Lys Ala Glu Lys Arg Asp Val Val Ser
                325                 330                 335

Leu Gln Glu Gln Val Phe Val Arg Lys Ile Ile Glu Leu His Asp Lys
            340                 345                 350

Tyr Leu Ala Tyr Val Asn Asp Cys Phe Thr Asn His Thr Leu Phe His
        355                 360                 365

Lys Ala Leu Lys Glu Ala Phe Glu Ile Phe Cys Asn Lys Gly Val Ala
    370                 375                 380

-continued

```
Gly Ser Ser Asn Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Lys Glu Asn Gln Ser Ser Phe Glu Glu Tyr Leu
                485                 490                 495

Gly Asn Asn Ala Asn Val Asn Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Lys Cys Val Glu Val Phe Arg Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Ile Glu Leu Ile Val
                565                 570                 575

Thr Thr Tyr Gln Ala Ser Ala Leu Leu Leu Phe Asn Thr Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620

Thr Lys Glu Pro Asn Asn Lys Thr Ile Ser Pro Thr Asp Tyr Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Ala Asn
                725                 730                 735

Leu Phe Arg Tyr Leu Ala
            740
```

<210> SEQ ID NO 62
<211> LENGTH: 742
<212> TYPE: PRT
<213> ORGANISM: Cichorium intybus

<400> SEQUENCE: 62

```
Met Asn Glu Arg Lys Thr Ile Asp Leu Glu Gln Gly Trp Asp Phe Met
1               5                   10                  15
```

-continued

```
Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
    50                  55                  60

Asp Lys Tyr Arg Glu Ser Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Arg Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Pro
        115                 120                 125

Leu Asn Glu Val Gly Leu Ala Cys Phe Arg Asp Leu Val Tyr Gln Glu
    130                 135                 140

Val Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Gln Met Glu Tyr Tyr Glu Asn Asp
            180                 185                 190

Phe Glu Ala Ser Met Leu Asn Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Ser Ser Ser Glu Pro Lys Leu Leu Glu Lys Val Gln Thr Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Gln Lys Gly Leu Asp Pro Val Ser Ser Met
    290                 295                 300

Phe Lys Gln His Val Thr Ala Glu Gly Thr Thr Leu Val Lys Gln Ala
305                 310                 315                 320

Glu Asp Ala Ala Ser Thr Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asp Cys Phe Met Asn His Thr Leu Phe His
        355                 360                 365

Lys Ala Leu Lys Glu Ala Phe Glu Ile Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Asp Thr
                405                 410                 415

Leu Glu Lys Val Val Lys Leu Leu Ala Tyr Ile Ser Asp Lys Asp Leu
            420                 425                 430
```

```
Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Lys Glu Asn Gln Ser His Phe Glu Glu Tyr Leu
                485                 490                 495

Asn Asn Asn Pro Asn Val Ser Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Lys Cys Val Glu Val Phe Arg Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Met Glu Leu Ile Val
                565                 570                 575

Thr Thr Tyr Gln Ala Ser Ala Leu Leu Leu Phe Asn Ser Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620

Leu Lys Glu Pro Asn Thr Lys Thr Ile Ser Pro Thr Asp Phe Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Glu Asn Pro Asn
                725                 730                 735

Leu Phe Arg Tyr Leu Ala
            740


<210> SEQ ID NO 63
<211> LENGTH: 742
<212> TYPE: PRT
<213> ORGANISM: Cichorium endivia

<400> SEQUENCE: 63

Met Asn Glu Arg Lys Thr Ile Asp Leu Glu Gln Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
    50                  55                  60
```

-continued

```
Asp Lys Tyr Arg Glu Ser Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Arg Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Pro
        115                 120                 125

Leu Asn Glu Val Gly Leu Ala Cys Phe Arg Asp Leu Val Tyr Gln Glu
    130                 135                 140

Val Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Gln Met Glu Tyr Tyr Glu Asn Asp
            180                 185                 190

Phe Glu Ala Ser Met Leu Asn Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Ser Ser Ser Glu Pro Lys Leu Leu Glu Lys Val Gln Thr Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Gln Lys Gly Leu Asp Pro Val Ser Ser Met
    290                 295                 300

Phe Lys Gln His Val Thr Ala Glu Gly Thr Thr Leu Val Lys Gln Ala
305                 310                 315                 320

Glu Asp Ala Ala Ser Thr Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asp Cys Phe Met Asn His Thr Leu Phe His
        355                 360                 365

Lys Ala Leu Lys Glu Ala Phe Glu Ile Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Asp Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480
```

-continued

```
Asp Leu Thr Leu Ala Lys Glu Asn Gln Ser His Phe Glu Glu Tyr Leu
                485                 490                 495

Asn Asn Asn Pro Asn Val Ser Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Lys Cys Val Glu Val Phe Arg Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Met Glu Leu Ile Val
                565                 570                 575

Thr Thr Tyr Gln Ala Ser Ala Leu Leu Leu Phe Asn Ser Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620

Leu Lys Glu Pro Asn Thr Lys Thr Ile Ser Pro Thr Asp Phe Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Glu Asn Pro Asn
                725                 730                 735

Leu Phe Arg Tyr Leu Ala
            740


<210> SEQ ID NO 64
<211> LENGTH: 744
<212> TYPE: PRT
<213> ORGANISM: Allium ampeloprasum

<400> SEQUENCE: 64

Met Ser Leu His Glu Arg Lys Thr Ile Asp Leu Glu Gln Gly Trp Ala
1               5                   10                  15

Phe Met Gln Lys Gly Ile Thr Lys Leu Lys Asn Ile Leu Asp Glu Leu
            20                  25                  30

Asn Glu Pro Gln Phe Ser Ser Glu Asp Tyr Met Met Leu Tyr Thr Thr
        35                  40                  45

Met Tyr Asn Met Cys Thr Gln Lys Pro Pro His Asp Tyr Ser Gln Glu
    50                  55                  60

Leu Tyr Asp Lys Tyr Arg Glu Ser Phe Glu Glu Tyr Ile Thr Thr Thr
65                  70                  75                  80

Val Leu Pro Ser Leu Arg Glu Lys His Asp Glu Tyr Met Leu Arg Glu
                85                  90                  95

Leu Val Arg Arg Trp Ser Asn His Lys Ile Met Val Arg Trp Leu Ser
            100                 105                 110
```

-continued

```
Arg Phe Phe His Tyr Leu Asp Arg Tyr Phe Ile Ala Arg Arg Ser Leu
        115                 120                 125

Pro Ala Leu Asn Glu Val Gly Leu Thr Cys Phe Arg Asp Leu Val Tyr
    130                 135                 140

Asn Glu Val His Gly Lys Val Lys Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Gly Ile Phe Val Glu Ile Gly Leu Gly Ser Met Glu Cys Tyr Glu
            180                 185                 190

Asn Asp Phe Glu Thr Ser Met Leu Asn Ala Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Lys His Glu Lys Asp Arg Val Ala His
225                 230                 235                 240

Tyr Leu His Ser Ser Ser Glu Gln Lys Leu Leu Glu Lys Val Gln His
                245                 250                 255

Glu Leu Leu Phe Val Tyr Ala Ser Gln Leu Leu Glu Lys Glu His Ser
            260                 265                 270

Gly Cys His Ala Leu Leu Arg Asp Asp Lys Val Gly Asp Leu Ser Arg
        275                 280                 285

Met Tyr Arg Leu Phe Cys Arg Ile Thr Arg Gly Leu Asp Pro Val Ser
    290                 295                 300

Gln Ile Phe Lys Gln His Val Thr Ala Glu Gly Thr Ala Leu Val Lys
305                 310                 315                 320

His Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Thr Asp Cys Phe Gln Asn His Ser Leu
        355                 360                 365

Phe His Lys Ala Leu Lys Glu Ala Phe Glu Val Phe Cys Asn Lys Gly
    370                 375                 380

Val Ala Gly Ser Ser Ser Ala Glu Leu Leu Ala Ala Phe Cys Asp Asn
385                 390                 395                 400

Ile Leu Lys Lys Gly Gly Ser Glu Lys Leu Ser Asp Glu Ala Ile Glu
                405                 410                 415

Asp Thr Leu Glu Lys Val Val Lys Leu Leu Ala Tyr Ile Ser Asp Lys
            420                 425                 430

Asp Leu Phe Ala Glu Phe Tyr Arg Lys Lys Leu Ala Arg Arg Leu Leu
        435                 440                 445

Phe Asp Lys Ser Ala Asn Asp Asp His Glu Arg Ser Ile Leu Thr Lys
    450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Ser Ser Phe Asp Asp
                485                 490                 495

Tyr Leu Ser Ser Asn Pro Lys Ala Asn Ser Gly Ile Asp Leu Thr Val
            500                 505                 510

Thr Val Leu Thr Thr Gly Phe Trp Pro Ser Tyr Lys Ser Phe Asp Leu
        515                 520                 525
```

```
Asn Leu Pro Asp Glu Met Val Lys Cys Val Glu Ile Phe Lys Glu Phe
    530                 535                 540

Tyr Glu Thr Lys Thr Lys His Arg Lys Leu Thr Trp Ile Tyr Ser Leu
545                 550                 555                 560

Gly Thr Cys Asn Ile Asn Gly Lys Phe Glu Thr Lys Thr Ile Glu Leu
                565                 570                 575

Val Val Thr Thr Tyr Gln Ala Ala Val Leu Leu Leu Phe Asn Ser Ala
            580                 585                 590

Asp Lys Leu Ser Tyr Ser Glu Ile Val Gln Gln Leu Asn Leu Ser Asp
        595                 600                 605

Asp Asp Val Ile Arg Leu Leu His Ser Leu Ser Cys Ala Lys Tyr Lys
    610                 615                 620

Ile Leu Asn Lys Glu Pro Ala Thr Lys Thr Ile Thr Pro Asn Asp His
625                 630                 635                 640

Phe Glu Phe Asn Ser Lys Phe Thr Asp Arg Met Arg Arg Ile Lys Ile
                645                 650                 655

Pro Leu Pro Pro Val Asp Glu Lys Lys Lys Val Ile Glu Asp Val Asp
            660                 665                 670

Lys Asp Arg Arg Tyr Ala Ile Asp Ala Ser Ile Val Arg Ile Met Lys
        675                 680                 685

Ser Arg Lys Val Leu Gly His Gln Gln Leu Val Leu Glu Cys Val Glu
    690                 695                 700

Gln Leu Gly Arg Met Phe Lys Pro Asp Phe Lys Ala Ile Lys Lys Arg
705                 710                 715                 720

Ile Glu Asp Leu Ile Ala Arg Asp Tyr Leu Glu Arg Asp Lys Asp Asn
                725                 730                 735

Pro Asn Leu Phe Lys Tyr Leu Ala
            740


<210> SEQ ID NO 65
<211> LENGTH: 742
<212> TYPE: PRT
<213> ORGANISM: Lactuca sativa

<400> SEQUENCE: 65

Met Asn Glu Arg Lys Thr Ile Asp Leu Glu Gln Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
    50                  55                  60

Asp Lys Tyr Arg Glu Ser Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Arg Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Pro
        115                 120                 125

Leu Asn Glu Val Gly Leu Ala Cys Phe Arg Asp Leu Val Tyr Gln Glu
    130                 135                 140

Val Asn Gly Lys Val Arg Asp Ala Val Ile Ser Leu Ile Asp Gln Glu
145                 150                 155                 160
```

-continued

```
Arg Glu Gly Glu Gln Ile Asp Arg Ala Leu Leu Lys Asn Val Leu Asp
                165                 170                 175

Ile Phe Val Glu Ile Gly Met Gly Gln Met Glu Tyr Tyr Glu Asn Asp
            180                 185                 190

Phe Glu Ala Ser Met Leu Asn Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Ser Ser Ser Glu Pro Lys Leu Leu Glu Lys Val Gln Asn Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Pro Lys Gly Leu Asp Pro Val Ser Ser Met
    290                 295                 300

Phe Lys Gln His Val Thr Ala Glu Gly Thr Thr Leu Val Lys Gln Ala
305                 310                 315                 320

Glu Asp Ala Ala Ser Thr Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asp Cys Phe Met Asn His Thr Leu Phe His
        355                 360                 365

Lys Ala Leu Lys Glu Ala Phe Glu Ile Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Asp Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Lys Glu Asn Gln Ser His Phe Glu Glu Tyr Leu
                485                 490                 495

Asn Asn Asn Pro Asn Val Ser Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Lys Cys Val Glu Val Phe Arg Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Met Glu Leu Ile Val
                565                 570                 575
```

-continued

Thr Thr Tyr Gln Ala Ser Ala Leu Leu Leu Phe Asn Leu Ser Asp Arg
580 585 590

Leu Ser Tyr Gln Glu Ile Met Thr Gln Leu Asn Leu Ser Asp Asp Asp
595 600 605

Val Val Arg Leu Leu His Ser Leu Ser Cys Ala Lys Tyr Lys Ile Leu
610 615 620

Leu Lys Glu Pro Asn Thr Lys Thr Ile Ser Pro Thr Asp Tyr Phe Glu
625 630 635 640

Phe Asn Ser Lys Phe Thr Asp Lys Met Arg Arg Ile Lys Ile Pro Leu
645 650 655

Pro Pro Val Asp Glu Lys Lys Lys Val Ile Glu Asp Val Asp Lys Asp
660 665 670

Arg Arg Tyr Ala Ile Asp Ala Ser Ile Val Arg Ile Met Lys Ser Arg
675 680 685

Lys Val Leu Gly Tyr Gln Gln Leu Val Met Glu Cys Val Glu Gln Leu
690 695 700

Gly Arg Met Phe Lys Pro Asp Val Lys Ala Ile Lys Lys Arg Ile Glu
705 710 715 720

Asp Leu Ile Thr Arg Asp Tyr Leu Glu Arg Asp Lys Glu Asn Pro Asn
725 730 735

Leu Phe Arg Tyr Leu Ala
740

<210> SEQ ID NO 66
<211> LENGTH: 738
<212> TYPE: PRT
<213> ORGANISM: Raphanus sativus

<400> SEQUENCE: 66

Met Glu Arg Lys Thr Ile Asp Leu Glu Gln Gly Trp Asp Tyr Met Gln
1 5 10 15

Thr Gly Ile Thr Lys Leu Lys Arg Ile Leu Glu Gly Leu Pro Glu Pro
20 25 30

Gln Phe Asp Ser Glu Gln Tyr Met Met Leu Tyr Thr Thr Met Tyr Asn
35 40 45

Met Cys Thr Gln Lys Pro Pro His Asp Tyr Ser Gln Gln Leu Tyr Asp
50 55 60

Lys Tyr Arg Glu Ala Phe Glu Glu Tyr Ile Asp Ser Thr Val Leu Pro
65 70 75 80

Ala Leu Lys Glu Lys His Asp Glu Tyr Met Leu Arg Glu Leu Val Lys
85 90 95

Arg Trp Ser Asn His Lys Val Met Val Arg Trp Leu Ser Arg Phe Phe
100 105 110

Tyr Tyr Leu Asp Arg Tyr Phe Ile Ala Arg Arg Ser Leu Pro Pro Leu
115 120 125

Asn Glu Val Gly Leu Thr Cys Phe Arg Asp Arg Val Tyr Lys Glu Leu
130 135 140

His Ser Lys Val Lys Asp Ala Val Ile Ala Leu Val Asp Lys Glu Arg
145 150 155 160

Glu Gly Glu Gln Ile Asp Arg Ala Leu Leu Lys Asn Val Leu Asp Ile
165 170 175

Tyr Val Glu Ile Gly Met Gly Gln Met Glu Arg Tyr Glu Val Asp Phe
180 185 190

Glu Ser Phe Met Leu Leu Asp Ser Ala Ser Tyr Tyr Ser Arg Lys Ala
195 200 205

```
Ser Asn Trp Ile Gln Glu Asp Ser Cys Pro Asp Tyr Met Leu Lys Ser
    210                 215                 220

Glu Glu Cys Leu Lys Lys Glu Arg Glu Arg Val Ala His Tyr Leu His
225                 230                 235                 240

Ser Ser Ser Glu Pro Lys Leu Val Glu Lys Val Gln His Glu Leu Leu
                245                 250                 255

Val Val Tyr Ala Asn Gln Leu Leu Glu Lys Glu His Ser Gly Cys Arg
            260                 265                 270

Ala Leu Leu Arg Asp Asp Lys Val Asp Asp Leu Ser Arg Met Tyr Arg
        275                 280                 285

Leu Tyr His Lys Ile Ala Lys Gly Leu Glu Pro Val Ala Asn Ile Phe
    290                 295                 300

Lys Gln His Val Thr Ala Glu Gly Asn Ala Leu Val Gln Gln Ala Glu
305                 310                 315                 320

Asp Thr Ala Thr Asn Gln Ala Ala Asn Thr Ala Ser Val Gln Glu Gln
                325                 330                 335

Val Leu Ile Arg Lys Val Ile Glu Leu His Asp Lys Tyr Met Val Tyr
            340                 345                 350

Val Val Glu Cys Phe Gln Asn His Thr Leu Phe His Lys Ala Leu Lys
        355                 360                 365

Glu Ala Phe Glu Ile Phe Cys Asn Lys Thr Val Ala Gly Ser Ser Ser
    370                 375                 380

Ala Glu Leu Leu Ala Thr Phe Cys Asp Asn Ile Leu Lys Lys Gly Gly
385                 390                 395                 400

Ser Glu Lys Leu Ser Asp Glu Ala Ile Glu Asp Thr Leu Glu Lys Val
                405                 410                 415

Val Lys Leu Leu Ala Tyr Ile Ser Asp Lys Asp Leu Phe Ala Glu Phe
            420                 425                 430

Tyr Arg Lys Lys Leu Ala Arg Arg Leu Leu Phe Asp Arg Ser Ala Asn
        435                 440                 445

Asp Asp His Glu Arg Ser Ile Leu Thr Lys Leu Lys Gln Gln Cys Gly
    450                 455                 460

Gly Gln Phe Thr Ser Lys Met Glu Gly Met Val Thr Asp Leu Thr Leu
465                 470                 475                 480

Ala Arg Glu Asn Gln Thr Ser Phe Glu Glu Tyr Leu Gly Asn Asn Pro
                485                 490                 495

Ala Ala Asn Pro Gly Ile Asp Leu Thr Val Thr Val Leu Thr Thr Gly
            500                 505                 510

Phe Trp Pro Ser Tyr Lys Ser Phe Asp Ile Asn Leu Pro Ser Glu Met
        515                 520                 525

Val Lys Cys Val Glu Val Phe Lys Gly Phe Tyr Glu Thr Lys Thr Lys
    530                 535                 540

His Arg Lys Leu Thr Trp Ile Tyr Ser Leu Gly Thr Cys His Leu Asn
545                 550                 555                 560

Gly Lys Phe Asp His Lys Pro Ile Glu Leu Val Val Ser Thr Tyr Gln
                565                 570                 575

Ala Ala Val Leu Leu Leu Phe Asn Thr Thr Asp Lys Leu Ser Tyr Asn
            580                 585                 590

Asp Ile Leu Thr Gln Leu Asn Leu Ser His Glu Asp Leu Val Arg Leu
        595                 600                 605

Leu His Ser Leu Ser Cys Ala Arg Tyr Lys Ile Leu Leu Lys Glu Pro
    610                 615                 620
```

```
Ser Thr Lys Thr Val Thr Gln Thr Asp Ser Phe Glu Phe Asn Ala Lys
625                 630                 635                 640

Phe Thr Asp Arg Met Arg Arg Ile Lys Ile Pro Leu Pro Pro Val Asp
                645                 650                 655

Glu Arg Lys Lys Val Val Glu Asp Val Asp Lys Asp Arg Arg Tyr Ala
            660                 665                 670

Ile Asp Ala Ala Ile Val Arg Ile Met Lys Ser Arg Lys Val Leu Gly
        675                 680                 685

His Gln Gln Leu Val Ser Glu Cys Val Glu Gln Leu Ser Arg Met Phe
    690                 695                 700

Lys Pro Asp Ile Lys Ala Ile Lys Lys Arg Met Glu Asp Leu Ile Thr
705                 710                 715                 720

Arg Asp Tyr Leu Glu Arg Asp Lys Glu Asn Pro Asn Met Phe Arg Tyr
                725                 730                 735

Leu Ala


<210> SEQ ID NO 67
<211> LENGTH: 740
<212> TYPE: PRT
<213> ORGANISM: Spinacia oleracea

<400> SEQUENCE: 67

Met Asn Asp Arg Lys Val Ile Glu Leu Glu Gln Gly Trp Glu Phe Met
1               5                   10                  15

Gly Lys Gly Ile Thr Lys Leu Lys Arg Ile Leu Glu Gly Leu Pro Glu
            20                  25                  30

Pro Pro Phe Asn Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
    50                  55                  60

Asp Asn Tyr Lys Glu Ala Phe Val Asp Tyr Ile His Ser Thr Val Leu
65                  70                  75                  80

Pro Ser Leu Gly Asp Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Ser
        115                 120                 125

Leu Asn Asp Val Gly Leu Thr Cys Phe Arg Asp Leu Val Tyr Gln Glu
    130                 135                 140

Ile Ser Gly Lys Ala Lys Asp Ala Val Ile Ala Leu Ile Asp Glu Glu
145                 150                 155                 160

Arg Glu Gly Gly Gln Ile Asp Arg Ala Leu Leu Lys Asn Val Leu Asp
                165                 170                 175

Ile Tyr Val Glu Ile Gly Met Thr Gln Met Asp Tyr Tyr Glu Lys Asp
            180                 185                 190

Phe Glu Ala His Met Leu Asp Asp Thr Ala Ala Tyr Tyr Ser Arg Lys
        195                 200                 205

Ala Ser Ser Trp Ile Leu Glu Asp Ser Cys Pro Glu Tyr Met Leu Lys
    210                 215                 220

Ser Glu Glu Cys Leu Lys Lys Glu Lys Asp Arg Val Ala His Tyr Leu
225                 230                 235                 240

His Ser Ser Ser Glu Pro Lys Leu Leu Glu Lys Val Gln Asn Glu Leu
                245                 250                 255
```

```
Leu Leu Val Tyr Glu Asn Gln Leu Leu Glu Lys Glu Asn Ser Gly Cys
            260                 265                 270

Arg Ala Leu Leu Lys Asp Asp Lys Val Glu Asp Leu Ser Arg Met Tyr
        275                 280                 285

Arg Leu Tyr Ser Lys Val Thr Lys Gly Leu Glu Pro Ile Gly Ser Ile
    290                 295                 300

Phe Lys Gln His Ile Thr Asp Glu Gly Thr Ala Leu Val Gln Gln Ala
305                 310                 315                 320

Glu Asp Ala Ala Ile Ser Lys Ala Glu Asn Ala Gly Gly Gly Ser His
                325                 330                 335

Glu Gln Val Phe Val Arg Lys Val Ile Glu Leu His Asp Lys Phe Met
            340                 345                 350

Thr Tyr Val Thr Asp Cys Phe Asn Ser His Thr Ile Phe His Lys Ala
        355                 360                 365

Leu Lys Glu Ala Phe Glu Val Phe Leu Asn Lys Gly Val Ala Gly Ser
    370                 375                 380

Ser Ser Ala Glu Leu Leu Ala Ser Phe Cys Asp Asn Ile Leu Lys Lys
385                 390                 395                 400

Gly Gly Ser Glu Lys Leu Ser Asp Glu Ala Ile Glu Asp Ser Leu Glu
                405                 410                 415

Lys Val Val Lys Leu Leu Ala Tyr Val Ser Asp Lys Asp Leu Phe Ala
            420                 425                 430

Glu Phe Tyr Arg Lys Lys Leu Ser Arg Arg Leu Leu Phe Asp Lys Ser
        435                 440                 445

Ala Asn Asp Asp His Glu Arg Ser Ile Leu Thr Lys Leu Lys Gln Gln
    450                 455                 460

Cys Gly Gly Gln Phe Thr Ser Lys Met Glu Gly Met Val Thr Asp Leu
465                 470                 475                 480

Thr Leu Ala Arg Glu Asn Gln Thr Asn Phe Glu Glu Tyr Leu Gly Gln
                485                 490                 495

Asn Thr Asp Ala Ser Pro Gly Leu Asp Leu Thr Val Thr Val Leu Thr
            500                 505                 510

Thr Gly Phe Trp Pro Ser Tyr Lys Ser Ser Asp Leu Asn Leu Pro Ala
        515                 520                 525

Glu Met Val Arg Cys Val Glu Val Phe Lys Gln Phe Tyr Gln Thr Lys
    530                 535                 540

Thr Lys His Arg Lys Leu Thr Trp Val Tyr Ser Leu Gly Ser Cys Asn
545                 550                 555                 560

Ile Asn Gly Lys Phe Gly Pro Lys Thr Ile Glu Leu Val Val Gly Thr
                565                 570                 575

Tyr Gln Ala Ala Ala Leu Met Leu Phe Asn Thr Ser Asp Arg Leu Ser
            580                 585                 590

Tyr Ser Glu Ile Thr Thr Gln Leu Asn Leu Ala Asp Glu Asp Leu Val
        595                 600                 605

Arg Val Leu Gln Ser Leu Ser Cys Ala Lys Tyr Lys Ile Leu Leu Lys
    610                 615                 620

Glu Pro Ser Thr Arg Asn Val Ile Ser Thr Asp Cys Phe Ser Phe Asn
625                 630                 635                 640

Ser Asn Phe Thr Asp Arg Met Arg Arg Ile Arg Ile Pro Leu Pro Pro
                645                 650                 655

Met Asp Glu Arg Lys Lys Val Val Glu Asp Val Asp Lys Asp Arg Arg
            660                 665                 670

Tyr Ala Ile Asp Ala Ser Ile Val Arg Ile Met Lys Ser Arg Lys Ala
```

675 680 685

Leu Gly Tyr Gln Gln Leu Ile Thr Glu Cys Val Glu Gln Leu Ser Arg
690 695 700

Met Phe Lys Pro Asp Phe Lys Ala Ile Lys Lys Arg Ile Glu Asp Leu
705 710 715 720

Ile Thr Arg Asp Tyr Ile Glu Arg Asp Lys Glu Asn Pro Gln Leu Phe
725 730 735

Arg Tyr Leu Ala
740

<210> SEQ ID NO 68
<211> LENGTH: 739
<212> TYPE: PRT
<213> ORGANISM: Beta vulgaris

<400> SEQUENCE: 68

Met Asn Asp Arg Lys Val Ile Glu Leu Glu Gln Gly Trp Glu Phe Met
1 5 10 15

Gly Lys Gly Ile Thr Lys Leu Lys Arg Ile Leu Glu Gly Leu Pro Glu
20 25 30

Pro Pro Phe Asn Ser Glu Asp Tyr Met Met Leu Tyr Thr Thr Met Tyr
35 40 45

Asn Met Cys Thr Gln Lys Pro Pro His Asp Tyr Ser Gln Gln Leu Tyr
50 55 60

Asp Asn Tyr Lys Gln Ala Phe Val Asp Tyr Ile Asn Ser Thr Val Leu
65 70 75 80

Pro Ser Leu Arg Glu Lys His Asp Glu Phe Met Leu Arg Glu Leu Val
85 90 95

Lys Arg Trp Ala Asn His Lys Val Met Val Arg Trp Leu Ser Arg Phe
100 105 110

Phe His Tyr Leu Asp Arg Tyr Phe Ile Ala Arg Arg Ser Leu Pro Ser
115 120 125

Leu Asn Glu Val Gly Leu Thr Cys Phe Arg Asp Leu Val Tyr Gln Glu
130 135 140

Ile Ser Gly Lys Ala Lys Asp Ala Val Ile Ala Leu Ile Asp Ile Glu
145 150 155 160

Arg Glu Gly Gly Gln Ile Asp Arg Ser Leu Leu Lys Asn Val Leu Asp
165 170 175

Ile Tyr Val Glu Ile Gly Met Gly Gln Met Asp His Tyr Glu Lys Asp
180 185 190

Phe Glu Ala His Met Leu Asp Asp Thr Ala Ala Tyr Tyr Ser Arg Lys
195 200 205

Ala Ser Ser Trp Ile Leu Glu Asp Ser Cys Pro Glu Tyr Met Leu Lys
210 215 220

Ser Glu Glu Cys Leu Lys Lys Glu Lys Glu Arg Val Ala Asn Tyr Leu
225 230 235 240

His Ser Ser Ser Glu Pro Lys Leu Leu Glu Lys Val Gln Asn Glu Leu
245 250 255

Leu Leu Val Tyr Glu Ser Gln Leu Leu Glu Lys Glu Asn Ser Gly Cys
260 265 270

Arg Ala Leu Leu Lys Asp Asp Lys Val Asp Asp Leu Ser Arg Met Tyr
275 280 285

Arg Leu Tyr Ser Lys Val Thr Lys Gly Leu Glu Pro Ile Gly Ser Ile
290 295 300

-continued

```
Phe Lys Gln His Ile Thr Asp Glu Gly Thr Ala Leu Val Gln Gln Ala
305                 310                 315                 320

Glu Asp Ala Ala Ile Ser Lys Ala Glu Asn Thr Gly Gly Ser His Glu
                325                 330                 335

Gln Val Phe Val Arg Lys Val Ile Glu Leu His Asp Lys Phe Met Thr
            340                 345                 350

Tyr Val Thr Asp Cys Phe Asn Ser His Thr Ile Phe His Lys Ala Leu
        355                 360                 365

Lys Glu Ala Phe Glu Val Phe Leu Asn Lys Gly Val Ala Gly Ser Ser
    370                 375                 380

Ser Ala Glu Leu Leu Ala Thr Phe Cys Asp Asn Ile Leu Lys Lys Gly
385                 390                 395                 400

Gly Ser Glu Lys Leu Ser Asp Glu Ala Ile Glu Asp Ser Leu Glu Lys
                405                 410                 415

Val Val Lys Leu Leu Ala Tyr Val Ser Asp Lys Asp Leu Phe Ala Glu
            420                 425                 430

Phe Tyr Arg Lys Lys Leu Ser Arg Arg Leu Leu Phe Asp Lys Ser Ala
        435                 440                 445

Asn Asp Asp His Glu Arg Ser Ile Leu Thr Lys Leu Lys Gln Gln Cys
    450                 455                 460

Gly Gly Gln Phe Thr Ser Lys Met Glu Gly Met Val Thr Asp Leu Thr
465                 470                 475                 480

Leu Ala Arg Glu Asn Gln Thr Asn Phe Glu Glu Tyr Leu Ser Gln Asn
                485                 490                 495

Pro Asp Ala Ser Pro Gly Leu Asp Leu Thr Val Thr Val Leu Thr Thr
            500                 505                 510

Gly Phe Trp Pro Ser Tyr Lys Ser Ser Asp Leu Asn Leu Pro Ala Glu
        515                 520                 525

Met Val Arg Cys Val Glu Val Phe Lys Gln Phe Tyr Ser Thr Lys Thr
    530                 535                 540

Lys His Arg Lys Leu Thr Trp Val Tyr Ser Leu Gly Ser Cys Asn Ile
545                 550                 555                 560

Asn Gly Lys Phe Gly Pro Lys Thr Ile Glu Leu Val Val Gly Thr Tyr
                565                 570                 575

Gln Ala Ala Ala Leu Met Leu Phe Asn Thr Ser Asp Arg Leu Ser Tyr
            580                 585                 590

Ser Glu Ile Ala Thr Gln Leu Asn Leu Ala Asp Glu Asp Leu Val Arg
        595                 600                 605

Val Leu Gln Ser Leu Ser Cys Ala Lys Tyr Lys Ile Leu Leu Lys Glu
    610                 615                 620

Pro Asn Thr Lys Thr Val Ser Pro Thr Asp Cys Phe Ser Phe Asn Ser
625                 630                 635                 640

Ser Phe Thr Asp Arg Met Arg Arg Ile Arg Ile Pro Leu Pro Pro Met
                645                 650                 655

Asp Glu Arg Lys Lys Val Val Glu Asp Val Asp Lys Asp Arg Arg Tyr
            660                 665                 670

Ala Ile Asp Ala Ser Ile Val Arg Ile Met Lys Ser Arg Lys Val Leu
        675                 680                 685

Gly Tyr Gln Gln Leu Ile Thr Glu Cys Val Glu Gln Leu Ser Arg Met
    690                 695                 700

Phe Lys Pro Asp Phe Lys Ala Ile Lys Lys Arg Ile Glu Asp Leu Ile
705                 710                 715                 720

Thr Arg Asp Tyr Ile Glu Arg Asp Lys Glu Asn Pro Gln Leu Phe Arg
```

725 730 735

Tyr Leu Ala

<210> SEQ ID NO 69
<211> LENGTH: 738
<212> TYPE: PRT
<213> ORGANISM: Arabidopsis

<400> SEQUENCE: 69

Met Glu Arg Lys Thr Ile Asp Leu Glu Gln Gly Trp Asp Tyr Met Gln
1 5 10 15

Thr Gly Ile Thr Lys Leu Lys Arg Ile Leu Glu Gly Leu Asn Glu Pro
20 25 30

Ala Phe Asp Ser Glu Gln Tyr Met Met Leu Tyr Thr Thr Ile Tyr Asn
35 40 45

Met Cys Thr Gln Lys Pro Pro His Asp Tyr Ser Gln Gln Leu Tyr Asp
50 55 60

Lys Tyr Arg Glu Ala Phe Glu Glu Tyr Ile Asn Ser Thr Val Leu Pro
65 70 75 80

Ala Leu Arg Glu Lys His Asp Glu Phe Met Leu Arg Glu Leu Phe Lys
85 90 95

Arg Trp Ser Asn His Lys Val Met Val Arg Trp Leu Ser Arg Phe Phe
100 105 110

Tyr Tyr Leu Asp Arg Tyr Phe Ile Ala Arg Arg Ser Leu Pro Pro Leu
115 120 125

Asn Glu Val Gly Leu Thr Cys Phe Arg Asp Leu Val Tyr Asn Glu Leu
130 135 140

His Ser Lys Val Lys Gln Ala Val Ile Ala Leu Val Asp Lys Glu Arg
145 150 155 160

Glu Gly Glu Gln Ile Asp Arg Ala Leu Leu Lys Asn Val Leu Asp Ile
165 170 175

Tyr Val Glu Ile Gly Met Gly Gln Met Glu Arg Tyr Glu Glu Asp Phe
180 185 190

Glu Ser Phe Met Leu Gln Asp Thr Ser Ser Tyr Tyr Ser Arg Lys Ala
195 200 205

Ser Ser Trp Ile Gln Glu Asp Ser Cys Pro Asp Tyr Met Leu Lys Ser
210 215 220

Glu Glu Cys Leu Lys Lys Glu Arg Glu Arg Val Ala His Tyr Leu His
225 230 235 240

Ser Ser Ser Glu Pro Lys Leu Val Glu Lys Val Gln His Glu Leu Leu
245 250 255

Val Val Phe Ala Ser Gln Leu Leu Glu Lys Glu His Ser Gly Cys Arg
260 265 270

Ala Leu Leu Arg Asp Asp Lys Val Asp Asp Leu Ser Arg Met Tyr Arg
275 280 285

Leu Tyr His Lys Ile Leu Arg Gly Leu Glu Pro Val Ala Asn Ile Phe
290 295 300

Lys Gln His Val Thr Ala Glu Gly Asn Ala Leu Val Gln Gln Ala Glu
305 310 315 320

Asp Thr Ala Thr Asn Gln Val Ala Asn Thr Ala Ser Val Gln Glu Gln
325 330 335

Val Leu Ile Arg Lys Val Ile Glu Leu His Asp Lys Tyr Met Val Tyr
340 345 350

Val Thr Glu Cys Phe Gln Asn His Thr Leu Phe His Lys Ala Leu Lys

-continued

```
        355                 360                 365

Glu Ala Phe Glu Ile Phe Cys Asn Lys Thr Val Ala Gly Ser Ser Ser
    370                 375                 380

Ala Glu Leu Leu Ala Thr Phe Cys Asp Asn Ile Leu Lys Lys Gly Gly
385                 390                 395                 400

Ser Glu Lys Leu Ser Asp Glu Ala Ile Glu Asp Thr Leu Glu Lys Val
                405                 410                 415

Val Lys Leu Leu Ala Tyr Ile Ser Asp Lys Asp Leu Phe Ala Glu Phe
            420                 425                 430

Tyr Arg Lys Lys Leu Ala Arg Arg Leu Leu Phe Asp Arg Ser Ala Asn
        435                 440                 445

Asp Asp His Glu Arg Ser Ile Leu Thr Lys Leu Lys Gln Gln Cys Gly
    450                 455                 460

Gly Gln Phe Thr Ser Lys Met Glu Gly Met Val Thr Asp Leu Thr Leu
465                 470                 475                 480

Ala Arg Glu Asn Gln Asn Ser Phe Glu Asp Tyr Leu Gly Ser Asn Pro
                485                 490                 495

Ala Ala Asn Pro Gly Ile Asp Leu Thr Val Thr Val Leu Thr Thr Gly
            500                 505                 510

Phe Trp Pro Ser Tyr Lys Ser Phe Asp Ile Asn Leu Pro Ser Glu Met
        515                 520                 525

Ile Lys Cys Val Glu Val Phe Lys Gly Phe Tyr Glu Thr Lys Thr Lys
    530                 535                 540

His Arg Lys Leu Thr Trp Ile Tyr Ser Leu Gly Thr Cys His Ile Asn
545                 550                 555                 560

Gly Lys Phe Asp Gln Lys Ala Ile Glu Leu Ile Val Ser Thr Tyr Gln
                565                 570                 575

Ala Ala Val Leu Leu Leu Phe Asn Thr Thr Asp Lys Leu Ser Tyr Thr
            580                 585                 590

Glu Ile Leu Ala Gln Leu Asn Leu Ser His Glu Asp Leu Val Arg Leu
        595                 600                 605

Leu His Ser Leu Ser Cys Ala Lys Tyr Lys Ile Leu Leu Lys Glu Pro
    610                 615                 620

Asn Thr Lys Thr Val Ser Gln Asn Asp Ala Phe Glu Phe Asn Ser Lys
625                 630                 635                 640

Phe Thr Asp Arg Met Arg Arg Ile Lys Ile Pro Leu Pro Pro Val Asp
                645                 650                 655

Glu Arg Lys Lys Val Val Glu Asp Val Asp Lys Asp Arg Arg Tyr Ala
            660                 665                 670

Ile Asp Ala Ala Ile Val Arg Ile Met Lys Ser Arg Lys Val Leu Gly
        675                 680                 685

His Gln Gln Leu Val Ser Glu Cys Val Glu Gln Leu Ser Arg Met Phe
    690                 695                 700

Lys Pro Asp Ile Lys Ala Ile Lys Lys Arg Met Glu Asp Leu Ile Thr
705                 710                 715                 720

Arg Asp Tyr Leu Glu Arg Asp Lys Glu Asn Pro Asn Met Phe Arg Tyr
                725                 730                 735

Leu Ala
```

MODIFIED CULLIN1 GENE

RELATED APPLICATIONS AND INCORPORATION BY REFERENCE

This application is a continuation-in-part application of international patent application Serial No. PCT/EP2016/071177 filed 8 Sep. 2016, which published as PCT Publication No. WO 2017/042270 on 16 Mar. 2017, which claims benefit of Dutch patent application Serial No. 2015409 filed 8 Sep. 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Feb. 8, 2018, is named 4310400234_SL.txt and is 322,107 bytes in size.

FIELD OF THE INVENTION

The present invention relates to a plant type that enables efficient cultivation, and to methods for identifying and developing such a plant. The present invention also relates to a plant type suitable for situations that require smaller portions, or reduces the labour, time and expenses involved with storing, handling and transporting of redundant plant leaves, and to methods for identifying and developing such plant.

BACKGROUND OF THE INVENTION

Plant breeders are continuously looking for more efficient ways to cultivate plants. One way to increase the efficiency is by high-wire cultivation. In the high-wire cultivation, higher planting densities are used to obtain higher yields per $m^2$. In addition, high-wire cultivation allows a longer cultivation period during which the plant produces fruits. Cucumber and tomato are crops that are suitable for high-wire cultivation. However, not all varieties are fit for this type of cultivation.

More efficient cultivation can also be achieved in other crops if the plants have a compact growth phenotype. Such a compact growth phenotype may be characterized by the plants showing shorter internodes and/or a smaller leave area. Because of this compact growth phenotype, the plants can be planted in higher densities, thereby saving a lot of space.

It is one goal of the present invention to provide a plant type that enables efficient cultivation. This goal has been achieved by providing a plant type showing a compact growth phenotype.

In the research leading to the present invention, it was found that a mutation in the Cullin1 gene leads to a modification in plant type that may be expressed as a compact growth phenotype. A plant that has the mutant gene is in particular suitable for efficient cultivation. Such a plant shows a shorter internode length and/or a smaller leaf area and may also display other characteristics that lead to a compact growth phenotype.

Cullin proteins are a family of proteins present in all eukaryotes, not only plants. The Cullin proteins combine with RING proteins to form so-called Cullin-RING ubiquitine ligases (CRLs). In general, Cullin proteins play an important role in protein ubiquitination and protein degradation.

Ubiquitination (also known as ubiquitylation) is an enzymatic, post-translational modification process in which an ubiquitin protein is ligated to substrate protein.

Ubiquitine is a highly conserved, small polypeptide, ubiquitously distributed among eukaryotes. An ATP-dependent reaction cascade (involving the sequential action of ubiquitine-activating (E1s), ubiquitine-conjugating (E2s) and ubiquitine-protein ligase (E3s) enzymes) performs the ligation of ubiquitine to other proteins. Proteins that are ligated with ubiquitine are subsequently degraded and broken down, or relocated.

The Cullin1 protein, which is a member of the Cullin protein family, is one out of the four subunits that make up the SCF complex. The abbreviation SCF stands for SKP1-CUL1-F-box protein E3 ubiquitin ligase complex, which mediates the ubiquitination of proteins involved in cell cycle progression, signal transduction and transcription. In the SCF complex, Cullin1 serves as a rigid scaffold that organizes the SKP1-F-box protein and RBX1 subunits. It may contribute to catalysis through positioning of the substrate and the ubiquitin-conjugating enzyme.

Citation or identification of any document in this application is not an admission that such document is available as prior art to the present invention.

SUMMARY OF THE INVENTION

Cullin proteins are present in all eukaryotes. Through its involvement in ubiquitination and subsequent processes it is engaged in a wide range of cellular processes. Surprisingly, the mutation of the invention causes shorter internode length and/or smaller leaf area without causing a deleterious effect on the plant, which would be expected based on the state of the art knowledge available on the conserved status of Cullin1 protein and its functionality.

The characterisation of the modified Cullin1 gene in the present research was performed in cucumber (*Cucumis sativus*). This enabled the identification of further crops having a Cullin1 gene, which when modified leads to plants with a compact growth phenotype, i.e. showing shorter internode length and/or a smaller leaf area, or a reduction in other plant parts when compared to plants not having the modified Cullin1 gene. These crops include those belonging to the family of Cucurbitacea, such as for instance melon (*Cucumis melo*), watermelon (*Citrullus lanatus*), and squash (*Cucurbita pepo*); fruit crops, such as pepper (*Capsicum annuum*), tomato (*Solanum lycopersicum*), and eggplant (*Solanum melongena*); leafy vegetables, such as lettuce (*Lactuca sativa*), spinach (*Spinacia oleracea*), chicory (*Cichorium intybus*), and cabbage (*Brassica oleracea*); root vegetables, such as for instance carrot (*Daucus carota*), radish (*Raphanus sativus*), and beetroot (*Beta vulgaris*); and other crops, such as celery (*Apium graveolens*) and leek (*Allium ampeloprasum*).

It is another goal of the present invention to provide a plant type that is suitable for situations that require smaller portions, or reduces the labour, time and expenses involved with storing, handling and transporting of redundant plant leaves.

The invention thus relates to a modified Cullin1 gene which may comprise a modification in the wild type Cullin1 nucleotide sequence which leads to a modification in the wild type Cullin1 amino acid sequence.

The Cullin1 gene can be modified by different means known in the art, including mutagenesis. Mutagenesis may comprise the random introduction of at least one modification to DNA by means of one or more chemical compounds, such as ethyl methanesulphonate (EMS), nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements. Mutagenesis also may comprise the more specific, targeted introduction of at least one modification by means of homologous recombination, oligonucleotide-based mutation induction, zinc-finger nucleases (ZFNs), transcription activator-like effector nucleases (TALENs) or Clustered Regularly Interspaced Short Palindromic Repeat (CRISPR) systems.

The modified Cullin1 gene may be an exogenous Cullin1 gene introduced into a plant by a transgenic method or a cisgenic method. Use of a modified Cullin1 gene of the invention for developing a plant that shows a compact growth phenotype, i.e. may comprise shorter internodes and/or smaller leaf area, may comprise the introduction of a modified exogenous Cullin1 gene by a transgenic or a cisgenic method.

The modified Cullin1 gene may be part of a gene construct, which gene construct may comprise a selectable marker, a promoter sequence, a Cullin1 gene sequence, and a terminator sequence.

The present invention is widely applicable to all plant species that have a functional orthologue of the Cullin1 gene in their genome, i.e. an orthologue that performs the same or a similar biological function. Identification of Cullin1 orthologues, i.e. Cullin1 genes in other species, can be performed in many crops, methods of which are known in the art. The present invention can for instance be applied to a plant belonging to a species selected from the group consisting of *Cucumis sativus, Cucumis melo, Cucurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea*, and *Beta vulgaris*.

Accordingly, the present invention relates to a modified Cullin1 gene which may comprise a modification in the wild type Cullin1 nucleotide sequence of SEQ ID No: 1, SEQ ID No: 2, SEQ ID No: 3, SEQ ID No: 4, SEQ ID No: 5, SEQ ID No: 6, SEQ ID No: 7, SEQ ID No: 8, SEQ ID No: 9, SEQ ID No: 10, SEQ ID No: 11, SEQ ID No: 12, SEQ ID NO: 13, SEQ ID NO: 14, SEQ ID NO: 15, SEQ ID NO: 16, SEQ ID NO: 17 which leads to a modification in the wild type Cullin1 amino acid sequence of SEQ ID No: 18, SEQ ID No: 19, SEQ ID No: 20, SEQ ID No: 21, SEQ ID No: 22, SEQ ID No: 23, SEQ ID No: 24, SEQ ID No: 25, SEQ ID No: 26, SEQ ID No: 27, SEQ ID No: 28, SEQ ID NO: 29, SEQ ID NO: 30, SEQ ID NO: 31, SEQ ID NO:32, SEQ ID NO. 33, SEQ ID NO: 34 respectively.

FIGS. 1-17 show the wild type Cullin1 nucleotide sequences SEQ ID NO. 1-17 of *Cucumis sativus, Cucumis melo, Cucurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea*, and *Beta vulgaris*, respectively. FIGS. 18-34 show the wild type Cullin1 amino acid sequences SEQ ID NO.18-34 of *Cucumis sativus, Cucumis melo, Cucurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea*, and *Beta vulgaris*, respectively.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 Cucumber Cullin1 coding sequence wildtype, SEQ ID NO. 1. The nucleotide between brackets and bold indicates the position of the SNP, 147 nucleotides from the start. The wildtype nucleotide is "A", as shown here.

FIG. 2 Melon Cullin1 coding sequence wildtype, SEQ ID NO. 2. The nucleotide between brackets and bold indicates the position of the SNP, 147 nucleotides from the start. The wildtype nucleotide is "A", as shown here.

FIG. 3 Squash Cullin1 coding sequence wildtype, SEQ ID NO. 3. The nucleotide between brackets and bold indicates the position of the SNP, 147 nucleotides from the start. The wildtype nucleotide is "A", as shown here.

FIG. 4 Watermelon Cullin1 coding sequence wildtype, SEQ ID NO. 4. The nucleotide between brackets and bold indicates the position of the SNP, 147 nucleotides from the start. The wildtype nucleotide is "A", as shown here.

FIG. 5 Eggplant Cullin1 coding sequence wildtype, SEQ ID NO. 5. The nucleotide between brackets and bold indicates the position of the SNP, 141 nucleotides from the start. The wildtype nucleotide is "T", as shown here.

FIG. 6 Tomato Cullin1 coding sequence wildtype, SEQ ID NO. 6. The nucleotide between brackets and bold indicates the position of the SNP, 141 nucleotides from the start. The wildtype nucleotide is "T", as shown here.

FIG. 7 Pepper Cullin1 coding sequence wildtype, SEQ ID NO. 7. The nucleotide between brackets and bold indicates the position of the SNP, 141 nucleotides from the start. The wildtype nucleotide is "T", as shown here.

FIG. 8 Cabbage Cullin1 coding sequence wildtype, SEQ ID NO. 8. The nucleotide between brackets and bold indicates the position of the SNP, 138 nucleotides from the start. The wildtype nucleotide is "C", as shown here.

FIG. 9 Carrot Cullin1 coding sequence wildtype, SEQ ID NO. 9. The nucleotide between brackets and bold indicates the position of the SNP, 144 nucleotides from the start. The wildtype nucleotide is "C", as shown here.

FIG. 10 Celery Cullin1 coding sequence wildtype, SEQ ID NO. 10. The nucleotide between brackets and bold indicates the position of the SNP, 141 nucleotides from the start. The wildtype nucleotide is "C", as shown here.

FIG. 11 Chicory Cullin1 coding sequence wildtype, SEQ ID NO. 11. The nucleotide between brackets and bold indicates the position of the SNP, 141 nucleotides from the start. The wildtype nucleotide is "C", as shown here.

FIG. 12 Endive Cullin1 coding sequence wildtype, SEQ ID NO. 12. The nucleotide between brackets and bold indicates the position of the SNP, 141 nucleotides from the start. The wildtype nucleotide is "C", as shown here.

FIG. 13 Leek Cullin1 coding sequence wildtype, SEQ ID NO. 13. The nucleotide between brackets and bold indicates the position of the SNP, 147 nucleotides from the start. The wildtype nucleotide is "C", as shown here.

FIG. 14 Lettuce Cullin1 coding sequence wildtype, SEQ ID NO. 14. The nucleotide between brackets and bold indicates the position of the SNP, 141 nucleotides from the start. The wildtype nucleotide is "C", as shown here.

FIG. 15 Radish Cullin1 coding sequence wildtype, SEQ ID NO. 15. The nucleotide between brackets and bold indicates the position of the SNP, 138 nucleotides from the start. The wildtype nucleotide is "C", as shown here.

FIG. 16 Spinach Cullin1 coding sequence wildtype, SEQ ID NO. 16. The nucleotide between brackets and bold indicates the position of the SNP, 141 nucleotides from the start. The wildtype nucleotide is "A", as shown here.

FIG. 17 Beetroot Cullin1 coding sequence wildtype, SEQ ID NO. 17. The nucleotide between brackets and bold indicates the position of the SNP, 141 nucleotides from the start. The wildtype nucleotide is "A", as shown here.

FIG. 18 Cucumber Cullin1 protein sequence wildtype, SEQ ID NO.18. The amino acid between brackets and bold indicates the position of the amino acid change caused by the SNP, 49 amino acids from the start. The wildtype amino acid is 'I', as shown here.

FIG. 19 Melon Cullin1 protein sequence wildtype, SEQ ID NO.19. The amino acid between brackets and bold indicates the position of the amino acid change caused by the SNP, 49 amino acids from the start. The wildtype amino acid is 'I', as shown here.

FIG. 20 Squash Cullin1 protein sequence wildtype, SEQ ID NO.20. The amino acid between brackets and bold indicates the position of the amino acid change caused by the SNP, 49 amino acids from the start. The wildtype amino acid is 'I', as shown here.

FIG. 21 Watermelon Cullin1 protein sequence wildtype, SEQ ID NO.21. The amino acid between brackets and bold indicates the position of the amino acid change caused by the SNP, 49 amino acids from the start. The wildtype amino acid is 'I', as shown here.

FIG. 22 Eggplant Cullin1 protein sequence wildtype, SEQ ID NO.22. The amino acid between brackets and bold indicates the position of the amino acid change caused by the SNP, 47 amino acids from the start. The wildtype amino acid is 'I', as shown here.

FIG. 23 Tomato Cullin1 protein sequence wildtype, SEQ ID NO.23. The amino acid between brackets and bold indicates the position of the amino acid change caused by the SNP, 47 amino acids from the start. The wildtype amino acid is 'I', as shown here.

FIG. 24 Pepper Cullin1 protein sequence wildtype, SEQ ID NO.24. The amino acid between brackets and bold indicates the position of the amino acid change caused by the SNP, 47 amino acids from the start. The wildtype amino acid is 'I', as shown here.

FIG. 25 Cabbage Cullin1 protein sequence wildtype, SEQ ID NO.25. The amino acid between brackets and bold indicates the position of the amino acid change caused by the SNP, 46 amino acids from the start. The wildtype amino acid is 'I', as shown here.

FIG. 26 Carrot Cullin1 protein sequence wildtype, SEQ ID NO.26. The amino acid between brackets and bold indicates the position of the amino acid change caused by the SNP, 48 amino acids from the start. The wildtype amino acid is 'I', as shown here.

FIG. 27 Celery Cullin1 protein sequence wildtype, SEQ ID NO.27. The amino acid between brackets and bold indicates the position of the amino acid change caused by the SNP, 47 amino acids from the start. The wildtype amino acid is 'I', as shown here.

FIG. 28 Chicory Cullin1 protein sequence wildtype, SEQ ID NO.28. The amino acid between brackets and bold indicates the position of the amino acid change caused by the SNP, 47 amino acids from the start. The wildtype amino acid is 'I', as shown here.

FIG. 29 Endive Cullin1 protein sequence wildtype, SEQ ID NO.29. The amino acid between brackets and bold indicates the position of the amino acid change caused by the SNP, 47 amino acids from the start. The wildtype amino acid is 'I', as shown here.

FIG. 30 Leek Cullin1 protein sequence wildtype, SEQ ID NO.30. The amino acid between brackets and bold indicates the position of the amino acid change caused by the SNP, 49 amino acids from the start. The wildtype amino acid is 'I', as shown here.

FIG. 31 Lettuce Cullin1 protein sequence wildtype, SEQ ID NO.31. The amino acid between brackets and bold indicates the position of the amino acid change caused by the SNP, 47 amino acids from the start. The wildtype amino acid is 'I', as shown here.

FIG. 32 Radish Cullin1 protein sequence wildtype, SEQ ID NO.32. The amino acid between brackets and bold indicates the position of the amino acid change caused by the SNP, 46 amino acids from the start. The wildtype amino acid is 'I', as shown here.

FIG. 33 Spinach Cullin1 protein sequence wildtype, SEQ ID NO.33. The amino acid between brackets and bold indicates the position of the amino acid change caused by the SNP, 47 amino acids from the start. The wildtype amino acid is 'I', as shown here.

FIG. 34 Beetroot Cullin1 protein sequence wildtype, SEQ ID NO.34. The amino acid between brackets and bold indicates the position of the amino acid change caused by the SNP, 47 amino acids from the start. The wildtype amino acid is 'I', as shown here.

FIG. 35 Cucumber Cullin1 coding sequence "modified" SEQ ID NO. 35. The nucleotide between brackets and bold and bold indicates the position of the SNP 147 bp from the start. The modified nucleotide is "G", as shown here.

FIG. 36 Melon Cullin1 coding sequence "modified" SEQ ID NO. 36. The nucleotide between brackets and bold indicates the position of the SNP 147 bp from the start. The modified nucleotide is "G", as shown here.

FIG. 37 Squash Cullin1 coding sequence "modified" SEQ ID NO. 37. The nucleotide between brackets and bold indicates the position of the SNP 147 bp from the start. The modified nucleotide is "G", as shown here.

FIG. 38 Watermelon Cullin1 coding sequence "modified" SEQ ID NO. 38. The nucleotide between brackets and bold indicates the position of the SNP 147 bp from the start. The modified nucleotide is "G", as shown here.

FIG. 39 Eggplant Cullin1 coding sequence "modified" SEQ ID NO. 39. The nucleotide between brackets and bold indicates the position of the SNP 141 bp from the start. The modified nucleotide is "G", as shown here.

FIG. 40 Tomato Cullin1 coding sequence "modified" SEQ ID NO. 40. The nucleotide between brackets and bold indicates the position of the SNP 141 bp from the start. The modified nucleotide is "G", as shown here.

FIG. 41 Pepper Cullin1 coding sequence "modified" SEQ ID NO. 41. The nucleotide between brackets and bold indicates the position of the SNP 141 bp from the start. The modified nucleotide is "G", as shown here.

FIG. 42 Cabbage Cullin1 coding sequence "modified" SEQ ID NO. 42. The nucleotide between brackets and bold indicates the position of the SNP 138 bp from the start. The modified nucleotide is "G", as shown here.

FIG. 43 Carrot Cullin1 coding sequence "modified" SEQ ID NO. 43. The nucleotide between brackets and bold indicates the position of the SNP 144 bp from the start. The modified nucleotide is "G", as shown here.

FIG. 44 Celery Cullin1 coding sequence "modified" SEQ ID NO. 44. The nucleotide between brackets and bold indicates the position of the SNP 141 bp from the start. The modified nucleotide is "G", as shown here.

FIG. 45 Chicory Cullin1 coding sequence "modified" SEQ ID NO. 45. The nucleotide between brackets and bold indicates the position of the SNP 141 bp from the start. The modified nucleotide is "G", as shown here.

FIG. 46 Endive Cullin1 coding sequence "modified" SEQ ID NO. 46. The nucleotide between brackets and bold indicates the position of the SNP 141 bp from the start. The modified nucleotide is "G", as shown here.

FIG. 47 Leek Cullin1 coding sequence "modified" SEQ ID NO. 47. The nucleotide between brackets and bold indicates the position of the SNP 147 bp from the start. The modified nucleotide is "G", as shown here.

FIG. 48 Lettuce Cullin1 coding sequence "modified" SEQ ID NO. 48. The nucleotide between brackets and bold indicates the position of the SNP 141 bp from the start. The modified nucleotide is "G", as shown here.

FIG. 49 Radish Cullin1 coding sequence "modified" SEQ ID NO. 49. The nucleotide between brackets and bold indicates the position of the SNP 138 bp from the start. The modified nucleotide is "G", as shown here.

FIG. 50 Spinach Cullin1 coding sequence "modified" SEQ ID NO. 50. The nucleotide between brackets and bold indicates the position of the SNP 141 bp from the start. The modified nucleotide is "G", as shown here.

FIG. 51 Beetroot Cullin1 coding sequence "modified" SEQ ID NO. 51. The nucleotide between brackets and bold indicates the position of the SNP 141 bp from the start. The modified nucleotide is "G", as shown here.

FIG. 52 Cucumber Cullin1 protein sequence "modified" SEQ ID NO. 52. The amino acid between brackets and bold indicates the position of the amino acid change caused by the SNP, 49 amino acids from the start. The modified amino acid is 'M', as shown here.

FIG. 53 Melon Cullin1 protein sequence "modified" SEQ ID NO. 53. The amino acid between brackets and bold indicates the position of the amino acid change caused by the SNP, 49 amino acids from the start. The modified amino acid is 'M', as shown here.

FIG. 54 Squash Cullin1 protein sequence "modified" SEQ ID NO. 54. The amino acid between brackets and bold indicates the position of the amino acid change caused by the SNP, 49 amino acids from the start. The modified amino acid is 'M', as shown here.

FIG. 55 Watermelon Cullin1 protein sequence "modified" SEQ ID NO. 55. The amino acid between brackets and bold indicates the position of the amino acid change caused by the SNP, 49 amino acids from the start. The modified amino acid is 'M', as shown here.

FIG. 56 Eggplant Cullin1 protein sequence "modified" SEQ ID NO. 56. The amino acid between brackets and bold indicates the position of the amino acid change caused by the SNP, 47 amino acids from the start. The modified amino acid is 'M', as shown here.

FIG. 57 Tomato Cullin1 protein sequence "modified" SEQ ID NO. 57. The amino acid between brackets and bold indicates the position of the amino acid change caused by the SNP, 47 amino acids from the start. The modified amino acid is 'M', as shown here.

FIG. 58 Pepper Cullin1 protein sequence "modified" SEQ ID NO. 58. The amino acid between brackets and bold indicates the position of the amino acid change caused by the SNP, 47 amino acids from the start. The modified amino acid is 'M', as shown here.

FIG. 59 Cabbage Cullin1 protein sequence "modified" SEQ ID NO. 59. The amino acid between brackets and bold indicates the position of the amino acid change caused by the SNP, 46 amino acids from the start. The modified amino acid is 'M', as shown here.

FIG. 60 Carrot Cullin1 protein sequence "modified" SEQ ID NO. 60. The amino acid between brackets and bold indicates the position of the amino acid change caused by the SNP, 48 amino acids from the start. The modified amino acid is 'M', as shown here.

FIG. 61 Celery Cullin1 protein sequence "modified" SEQ ID NO. 61. The amino acid between brackets and bold indicates the position of the amino acid change caused by the SNP, 47 amino acids from the start. The modified amino acid is 'M', as shown here.

FIG. 62 Cichory Cullin1 protein sequence "modified" SEQ ID NO. 62. The amino acid between brackets and bold indicates the position of the amino acid change caused by the SNP, 47 amino acids from the start. The modified amino acid is 'M', as shown here.

FIG. 63 Endive Cullin1 protein sequence "modified" SEQ ID NO. 63. The amino acid between brackets and bold indicates the position of the amino acid change caused by the SNP, 47 amino acids from the start. The modified amino acid is 'M', as shown here.

FIG. 64 Leek Cullin1 protein sequence "modified" SEQ ID NO. 64. The amino acid between brackets and bold indicates the position of the amino acid change caused by the SNP, 49 amino acids from the start. The modified amino acid is 'M', as shown here.

FIG. 65 Lettuce Cullin1 protein sequence "modified" SEQ ID NO. 65. The amino acid between brackets and bold indicates the position of the amino acid change caused by the SNP, 47 amino acids from the start. The modified amino acid is 'M', as shown here.

FIG. 66 Radish Cullin1 protein sequence "modified" SEQ ID NO. 66. The amino acid between brackets and bold indicates the position of the amino acid change caused by the SNP, 46 amino acids from the start. The modified amino acid is 'M', as shown here.

FIG. 67 Spinach Cullin1 protein sequence "modified" SEQ ID NO. 67. The amino acid between brackets and bold indicates the position of the amino acid change caused by the SNP, 47 amino acids from the start. The modified amino acid is 'M', as shown here.

FIG. 68 Beetroot Cullin1 protein sequence "modified" SEQ ID NO. 68. The amino acid between brackets and bold indicates the position of the amino acid change caused by the SNP, 47 amino acids from the start. The modified amino acid is 'M', as shown here.

FIGS. 69A-S The multiple sequence alignment of the Cullin1 coding sequence orthologues (wild type) of various crops: *brassica* (SEQ ID NO. 8), radish (SEQ ID NO. 15), beet (SEQ ID NO. 17), spinach (SEQ ID NO. 16), leek (SEQ ID NO. 13), squash (SEQ ID NO. 3), watermelon (SEQ ID NO. 4), cucumber (SEQ ID NO. 1), melon (SEQ ID NO. 2), tomato (SEQ ID NO. 6), eggplant (SEQ ID NO. 5), pepper (SEQ ID NO. 7), lettuce (SEQ ID NO. 14), chicory (SEQ ID NO. 11), endive (SEQ ID NO. 12), carrot (SEQ ID NO. 9), celery (SEQ ID NO. 10). Between brackets and bold is indicated the SNP on position 147 in the Cucumber coding sequence and for other crops on a position corresponding to this position.

FIGS. 70A-F The multiple sequence alignment of the Cullin1 amino acid orthologues (wild type) of various crops: beet (SEQ ID NO. 34), spinach (SEQ ID NO. 33), arabidopsis (SEQ ID NO. 69), *brassica* (SEQ ID NO. 25), radish (SEQ ID NO. 32), leek (SEQ ID NO. 30), eggplant (SEQ ID NO. 22), tomato (SEQ ID NO. 23), pepper (SEQ ID NO. 24), cucumber (SEQ ID NO. 18), melon (SEQ ID NO. 19), watermelon (SEQ ID NO. 21), squash (SEQ ID NO. 20), celery (SEQ ID NO. 27), lettuce (SEQ ID NO. 31), endive (SEQ ID NO. 29), chicory (SEQ ID NO. 28), carrot (SEQ ID NO. 26). Between brackets and bold is indicated the SNP on position 49 in the Cucumber amino acid sequence and for other crops on a position corresponding to this position.

DETAILED DESCRIPTION OF THE INVENTION

The term "wild type" as used herein refers in general to the form of an organism, gene, protein, or trait as it would occur in nature, as opposed to a mutated or modified form. In this application wild type refers specifically to the naturally occurring form of the Cullin1 gene, the naturally occurring form of the nucleotide sequence of Cullin1 and the naturally occurring form of the Cullin1 amino acid sequence. The naturally occurring forms of the Cullin1 gene and Cullin1 protein of several crops are shown in FIGS. 1-17 and FIGS. 18-34 respectively.

The terms "mutant", "mutation", "modification", "modified", "mutated Cullin1 gene" and "modified Cullin1 gene" as used herein refer to nucleotide changes and amino acid changes to the wild type Cullin1 gene thereof that lead to a modified version of the wild type gene. The modification can be any modification, including but not limited to a SNP.

The modified Cullin1 gene is also referred to herein as "the gene of the invention", "the modified Cullin1 gene", or "the modified Cullin1 gene of the invention". These terms are used interchangeably herein. As used herein the phrase "the modified Cullin1 gene" is intended to encompass the Cullin1 gene with any modification that leads to the compact growth phenotype.

The terms "compact gene phenotype", "compact phenotype" or "compact growth phenotype" are used interchangeably herein and refer to a phenotype of a shorter internode length and/or a smaller leaf area. Crops which may comprise the modified Cullin1 gene and which have internodes, such as for instance cucumber, may show shorter internodes or a smaller leaf area. They may also show shorter internodes and a smaller leaf area. Crops which may comprise the modified Cullin1 gene but which do not have internodes, such as for instance lettuce, may show a smaller leaf area.

The term "smaller leaf area" as used herein is the leaf area that displays a reduction in individual leaf area of, in order of increased preference, at least 10%, at least 20%, at least 30%, at least 40%, at least 50%, at least 60%, at least 70%, at least 80% as a result of the homozygous or heterozygous presence of the modified gene of the invention. To investigate the influence of the gene of the invention on the smaller leaf area, a skilled person would have to compare plants having the gene of the invention homozygously or heterozygously with plants that are isogenic to first mentioned plants but do not have the gene of the invention.

With the term "leaf" is meant the part of the plant consisting of the petiole and leaf blade. With the term "leaf area" is meant the surface of the part of the plant consisting of the leaf blade.

The term "shorter internodes" or "shorter internode length" as used herein is internode length that has a reduction in individual length of, in order of increased preference, at least 10%, at least 20%, at least 30%, at least 40%, at least 50%, at least 60%, at least 70%, at least 80% as a result of the homozygous or heterozygous presence of the gene of the invention. To investigate the influence of the gene of the invention on the shorter internode length, a skilled person would have to compare plants having the gene of the invention homozygously or heterozygously with plants that are isogenic to first mentioned plants but without the gene of the invention.

The modification leading to the modified Cullin1 gene may be selected from a modification that changes the mRNA level of the Cullin1 gene, a modification that changes the Cullin1 protein structure and/or levels, and/or a modification that changes the Cullin1 protein activity.

One aspect of the invention relates to a modified Cullin1 gene, which may comprise a mutation as compared to its wild type genomic sequence, which mutation leads to a change in the Cullin1 protein and/or protein activity, wherein the modified Cullin1 gene is capable of causing a compact growth phenotype.

In one embodiment, the mutation is a Single Nucleotide Polymorphism (SNP).

In one embodiment of the present invention, the change in the amino acid sequence is a substitution.

In a preferred embodiment of the present invention, the change in the amino acid sequence is found in the part of the Cullin1 protein between the amino acids on position 30-60, preferably in the part between the amino acids on positions 40-55 of the cucumber amino acid sequence of SEQ ID No: 18, or on a part corresponding thereto.

In a further preferred embodiment of the present invention, the change in the amino acid sequence is found in the part of the Cullin1 protein that binds SKP1 and/or ETA2.

Preferably, the physical location of the amino acid substitution in the Cullin1 protein lies in the region of the protein where the Cullin1 protein binds to SKP1 and/or ETA2. The Cullin1 protein forms a so-called SCF complex, together with SKP1, RBX1 and a F-box protein, which has important functionalities such as a role in leaf development. ETA2 is according to some theories, required to sustain the SCF complex activity, most probably by facilitating cycles of assembly and disassembly of the SCF complex.

In a specific embodiment, the modified Cullin1 gene includes, a Cullin1 gene which may comprise a SNP on position 147 of SEQ ID NO.1 of cucumber, or on a position corresponding thereto in the Cullin1 gene of other crops, wherein the modification may comprise a change in the nucleotide on that position and wherein the modification leads to an amino acid substitution in the Cullin1 protein on position 49 of the wildtype protein sequence SEQ ID NO: 18. of cucumber, or on a position corresponding thereto, in other crops. In cucumber the change is from A to G and from Isoleucine to Methionine. In other crops the change in nucleotide and amino acid may be different.

In a preferred embodiment of the present invention, the modification of the nucleotide sequence may comprise a change from Adenine, Cytosine or Thymine to Guanine.

The definition "coding sequence" as used herein is the portion of the gene's DNA composed of exons that code for the protein.

In a further embodiment of the present invention, the modification in the amino acid sequence is a substitution on position 49 of the cucumber amino acid sequence of SEQ ID No: 18, or, in case of a crop other than cucumber, on a position corresponding to position 49 of the cucumber amino acid sequence of SEQ ID No: 18.

The amino acid substitution caused by the mutation of the current invention was found to be present on position 49 of the cucumber amino acid sequence of SEQ ID No: 18, or, in case of a crop other than cucumber, on a position corresponding to position 49 of the wild type amino acid sequence SEQ ID NO. 18 of cucumber. This nucleotide mutation is considered to be non-conservative, and the amino acid change can be considered non-conservative.

Amino acid changes in a protein occur when the mutation of one or more base pairs in the coding DNA sequence result in an altered codon triplet that encodes a different amino acid. Not all point mutations in the coding DNA sequence lead to amino acid changes, due to the redundancy of the genetic code. Mutations in the coding sequence that do not lead to amino acid changes are called "silent mutations". Other mutations are called "conservative", they lead to the replacement of one amino acid by another amino acid with comparable properties, such that the mutations are unlikely to change the folding of the mature protein, or influence its function. As used herein a "non-conservative amino acid change" refers to an amino acid that is replaced by another amino acid that has different chemical properties that may lead to decreased stability, changed functionality and/or structural effects of the encoded protein.

In a further preferred embodiment of the present invention, the modification in the amino acid sequence is a substitution and consists of a change from Isoleucine to Methionine The invention further relates to a plant which may comprise the modified Cullin1 gene.

A *Cucumis sativus* plant which may comprise the modified Cullin1 gene with the nucleotide sequence of SEQ ID No: 35 is not part of this invention and is therefore disclaimed herewith.

A plant which may comprise the modified Cullin1 gene shows a compact growth phenotype, i.e. may comprise a shorter internode length and/or a smaller leaf area, compared to an isogenic plant of the same species not comprising the modified Cullin1 gene. For example, a *Cucumis sativus* plant a *Cucumis melo* plant, a *Cucurbita pepo* plant, a *Citrullus lanatus* plant, a *Solanum melongena* plant, a, *Solanum lycopersicum* plant, and a *Capsicum annuum* plant which may comprise the modified Cullin1 gene show a shorter internode length and/or a smaller leaf area. These plants are therefore particularly suitable for efficient cultivation. A *Cichorium intybus* plant, a *Cichorium endivia* plant, a *Lactuca sativa* plant, a *Brassica oleracea* plant and a *Spinacia oleracea* plant which may comprise the modified Cullin1 gene show for example a smaller leaf area. As such, the parts of these plants harvested for consumption are smaller in size. These plants are therefore particularly suitable for a situation in which smaller portions are required. A *Daucus carota* plant which may comprise the modified Cullin1 gene shows a shorter internode length and/or a smaller leaf area. As such, the plant may comprise less foliage that needs to be removed before the product is sold and/or consumed. An *Apium graveolens* plant which may comprise the modified Cullin1 gene shows a shorter internode length and/or a smaller leaf area. As such, the plant is of a more compact size suitable for a situation in which smaller portions are required and/or may comprise less foliage that needs to be removed before the product is sold and/or consumed. An *Allium ampeloprasum* plant which may comprise the modified Cullin1 gene shows a smaller leaf area. As such, the leaves that are not consumed do not need to be removed before the product is sold and/or consumed. A *Raphanus sativus* plant and a *Beta vulgaris* plant which may comprise the modified Cullin1 gene show a smaller leaf area. As such, less foliage needs to be removed before the product is sold and/or consumed.

The plant of the invention which may comprise the modified Cullin1 gene either homozygously or heterozygously may be a plant of an inbred line, a hybrid, a doubled haploid, or a plant of a segregating population.

The plant of the invention may have the modified Cullin1 gene in heterozygous state since such a plant shows the trait in an intermediate level. Furthermore such plant may be a potential source of the gene and when crossed with another plant that optionally also has the modified gene either homozygously or heterozygously can result in progeny plants that have the modified gene homozygously or heterozygously and show the trait of having a compact growth phenotype.

The invention also relates to a method for the production of a plant having the modified Cullin1 gene that leads to a compact growth phenotype by using a seed that may comprise the modified Cullin1 gene for growing the said plant.

The invention further relates to a method for the production of a plant having the modified Cullin1 gene by using tissue culture of plant material that carries the modified Cullin1 gene in its genome.

The invention furthermore relates to a method for the production of a plant having the modified Cullin1 gene which leads to a compact growth phenotype, by using vegetative reproduction of plant material that carries the modified Cullin1 gene in its genome.

The invention further provides a method for the production of a plant having the modified Cullin1 gene by using a doubled haploid generation technique to generate a doubled haploid line from a cucumber plant which may comprise the modified Cullin1 gene.

The invention further relates to a plant seed which may comprise the modified Cullin1 gene of the invention, wherein the plant that can be grown from the seed shows a compact growth phenotype.

The invention also relates to a method for seed production which may comprise growing plants from seeds of the invention, allowing the plants to produce seeds by allowing pollination to occur, and harvesting those seeds. Production of the seeds is suitably done by crossing or selfing. Seeds produced in that manner result in a compact growth phenotype of the plants grown thereof.

The invention furthermore relates to hybrid seed and to a method for producing such hybrid seed which may comprise crossing a first parent plant with a second parent plant and harvesting the resultant hybrid seed, wherein said first parent plant and/or said second parent plant has the modified Cullin1 gene of the invention. A hybrid plant resulting from growing the resulting seed that may comprise the modified Cullin1 gene of the invention, showing the compact growth phenotype of the invention is also a plant of the invention.

Another aspect of the invention relates to propagation material capable of developing into and/or being derived from a plant which may comprise a modified Cullin1 gene, wherein the plant shows a compact growth phenotype, compared to an isogenic plant of the same species not comprising the modified Cullin1 gene, wherein the propagation material may comprise the modified Cullin1 gene of the invention and wherein the propagation material is selected from the group consisting of microspores, pollen, ovaries, ovules, embryos, embryo sacs, egg cells, cuttings, roots, hypocotyls, cotyledons, stems, leaves, flowers, anthers, seeds, meristematic cells, protoplasts and cells, or tissue culture thereof.

The invention thus further relates to parts of a claimed plant that are suitable for sexual reproduction. Such parts are for example selected from the group consisting of microspores, pollen, ovaries, ovules, embryo sacs, and egg cells. In addition, the invention relates to parts of a claimed plant that are suitable for vegetative reproduction, which are in particular cuttings, roots, stems, cells, protoplasts. The parts of the plants as mentioned above are considered propagation material. The plant that is produced from the propagation material may comprise the modified Cullin1 gene that leads to a compact growth phenotype and thus enables efficient cultivation and/or is suitable for the production for market segments that require a smaller product.

According to a further aspect thereof, the invention provides a tissue culture of a plant carrying the modified Cullin1 gene of the invention, which is also propagation material. The tissue culture may comprise regenerable cells. Such tissue culture can be selected or derived from any part of the plant, in particular from leaves, pollen, embryos, cotyledon, hypocotyls, meristematic cells, roots, root tips, anthers, flowers, seeds, and stems. The tissue culture can be regenerated into a plant carrying the modified Cullin1 gene of the invention, which regenerated plant expresses the trait of the invention and is also part of the invention.

The invention further relates to the use of the modified Cullin1 gene for the development of a plant showing a compact growth phenotype. A skilled person is familiar with introducing a new trait into a plant already having other desired agricultural properties, for instance by introgression. Introgression can be done by means of standard breeding techniques, wherein selection can be done either phenotypically or with the use of markers or a combination thereof.

The invention further relates to the use of the modified Cullin1 gene, or a part thereof which may comprise the modification, as a marker for identifying a plant showing a compact growth phenotype.

The 'use for identifying' or a 'method for identifying' as used in the current application may comprise the use of the described (causal) SNP in the Cullin1 gene as a marker. The invention also relates to other markers that can be developed based on a modification, including the causal SNP, in the Cullin1 gene, as well as to other markers that can be developed based on the wildtype sequence of the Cullin1 gene.

The invention further relates to the use of any of the sequences of SEQ ID NOs. 35-51, or a part thereof, as a marker for identifying a plant showing a compact growth phenotype, i.e. which may comprise a shorter internode length and/or a smaller leaf area. If a part of any of these sequences is used, the part must comprise the modification. For example, SEQ ID No. 35 or a part thereof may be used to identify a *Cucumis sativus* plant showing a shorter internode length and/or a smaller leaf area; SEQ ID No. 36 or a part thereof may be used to identify a *Cucumis melo* plant showing a shorter internode length and/or a smaller leaf area; SEQ ID No. 37 or a part thereof may be used to identify a *Cucurbita pepo* plant showing a shorter internode length and/or a smaller leaf area; SEQ ID No. 38 or a part thereof may be used to identify a *Citrullus lanatus* plant showing a shorter internode length and/or a smaller leaf area; SEQ ID No. 39 or a part thereof may be used to identify a *Solanum melongena* plant showing a shorter internode length and/or a smaller leaf area; SEQ ID No. 40 or a part thereof may be used to identify a *Solanum lycopersicum* plant showing a shorter internode length and/or a smaller leaf area; SEQ ID No. 41 or a part thereof may be used to identify a *Capsicum annuum* plant showing a shorter internode length and/or a smaller leaf area; SEQ ID No. 42 or a part thereof may be used to identify a *Brassica oleracea* plant showing a smaller leaf area; SEQ ID No. 43 or a part thereof may be used to identify a *Daucus carota* plant showing a shorter internode length and/or a smaller leaf area; SEQ ID No. 44 or a part thereof may be used to identify a *Apium graveolens* plant showing a shorter internode length and/or a smaller leaf area; SEQ ID No. 45 or a part thereof may be used to identify a *Cichorium intybus* plant showing a smaller leaf area; SEQ ID No. 46 or a part thereof may be used to identify a *Cichorium endivia* plant showing a smaller leaf area; SEQ ID No. 47 or a part thereof may be used to identify an *Allium ampeloprasum* plant showing a smaller leaf area; SEQ ID No. 48 or a part thereof may be used to identify a *Lactuca sativa* plant showing a smaller leaf area; SEQ ID No. 49 or a part thereof may be used to identify a *Raphanus sativus* plant showing a shorter internode length and/or a smaller leaf area; SEQ ID No. 50 or a part thereof may be used to identify a *Spinacia oleracea* plant showing a smaller leaf area; SEQ ID No. 51 or a part thereof may be used to identify a *Beta vulgaris* plant showing a shorter internode length and/or a smaller leaf area. The invention also relates to the use of any markers that are derived from SEQ ID Nos. 1-17 or SEQ ID NOs. 36-51 for identifying a plant showing a compact growth phenotype. Any such derived marker must comprise the modification that leads to the phenotype of the invention.

In general, to identify a plant showing a compact growth phenotype, it is thus determined in the Cullin1 gene whether there is an A, C, or T (SEQ ID Nos. 1-17) or a G (SEQ ID Nos. 35-51) on position 147, or a position corresponding thereto.

The invention further relates to a method for obtaining a plant which shows a compact growth phenotype which may comprise;

a) crossing a plant which may comprise the modified Cullin1 gene of the current invention with a plant not comprising the modified Cullin1 gene, to obtain an F1 population;
b) optionally performing one or more rounds of selfing and/or crossing a plant from the F1 to obtain a further generation population; and
c) selecting a plant that has a compact growth phenotype and the modified Cullin1 gene of the invention.

The invention also relates to a method for obtaining a plant which shows a compact growth phenotype which may comprise;

a) crossing a plant which may comprise the modified Cullin1 gene of the current invention with another plant which may comprise the modified Cullin1 gene, to obtain an F1 population;
b) optionally performing one or more rounds of selfing and/or crossing a plant from the F1 to obtain a further generation population; and
c) selecting a plant that has a compact growth phenotype and the modified Cullin1 gene of the invention.

The invention further relates to a marker for identifying a plant showing a compact growth phenotype, which may comprise the modified Cullin1, or a part thereof that may comprise the modification. Preferably, the modification is a nucleotide substitution on or around position 147 of SEQ ID No:1 of cucumber, or, in case of a crop other than cucumber, on or around a position corresponding to position 147 of SEQ ID No:1 of cucumber, which modification leads to an amino acid substitution in the Cullin1 protein.

The invention also relates to a method for selecting a plant showing a compact growth phenotype from a population of plants, which may comprise detecting the presence or absence of a guanine on position 147 of the cucumber nucleotide sequence of SEQ ID NO:1, or, for a crop other than cucumber, on a position corresponding to position 147 of the cucumber nucleotide sequence of SEQ ID No: 1, in the genome of a plant of a population of plants, and selecting a plant which may comprise a guanine on position 147 of SEQ ID NO:1, as shown in SEQ ID NO. 35, or, for a crop other than cucumber, on a position corresponding to position 147 of the cucumber nucleotide sequence of SEQ ID No: 1, as shown in any of SEQ ID Nos. 36-51.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1. Identification of the Cullin1 Gene Modification in *Cucumis Sativus*

A F2 crossing population made from a commercially available "high wire" cucumber variety, "Hi Lisa", was used to create a new genetic map. In total, 375 markers and 398 F2 lines are used. A QTL analysis performed on these crossing populations revealed a major QTL on chromosome 6 that causes a smaller internode length and a smaller leaf surface. Sequencing of the peak marker of the QTL revealed a SNP present in the marker sequence. The particular sequence was polymorphic in the crossing population. The nucleotide sequence of the major QTL on chromosome 6 was identified by means of BLAST. The best BLAST hits for the sequence all resembled the sequence of the Cullin1 gene.

Example 2. Validation of the Effect of SNP in the Cullin1 Gene on Internode Length and Plant Leaf Area Different populations of *Cucumis sativus* plants, each made with different commercially available 'high wire' varieties, having the phenotype of shorter internodes, and smaller leaves, were phenotypically and genetically analysed. See Table 1 for the phenotypic and genetic data.

Plants were measured 3 weeks after sowing. For estimating the leaf area, from the second leaf on (not the cotyledons) all leafs present were measured, and the width and the length of a leaf were measured and multiplied with each other to obtain a (roughly estimation) score for leaf area. In the third column of Table 1, the different haplotypes for the Cullin1 gene SNP are given. The score A means that the SNP marker scored homozygous wildtype Cullin1 gene, B means homozygous modified Cullin1 gene.

In the first population, plants that are homozygous for the modified Cullin1 gene (B), show an internode length that is on average 63% of the length of the plants that score homozygous for the wild type Cullin1 gene (A). The B plants (homozygous for the modified Cullin1 gene) show a leaf area that is on average 38% of the length of the A plants (homozygous for the wild type Cullin1 gene).

In the second population, B plants show on average an internode length that is 78% and a leaf area that is 39% of the A plants of the same population.

In the third population, the B plants show on average an internode length of 66% and a leaf area of 47%, compared to the average of the A plants.

TABLE 1

Results of phenotypic and genotypic analyses of 3 different cucumber lines derived from commercially available high wire varieties. The internode length is defined as the length of the main stem divided by the number of internodes. The leaf area is roughly estimated by measuring from all leafs present on a plant starting with the second leaf (not the cotyledons) the length and the width, multiplying length and width, and computing the average per plant. For the scores of the Cullin1 SNP, score A means that the marker scored A homozygous (wildtype), B means homozygous (modified).

| Plant material | Cullin1 haplotype | Internode length (H/I) | Leaf area (J × K) |
|---|---|---|---|
| BPQ -3 | B | 6 | 210 |
| BPQ -8 | B | 4, 7 | 210 |
| BPQ -10 | B | 5, 8 | 289 |
| BPQ -12 | B | 4, 8 | 210 |

TABLE 1-continued

Results of phenotypic and genotypic analyses of 3 different cucumber lines derived from commercially available high wire varieties. The internode length is defined as the length of the main stem divided by the number of internodes. The leaf area is roughly estimated by measuring from all leafs present on a plant starting with the second leaf (not the cotyledons) the length and the width, multiplying length and width, and computing the average per plant. For the scores of the Cullin1 SNP, score A means that the marker scored A homozygous (wildtype), B means homozygous (modified).

| Plant material | Cullin1 haplotype | Internode length (H/I) | Leaf area (J × K) |
|---|---|---|---|
| BPQ -5 | A | 6, 6 | 462 |
| BPQ -6 | A | 9, 3 | 550 |
| BPQ -4 | A | 7, 6 | 575 |
| BPQ -7 | A | 8, 4 | 650 |
| BPQ -1 | A | 8, 3 | 725 |
| BPQ -11 | A | 8, 5 | 676 |
| BPQ -9 | A | 10, 3 | 650 |
| 13L.3402-2 pl-1 | B | 4, 3 | 208 |
| 13L.3402-2 pl-15 | B | 5, 7 | 285 |
| 13L.3402-2 pl-7 | B | 5, 8 | 238 |
| 13L.3402-2 pl-9 | B | 6, 1 | 216 |
| 13L.3402-2 pl-17 | B | 6, 6 | 238 |
| 13L.3402-2 pl-6 | A | 6, 7 | 550 |
| 13L.3402-2 pl-3 | A | 6, 8 | 616 |
| 13L.3402-2 pl-10 | A | 6, 8 | 567 |
| 13L.3402-2 pl-13 | A | 7, 2 | 675 |
| 13L.3402-2 pl-5 | A | 8 | 690 |
| 13L.3402-2 pl-8 | A | 8, 6 | 546 |
| 12L. 1480-2 pl-4 | B | 3, 9 | 156 |
| 12L. 1480-2 pl-8 | B | 4, 1 | 195 |
| 12L. 1480-2 pl-6 | B | 4, 3 | 238 |
| 12L. 1480-2 pl-2 | B | 4, 4 | 195 |
| 12L. 1480-2 pl-11 | B | 4, 8 | 208 |
| 12L. 1480-2 pl-5 | B | 4, 9 | 224 |
| 12L. 1480-2 pl-9 | A | 5, 1 | 336 |
| 12L. 1480-2 pl-10 | A | 7 | 480 |
| 12L. 1480-2 pl-14 | A | 7, 3 | 437 |
| 12L. 1480-2 pl-12 | A | 7, 4 | 483 |

Example 3

Creation of a Melon Plant with a Cullin1 Gene Mutation; Genetic Modification of Plants by Ethyl Methane Sulfonate (EMS) and Identification of Plants which Have the Mutated Cullin1 Gene Melon seeds were treated with EMS by submergence of approximately 5000 seeds into an aerated solution of 0.07% (w/v) EMS during 24 hours at room temperature. The treated seeds were germinated on paper in a small plastic container and the resulting plants were grown and self-pollinated in a greenhouse to produce seeds. After maturation, these seeds were harvested and bulked in one pool. The resulting pool of seeds was used as starting material to identify the individual plants that show smaller internode length and/or smaller leaf area.

The Cullin1 mutants which were obtained were grown in a greenhouse in order to produce lines by self-fertilisation. Melon plant lines were analysed to confirm the smaller internode length and smaller leaf area. When a line was segregating for smaller internode length and/or smaller leaf area, plants were selected and after an additional cycle of inbreeding Cullin1 lines were selected. Cullin1 mutants were identified by their shorter internodes and/or smaller leaf area in comparison with control lines.

Example 4. Identification of Crops Comprising the Cullin1 Gene

A Basic Local Alignment Search Tool (BLAST) program was used to compare the Cullin1 gene as identified in SEQ ID NO:1 and the protein sequence as identified in SEQ ID NO:18 against the nucleotide coding sequences and protein sequences of other crop plants. This resulted in the identification of candidate Cullin1 orthologous genes in other plants. The multiple sequence alignment of the Cullin1 coding sequence confirmed that these were orthologous Cullin1 genes, see FIG. 69. Multiple sequence alignment of the protein sequences confirmed that these were orthologous Cullin1 proteins, see FIG. 70.

The invention is further described by the following numbered paragraphs:

1. Modified Cullin1 gene comprising a modification in the wild type Cullin1 nucleotide sequence of SEQ ID No: 1, SEQ ID No: 2, SEQ ID No: 3, SEQ ID No: 4, SEQ ID No: 5, SEQ ID No: 6, SEQ ID No: 7, SEQ ID No: 8, SEQ ID No: 9, SEQ ID No: 10, SEQ ID No: 11, SEQ ID No: 12, SEQ ID NO: 13, SEQ ID NO: 14, SEQ ID NO: 15, SEQ ID NO: 16, SEQ ID NO: 17 which leads to a change in the wild type Cullin1 amino acid sequence of SEQ ID No: 18, SEQ ID No: 19, SEQ ID No: 20, SEQ ID No: 21, SEQ ID No: 22, SEQ ID No: 23, SEQ ID No: 24, SEQ ID No: 25, SEQ ID No: 26, SEQ ID No: 27, SEQ ID No: 28, SEQ ID NO: 29, SEQ ID NO: 30, SEQ ID NO: 31, SEQ ID NO:32, SEQ ID NO. 33, SEQ ID NO: 34 respectively.

2. Modified Cullin1 gene of paragraph 1, wherein the modification of the nucleotide sequence is a SNP on a position that leads to a change in the amino acid sequence of the Cullin1 protein.

3. Modified Cullin1 gene of paragraph 1 or 2, wherein the change in the amino acid sequence is a substitution.

4. Modified Cullin1 gene of any one of the paragraphs 1-3, wherein the change in the amino acid sequence is found in the part of the Cullin1 protein between the amino acids on positions 30-60, preferably in the part between the amino acids on positions 40-55 of the cucumber amino acid sequence of SEQ ID No: 18, or, on a position corresponding thereto, for other crops.

5. Modified Cullin1 gene of any one of the paragraphs 1-4, wherein the modification in the amino acid sequence is found in the part of the Cullin1 protein that binds SKP1 and/or ETA-2.

6. Modified Cullin1 gene of any of the paragraphs 1-5, wherein the modification of the nucleotide sequence is a SNP on position 147 of the cucumber nucleotide sequence of SEQ ID No: 1, or, for a crop other than cucumber, on a position corresponding to position 147 of the cucumber nucleotide sequence of SEQ ID No: 1, leading to an amino acid change on position 49 of the cucumber amino acid sequence of SEQ ID No: 18, or, for a crop other than cucumber, on a position corresponding to position 49 of the cucumber amino acid sequence of SEQ ID No: 18.

7. Modified Cullin1 gene of paragraph 6, wherein the SNP comprises a change from Adenine, Cytosine or Thymine to Guanine.

8. Modified Cullin1 gene of any of the paragraphs 1-7, wherein in cucumber the SNP comprises a change from Adenine, Cytosine or Thymine to Guanine and the amino acid substitution comprises a change from Isoleucine to Methionine.

9. Plant, comprising the modified Cullin1 gene of any one of the paragraphs 1-8.

10. Plant of paragraph 9, wherein the plant belongs to a species selected from the group consisting of *Cucumis sativus, Cucumis melo, Curcurbita pepo, Citrullus lanatus, Solanum melongena, Solanum lycopersicum, Capsicum annuum, Brassica oleracea, Daucus carota, Apium graveo-*

*lens, Cichorium intybus, Cichorium endivia, Allium ampeloprasum, Lactuca sativa, Raphanus sativus, Spinacia oleracea*, and *Beta vulgaris*.

11. Plant of paragraph 9 or 10, wherein the modified Cullin1 gene results in the plant showing a compact growth phenotype as compared to an isogenic plant of the same species not comprising the modification of the Cullin 1 gene.

12. Plant seed, comprising the modified Cullin1 gene of any of the paragraphs 1-8.

13. Plant seed of paragraph 12, wherein the plant seed belongs to a species selected from the group consisting of *Cucumis sativus, Cucumis melo, Curcurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea*, and *Beta vulgaris*.

14. Propagation material capable of developing into and/or being derived from a plant of any of the paragraphs 9-11, wherein the propagation material comprises the modified Cullin1 gene of any of the paragraphs 1-8 and wherein the propagation material is selected from a microspore, pollen, ovary, ovule, embryo, embryo sac, egg cell, cutting, root, hypocotyl, cotyledon, stem, leaf, flower, anther, seed, meristematic cell, protoplast, or cell, or tissue culture thereof.

15. Use of the modified Cullin1 gene of any of the paragraphs 1-8 for the development of a plant showing a compact growth phenotype as compared to an isogenic plant not comprising the modified Cullin 1 gene.

16. Use of the modified Cullin1 gene of any of the paragraphs 1-8 or a part thereof for identifying a plant showing a compact growth phenotype as compared to an isogenic plant not comprising the modified Cullin 1 gene.

17. Use of any of the sequences of SEQ ID No: 1-SEQ ID No: 17 and/or SEQ ID No: 35-SEQ ID No: 51 or a part thereof, or a marker derived thereof, as a marker for identifying a plant showing a compact growth phenotype as compared to an isogenic plant not comprising the modified Cullin 1 gene.

18. Use of any of the paragraphs 15-17, wherein the plant belongs to a species selected from the group consisting of *Cucumis sativus, Cucumis melo, Cucurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea*, and *Beta vulgaris*.

19. Method for obtaining a plant which shows a compact growth phenotype comprising;

a) crossing a plant comprising the modified Cullin1 gene of any one of the paragraphs 1-8 with a plant not comprising the modified Cullin1 gene, to obtain an F1 population;
b) optionally performing one or more rounds of selfing and/or crossing a plant from the F1 to obtain a further generation population;
c) selecting a plant that has a compact growth phenotype and the modified Cullin1 gene of the invention.

20. Method for obtaining a plant which shows a compact growth phenotype comprising;

a) crossing a plant comprising the modified Cullin1 gene of the current invention with another plant comprising the modified Cullin1 gene, to obtain an F1 population;
b) optionally performing one or more rounds of selfing and/or crossing a plant from the F1 to obtain a further generation population; and
c) selecting a plant that has a compact growth phenotype and the modified Cullin1 gene of the invention.

21. Method of paragraph 19 or 20, wherein the plant belongs to a species selected from the group consisting of *Cucumis sativus, Cucumis melo, Curcurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea*, and *Beta vulgaris*.

22. Marker for identifying a plant showing a compact growth phenotype, comprising the modified Cullin1 gene of any one of the paragraphs 1-8 or a part thereof that comprises the modification.

23. Marker of paragraph 22, wherein the modification is a nucleotide substitution on or around position 147 of SEQ ID No:1 of cucumber, or, in case of a crop other than cucumber, on or around a position corresponding to position 147 of SEQ ID No:1 of cucumber, which modification leads to an amino acid substitution in the Cullin1 protein.

24. Method for selecting a plant showing a compact growth phenotype from a population of plants, comprising detecting the presence or absence of a guanine on position 147 of the cucumber nucleotide sequence of SEQ ID NO:1, or, for a crop other than cucumber, on a position corresponding to position 147 of the cucumber nucleotide sequence of SEQ ID No: 1, in the genome of a plant of a population of plants, and selecting a plant comprising a guanine on position 147 of SEQ ID NO:1, or, for a crop other than cucumber, on a position corresponding to position 147 of the cucumber nucleotide sequence of SEQ ID No: 1.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A mutant *Cucumis* plant comprising a modified Cullin1 gene comprising a modification in the wild type nucleotide sequence of SEQ ID NO: 1 which leads to a change in the wild type Cullin1 amino acid sequence of SEQ ID NO: 18, wherein the modification of the nucleotide sequence is a SNP at position 147 of the nucleotide sequence of SEQ ID NO: 1 leading to an amino acid change at position 49 of the amino acid sequence of SEQ ID NO: 18, wherein the change is a replacement of the amino acid isoleucine with methionine.

2. The plant as claimed in claim 1, wherein the plant belongs to a species selected from the group consisting of *Cucumis sativus* and *Cucumis melo*.

3. The plant as claimed in claim 1, wherein the modified Cullin1 gene results in the plant showing a compact growth phenotype as compared to an isogenic plant of the same species not comprising the modification of the Cullin1 gene.

4. A mutant *Cucumis* plant seed comprising a modified Cullin1 gene comprising a modification in the wild type nucleotide sequence of SEQ ID NO: 1 which leads to a change in the wild type Cullin1 amino acid sequence of SEQ ID NO: 18, wherein the modification of the nucleotide sequence is a SNP at position 147 of the nucleotide sequence of SEQ ID NO: 1 leading to an amino acid change at position 49 of the cucumber amino acid sequence of SEQ ID NO: 18, wherein the change is a replacement of the amino acid isoleucine with methionine.

5. The plant seed as claimed in claim 3, wherein the plant seed belongs to a species selected from the group consisting of *Cucumis sativus* and *Cucumis melo*.

6. A propagation material capable of developing into the plant as claimed in claim 1, wherein the propagation material comprises the modified Cullin1 gene.

7. The plant of claim 1, wherein the modified Cullin1 gene is introgressed into the plant.

8. The propagation material of claim 6, wherein the propagation material comprises a microspore, pollen, ovary, ovule, embryo, embryo sac, egg cell, cutting, root, hypocotyl, cotyledon, stem, leaf, flower, anther, seed, meristematic cell, protoplast, cell, or tissue culture thereof.

* * * * *

UNITED STATES PATENT AND TRADEMARK OFFICE

CERTIFICATE OF CORRECTION

PATENT NO. : 10,856,482 B2
APPLICATION NO. : 15/892500
DATED : December 8, 2020
INVENTOR(S) : Lilian Van Der Linde et al.

It is certified that error appears in the above-identified patent and that said Letters Patent is hereby corrected as shown below:

In the Claims

Column 230, Lines 7-9, should read:
The plant seed as claimed in claim 4, wherein the plant seed belongs to a species selected from the group consisting of Cucumis sativus and Cucumis melo.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*